(12) United States Patent
Bandarage et al.

(10) Patent No.: US 7,442,802 B2
(45) Date of Patent: *Oct. 28, 2008

(54) CYCLOOXYGENASE-2 SELECTIVE INHIBITORS, COMPOSITIONS AND METHODS OF USE

(75) Inventors: Upul K. Bandarage, Lexington, MA (US); Richard A. Earl, Westford, MA (US); Maiko Ezawa, Acton, MA (US); Xinqin Fang, Lexington, MA (US); David S. Garvey, Dover, MA (US); Subhash P. Khanapure, Clinton, MA (US); Ramani R. Ranatunge, Lexington, MA (US); Stewart K. Richardson, Tolland, CT (US); Joseph D. Schroeder, Minneapolis, MA (US); Cheri A. Stevenson, Haverhill, MA (US); Shiow-Jyi Wey, Woburn, MA (US)

(73) Assignee: NitroMed, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/418,187

(22) Filed: May 5, 2006

(65) Prior Publication Data
US 2006/0194861 A1 Aug. 31, 2006

Related U.S. Application Data

(62) Division of application No. 10/603,098, filed on Jun. 25, 2003, now Pat. No. 7,087,630.

(60) Provisional application No. 60/454,307, filed on Mar. 14, 2003, provisional application No. 60/391,769, filed on Jun. 27, 2002.

(51) Int. Cl.
*A61K 31/415* (2006.01)
*C07D 231/12* (2006.01)

(52) U.S. Cl. .................... 548/375.1; 514/406

(58) Field of Classification Search .............. 548/375.1
See application file for complete search history.

(56) References Cited

U.S. PATENT DOCUMENTS

| | | | |
|---|---|---|---|
| 5,474,995 A | 12/1995 | Ducharme et al. | |
| 5,536,752 A | 7/1996 | Ducharme et al. | |
| 5,550,142 A | 8/1996 | Ducharme et al. | |
| 5,633,272 A | 5/1997 | Talley et al. | |
| 5,710,140 A | 1/1998 | Ducharme et al. | |
| 5,719,163 A | 2/1998 | Norman et al. | |
| 5,859,257 A | 1/1999 | Talley | |
| 5,945,539 A | 8/1999 | Haruta et al. | |
| 5,985,902 A | 11/1999 | Talley et al. | |
| 5,994,381 A | 11/1999 | Haruta et al. | |
| 6,002,014 A | 12/1999 | Haruta et al. | |
| 6,040,341 A | 3/2000 | Del Soldato et al. | |
| 6,297,260 B1 | 10/2001 | Bandarage et al. | |
| 6,436,967 B1 | 8/2002 | Talley et al. | |
| 6,482,956 B2 | 11/2002 | Luengo et al. | |
| 6,362,209 B1 | 3/2003 | Haruta et al. | |
| 6,649,629 B2 * | 11/2003 | Bandarage et al. ......... 514/326 |
| 6,673,818 B2 | 1/2004 | Brown et al. | |
| 6,699,884 B2 | 3/2004 | Brown et al. | |
| 7,211,598 B2 * | 5/2007 | Garvey et al. ............... 514/406 |
| 2004/0006133 A1 | 1/2004 | Ranatunge et al. | |
| 2004/0072883 A1 | 4/2004 | Garvey et al. | |
| 2004/0082652 A1 | 4/2004 | Del Soldato et al. | |
| 2005/0032851 A1 | 2/2005 | Talley et al. | |
| 2005/0032852 A1 | 2/2005 | Carter | |
| 2005/0101661 A1 | 5/2005 | Del Soldato et al. | |

FOREIGN PATENT DOCUMENTS

| | | |
|---|---|---|
| WO | WO 95/15316 | 6/1995 |
| WO | WO 95/18799 | 7/1995 |
| WO | WO 96/25405 | 8/1996 |

(Continued)

OTHER PUBLICATIONS

Jul. 11, 2005. Supplementary European Search Report for European Patent Application No. 03762000.2.

(Continued)

*Primary Examiner*—Laura L. Stockton
(74) *Attorney, Agent, or Firm*—Wilmer Cutler Pickering Hale and Dorr LLP

(57) ABSTRACT

The invention describes novel cyclooxygenase 2 (COX-2) selective inhibitors and novel compositions comprising at least one cyclooxygenase 2 (COX-2) selective inhibitor, and, optionally, at least one compound that donates, transfers or releases nitric oxide, stimulates endogenous synthesis of nitric oxide, elevates endogenous levels of endothelium-derived relaxing factor or is a substrate for nitric oxide synthase, and/or at least one therapeutic agent. The invention also provides novel kits comprising at least one COX-2 selective inhibitor, optionally nitrosated and/or nitrosylated, and, optionally, at least one nitric oxide donor, and/or, optionally, at least one therapeutic agent. The novel cyclooxygenase 2 selective inhibitors of the invention can be optionally nitrosated and/or nitrosylated. The invention also provides methods for treating inflammation, pain and fever; for treating and/or improving the gastrointestinal properties of COX-2 selective inhibitors; for facilitating wound healing; for treating and/or preventing renal and/or respiratory toxicity; for treating and/or preventing other disorders resulting from elevated levels of cyclooxygenase-2; and for improving the cardiovascular profile of COX-2 selective inhibitors.

25 Claims, No Drawings

FOREIGN PATENT DOCUMENTS

| | | |
|---|---|---|
| WO | WO 96/36617 | 11/1996 |
| WO | WO 97/38986 | 10/1997 |
| WO | WO 00/25776 | 5/2000 |
| WO | WO 01/45703 | 6/2001 |
| WO | WO 04/000300 | 12/2003 |
| WO | WO 04/000781 | 12/2003 |
| WO | WO 2004/024186 | 3/2004 |
| WO | WO 2005/030224 | 4/2005 |

OTHER PUBLICATIONS

Jun. 9, 2004. International Search Report from PCT/US03/19850.

* cited by examiner

CYCLOOXYGENASE-2 SELECTIVE INHIBITORS, COMPOSITIONS AND METHODS OF USE

RELATED APPLICATIONS

This application is a divisional of U.S. application Ser. No. 10/603,098, filed Jun. 25, 2003, issued as U.S. Pat. No. 7,087,630, which claims priority under 35 USC § 119 to U.S. Application No. 60/391,769 filed Jun. 27, 2002, and U.S. Application No. 60/454,307 filed Mar. 14, 2003.

FIELD OF THE INVENTION

The invention describes novel nitrosated and/or nitrosylated cyclooxygenase 2 (COX-2) selective inhibitors and novel compositions comprising at least one nitrosated and/or nitrosylated cyclooxygenase 2 (COX-2) selective inhibitor, and, optionally, at least one compound that donates, transfers or releases nitric oxide, stimulates endogenous synthesis of nitric oxide, elevates endogenous levels of endothelium-derived relaxing factor or is a substrate for nitric oxide synthase, and/or at least one therapeutic agent. The invention also provides novel compositions comprising at least one COX-2 selective inhibitor, that is optionally nitrosated and/or nitrosylated, and at least one compound that donates, transfers or releases nitric oxide, elevates endogenous levels of endothelium-derived relaxing factor, stimulates endogenous synthesis of nitric oxide or is a substrate for nitric oxide synthase and/or at least one therapeutic agent. The invention also provides novel kits comprising at least one COX-2 selective inhibitor, that is optionally nitrosated and/or nitrosylated, and, optionally, at least one nitric oxide donor and/or at least one therapeutic agent. The invention also provides methods for treating inflammation, pain and fever; for treating gastrointestinal disorders and/or improving the gastrointestinal properties of COX-2 selective inhibitors; for facilitating wound healing; for treating and/or preventing renal and/or respiratory toxicities; for treating and/or preventing other disorders resulting from elevated levels of cyclooxygenase-2; and for improving the cardiovascular profile of COX-2 selective inhibitors.

BACKGROUND OF THE INVENTION

Nonsteroidal anti-inflammatory compounds (NSAIDs) are widely used for the treatment of pain, inflammation, and acute and chronic inflammatory disorders such as osteoarthritis and rheumatoid arthritis. These compounds inhibit the activity of the enzyme cyclooxygenase (COX), also known as prostaglandin G/H synthase, which is the enzyme that converts arachidonic acid into prostanoids. The NSAIDs also inhibit the production of other prostaglandins, especially prostaglandin $G_2$, prostaglandin $H_2$ and prostaglandin $E_2$, thereby reducing the prostaglandin-induced pain and swelling associated with the inflammation process. The chronic use of NSAIDs has been associated with adverse effects, such as gastrointestinal ulceration and renal toxicity. The undesirable side effects are also due to the inhibition of prostaglandin in the affected organ.

Recently two isoforms of cyclooxygenase, encoded by two distinct genes (Kujubu et al, *J. Biol. Chem.*, 266, 12866-12872 (1991)), have been identified—a constitutive form, cyclooxygenase-1 (COX-1), and an inductive form, cyclooxygenase-2 (COX-2). It is thought that the antiinflammatory effects of NSAIDs are mediated by the inhibition of COX-2, whereas the side effects seem to be caused by the inhibition of COX-1. The NSAIDs currently on the market either inhibit both isoforms of COX with little selectivity for either isoform or are COX-1 selective. Recently compounds that are COX-2 selective inhibitors have been developed and marketed. These COX-2 selective inhibitors have the desired therapeutic profile of an antiinflammatory drug without the adverse effects commonly associated with the inhibition of COX-1. However, these compounds can result in dyspepsia and can cause gastropathy (Mohammed et al, *N. Engl. J. Med.*, 340(25) 2005 (1999)). Additionally the COX-2 selective inhibitors can increase the risk of cardiovascular events in a patient (Mukherjee et al., *JAMA* 286(8) 954-959 (2001)); Hennan et al., *Circulation*, 104:820-825 (2001)).

There is still a need in the art for novel COX-2 selective inhibitor compounds that have gastroprotective properties, facilitate wound healing, decreased renal toxicity and dyspepsia, improved cardiovascular profile and that can be used at low dosages. The invention is directed to these, as well as other, important ends.

SUMMARY OF THE INVENTION

The invention provides novel COX-2 selective inhibitors, or a pharmaceutically acceptable salt thereof. These compounds are potent analgesics, have antiinflammatory properties and have an unexpected potential for facilitating wound healing. The novel compounds also have unexpected properties in the treatment and/or prevention of renal and/or respiratory toxicity and for improving the cardiovascular profile of COX-2 selective inhibitors. The COX-2 selective inhibitor, or a pharmaceutically acceptable salt thereof, can be nitrosated and/or nitrosylated through one or more sites, such as oxygen (hydroxyl condensation), sulfur (sulfhydryl condensation) and/or nitrogen. The invention also provides compositions comprising the novel compounds described herein in a pharmaceutically acceptable carrier.

The invention is also based on the discovery that administering at least one COX-2 selective inhibitor and at least one nitric oxide donor or administering at least one nitrosated and/or nitrosylated COX-2 selective inhibitor, and, optionally, at least one nitric oxide donor reduces the gastrointestinal toxicity induced by COX-2-selective inhibitors. Nitric oxide donors include, for example, S-nitrosothiols, nitrites, nitrates, N-oxo-N-nitrosamines, SPM 3672, SPM 5185, SPM 5186 and analogues thereof, and substrates of the various isozymes of nitric oxide synthase. Thus, another aspect of the invention provides compositions comprising at least one COX-2 selective inhibitor, that is optionally substituted with at least one NO and/or $NO_2$ group (i.e., nitrosylated and/or nitrosated), and at least one compound that donates, transfers or releases nitric oxide as a charged species, i.e., nitrosonium ($NO^+$) or nitroxyl (NO—), or as the neutral species, nitric oxide (NO•), and/or stimulates endogenous production of nitric oxide or EDRF in vivo and/or is a substrate for nitric oxide synthase. The invention also provides for such compositions in a pharmaceutically acceptable carrier.

Yet another aspect of the invention provides compositions comprising at least one COX-2 selective inhibitor, that is optionally substituted with at least one $NO_2$ group and/or at least one NO group (i.e., nitrosated and/or nitrosylated respectively), and, optionally, at least one compound that donates, transfers or releases nitric oxide as a charged species, i.e., nitrosonium ($NO^+$) or nitroxyl (NO—), or as the neutral species, nitric oxide (NO.), and/or stimulates endogenous production of nitric oxide or EDRF in vivo and/or is a substrate for nitric oxide synthase, and/or, optionally, at least one therapeutic agent, including but not limited to, steroids, nonsteroidal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, HMG CoA inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and the like. The invention also provides for such compositions in a pharmaceutically acceptable carrier.

Yet another aspect of the present invention provides methods for treating and/or preventing inflammation, pain and fever; for treating gastrointestinal disorders and/or improving gastrointestinal properties of COX-2 inhibitors; for facilitating wound healing; for treating and/or preventing renal and/or respiratory toxicity; and for treating and/or preventing COX-2 mediated disorders (i.e., disorders resulting from elevated levels of COX-2) in a patient in need thereof which comprises administering to the patient a therapeutically effective amount of at least one COX-2 selective inhibitor, that is optionally substituted with at least one $NO_2$ group and/or at least one NO group (i.e., nitrosated and/or nitrosylated respectively), and, optionally, at least one compound that donates, transfers or releases nitric oxide as a charged species, i.e., nitrosonium ($NO^+$) or nitroxyl (NO—), or as the neutral species, nitric oxide (NO.), and/or stimulates endogenous production of nitric oxide or EDRF in vivo and/or is a substrate for nitric oxide synthase and/or stimulates endogenous production of NO or EDRF in vivo and/or is a substrate for nitric oxide synthase (i.e., NO donors). The methods can optionally further comprise the administration of at least one therapeutic agent, such as, for example, steroids, nonsteroidal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, HMG CoA inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and mixtures of two or more thereof. In this aspect of the invention, the methods can involve administering the COX-2 selective inhibitors, that are optionally nitrosated and/or nitrosyalted, administering the COX-2 selective inhibitors, that are optionally nitrosated and/or nitrosylated and NO donors, administering the COX-2 selective inhibitors, that are optionally nitrosated and/or nitrosylated, and therapeutic agents, or administering the COX-2 selective inhibitors, that are optionally nitrosated and/or nitrosylated, NO donors and therapeutic agents. The selective COX-2 inhibitors, nitric oxide donors, and/or therapeutic agents can be administered separately or as components of the same composition in one or more pharmaceutically acceptable carriers.

Yet another aspect of the invention provides methods for improving the cardiovascular profile of COX-2 selective inhibitors in a patient in need thereof which comprises administering to the patient a therapeutically effective amount of at least one COX-2 selective inhibitor, optionally substituted with at least one $NO_2$ and/or NO group (i.e. nitrosated and/or nitrosylated), and, optionally, at least one compound that donates, transfers or releases nitric oxide as a charged species, i.e., nitrosonium ($NO^+$) or nitroxyl (NO—), or as the neutral species, nitric oxide (NO.), and/or stimulates endogenous production of nitric oxide or EDRF in vivo and/or is a substrate for nitric oxide synthase and/or stimulates endogenous production of NO or EDRF in vivo and/or is a substrate for nitric oxide synthase (i.e. NO donor). The methods can optionally further comprise the administration of at least one of 3-hydroxy-3-methylglutaryl coenzyme A (HMG-CoA) inhibitors, antiplatelet agents, thrombin-inhibitors,-thromboxane inhibitors, and mixtures of two or more thereof. In this aspect of the invention, the methods can involve administering the nitrosated and/or nitrosylated COX-2 selective inhibitors, administering the COX-2 selective inhibitors, that are optionally nitrosated and/or nitrosylated, and NO donors, administering the COX-2 selective inhibitors, that are optionally nitrosated and/or nitrosylated, and at least one of 3-hydroxy-3-methylglutaryl coenzyme A (HMG-CoA) inhibitors, antiplatelet agents, thrombin inhibitors or thromboxane inhibitors, or administering the COX-2 selective inhibitors, that are optionally nitrosated and/or nitrosylated, NO donors, and at least one of 3-hydroxy-3-methylglutaryl coenzyme A (HMG-CoA) inhibitors, antiplatelet agents, thrombin inhibitors or thromboxane inhibitors. The COX-2 inhibitors, nitric oxide donors, and/or 3-hydroxy-3-methylglutaryl coenzyme A (HMG-CoA) inhibitors, antiplatelet agents, thrombin inhibitors or thromboxane inhibitors can be administered separately or as components of the same composition in one or more pharmaceutically acceptable carriers.

In yet another aspect the invention provides kits comprising at least one COX-2 selective inhibitor, that is optionally substituted with at least one $NO_2$ group and/or at least one NO group (i.e., nitrosated and/or nitrosylated respectively), and, optionally, at least one compound that donates, transfers or releases nitric oxide as a charged species, i.e., nitrosonium ($NO^+$) or nitroxyl (NO—), or as the neutral species, nitric oxide (NO.), and/or stimulates endogenous production of nitric oxide or EDRF in vivo and/or is a substrate for nitric oxide synthase. The kit can further comprise at least one therapeutic agent, such as, for example, steroids, nonsteroidal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, 3-hydroxy-3-methylglutaryl coenzyme A (HMG-CoA) inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and mixtures of two or more thereof. The COX-2 selective inhibitor, the nitric oxide donor and/or therapeutic agent, can be separate components in the kit or can be in the form of a composition in the kit in one or more pharmaceutically acceptable carriers.

DETAILED DESCRIPTION OF THE INVENTION

As used throughout the disclosure, the following terms, unless otherwise indicated, shall be understood to have the following meanings.

"NSAID" refers to a nonsteroidal anti-inflammatory compound or a nonsteroidal anti-inflammatory drug. NSAIDs inhibit cyclooxygenase, the enzyme responsible for the biosyntheses of the prostaglandins and certain autocoid inhibitors, including inhibitors of the various isozymes of cyclooxygenase (including but not limited to cyclooxygenase-1 and -2), and as inhibitors of both cyclooxygenase and lipoxygenase.

"Cyclooxygenase-2 (COX-2) selective inhibitor" refers to a compound that selectively inhibits the cyclooxygenase-2 enzyme over the cyclooxygenase-1 enzyme. In one embodiment, the compound has a cyclooxygenase-2 $IC_{50}$ of less than about 2 μM and a cyclooxygenase-1 $IC_{50}$ of greater than about 5 μM, in the human whole blood COX-2 assay (as described in Brideau et al., *Inflamm Res.*, 45: 68-74 (1996)) and also has a selectivity ratio of cyclooxygenase-2 inhibition over cyclooxygenase-1 inhibition of at least 10, and preferably of at least 40. In another embodiment, the compound has a cyclooxygenase-1 $IC_{50}$ of greater than about 1 μM, and preferably of greater than 20 μM. The compound can also inhibit the enzyme, lipoxygenase. Such selectivity may indicate an ability to reduce the incidence of common NSAID-induced side effects.

"Parent COX-2 inhibitor" refers to a non-nitrosated and/or non-nitrosylated COX-2 inhibitor, or pharmaceutically acceptable salts thereof or pharmaceutically acceptable esters thereof. "Parent COX-2 inhibitor" includes the compounds of Formulas (I), (II) and (III) before they are nitrosated and/or nitrosylated by the methods described herein.

"Therapeutic agent" includes any therapeutic agent that can be used to treat or prevent the diseases described herein. "Therapeutic agents" include, for example, steroids, nonsteroidal antiinflammatory compounds, 5-lipoxygenase inhibitors, leukotriene $B_4$ receptor antagonists, leukotriene $A_4$ hydrolase inhibitors, 3-hydroxy-3-methylglutaryl coenzyme A inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and the like. Therapeutic agent includes the pro-drugs and pharmaceutical derivatives thereof including but not limited to the corresponding nitrosated and/or nitrosylated derivatives. Although nitric oxide donors have therapeutic activity, the term "therapeutic agent" does not include the nitric oxide donors described herein, since nitric oxide donors are separately defined.

"Cardiovascular disease or disorder" refers to any cardiovascular disease or disorder known in the art, including, but not limited to, restenosis, atherosclerosis, atherogenesis, angina, (particularly chronic, stable angina pectoris), ischemic disease, congestive heart failure or pulmonary edema associated with acute myocardial infarction, thrombosis, controlling blood pressure in hypertension (especially hypertension associated with cardiovascular surgical procedures), thromboembolic events, platelet aggregation, platelet adhesion, smooth muscle cell proliferation, vascular complications associated with the use of medical devices, wounds associated with the use of medical devices, cerebrovascular ischemic events, and the like. Complications associated with the use of medical devices may occur as a result of increased platelet deposition, activation, thrombus formation or consumption of platelets and coagulation proteins. Such complications, which are within the definition of "cardiovascular disease or disorder," include, for example, myocardial infarction, ischemic stroke, transient ischemic stroke, thromboembolic events, pulmonary thromboembolism, cerebral thromboembolism, thrombophlebitis, thrombocytopenia, bleeding disorders and/or any other complications which occur either directly or indirectly as a result of the foregoing disorders.

"Restenosis" is a cardiovascular disease or disorder that refers to the closure of a peripheral or coronary artery following trauma to the artery caused by an injury such as, for example, angioplasty, balloon dilation, atherectomy, laser ablation treatment or stent insertion. Restenosis can also occur following a number of invasive surgical techniques, such as, for example, transplant surgery, vein grafting, coronary artery bypass surgery, endarterectomy, heart transplantation, balloon angioplasty, atherectomy, laser ablation, endovascular stenting, and the like.

"Atherosclerosis" is a form of chronic vascular injury in which some of the normal vascular smooth muscle cells in the artery wall, which ordinarily control vascular tone regulating blood flow, change their nature and develop "cancer-like" behavior. These vascular smooth muscle cells become abnormally proliferative, secreting substances such as growth factors, tissue-degradation enzymes and other proteins, which enable them to invade and spread into the inner vessel lining, blocking blood flow and making that vessel abnormally susceptible to being completely blocked by local blood clotting, resulting in the death of the tissue served by that artery. Atherosclerotic cardiovascular disease, coronary heart disease (also known as coronary artery disease or ischemic heart disease), cerebrovascular disease and peripheral vessel disease are all common manifestations of atherosclerosis and are therefore encompassed by the terms "atherosclerosis" and "atherosclerotic disease".

"Improving the cardiovascular profile" refers to and includes reducing the risk of lic events, reducing the risk of developing atherosclerosis and atherosclerotic diseases, and inhibiting platelet aggregation of the parent COX-2 inhibitor.

"Thromboembolic events" includes, but is not limited to, ischemic stroke, transient ischemic stroke, myocardial infarction, angina pectoris, thrombosis, thromboembolism, thrombotic occlusion and reocclusion, acute vascular events, restenosis, transient ischemic attacks, and first and subsequent thrombotic stroke. Patients who are at risk of developing thromboembolic events, may include those with a familial history of, or genetically predisposed to, thromboembolic disorders, who have had ischemic stroke, transient ischemic stroke, myocardial infarction, and those with unstable angina pectoris or chronic stable angina pectoris and patients with altered prostacyclin/thromboxane $A_2$ homeostasis or higher than normal thromboxane $A_2$ levels leading to increase risk for thromboembolism, including patients with diabetes and rheumatoid arthritis.

"Thromboxane inhibitor" refers to any compound that reversibly or irreversibly inhibits thromboxane synthesis, and includes compounds which are the so-called thromboxane $A_2$ receptor antagonists, thromboxane $A_2$ antagonists, thromboxane $A_2$/prostaglandin endoperoxide antagonists, thromboxane receptor (TP) antagonists, thromboxane antagonists, thromboxane synthase inhibitors, and dual acting thromboxane synthase inhibitors and thromboxane receptor antagonists. The characteristics of the preferred thromboxane inhibitor should include the suppression of thromboxane $A_2$ formation (thromboxane synthase inhibitors) and/or blockade of thromboxane $A_2$ and prostaglandin $H_2$ platelet and vessel wall (thromboxane receptor antagonists). The effects should block platelet activation and therefore platelet function.

"Thromboxane $A_2$ receptor antagonist" refers to any compound that reversibly or irreversibly blocks the activation of any thromboxane $A_2$ receptor.

"Thromboxane synthase inhibitor" refers to any compound that reversibly or irreversibly inhibits the enzyme thromboxane synthesis thereby reducing the formation of thromboxane $A_2$. Thromboxane synthase inhibitors may also increase the synthesis of antiaggregatory prostaglandins including prostacyclin and prostaglandin $D_2$. Thromboxane $A_2$ receptor antagonists and thromboxane synthase inhibitors and can be identified using the assays described in Tai, Methods of Enzymology, Vol. 86, 110-113 (1982); Hall, *Medicinal Research Reviews,* 11:503-579 (1991) and Coleman et al., *Pharmacol*

Rev., 46: 205-229 (1994) and references therein, the disclosures of which are incorporated herein by reference in its entirety.

"Dual acting thromboxane receptor antagonist and thromboxane synthase inhibitor" refers to any compound that simultaneously acts as a thromboxane $A_2$ receptor antagonist and a thromboxane synthase inhibitor.

"Thrombin inhibitors" refers to and includes compounds that inhibit hydrolytic activity of thrombin, including the catalytic conversion of fibrinogen to fibrin, activation of Factor V to Va, Factor VIII to VIIIa, Factor XIII to XIIIa and platelet activation. Thrombin inhibitors may be identified using assays described in Lewis et at., Thrombosis Research. 70: 173-190 (1993).

"Platelet aggregation" refers to the binding of one or more platelets to each other. Platelet aggregation is commonly referred to in the context of generalized atherosclerosis, not with respect to platelet adhesion on vasculature damaged as a result of physical injury during a medical procedure. Platelet aggregation requires platelet activation which depends on the interaction between the ligand and its specific platelet surface receptor.

"Platelet activation" refers either to the change in conformation (shape) of a cell, expression of cell surface proteins (e.g., the IIb/IIIa receptor complex, loss of GPIb surface protein), and secretion of platelet derived factors (e.g., serotonin, growth factors).

"Patient" refers to animals, preferably mammals, most preferably humans, and includes males and females, and children and adults.

"Therapeutically effective amount" refers to the amount of the compound and/or composition that is effective to achieve its intended purpose.

"Transdermal" refers to the delivery of a compound by passage through the skin and into the blood stream.

"Transmucosal" refers to delivery of a compound by passage of the compound through the mucosal tissue and into the blood stream.

"Penetration enhancement" or "permeation enhancement" refers to an increase in the permeability of the skin or mucosal tissue to a selected pharmacologically active compound such that the rate at which the compound permeates through the skin or mucosal tissue is increased.

"Carriers" or "vehicles" refers to carrier materials suitable for compound administration and include any such material known in the art such as, for example, any liquid, gel, solvent, liquid diluent, solubilizer, or the like, which is non-toxic and which does not interact with any components of the composition in a deleterious manner.

"Nitric oxide adduct" or "NO adduct" refers to compounds and functional groups which, under physiological conditions, can donate, release and/or directly or indirectly transfer any of the three redox forms of nitrogen monoxide ($NO^+$, $NO^-$, NO.), such that the biological activity of the nitrogen monoxide species is expressed at the intended site of action.

"Nitric oxide releasing" or "nitric oxide donating" refers to methods of donating, releasing and/or directly or indirectly transferring any of the three redox forms of nitrogen monoxide ($NO^+$, NO—, NO.), such that the biological activity of the nitrogen monoxide species is expressed at the intended site of action.

"Nitric oxide donor" or "NO donor" refers to compounds that donate, release and/or directly or indirectly transfer a nitrogen monoxide species, and/or stimulate the endogenous production of nitric oxide or endothelium-derived relaxing factor (EDRF) in vivo and/or elevate endogenous levels of nitric oxide or EDRF in vivo. "NO donor" also includes compounds that are substrates for nitric oxide synthase.

"Alkyl" refers to a lower alkyl group, a haloalkyl group, a hydroxyalkyl group, an alkenyl group, an alkynyl group, a bridged cycloalkyl group, a cycloalkyl group or a heterocyclic ring, as defined herein. An alkyl group may also comprise one or more radical species, such as, for example a cycloalkylalkyl group or a heterocyclicalkyl group.

"Lower alkyl" refers to branched or straight chain acyclic alkyl group comprising one to about ten carbon atoms (preferably one to about eight carbon atoms, more preferably one to about six carbon atoms). Exemplary lower alkyl groups include methyl, ethyl, n-propyl, isopropyl, n-butyl, isobutyl, sec-butyl, t-butyl, pentyl, neopentyl, iso-amyl, hexyl, octyl, and the like.

"Substituted lower alkyl" refers to a lower alkyl group, as defined herein, wherein one or more of the hydrogen atoms have been replaced with one or more $R^{100}$ groups, wherein each $R^{100}$ is independently a hydroxy, an oxo, a carboxyl, a carboxamido, a halo, a cyano or an amino group, as defined herein.

"Haloalkyl" refers to a lower alkyl group, an alkenyl group, an alkynyl group, a bridged cycloalkyl group, a cycloalkyl group or a heterocyclic ring, as defined herein, to which is appended one or more halogens, as defined herein. Exemplary haloalkyl groups include trifluoromethyl, chloromethyl, 2-bromobutyl, 1-bromo-2-chloro-pentyl, and the like.

"Alkenyl" refers to a branched or straight chain $C_2$-$C_{10}$ hydrocarbon (preferably a $C_2$-$C_8$ hydrocarbon, more preferably a $C_2$-$C_6$ hydrocarbon) that can comprise one or more carbon-carbon double bonds. Exemplary alkenyl groups include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Lower alkenyl" refers to a branched or straight chain $C_2$-$C_4$ hydrocarbon that can comprise one or two carbon-carbon double bonds.

"Substituted alkenyl" refers to a branched or straight chain $C_2$-$C_{10}$ hydrocarbon (preferably a $C_2$-$C_8$ hydrocarbon, more preferably a $C_2$-$C_6$ hydrocarbon) which can comprise one or more carbon-carbon double bonds, wherein one or more of the hydrogen atoms have been replaced with one or more $R^{100}$ groups, wherein each $R^{100}$ is independently a hydroxy, an oxo, a carboxyl, a carboxamido, a halo, a cyano or an amino group, as defined herein.

"Alkynyl" refers to an unsaturated acyclic $C_2$-$C_{10}$ hydrocarbon (preferably a $C_2$-$C_8$ hydrocarbon, more preferably a $C_2$-$C_6$ hydrocarbon) that can comprise one or more carbon-carbon triple bonds. Exemplary alkynyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl, 3,3-dimethyl-butyn-1-yl, and the like.

"Bridged cycloalkyl" refers to two or more cycloalkyl groups, heterocyclic groups, or a combination thereof fused via adjacent or non-adjacent atoms. Bridged cycloalkyl groups can be unsubstituted or substituted with one, two or three substituents independently selected from alkyl, alkoxy, amino, alkylamino, dialkylamino, hydroxy, halo, carboxyl, alkylcarboxylic acid, aryl, amidyl, ester, alkylcarboxylic ester, carboxamido, alkylcarboxamido, oxo and nitro. Exemplary bridged cycloalkyl groups include adamantyl, decahydronapthyl, quinuclidyl, 2,6-dioxabicyclo(3.3.0)octane, 7-oxabycyclo(2.2.1)heptyl, 8-azabicyclo(3,2,1)oct-2-enyl and the like.

"Cycloalkyl" refers to a saturated or unsaturated cyclic hydrocarbon comprising from about 3 to about 10 carbon atoms. Cycloalkyl groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo, alkylsulfinyl, and nitro. Exemplary cycloalkyl groups include cyclopropyl, cyclobutyl, cyclopentyl, cyclohexyl, cyclohexenyl, cyclohepta-1,3-dienyl, and the like.

"Heterocyclic ring or group" refers to a saturated or unsaturated cyclic hydrocarbon group having about 2 to about 10 carbon atoms (preferably about 4 to about 6 carbon atoms) where 1 to about 4 carbon atoms are replaced by one or more nitrogen, oxygen and/or sulfur atoms. Sulfur maybe in the thio, sulfinyl or sulfonyl oxidation state. The heterocyclic ring or group can be fused to an aromatic hydrocarbon group. Heterocyclic groups can be unsubstituted or substituted with one, two or three substituents independently selected from alkyl, alkoxy, amino, alkylthio, aryloxy, arylthio, arylalkyl, hydroxy, oxo, thial, halo, carboxyl, carboxylic ester, alkylcarboxylic acid, alkylcarboxylic ester, aryl, arylcarboxylic acid, arylcarboxylic ester, amidyl, ester, alkylcarbonyl, arylcarbonyl, alkylsulfinyl, carboxamido, alkylcarboxamido, arylcarboxamido, sulfonic acid, sulfonic ester, sulfonamido and nitro. Exemplary heterocyclic groups include pyrrolyl, furyl, thienyl, 3-pyrrolinyl,4,5,6-trihydro-2H-pyranyl, pyridinyl, 1,4-dihydropyridinyl, pyrazolyl, triazolyl, pyrimidinyl, pyridazinyl, oxazolyl, thiazolyl, imidazolyl, indolyl, thiophenyl, furanyl, tetrhydrofuranyl, tetrazolyl, pyrrolinyl, pyrrolindinyl, oxazolindinyl 1,3-dioxolanyl, imidazolinyl, imidazolindinyl, pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyl, benzothiazolinyl, quinolinyl, and the like.

"Heterocyclic compounds" refer to mono- and polycyclic compounds comprising at least one aryl or heterocyclic ring.

"Aryl" refers to a monocyclic, bicyclic, carbocyclic or heterocyclic ring system comprising one or two aromatic rings. Exemplary aryl groups include phenyl, pyridyl, napthyl, quinoyl, tetrahydronaphthyl, furanyl, indanyl, indenyl, indoyl, and the like. Aryl groups (including bicyclic aryl groups) can be unsubstituted or substituted with one, two or three substituents independently selected from alkyl, alkoxy, alkylthio, amino, alkylamino, dialkylamino, arylamino, diarylamino, alkylarylamino, halo, cyano, alkylsulfinyl, hydroxy, carboxyl, carboxylic ester, alkylcarboxylic acid, alkylcarboxylic ester, aryl, arylcarboxylic acid, arylcarboxylic ester, alkylcarbonyl, arylcarbonyl, amidyl, ester, carboxamido, alkylcarboxamido, carbomyl, sulfonic acid, sulfonic ester, sulfonamido and nitro. Exemplary substituted aryl groups include tetrafluorophenyl, pentafluorophenyl, sulfonamide, alkylsulfonyl, arylsulfonyl, and the like.

"Cycloalkenyl" refers to an unsaturated cyclic $C_2$-$C_{10}$ hydrocarbon (preferably a $C_2$-$C_8$ hydrocarbon, more preferably a $C_2$-$C_6$ hydrocarbon) which can comprise one or more carbon-carbon double bonds.

"Alkylaryl" refers to an alkyl group, as defined herein, to which is appended an aryl group, as defined herein. Exemplary alkylaryl groups include benzyl, phenylethyl, hydroxybenzyl, fluorobenzyl, fluorophenylethyl, and the like.

"Arylalkyl" refers to an aryl radical, as defined herein, attached to an alkyl radical, as defined herein. Exemplary arylalkyl groups include benzyl, phenylethyl, 4-hydroxybenzyl, 3-fluorobenzyl, 2-fluorophenylethyl, and the like.

"Arylalkenyl" refers to an aryl radical, as defined herein, attached to an alkenyl radical, as defined herein. Exemplary arylalkenyl groups include styryl, propenylphenyl, and the like.

"Cycloalkylalkyl" refers to a cycloalkyl radical, as defined herein, attached to an alkyl radical, as defined herein.

"Cycloalkylalkoxy" refers to a cycloalkyl radical, as defined herein, attached to an alkoxy radical, as defined herein.

"Cycloalkylalkylthio" refers to a cycloalkyl radical, as defined herein, attached to an alkylthio radical, as defined herein.

"Heterocyclicalkyl" refers to a heterocyclic ring radical, as defined herein, attached to an alkyl radical, as defined herein.

"Arylheterocyclic ring" refers to a bi- or tricyclic ring comprised of an aryl ring, as defined herein, appended via two adjacent carbon atoms of the aryl ring to a heterocyclic ring, as defined herein. Exemplary arylheterocyclic rings include dihydroindole, 1,2,3,4-tetra-hydroquinoline, and the like.

"Alkylheterocyclic ring" refers to a heterocyclic ring radical, as defined herein, attached to an alkyl radical, as defined herein. Exemplary alkylheterocyclic rings include 2-pyridylmethyl, 1-methylpiperidin-2-one-3-methyl, and the like.

"Alkoxy" refers to $R_{50}O$—, wherein $R_{50}$ is an alkyl group, as defined herein (preferably a lower alkyl group or a haloalkyl group, as defined herein). Exemplary alkoxy groups include methoxy, ethoxy, t-butoxy, cyclopentyloxy, trifluoromethoxy, and the like.

"Aryloxy" refers to $R_{55}O$—, wherein $R_{55}$ is an aryl group, as defined herein. Exemplary arylkoxy groups include napthyloxy, quinolyloxy, isoquinolizinyloxy, and the like.

"Alkylthio" refers to $R_{50}S$—, wherein $R_{50}$ is an alkyl group, as defined herein.

"Lower alkylthio" refers to a lower alkyl group, as defined herein, appended to a thio group, as defined herein.

"Arylalkoxy" or "alkoxyaryl" refers to an alkoxy group, as defined herein, to which is appended an aryl group, as defined herein. Exemplary arylalkoxy groups include benzyloxy, phenylethoxy, chlorophenylethoxy, and the like.

"Alkoxyalkyl" refers to an alkoxy group, as defined herein, appended to an alkyl group, as defined herein. Exemplary alkoxyalkyl groups include methoxymethyl, methoxyethyl, isopropoxymethyl, and the like.

"Alkoxyhaloalkyl" refers to an alkoxy group, as defined herein, appended to a haloalkyl group, as defined herein. Exemplary alkoxyhaloalkyl groups include 4-methoxy-2-chlorobutyl and the like.

"Cycloalkoxy" refers to $R_{54}O$—, wherein $R_{54}$ is a cycloalkyl group or a bridged cycloalkyl group, as defined herein. Exemplary cycloalkoxy groups include cyclopropyloxy, cyclopentyloxy, cyclohexyloxy, and the like.

"Cycloalkylthio" refers to $R_{54}S$—, wherein $R_{54}$ is a cycloalkyl group or a bridged cycloalkyl group, as defined herein. Exemplary cycloalkylthio groups include cyclopropylthio, cyclopentylthio, cyclohexylthio, and the like.

"Haloalkoxy" refers to an alkoxy group, as defined herein, in which one or more of the hydrogen atoms on the alkoxy group are substituted with halogens, as defined herein. Exemplary haloalkoxy groups include 1,1,1-trichloroethoxy, 2-bromobutoxy, and the like.

"Hydroxy" refers to —OH.

"Oxo" refers to =O.

"Oxy" refers to —$O^- R_{77}^+$ wherein $R_{77}$ is an organic or inorganic cation.

"Oxime" refers to =N—$OR_{81}$ wherein $R_{81}$ is a hydrogen, an alkyl group, an aryl group, an alkylsulfonyl group, an arylsulfonyl group, a carboxylic ester, an alkylcarbonyl group, an arylcarbonyl group, a carboxamido group, an alkoxyalkyl group or an alkoxyaryl group.

"Hydrazone refers to =N—N($R_{81}$)($R'_{81}$) wherein $R'_{81}$ is independently selected from $R_{81}$, and $R_{81}$ is as defined herein.

"Organic cation" refers to a positively charged organic ion. Exemplary organic cations include alkyl substituted ammonium cations, and the like.

"Inorganic cation" refers to a positively charged metal ion. Exemplary inorganic cations include Group I metal cations such as for example, sodium, potassium, and the like.

"Hydroxyalkyl" refers to a hydroxy group, as defined herein, appended to an alkyl group, as defined herein.

"Nitrate" refers to —O—$NO_2$.

"Nitrite" refers to —O—NO.

"Thionitrate" refers to —S—$NO_2$.

"Thionitrite" and "nitrosothiol" refer to —S—NO.

"Nitro" refers to the group —$NO_2$ and "nitrosated" refers to compounds that have been substituted therewith.

"Nitroso" refers to the group —NO and "nitrosylated" refers to compounds that have been substituted therewith.

"Nitrile" and "cyano" refer to —CN.

"Halogen" or "halo" refers to iodine (I), bromine (Br), chlorine (Cl), and/or fluorine (F).

"Amino " refers to —$NH_2$, an alkylamino group, a dialkylamino group, an arylamino group, a diarylamino group, an alkylarylamino group or a heterocyclic ring, as defined herein.

"Alkylamino" refers to $R_{50}$NH—, wherein $R_{50}$ is an alkyl group, as defined herein. Exemplary alkylamino groups include methylamino, ethylamino, butylamino, cyclohexylamino, and the like.

"Arylamino" refers to $R_{55}$NH—, wherein $R_{55}$ is an aryl group, as defined herein.

"Dialkylamino" refers to $R_{52}R_{53}$N—, wherein $R_{52}$ and $R_{53}$ are each independently an alkyl group, as defined herein. Exemplary dialkylamino groups include dimethylamino, diethylamino, methyl propargylamino, and the like.

"Diarylamino" refers to $R_{55}R_{60}$N—, wherein $R_{55}$ and R60 are each independently an aryl group, as defined herein.

"Alkylarylamino or arylalkylamino" refers to $R_{52}R_{55}$N—, wherein $R_{52}$ is an alkyl group, as defined herein, and $R_{55}$ is an aryl group, as defined herein.

"Alkylarylalkylamino" refers to $R_{52}R_{79}$N—, wherein $R_{52}$ is an alkyl group, as defined herein, and $R_{79}$ is an arylalkyl group, as defined herein.

"Alkylcycloalkylamino" refers to $R_{52}R_{80}$N—, wherein $R_{52}$ is an alkyl group, as defined herein, and $R_{80}$ is an cycloalkyl group, as defined herein.

"Aminoalkyl" refers to an amino group, an alkylamino group, a dialkylamino group, an arylamino group, a diarylamino group, an alkylarylamino group or a heterocyclic ring, as defined herein, to which is appended an alkyl group, as defined herein. Exemplary aminoalkyl groups include dimethylaminopropyl, diphenylaminocyclopentyl, methylaminomethyl, and the like.

"Aminoaryl" refers to an aryl group to which is appended an alkylamino group, a arylamino group or an arylalkylamino group. Exemplary aminoaryl groups include anilino, N-methylanilino, N-benzylanilino, and the like.

"Thio" refers to —S—.

"Sulfinyl" refers to —S(O)—.

"Methanthial" refers to —C(S)—.

"Thial" refers to =S.

"Sulfonyl" refers to —$S(O)_2^-$.

"Sulfonic acid" refers to —$S(O)_2OR_{76}$, wherein $R_{76}$ is a hydrogen, an organic cation or an inorganic cation, as defined herein.

"Alkylsulfonic acid" refers to a sulfonic acid group, as defined herein, appended to an alkyl group, as defined herein.

"Arylsulfonic acid" refers to a sulfonic acid group, as defined herein, appended to an aryl group, as defined herein.

"Sulfonic ester" refers to —$S(O)_2OR_{58}$, wherein $R_{58}$ is an alkyl group, an aryl group, or an aryl heterocyclic ring, as defined herein.

"Sulfonamido" refers to —$S(O)_2$—N($R_{51}$)($R_{57}$), wherein $R_{51}$ and $R_{57}$ are each independently a hydrogen atom, an alkyl group, an aryl group or an arylheterocyclic ring, as defined herein, or $R_{51}$ and $R_{57}$ when taken together are a heterocyclic ring, a cycloalkyl group or a bridged cycloalkyl group, as defined herein.

"Alkylsulfonamido" refers to a sulfonamido group, as defined herein, appended to an alkyl group, as defined herein.

"Arylsulfonamido" refers to a sulfonamido group, as defined herein, appended to an aryl group, as defined herein.

"Alkylthio" refers to $R_{50}$S—, wherein $R_{50}$ is an alkyl group, as defined herein (preferably a lower alkyl group, as defined herein).

"Arylthio" refers to $R_{55}$S—, wherein $R_{55}$ is an aryl group, as defined herein.

"Arylalkylthio" refers to an aryl group, as defined herein, appended to an alkylthio group, as defined herein.

"Alkylsulfinyl" refers to $R_{50}$—S(O)—, wherein $R_{50}$ is an alkyl group, as defined herein.

"Alkylsulfonyl" refers to $R_{50}$—$S(O)_2$—, wherein $R_{50}$ is an alkyl group, as defined herein.

"Alkylsulfonyloxy" refers to $R_{50}$—$S(O)_2$—O—, wherein $R_{50}$ is an alkyl group, as defined herein.

"Arylsulfinyl" refers to $R_{55}$—S(O)—, wherein $R_{55}$ is an aryl group, as defined herein.

"Arylsulfonyl" refers to $R_{55}$—$S(O)_2$—, wherein $R_{55}$ is an aryl group, as defined herein.

"Arylsulfonyloxy" refers to $R_{55}$—$S(O)_2$—O—, wherein $R_{55}$ is an aryl group, as defined herein.

"Amidyl" refers to $R_{51}$C(O)N($R_{57}$)— wherein $R_{51}$ and $R_{57}$ are each independently a hydrogen atom, an alkyl group, an aryl group or an arylheterocyclic ring, as defined herein.

"Ester" refers to $R_{51}$C(O)O— wherein $R_{51}$ is a hydrogen atom, an alkyl group, an aryl group or an arylheterocyclic ring, as defined herein.

"Carbamoyl" refers to —O—C(O)N($R_{51}$)($R_{57}$), wherein $R_{51}$ and $R_{57}$ are each independently a hydrogen atom, an alkyl group, an aryl group or an arylheterocyclic ring, as defined herein, or $R_{51}$ and $R_{57}$ taken together are a heterocyclic ring, a cycloalkyl group or a bridged cycloalkyl group, as defined herein.

"Carboxyl" refers to —C(O)$OR_{76}$, wherein $R_{76}$ is a hydrogen, an organic cation or an inorganic cation, as defined herein.

"Carbonyl" refers to —C(O)—.

"Alkylcarbonyl" refers to $R_{52}$—C(O)—, wherein $R_{52}$ is an alkyl group, as defined herein.

"Arylcarbonyl" refers to $R_{55}$—C(O)—, wherein $R_{55}$ is an aryl group, as defined herein.

"Arylalkylcarbonyl" refers to $R_{55}$—$R_{52}$—C(O)—, wherein $R_{55}$ is an aryl group, as defined herein, and $R_{52}$ is an alkyl group, as defined herein.

"Alkylarylcarbonyl" refers to $R_{52}$—$R_{55}$—C(O)—, wherein $R_{55}$ is an aryl group, as defined herein, and $R_{52}$ is an alkyl group, as defined herein.

"Heterocyclicalkylcarbonyl" refer to $R_{78}$C(O)— wherein $R_{78}$ is a heterocyclicalkyl group, as defined herein.

"Carboxylic ester" refers to —C(O)$OR_{58}$, wherein $R_{58}$ is an alkyl group, an aryl group or an aryl heterocyclic ring, as defined herein.

"Alkylcarboxylic acid" and "alkylcarboxyl" refer to an alkyl group, as defined herein, appended to a carboxyl group, as defined herein.

"Alkylcarboxylic ester" refers to an alkyl group, as defined herein, appended to a carboxylic ester group, as defined herein.

"Arylcarboxylic acid" refers to an aryl group, as defined herein, appended to a carboxyl group, as defined herein.

"Arylcarboxylic ester" and "arylcarboxyl" refer to an aryl group, as defined herein, appended to a carboxylic ester group, as defined herein.

"Carboxamido" refers to —C(O)N($R_{51}$)($R_{57}$), wherein $R_{51}$ and $R_{57}$ are each independently a hydrogen atom, an alkyl group, an aryl group or an arylheterocyclic ring, as defined herein, or $R_{51}$ and $R_{57}$ when taken together are a heterocyclic ring, a cycloalkyl group or a bridged cycloalkyl group, as defined herein.

"Alkylcarboxamido" refers to an alkyl group, as defined herein, appended to a carboxamido group, as defined herein.

"Arylcarboxamido" refers to an aryl group, as defined herein, appended to a carboxamido group, as defined herein.

"Urea" refers to —N($R_{59}$)—C(O)N($R_{51}$)($R_{57}$) wherein $R_{51}$, $R_{57}$, and $R_{59}$ are each independently a hydrogen atom, an alkyl group, an aryl group or an arylheterocyclic ring, as defined herein, or $R_{51}$ and $R_{57}$ taken together are a heterocyclic ring, a cycloalkyl group or a bridged cycloalkyl group, as defined herein.

"Phosphoryl" refers to —P($R_{70}$)($R_{71}$)($R_{72}$), wherein $R_{70}$ is a lone pair of electrons, thial or oxo, and $R_{71}$ and $R_{72}$ are each independently a covalent bond, a hydrogen, a lower alkyl, an alkoxy, an alkylamino, a hydroxy, an oxy or an aryl, as defined herein.

Compounds that donate, transfer or release nitric oxide species in vivo have been recognized as having a wide spectrum of advantages and applications. The invention is based on the unexpected discovery of the effects of such compounds alone and together with one or more COX-2 inhibitors. Treatment or prevention of inflammation, pain and fever; treatment of gastrointestinal disorders and/or improvement of the gastrointestinal properties of COX-2 inhibitors; facilitation of wound healing; and treatment and/or prevention of renal and/or respiratory toxicity and cyclooxygenase-2 mediated disorders can be obtained by the use of COX-2 inhibitors of the invention; or by the use of COX-2 inhibitors in conjunction with one or more compounds that donate, release or transfer nitric oxide and/or stimulate endogenous production of NO and/or EDRF in vivo and/or is a substrate for nitric oxide synthase, and, optionally, with one or more therapeutic agents.

The COX-2 selective inhibitors, that are optionally nitrosated and/or nitrosylated, can be used alone or in conjunction with one or more compounds that donate, release or transfer nitric oxide and/or stimulate endogenous production of NO and/or EDRF in vivo and/or is a substrate for nitric oxide synthase, and/or with one or more therapeutic agents, such as for example, steroids, nonsterodal antiinflammatory compounds (NSAID), 5-lipoxygenase (5-LO) inhibitors, leukotriene $B_4$ (LTB$_4$) receptor antagonists, leukotriene $A_4$ (LTA$_4$) hydrolase inhibitors, 3-hydroxy-3-methylglutaryl coenzyme A (HMG-CoA) inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, analgesics, *Helicobacter pylori* inhibitors, proton pump inhibitors, isoprostane inhibitors, and mixtures of two or more thereof. These novel compounds and novel compositions of the present invention are described in more detail herein.

In one embodiment, the invention describes COX-2 inhibitors of Formula (I), and pharmaceutically acceptable salts thereof:

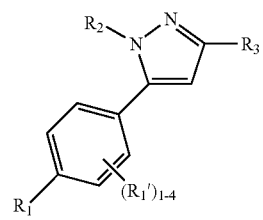

wherein:
$R_1$ is —S(O)$_2$—CH$_3$ or —S(O)$_2$—NH$_2$;
$R_1'$ at each occurrence is independently a hydrogen, a halogen, a methyl or CH$_2$OH;
$R_2$ is a substituted lower alkyl group, a cycloalkyl group, an aryl group or a heterocyclic ring;
$R_3$ is:
(a) —(C($R_4$)($R'_4$))$_k$—Y—(C($R_4$)($R'_4$))$_n$—O—V;
(b) —C(Z)-(C($R_4$)($R'_4$))$_k$—O—V;
(c) —C(Z)-(C($R_4$)($R'_4$))$_k$—Y—(C($R_4$)($R'_4$))$_n$—O—V;
(d) —(C($R_4$)($R'_4$))$_k$—Y—(C($R_4$)($R'_4$))$_n$—C(Z)-(C($R_4$)($R'_4$))$_n$—O—V;
(e) —(C($R_4$)($R'_4$))$_k$—CH=CH—(C($R_4$)($R'_4$))$_p$—O—V;
(f) —(C($R_4$)($R'_4$))$_n$—O—V;
(g) —(C($R_4$)($R'_4$))$_n$—W-Q-(C($R_4$)($R'_4$))$_k$—O—V;
(h) —C(Z)-W-Q-(C($R_4$)($R'_4$))$_k$—O—V;
(i) —C(O)—N($R_i$)—O—(C($R_4$)($R'_4$))$_n$—O—V;
(j) —(C($R_4$)($R'_4$))$_k$—C≡C—(C($R_4$)($R'_4$))$_p$—O—V;
(k) —(C($R_4$)($R'_4$))$_k$—Y—(C($R_4$)($R'_4$))$_k$—Y—(C($R_4$)($R'_4$))$_k$—O—V;
(l) —(C($R_4$)($R'_4$))$_p$-E-N($R_i$)—O—W-Q-(C($R_4$)($R'_4$))$_k$—O—V;
(m) —(C($R_4$)($R'_4$))$_p$-E-N($R_i$)—O—(C($R_4$)($R'_4$))$_k$—O—V;
(n) —(C($R_4$)($R'_4$))$_p$—N($R_i$)—O—(C($R_4$)($R'_4$))$_k$—O—V;
(o) —(C($R_4$)($R'_4$))$_p$—O—N($R_i$)—(C($R_4$)($R'_4$))$_k$—O—V;
(p) —(C($R_4$)($R'_4$))$_p$—O—N($R_i$)-E-(C($R_4$)($R'_4$))$_k$—O—V;
(q) —(C($R_4$)($R'_4$))$_p$—O—N($R_i$)-E-W-Q-(C($R_4$)($R'_4$))$_k$—O—V;
(r) —(C($R_4$)($R'_4$))$_p$—C(Z)-Y—(C($R_4$)($R'_4$))$_k$—O—V;
(s) —(C($R_4$)($R'_4$))$_p$—Y—C(Z)-(C($R_4$)($R'_4$))$_k$—O—V; or
(t) —(C($R_4$)($R'_4$))$_p$—Y—C(Z)-Y—(C($R_4$)($R'_4$))$_k$—O—V;
$R_4$ and $R'_4$ at each occurrence are independently a hydrogen, a halogen, a lower alkyl group, an alkoxy group; or $R_4$ and $R'_4$ taken together with the carbon atom to which they are attached are a cycloalkyl group, an aryl group or a heterocyclic ring;

V is —NO, —NO$_2$, or a hydrogen;
Y at each occurrence is independently an oxygen, —S(O)$_o$— or —N($R_a$)$R_i$—;
Z is an oxo, a thial, an oxime or a hydrazone;
Q is Y or a covalent bond;
W at each occurrence is independently an aryl group, an alkylaryl group, a heterocyclic ring or an alkylheterocyclic ring;
E is —C(O) or —S(O)$_o$;

$R_a$ is a lone pair of electron a hydrogen or a lower alkyl group;

$R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylaryl, an alkylsulfinyl, an alkylsulfonyl, an alkylsulfonyloxy, an arylsulfinyl, an arylsulfonyl, arylsulphonyloxy, a sulfonamido, a carboxamido, a carboxylic ester, an aminoalkyl, an aminoaryl, —$(C(R_4)(R'_4))_n$—O—V, a bond to an adjacent atom creating a double bond to that atom, —$(N_2O_2$—$)^-.M^+$, wherein $M^+$ is an organic or inorganic cation;

o is an integer from 0 to 2;

k is an integer from 1 to 6;

p at each occurrence is independently an integer from 0 to 10;

n at each occurrence is independently an integer from 2 to 10; and with the proviso that when $R_2$ is cycloalkyl, aryl or a heterocyclic ring, $R_3$ cannot be —$(C(R_4)(R'_4))_n$—O—V, where $R_4$ and $R'_4$ at each occurrence are independently a hydrogen, a halogen, a lower alkyl group, an alkoxy group and V is hydrogen, as disclosed in, for example, WO 98/47509 and WO 99/22720.

In cases where multiple designations of variables that reside in sequence are chosen as a "covalent bond" or the integer chosen is 0, the intent is to denote a single covalent bond connecting one radical to another. For example, $E_0$ would denote a covalent bond, while $E_2$ denotes (E-E) and $(C(R_4)(R'_4))_2$ denotes —$C(R_4)(R'_4)$—$C(R_4)(R'_4)$—.

Another embodiment of the invention describes COX-2 inhibitors of Formula (II), and pharmaceutically acceptable salts thereof:

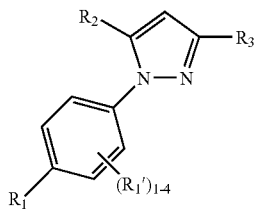

II wherein $R_1$, $R_1'$, $R_2$ and $R_3$ are as defined herein and with the proviso that when $R_2$ is cycloalkyl, aryl or a heterocyclic ring, $R_3$ cannot be —$(C(R_4)(R'_4))_n$—O—V, where $R_4$ and $R'_4$ at each occurrence are independently a hydrogen, a halogen, a lower alkyl group, an alkoxy group and V is hydrogen, as disclosed in, for example, U.S. Pat. Nos. 5,516,907, 5,753,688, 5,760,068 and in WO 95/15316.

Another embodiment of the invention describes COX-2 inhibitors of Formula (III), and pharmaceutically acceptable salts thereof:

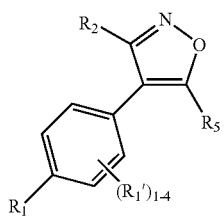

III wherein:

$R_5$ is:

(a) —$(C(R_4)(R'_4))_k$—Y—$(C(R_4)(R'_4))_k$—B—$(C(R_4)(R'_4))_k$—O—V;

(b) —$(C(R_4)(R'_4))_k$—Y—$(C(R_4)(R_4))_k$-D-$(C(R_4)(R'_4))_k$—O—V;

(c) —C(Z)-$(C(R_4)(R'_4))_k$—Y—$(C(R_4)(R'_4))_k$—O—V;

(d) —$C(R_4)(R'_4))_k$—Y—W-Q-$C(R_4)(R'_4))_k$—O—V;

(e) —C(Z)-W-Q-$(C(R_4)(R'_4))_k$—O—V;

(f) —$(C(R_4)(R'_4))_p$-E-N$(R_i)$—O—W-Q-$(C(R_4)(R'_4))_k$—O—V;

(g) —$(C(R_4)(R'_4))_p$-E-N$(R_i)$—O—$(C(R_4)(R'_4))_k$—O—V;

(h) —$(C(R_4)(R'_4))_p$—N$(R_i)$—O—$(C(R_4)(R'_4))_k$—O—V;

(i) —$(C(R_4)(R'_4))_p$—O—N$(R_i)$—$(C(R_4)(R'_4))_k$—O—V;

(j) —$(C(R_4)(R'_4))_p$—O—N$(R_i)$-E-$(C(R_4)(R'_4))_k$—O—V; or (k) —$(C(R_4)(R'_4))_p$—O—N$(R_i)$-E-W-Q-$(C(R_4)(R'_4))_k$—O—V;

B is —C(Z)-, —Y— or a covalent bond;

D is —S(O)$_o$ or —N$(R_a)(R_i)$; and $R_1$, $R_1'$, $R_2$, $R_4$, $R'_4$, $R_a$, $R_i$, E, Y, V, Z, W, Q, o and k are as defined herein.

In preferred embodiments for the compounds of Formula (I), (II) and (III), $R_2$ is a cyclopentyl group, a cyclohexyl group, a cycloheptyl group or a cyclooctyl group optionally substituted with one, two or three substituents independently selected from a lower alkyl group, an alkoxy group, an amino group, a hydroxy group, a nitro group or a halo group; a phenyl or a pyridyl optionally substituted with one, two or three substituents independently selected from a lower alkyl group, an alkoxy group, an amino group, a hydroxy group, a nitro group or a halo group.

In more preferred embodiments the compounds of Formulas (I) are:

1-(1-cyclohexyl-5-(4-(methylsulfonyl)phenyl)pyrazol-3-yl)-4-hydroxybutan-1-one;

1-(3-((1Z)-4-(hydroxy)but-1-enyl)-1-cyclohexylpyrazol-5-yl-4-methylsulfonyl)benzene; 4-(3-((3-hydroxypropoxy)methyl)-1-phenylpyrazol-5-yl)-1-(methylsulfonyl)benzene; 1-(3-(difluoro(3-hydroxypropoxy)methyl)-1-phenylpyrazol-5-yl)-4-(methylsulfonyl)benzene;

1-(1-(4-chlorophenyl)-3-((3-hydroxypropoxy)methyl)pyrazol-5-yl)-4-(methylsulfonyl)benzene;

1-(3-((3-hydroxypropoxy)methyl)-1-(4-methylphenyl)pyrazol-5-yl)-4-(methylsulfonyl)benzene;

1-(3-((3-hydroxypropoxy)methyl)-1-(4-(trifluoromethyl)phenyl)pyrazol-5-yl)-4-(methylsulfonyl)benzene;

1-(3-((3-hydroxypropoxy)methyl)-1-(4-methoxyphenyl)pyrazol-5-yl)-4-(methylsulfonyl)benzene;

1-(3-((1Z)-4-(hydroxy)but-1-enyl)-1-phenylpyrazol-5-yl)-4-methylsulfonyl)benzene;

4-hydroxy-1-(1-(4-methylphenyl)-5-(4-(methylsulfonyl)phenyl)pyrazol-3-yl)butan-1-one;

1-(1-(4-fluorophenyl)-5-(4-(methylsulfonyl)phenyl)pyrazol-3-yl)-4-hydroxybutan--one; 1-(1-(4-bromophenyl)-5-(4-(methylsulfonyl)phenyl)pyrazol-3-yl)-4-hydroxybutan-1-one;

1-(1-cyclohexyl-3-((2-hydroxyethoxy)methyl)pyrazol-5-yl)-4-(methylsulfonyl)benzene;

1-(1-cyclohexyl-3-((3-hydroxypropoxy)methyl)pyrazol-5-yl)-4-(methylsulfonyl)benzene;

1-(1-cyclohexyl-3-((3-(hydroxymethyl)phenoxy)methyl)pyrazol-5-yl)-4-(methylsulfonyl)benzene;

1-(1-(4-fluorophenyl)-3-((3-hydroxypropoxy)methyl)pyrazol-5-yl)-4-(methylsulfonyl)benzene;

1-(3-((3-hydroxybutoxy)methyl)-1-phenylpyrazol-5-yl)-4-(methylsulfonyl)benzene;

1-(3-((1E)-4-(hydroxy)but-1-enyl)-1-cyclohexylpyrazol-5-yl)-4-methylsulfonyl)benzene;
1-(1-cyclohexyl-5-(4-(methylsulfonyl)phenyl)-pyrazol-3-yl)-6-hydroxyhexan-1-one;
4-hydroxy-1-(5-(4-(methylsulfonyl)phenyl)-1-(4-(trifluoromethyl)-phenyl)pyrazol-3-yl)butan-1-one;
4-hydroxy-1-(1-(4-methoxyphenyl)-5-(4-(methylsulfonyl)phenyl)-pyrazol-3-yl)butan-1-one;
4-(3-((1E)-3-hydroxyprop-1-enyl)-1-cyclohexylpyrazol-5-yl)-1(methylsulfonyl)benzene;
1-(1-cyclohexyl-3-(((2-hydroxyethyl)amino)methyl)pyrazol-5-yl)-4-(methylsulfonyl)benzene;
4-(3-(4-hydroxybutanoyl)-5-(4-(methylsulfonyl)phenyl)pyrazolyl)benzenecarbonitrile;
4-(1-cyclohexyl-3-(4-hydroxybutanoyl)pyrazol-5-yl)benzenesulfonamide;
1-(1-(4-chloroophenyl)-5-(4-(methylsulfonyl)phenyl)pyrazol-3-yl)-4-hydroxybutan-1-one;
(1-cyclohexyl-5-(4-(methylsulfonyl)phenyl)pyrazol-3-yl)-N-(2-hydroxyethyl)carboxamide;
(1-cyclohexyl-5-(4-(methylsulfonyl)phenyl)pyrazol-3-yl)-N-(3-hydroxypropyl)carboxamide;

the nitrosated compounds of Formula (I) are:
1-(1-cyclooctyl-3-((nitrooxy)methyl)pyrazol-5-yl)-4-methylsulfonyl)benzene;
1-(1-cycloheptyl-3-((nitrooxy)methyl)pyrazol-5-yl)-4-(methylsulfonyl)benzene;
1-(1-cyclohexyl-5-(4-(methylsulfonyl)phenyl)pyrazol-3-yl)-4-(nitrooxy)butan-1-one
1-(3-((1Z)-4-(nitrooxy)but-1-enyl)-1-cyclohexylpyrazol-5-yl)-4-(methylsulfonyl)benzene;
4-(3-((3-(nitrooxy)propoxy)methyl)-1-phenylpyrazol-5-yl)-1-(methylsulfonyl)benzene;
1-(3-(difluoro(3-(nitrooxy)propoxy)methyl)-1-phenylpyrazol-5-yl)-4-(methylsulfonyl)benzene;
1-(1-(4-chlorophenyl)-3-((3-(nitrooxy)propoxy)methyl)pyrazol-5-yl)-4-(methylsulfonyl)benzene;
1-(1-(4-methylphenyl)-3-((3-(nitrooxy)propoxy)methyl)pyrazol-5-yl)-4-(methylsulfonyl)benzene;
4-(methylsulfonyl)-1-(3-((3-(nitrooxy)propoxy)methyl)-1-(4-(trifluoromethyl)phenyl)pyrazol-5-yl)benzene;
1-(1-(4-methoxy-3-nitrophenyl)-3-((3-(nitrooxy)propoxy)methyl)pyrazol-5-yl)-4-(methylsulfonyl)benzene;
1-(3-((1Z)-4-(nitrooxy)but-1-enyl)-1-phenylpyrazol-5-yl)-4-(methylsulfonyl)benzene;
1-(3-((1E)-4-(nitrooxy)but-1-enyl)-1-phenylpyrazol-5-yl)-4-(methylsulfonyl)benzene;
1-(1-(4-methylphenyl)-5-(4-(methylsulfonyl)phenyl)pyrazol-3-yl)-4-(nitrooxy)butan-1-one;
1-(1-(4-fluorophenyl)-5-(4-(methylsulfonyl)phenyl)pyrazol-3-yl)-4-(nitrooxy)butan-1-one
1-(1-(4-bromophenyl)-5-(4-(methylsulfonyl)phenyl)pyrazol-3-yl)-4-(nitrooxy)butan-1-one;
1-(1-cyclohexyl-3-((2-(nitrooxy)ethoxy)methyl)pyrazol-5-yl)-4-(methylsulfonyl)benzene;
1-(1-cyclohexyl-3-((3-(nitrooxy)propoxy)methyl)pyrazol-5-yl)-4-(methylsulfonyl)benzene;
1-(1-cyclohexyl-3-((3-((nitrooxy)methyl)phenoxy)methyl)pyrazol-5-yl)-4-(methylsulfonyl)benzene;
1-(1-(4-fluorophenyl)-3-((3-(nitrooxy)propoxy)methyl)pyrazol-5-yl)-4-(methylsulfonyl)benzene;
4-(methylsulfonyl)-1-(3-((3-(nitrooxy)butoxy)methyl)-1-phenylpyrazol-5-yl)benzene;
1-(3-((1E)-4-(nitrooxy)but-1-enyl)-1-cyclohexylpyrazol-5-yl)-4-(methylsulfonyl)benzene;
1-(1-cyclohexyl-5-(4-(methylsulfonyl)pyrazol-3-yl)-6-(nitrooxy)hexan-1-one;
1-(5-(4-(methylsulfonyl)phenyl)-1-(4-(trifluoromethyl)phenyl)pyrazol-3-yl)-4-(nitrooxy)butan-1-one;
1-(1-(4-methoxyphenyl)-5-(4-(methylsulfonyl)phenyl)pyrazol-3-yl-4-(nitrooxy)butan-1-one;
4-(1-cyclohexyl-3-(2-(nitrooxy)ethyl)pyrazol-5-yl)-1-(methylsulfonyl)benzene;
4-(1-cyclohexyl-3-(3-(nitrooxy)propyl)pyrazol-5-yl)-1-(methylsulfonyl)benzene;
1-(5-(4-(methysulfonyl)phenyl)-1-(2-pyridyl)pyrazol-3-yl)-2-(nitrooxy)ethan-1-one;
4-(1-(4-methoxyphenyl)-3-((3-(nitrooxy)propoxy)methyl)pyrazol-5-yl)-1-(methylsulfonyl)benzene;
4-(1-(4-methyl-3-nitrophenyl)-3-((3-(nitrooxy)propoxy)methyl)pyrazol-5-yl)-1-(methylsulfonyl)benzene;
1-(3-((1E)-3-(nitrooxy)prop-1-enyl)-1-cyclohexylpyrazol-5-yl)-4-(methylsulfonyl)benzene;
4-(5-(4-(methylsulfonyl)phenyl)-3-(4-(nitrooxy)butanoyl)pyrazolyl)benzenecarbonitrile;
4-(1-cyclohexyl-3-(4-(nitrooxy)butanoyl)pyrazol-5-yl)benzenesulfonamide;
1-(1-(4-chlorophenyl)-5-(4-(methylsulfonyl)phenyl)pyrazol-3-yl)-4-(nitrooxy)butan-1-one;
(1-cyclohexyl-5-(4-(methylsulfonyl)phenyl)pyrazol-3-yl)-N-(2-(nitrooxy)ethyl)carboxamide;
(1-cyclohexyl-5-(4-(methylsulfonyl)phenyl)pyrazol-3-yl)-N-(3(nitrooxy)propyl)carboxamide;
3-(nitrooxy)propyl 4-(5-(4-(methylsulfonyl)phenyl)-1-(4-(trifluoromethyl)-phenyl)pyrazol-3-yl)butanoate;

the compounds of Formula (II) are:
4-(3-((3-hydroxypropoxy)methyl)-5-(4-methylphenyl)pyrazolyl)benzenesulfonamide;
1-(3-((1Z)-4-hydroxybut-1-enyl)-5-(3-pyridnyl)pyrazolyl)-4-(methylsulfonyl)benzene;
4-(5-(4-chlorophenyl)-3-((3-hydroxypropoxy)methyl)pyrazolyl)benzenesulfonamide;
4-(3-((3-hydroxypropoxy)methyl)-5-phenylpyrazolyl)benzenesulfonamide;
4-(5-(4-chlorophenyl)-3-((3-hydroxypropoxy)methyl)pyrazolyl)-benzenesulfonamide;

the nitrosated compounds of Formula (II) are:
4-(5-(4-methylphenyl)-3-((3-(nitrooxy)propoxy)methyl)pyrazolyl)benzenesulfonamide;
1-(3-((1Z)-4-(nitrooxy)but-1-enyl)-5-(3-pyridyl)pyrazolyl)-4-(methylsulfonyl)benzene;
4-(5-(4-chlorophenyl)-3-((3-(nitrooxy)propoxy)methyl)pyrazolyl)benzenesulfonamide;
4-(3-((3-(nitrooxy)propoxy)methyl)-5-phenylpyrazolyl)benzenesulfonamide;
4-(5-(chlorophenyl)-3-((3-(nitrooxy)propoxy)methyl)benzene-sulfonamide the compounds of Formula (III) are:
4-(5-(3-hydroxypropoxy)methyl)-3-phenylisoxazol-4-yl)benzenesulfonamide;
4-(5-(2-hydroxyethoxy)methyl)-3-phenylisoxazol-4-yl)benzenesulfonamide;
4-(5-((2,2-difluoro-3-hydroxypropoxy)methyl)-3-phenylisoxazol-4-yl)benzenesulfonamide;
4-(3-phenyl-5-(2,2,3,3-tetrafluoro-4-hydroxy)methyl)isoxazol-4-yl)benzenesulfonamide;
4-(5-((2,2,3,3,4,4-hexafluoro-5-hydroxypentyloxy)methyl)-3-phenylisoxazol-4-yl)benzenesulfonamide;
4-(5-((2-((2-hydroxyethyl)sulfonyl)ethoxy)methyl)-3-phenylisoxazol-4-yl)benzenesulfonamide;

the nitrosated compounds of Formula (III) are:
4-(5-(3-nitrooxy)propoxy)methyl)-3-phenylisoxazol-4-yl) benzenesulfonamide;
4-(5-(2-nitrooxy)ethoxy)methyl-3-phenylisoxazol-4-yl)benzenesulfonamide;
4-(5-((2,2-difluoro-3-(nitrooxy)propoxy)methyl)-3-phenylisoxazol-4-yl)benzenesulfoamide;
4-(3-phenyl-5-(2,2,3,3-tetrafluoro-4-hydroxy)methyl)isoxazol-4-yl)benzenesulfonamide; and
4-(5-((2,2,3,3,4,4-hexafluoro-5-(nitrooxy)pentyloxy)methyl)-3-phenylisoxazol-4-yl)benzenesulfonamide;
4-(5-((2-(nitrooxy)ethyl)sulfonyl)ethoxy)methyl)-3-phenylisoxazol-4-yl)benzenesulfonamide;

and pharmaceutically acceptable salts thereof.

Another embodiment of the invention describes the metabolites of the compounds of Formulas (I), (II) and (III) and pharmaceutically acceptable salts thereof. These metabolites, include but are not limited to, the non-nitrosated and/or non-nitrosylated derivatives, degradation products, hydrolysis products, and the like, of the compounds of Formulas (I), (II) and (III) and pharmaceutically acceptable salts thereof.

Compounds of the invention that have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. The invention includes within its scope all such isomers and mixtures thereof.

Another embodiment of the invention provides processes for making the novel compounds of the invention and to the intermediates useful in such processes. The reactions are performed in solvents appropriate to the reagents and materials used are suitable for the transformations being effected. It is understood by one skilled in the art of organic synthesis that the functionality present in the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to one skilled in the art. The use of sulfur and oxygen protecting groups is well known for protecting thiol and alcohol groups against undesirable reactions during a synthetic procedure and many such protecting groups are known and described by, for example, Greene and Wuts, *Protective Groups in Organic Synthesis,* Third Edition, John Wiley & Sons, New York (1999).

The chemical reactions described herein are generally disclosed in terms of their broadest application to the preparation of the compounds of this invention. Occasionally, the reactions may not be applicable as described to each compound included within the disclosed scope. The compounds for which this occurs will be readily recognized by one skilled in the art. In all such cases, either the reactions can be successfully performed by conventional modifications known to one skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials.

The compounds of Formulas (I), (II) and (III) can be synthesized by one skilled in the art following the methods and examples described herein. The synthesis of the non-nitrosated and/or non-nitrosylated COX-2 inhibitors are disclosed in, for example, U.S. Pat. Nos. 5,344,991, 5,393,790, 5,466,823, 5,474,995, 5,486,534, 5,504,215, 5,508,426, 5,510,496, 5,516,907, 5,521,207, 5,536,752, 5,550,142, 5,563,165, 5,616,601, 5,620,999, 5,677,318, 5,668,161, 5,691,374, 5,698,584, 5,710,140, 5,753,688, 5,859,257, 5,908,858, 5,945,539, 5,994,381, 6,080,876, 6,083,969 and 6,071,954 and in WO 91/19708, WO 94/15932, WO 94/26731, WO 94/27980, WO 95/00501, WO 95/11883, WO 95/15315, WO 95/15316, WO 95/15317, WO 95/15318, WO 95/18799, WO 95/21817, WO 95/30652, WO 96/30656, WO 96/03387, WO 96/03392, WO 96/03385, WO 96/03387, WO 96/03388, WO 96/09293, WO 96/09304, WO 96/16934, WO 96/19462, WO 96/19463, WO 96/19469, WO 96/25405, WO 96/36617, WO 96/36623, WO 97/11704, WO 97/13755, WO 97/27181, WO 97/14691, WO 97/16435, WO 97/34882, WO 97/36863, WO 97/40012, WO 97/45420, WO 98/00416, WO 98/11080, WO 98/22422, WO 98/41516, WO 98/46594, WO 98/52937, WO 99/15531, WO 99/23087, WO 99/33796, WO 99/25695, WO 99/61016, WO 99/62884 and WO 99/64415 and in EP 0 745 596 A1, EP 0 087 629 B1, EP 0 418 845 B1, EP 0 554 829 A2, EP 0 863 134 A1, EP 1 006 114 A1; the disclosures of each of which are incorporated by reference herein in their entirety. The COX-2 inhibitor compounds can then be nitrosated and/or nitrosylated through one or more sites such as oxygen, sulfur and/or nitrogen using the methods described in the examples herein and using conventional methods known to one skilled in the art. For example, known methods for nitrosating and/or nitrosylating compounds are described in U.S. Pat. Nos. 5,380,758 and 5,703,073; WO 94/03421, WO 94/04484, WO 94/12463, WO 95/09831, WO 95/30641, WO 97/27749, WO 98/19672, WO 00/25776, WO 01/00563 and WO 01/04082, WO 01/10814, WO 01/45703 and Oae et al, *Org. Prep. Proc. Int.,* 15(3):165-198 (1983), the disclosures of each of which are incorporated by reference herein in their entirety. The methods of nitrosating and/or nitrosylating the compounds described in the examples herein and in these references can be applied by one skilled in the art to produce any of the nitrosated and/or nitrosylated COX-2 inhibitors described herein.

The compounds of the invention include the COX-2 inhibitors, which have been nitrosated and/or nitrosylated through one or more sites such as oxygen (hydroxyl condensation), sulfur (sulfhydryl condensation) and/or nitrogen. The nitrosated and/or nitrosylated COX-2 inhibitors of the invention donate, transfer or release a biologically active form of nitrogen monoxide (i.e., nitric oxide).

Nitrogen monoxide can exist in three forms: NO— (nitroxyl), NO. (uncharged nitric oxide) and NO$^+$ (nitrosonium). NO. is a highly reactive short-lived species that is potentially toxic to cells. This is critical because the pharmacological efficacy of NO depends upon the form in which it is delivered. In contrast to the nitric oxide radical (NO.), nitrosonium (NO$^+$) does not react with O$_2$ or O$_2^-$ species, and functionalities capable of transferring and/or releasing NO$^+$ and NO— are also resistant to decomposition in the presence of many redox metals. Consequently, administration of charged NO equivalents (positive and/or negative) is a more effective means of delivering a biologically active NO to the desired site of action.

Compounds contemplated for use in the invention (e.g., COX-2 selective inhibitor, that can be optionally nitrosated and/or nitrosylated), are, optionally, used in combination with nitric oxide and compounds that release nitric oxide or otherwise directly or indirectly deliver or transfer a biologically active form of nitrogen monoxide to a site of its intended activity, such as on a cell membrane in vivo.

The term "nitric oxide" encompasses uncharged nitric oxide (NO.) and charged nitrogen monoxide species, preferably charged nitrogen monoxide species, such as nitrosonium ion (NO$^+$) and nitroxyl ion (NO—). The reactive form of nitric oxide can be provided by gaseous nitric oxide. The nitrogen monoxide releasing, delivering or transferring compounds have the structure F—NO, wherein F is a nitrogen monoxide releasing, delivering or transferring moiety, and include any and all such compounds which provide nitrogen monoxide to its intended site of action in a form active for its intended purpose. The term "NO adducts" encompasses any nitrogen monoxide releasing, delivering or transferring compounds, including, for example, S-nitrosothiols, nitrites, nitrates, S-nitrothiols, sydnonimines, 2-hydroxy-2-nitrosohydrazines, (NONOates), (E)-alkyl-2-((E)-hydroxyimino)-5-nitro-3-hexeneamide (FK-409), (E)-alkyl-2-((E)-hydroxyimino)-5-nitro-3-hexeneamines, N-((2Z,3E)-4-ethyl-2-(hydroxyimino)-6-methyl-5-nitro-3-heptenyl)-3-pyridinecarboxamide (FR 146801), nitrosoamines, furoxans as well as substrates for the endogenous enzymes which synthesize nitric oxide. NONOates include, but are not limited to, (Z)-1-(N-methyl-N-(6-(N-methyl-ammoniohexyl)amino))diazen-1-ium-1,2-diolate ("MAHMA/NO"), (Z)-1-(N-(3-ammoniopropyl)-N-(n-propyl)amino)diazen-1-ium-1,2-diolate ("PAPA/NO"), (Z)-1-(N-(3-aminopropyl)-N-(4-(3-aminopropylammonio)butyl)-amino)diazen-1-ium-1,2-diolate (spermine NONOate or "SPER/NO") and sodium(Z)-1-(N,N-diethylamino)diazenium-1,2-diolate (diethylamine NONOate or "DEA/NO") and derivatives thereof. NONOates are also described in U.S. Pat. Nos. 6,232,336, 5,910,316 and 5,650,447, the disclosures of which are incorporated herein by reference in their entirety. The "NO adducts" can be mono-nitrosylated, poly-nitrosylated, mono-nitrosated and/or poly-nitrosated at a variety of naturally susceptible or artificially provided binding sites for biologically active forms of nitrogen monoxide.

One group of NO adducts is the S-nitrosothiols, which are compounds that include at least one —S—NO group. These compounds include S-nitroso-polypeptides (the term "polypeptide" includes proteins and polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars; S-nitrosylated, modified and unmodified, oligonucleotides (preferably of at least 5, and more preferably 5-200 nucleotides); straight or branched, saturated or unsaturated, aliphatic or aromatic, substituted or unsubstituted S-nitrosylated hydrocarbons; and S-nitroso heterocyclic compounds. S-nitrosothiols and methods for preparing them are described in U.S. Pat. Nos. 5,380,758 and 5,703,073; WO 97/27749; WO 98/19672; and Oae et al, *Org. Prep. Proc. Int.*, 15(3): 165-198 (1983), the disclosures of each of which are incorporated by reference herein in their entirety.

Another embodiment of the invention is S-nitroso amino acids where the nitroso group is linked to a sulfur group of a sulfur-containing amino acid or derivative thereof. Such compounds include, for example, S-nitroso-N-acetylcysteine, S-nitroso-captopril, S-nitroso-N-acetylpenicillamine, S-nitroso-homocysteine, S-nitroso-cysteine, S-nitroso-glutathione, S-nitroso-cysteinyl-glycine, and the like.

Suitable S-nitrosylated proteins include thiol-containing proteins (where the NO group is attached to one or more sulfur groups on an amino acid or amino acid derivative thereof) from various functional classes including enzymes, such as tissue-type plasminogen activator (TPA) and cathepsin B; transport proteins, such as lipoproteins; heme proteins, such as hemoglobin and serum albumin; and biologically protective proteins, such as immunoglobulins, antibodies and cytokines. Such nitrosylated proteins are described in WO 93/09806, the disclosure of which is incorporated by reference herein in its entirety. Examples include polynitrosylated albumin where one or more thiol or other nucleophilic centers in the protein are modified.

Other examples of suitable S-nitrosothiols include:
(i) HS(C($R_e$)($R_f$))$_m$SNO;
(ii) ONS(C($R_e$)($R_f$))$_m R_e$; or
(iii) $H_2N$—CH($CO_2H$)—$(CH_2)_m$—C(O)NH—CH($CH_2$SNO)—C(O)NH—$CH_2$—$CO_2H$;

wherein m is an integer from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring. a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cyano, an aminoalkyl, an aminoaryl, an aryl, an arylalkyl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, an alkylsulfonyl, an alkylsulfonyloxy, an arylsulfonyl, an arylsulfonyloxy, a urea, a nitro, -T-Q-, or —(C($R_g$)($R_h$))$_k$-T-Q or $R_e$ and $R_f$ taken together are an oxo, a thial, a heterocyclic ring, a cycloalkyl group, an oxime, a hydrazone or a bridged cycloalkyl group; Q is —NO or —$NO_2$; and T is independently a covalent bond, a carbonyl, an oxygen, —S(O)$_o$— or —N($R_a$)$R_i$—, wherein o is an integer from 0 to 2, $R_a$ is a lone pair of electrons, a hydrogen or an alkyl group; $R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylsulfinyl, an alkylsulfonyl, an alkylsulfonyloxy, an arylsulfinyl, an arylsulfonyloxy, an arylsulfonyl, a sulfonamido, a carboxamido, a carboxylic ester, an aminoalkyl, an aminoaryl, —$CH_2$—C(T-Q)($R_g$)($R_h$), or —($N_2O_2$—)$^-$.M$^+$, wherein M$^+$ is an organic or inorganic cation; with the proviso that when $R_i$ is —$CH_2$—C(T-Q)($R_g$)($R_h$) or —($N_2O_2$—).M$^+$; then "-T-Q" can be a hydrogen, an alkyl group, an alkoxyalkyl group, an aminoalkyl group, a hydroxy group or an aryl group; and $R_g$ and $R_h$ at each occurrence are independently $R_e$;

In cases where $R_e$ and $R_f$ are a heterocyclic ring or taken together $R_e$ and $R_f$ are a heterocyclic ring, then $R_i$ can be a substituent on any disubstituted nitrogen contained within the radical wherein $R_i$ is as defined herein.

Nitrosothiols can be prepared by various methods of synthesis. In general, the thiol precursor is prepared first, then converted to the S-nitrosothiol derivative by nitrosation of the thiol group with NaNO$_2$ under acidic conditions (pH is about 2.5) which yields the S-nitroso derivative. Acids which can be used for this purpose include aqueous sulfuric, acetic and hydrochloric acids. The thiol precursor can also be nitrosylated by reaction with an organic nitrite such as tert-butyl nitrite, or a nitrosonium salt such as nitrosonium tetrafluorborate in an inert solvent.

Another group of NO adducts for use in the invention, where the NO adduct is a compound that donates, transfers or releases nitric oxide, include compounds comprising at least one ON—O— or ON—N— group. The compounds that include at least one ON—O— or ON—N— group are preferably ON—O— or ON—N-polypeptides (the term "polypeptide" includes proteins and polyamino acids that do not possess an ascertained biological function, and derivatives thereof); ON—O— or ON—N-amino acids (including natural and synthetic amino acids and their stereoisomers and racemic mixtures); ON—O— or ON—N-sugars; ON—O— or —ON—N— modified or unmodified oligonucleotides (comprising at least 5 nucleotides, preferably 5-200 nucleotides); ON—O— or ON—N— straight or branched, saturated or unsaturated, aliphatic or aromatic, substituted or unsubstituted hydrocarbons; and ON—O—, ON—N— or ON—C-heterocyclic compounds.

Another group of NO adducts for use in the invention include nitrates that donate, transfer or release nitric oxide, such as compounds comprising at least one $O_2N$—O—, $O_2N$—N— or $O_2N$—S— group. Preferred among these compounds are $O_2N$—O—, $O_2N$—N— or $O_2N$—S— polypeptides (the term "polypeptide" includes proteins and also polyamino acids that do not possess an ascertained biological function, and derivatives thereof); $O_2N$—O—, $O_2N$—N— or $O_2N$—S— amino acids (including natural and synthetic amino acids and their stereoisomers and racemic mixtures); $O_2N$—O—, $O_2N$—N— or $O_2N$—S— sugars; $O_2N$—O—, $O_2N$—N— or $O_2N$—S— modified and unmodified oligonucleotides (comprising at least 5 nucleotides, preferably 5-200 nucleotides); $O_2N$—O—, $O_2N$—N— or $O_2N$—S— straight or branched, saturated or unsaturated, aliphatic or aromatic, substituted or unsubstituted hydrocarbons; and $O_2N$—O—, $O_2N$—N— or $O_2N$—S— heterocyclic compounds. Preferred examples of compounds comprising at least one $O_2N$—O—, $O_2N$—N— or $O_2N$—S— group include isosorbide dinitrate, isosorbide mononitrate, clonitrate, erythrityl tetranitrate, mannitol hexanitrate, nitroglycerin, pentaerythritoltetranitrate, pentrinitrol, propatylnitrate and organic nitrates with a sulfhydryl-containing amino acid such as, for example SPM 3672, SPM 5185, SPM 5186 and those disclosed in U.S. Pat. Nos. 5,284,872, 5,428,061, 5,661, 129, 5,807,847 and 5,883,122 and in WO 97/46521, WO 00/54756 and in WO 03/013432, the disclosures of each of which are incorporated by reference herein in their entirety.

Another group of NO adducts are N-oxo-N-nitrosoamines that donate, transfer or release nitric oxide and are represented by the formula: $R^{1''}R^{2''}N$—$N(O-M^+)$—NO, where $R^{1''}$ and $R^{2''}$ are each independently a polypeptide, an amino acid, a sugar, a modified or unmodified oligonucleotide, a straight or branched, saturated or unsaturated, aliphatic or aromatic, substituted or unsubstituted hydrocarbon, or a heterocyclic group, and where $M^+$ is an organic or inorganic cation, such as, for example, an alkyl substituted ammonium cation or a Group I metal cation.

The invention is also directed to compounds that stimulate endogenous NO or elevate levels of endogenous endothelium-derived relaxing factor (EDRF) in vivo or are substrates for nitric oxide synthase. Such compounds include, for example, L-arginine, L-homoarginine, and N-hydroxy-L-arginine, including their nitrosated and nitrosylated analogs (e.g., nitrosated L-arginine, nitrosylated L-arginine, nitrosated N-hydroxy-L-arginine, nitrosylated N-hydroxy-L-arginine, nitrosated L-homoarginine and nitrosylated L-homoarginine), precursors of L-arginine and/or physiologically acceptable salts thereof, including, for example, citrulline, ornithine, glutamine, lysine, polypeptides comprising at least one of these amino acids, inhibitors of the enzyme arginase (e.g., N-hydroxy-L-arginine and 2(S)-amino-6-boronohexanoic acid), nitric oxide mediators and/or physiologically acceptable salts thereof, including, for example, pyruvate, pyruvate precursors, α-keto acids having four or more carbon atoms, precursors of α-keto acids having four or more carbon atoms (as disclosed in WO 03/017996, the disclosure of which is incorporated herein in its entirety), and the substrates for nitric oxide synthase, cytokines, adenosin, bradykinin, calreticulin, bisacodyl, and phenolphthalein. EDRF is a vascular relaxing factor secreted by the endothelium, and has been identified as nitric oxide (NO) or a closely related derivative thereof (Palmer et al, *Nature,* 327:524-526 (1987); Ignarro et al, *Proc. Natl. Acad. Sci. USA,* 84:9265-9269 (1987)).

The invention is also based on the discovery that compounds and compositions of the invention may be used in conjunction with other therapeutic agents for co-therapies, partially or completely, in place of other conventional antiinflammatory compounds, such as, for example, together with steroids, NSAIDs, 5-lipoxygenase (5-LO) inhibitors, leukotriene $B_4$ (LTB$_4$) receptor antagonists, leukotriene $A_4$ (LTA$_4$) hydrolase inhibitors, 5-HT agonists, HMG-CoA inhibitors, $H_2$ receptor antagonists, antineoplastic agents, antiplatelet agents, thrombin inhibitors, thromboxane inhibitors, decongestants, diuretics, sedating or non-sedating anti-histamines, inducible nitric oxide synthase inhibitors, opiods, analgesics, *Helicobacter pylori* inhibitors, proton pump inhibitors, isoprostane inhibitors, and mixtures of two or more thereof.

Leukotriene $A_4$ (LTA$_4$) hydrolase inhibitors refer to compounds that selectively inhibit leukotriene $A_4$ hydrolase with an IC$_{50}$ of less than about 10 μM, and preferably with an IC$_{50}$ of less than about 1 μM. Suitable LTA$_4$ hydrolase inhibitors include, but are not limited to, RP-64966, (S,S)-3-amino-4-(4-benzyloxyphenyl)-2-hydroxybutyric acid benzyl ester, N-(2(R)-(cyclohexylmethyl)-3-(hydroxycarbamoyl)propionyl)-L-alanine, 7-(4-(4-ureidobenzyl)phenyl)heptanoic acid and 3(3-(1E,3E-tetradecadienyl)-2-oxiranyl)benzoic acid lithium salt, and mixtures of two or more thereof.

Suitable LTB$_4$ receptor antagonists include, but are not limited to, ebselen, linazolast, ontazolast; WAY 121006; Bay-x-1005; BI-RM-270; CGS-25019C; ETH-615; MAFP; TMK-688; T-0757; LY 213024, LY 210073, LY 223982, LY 233469, LY 255283, LY 264086, LY 292728 and LY 293111; ONO-LB457, ONO-4057, and ONO-LB-448, S-2474, calcitrol; PF 10042; Pfizer 105696; RP 66153; SC-53228, SC-41930, SC-50605, SC-51146 and SC-53228; SB-201146 and SB-209247; SKF-104493; SM 15178; TMK-688; BPC 15, and mixtures of two or more thereof. The preferred LTB$_4$ receptor antagonists are calcitrol, ebselen, Bay-x-1005, CGS-25019C, ETH-615, LY-293111, ONO-4057 and TMK-688, and mixtures of two or more thereof.

Suitable 5-LO inhibitors include, but are not limited to, A-76745, 78773 and ABT761; Bay-x-1005; CMI-392; E-3040; EF-40; F-1322; ML-3000; PF-5901; R-840; rilopirox, flobufen, linasolast, lonapolene, masoprocol, ontasolast, tenidap, zileuton, pranlukast, tepoxalin, rilopirox, flezelastine hydrochloride, enazadrem phosphate, and bunaprolast, and mixtures of two or more thereof. Suitable 5-LO inhibitors are also described more fully in WO 97/29776, the disclosure of which is incorporated herein by reference in its entirety.

Suitable 5-HT agonists, include, but are not limited to, rizatriptan, sumatriptan, naratriptan, zolmitroptan, eleptriptan, almotriptan, ergot alkaloids. ALX 1323, Merck L 741604 SB 220453 and LAS 31416. Suitable 5-HT agonists are described-more fully in WO 0025779, and in WO 00/48583. 5-HT agonists refers to a compound that is an agonist to any 5-HT receptor, including but not limited to, 5-HT$_1$ agonists, 5-HT$_{1B}$ agonists and 5-HT$_{1D}$ agonists, and the like.

Suitable steroids, include, but are not limited to, budesonide, dexamethasone, corticosterone, prednisolone, and the like. Suitable steroids are described more fully in the literature, such as in the Merck Index on CD-ROM, 13$^{th}$ Edition.

Suitable HMG CoA inhibitors, include, but are not limited to, reductase and synthase inhibitors, such as, for example, squalene synthetase inhibitors, benzodiazepine squalene synthase inhibitors, squalene epoxidase inhibitors, acyl-coenzyme A, bile acid sequestrants, cholesterol absorption inhibitors, and the like. Suitable HMG CoA inhibitors include simvastatin, pravastatin, lovastatin, mevastatin, fluvastatin, atorvastatin, cerivastatin, and the like, and are described more fully in U.S. Pat. No. 6,245,797 and WO 99/20110, the disclosures of which are incorporated herein by reference in their entirety.

Suitable NSAIDs, include, but are not limited to, acetaminophen, aspirin, diclofenac, ibuprofen, ketoprofen, naproxen, indomethacin, including but not limited to prodrugs thereof, and the like. Suitable NSAIDs are described more fully in the literature, such as in Goodman and Gilman, The Pharmacological Basis of Therapeutics (9th Edition), McGraw-Hill, 1995, Pgs. 617-657; the Merck Index on CD-ROM, 13$^{th}$ Edition; and in U.S. Pat. Nos. 6,057,347 and 6,297,260 assigned to NitroMed Inc., the disclosures of which are incorporated herein by reference in their entirety.

Suitable $H_2$ receptor anatgonists, include, but are not limited to, cimetidine, roxatidine, rantidine and the like. Suitable $H_2$ receptor antagonists are described more fully in the literature, such as in Goodman and Gilman, The Pharmacological Basis of Therapeutics (9th Edition), McGraw-Hill, 1995, Pgs. 901-915; the Merck Index on CD-ROM, 13$^{th}$ Edition; and in WO 00/28988 assigned to NitroMed Inc., the disclosures of which are incorporated herein by reference in their entirety.

Suitable antineoplastic agents, include but are not limited to, 5-FU-fibrinogen, acanthifolic acid, aminothiadiazole, altretamine, anaxirone, aclarubicin and the like. Suitable antineoplastic agents are also described in U.S. Pat. No. 6,025,353 and WO 00/38730, the disclosures of which are incorporated herein by reference in their entirety.

Suitable antiplatelet agents, include but are not limited to, aspirin, ticlopidine, dipyridamole, clopidogrel, glycoprotein IIb/IIIa receptor antagonists, and the like. Suitable antineoplastic agents are also described in WO 99/45913, the disclosure of which is incorporated herein by reference in its entirety. In a preferred embodiment of the invention, the antiplatelet agent is aspirin, more preferably, low-dose aspirin (i.e. 75 mg-100 mg/day).

Suitable thrombin inhibitors, include but are not limited to, N'-((1-(aminoiminomethyl)-4-piperidinyl)methyl)-N-(3,3-diphenylpropinyl)-L-proline amide),3-(2-phenylethylamino)-6-methyl-1-(2-amino-6-methyl-5-methylene-carboxamidomethylpyridinyl)-2-pyrazinone, 3-(2-phenethylamino)-6-methyl-1-(2-amino-6-methyl-5-methylenecarboxamidomethylpyridinyl)-2-pyridinone, and the like. Suitable thrombin inhibitors are also described in WO 00/18352, the disclosure of which is incorporated herein by reference in its entirety.

Suitable thromboxane inhibitors, include but are not limited to thromboxane synthase inhibitors, thromboxane receptor antagonists, and the like. Suitable thromboxane inhibitors, are also described in WO 01/87343, the disclosure of which is incorporated herein by reference in its entirety.

Suitable decongestants include, but are not limited to, phenylephrine, phenylpropanolamine, pseudophedrine, oxymetazoline, ephinephrine, naphazoline, xylometazoline, propylhexedrine, levo-desoxyephedrine, and the like.

Suitable antitussives include, but are not limited to, codeine, hydrocodone, caramiphen, carbetapentane, dextramethorphan, and the like.

Suitable proton pump inhibitors, include, but are not limited to, omeprazole, esomeprazole, lansoprazole, rabeprazole, pantoprazole, and the like. Suitable proton pump inhibitors are described more fully in the literature, such as in Goodman and Gilman, The Pharmacological Basis of Therapeutics (9th Edition), McGraw-Hill, 1995, Pgs. 901-915; the Merck Index on CD-ROM, 13$^{th}$ Edition; and in WO 00/50037 assigned to NitroMed Inc., the disclosures of which are incorporated herein by reference in their entirety.

The compounds and compositions of the invention, may also be used in combination therapies with opioids and other analgesics, including, but not limited to, narcotic analgesics, Mu receptor antagonists, Kappa receptor antagonists, non-narcotic (i.e. non-addictive) analgesics, monoamine uptake inhibitors, adenosine regulating agents, cannabinoid derivatives, neurokinin 1 receptor antagonists, Substance P antagonists, neurokinin-1 receptor antagonists, sodium channel blockers, N-methyl-D-aspartate receptor antagonists, and mixtures of two or more thereof. Preferred combination therapies would be with morphine, meperidine, codeine, pentazocine, buprenorphine, butorphanol, dezocine, meptazinol, hydrocodone, oxycodone, methadone, Tramadol ((+) enantiomer), DuP 747, Dynorphine A, Enadoline, RP-60180, HN-11608, E-2078, ICI-204448, acetominophen (paracetamol), propoxyphene, nalbuphine, E-4018, filenadol, mirtentanil, amitriptyline, DuP631, Tramadol ((−) enantiomer), GP-531, acadesine, AKI-1, AKI-2, GP-1683, GP-3269, 4030W92, tramadol racemate, Dynorphine A, E-2078, AXC3742, SNX-111, ADL2-1294, ICI-204448, CT-3, CP-99,994, CP-99,994, and mixtures of two or more thereof.

The compounds and compositions of the invention can also be used in combination with inducible nitric oxide synthase (iNOS) inhibitors. Suitable iNOS inhibitors are disclosed in U.S. Pat. Nos. 5,132,453 and 5,273,875, and in WO 97/38977 and WO 99/18960, the disclosures of each of which are incorporated by reference herein in their entirety.

The invention is also based on the discovery that the administration of a therapeutically effective amount of the compounds and compositions described herein is effective for treating inflammation, pain (both chronic and acute), and fever, such as, for example, analgesic in the treatment of pain, including, but not limited to headaches, migraines, postoperative pain, dental pain, muscular pain, and pain resulting from cancer; as an antipyretic for the treatment of fever, including but not limited to, rheumatic fever, symptoms associated with influenza or other viral infections, common cold, low back and neck pain, dysmenorrhea, headache, toothache, sprains, strains, myositis, neuralgia, synovitis; arthritis, including but not limited to rheumatoid arthritis, degenerative joint disease (osteoarthritis), spondyloarthropathies, gouty arthritis, systemic lupus erythematosus and juvenile arthritis. For example, the patient can be administered a therapeutically effective amount of at least one COX-2 selective inhibitor, that is optionally nitrosated and/or nitrosylated. In another embodiment, the patient can be administered a therapeutically effective amount of at least one COX-2 selective inhibitor, that is optionally nitrosated and/or nitrosylated, and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one COX-2 selective inhibitor, that is optionally nitrosated and/or nitrosylated, and, at least one therapeutic agent, including but not limited to, steroids, nonsterodal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, 3-hydroxy-3-methylglutaryl coenzyme A (HMG-CoA) inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and, optionally, at least one compound that donates, transfers or releases nitric oxide, or elevates levels of endogenous EDRF or nitric oxide, or is a substrate for nitric oxide synthase. The compounds can be administered separately or in the form of a composition.

Another embodiment of the invention provides methods for treating gastrointestinal disorders and/or improving the gastrointestinal properties of the COX-2 selective inhibitor by administering to the patient in need thereof a therapeutically effective amount of the compounds and/or compositions described herein. Such gastrointestinal disorders refer to any disease or disorder of the upper gastrointestinal tract (e.g., esophagus, the stomach, the duodenum, jejunum) including, for example, inflammatory bowel disease, Crohn's disease, gastritis, irritable bowel syndrome, ulcerative colitis, peptic ulcers, stress ulcers, gastric hyperacidity, dyspepsia, gastroparesis, Zollinger-Ellison syndrome, gastroesophageal reflux disease, bacterial infections (including, for example, a *Helicobacter Pylori* associated disease), short-bowel (anastomosis) syndrome, hypersecretory states associated with systemic mastocytosis or basophilic leukemia and hyperhistaminemia, and bleeding peptic ulcers that result, for example, from neurosurgery, head injury, severe body trauma or burns. For example, the patient can be administered a therapeutically effective amount of at least one COX-2 selective inhibitor, that is optionally nitrosated and/or nitrosylated In another embodiment, the patient can be administered a therapeutically effective amount of at least one COX-2 selective inhibitor, that is optionally nitrosated and/or nitrosylated, and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one COX-2 selective inhibitor, that is optionally nitrosated and/or nitrosylated, and, at least one therapeutic agent, including but not limited to, including but not limited to, steroids, nonsterodal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, 3-hydroxy-3-methylglutaryl coenzyme A (HMG-CoA) inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and, optionally, at least one compound that donates, transfers or releases nitric oxide, or elevates levels of endogenous EDRF or nitric oxide, or is a substrate for nitric oxide synthase. The compounds can be administered separately or in the form of a composition.

Yet another embodiment of the invention provides methods for facilitating wound healing (such as, for example, ulcer healing, bone healing including osteoporosis) by administering to the patient in need thereof a therapeutically effective amount of the compounds and/or compositions described herein. Wound refers to, and includes, any lesion that is characterized by loss of tissue, and, includes, but is not limited to, ulcers, cuts, burns, bone fractures, orthopedic procedure, wound infliction, and the like. Ulcers refers to lesions of the upper gastrointestinal tract lining that are characterized by loss of tissue, and, include, but are not limited to, gastric ulcers, duodenal ulcers, gastritis, and the like. For example, the patient can be administered a therapeutically effective amount of at least one COX-2 selective inhibitor, that is optionally nitrosated and/or nitrosylated In another embodiment, the patient can be administered a therapeutically effective amount of at least one COX-2 selective inhibitor, that is optionally nitrosated and/or nitrosylated, and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one COX-2 selective inhibitor, that is optionally nitrosated and/or nitrosylated, and, at least one therapeutic agent, and, optionally, at least one nitric oxide donor. The compounds can be administered separately or in the form of a composition.

Another embodiment of the invention provides methods to decrease or reverse renal and/or other toxicities (such as, for example, kidney toxicity, respiratory toxicity) by administering to a patient in need thereof a therapeutically effective amount of the compounds and/or compositions described herein. For example, the patient can be administered a therapeutically effective amount of at least one COX-2 selective inhibitor, that is optionally nitrosated and/or nitrosylated. In another embodiment, the patient can be administered a therapeutically effective amount of at least one COX-2 selective inhibitor, that is optionally nitrosated and/or nitrosylated, and at least one nitric oxide donor. In yet another embodiment, the patient can be administered a therapeutically effective amount of at least one COX-2 selective inhibitor, that is optionally nitrosated and/or nitrosylated, and at least one therapeutic agent, and, optionally, at least one nitric oxide donor. The compounds can be administered separately or in the form of a composition.

Another embodiment of the invention provides methods to treat or prevent disorders resulting from elevated levels of COX-2 by administering to a patient in need thereof a therapeutically effective amount of the compounds and/or compositions described herein. For example, the patient can be administered a therapeutically effective amount of at least one COX-2 selective inhibitor, that is optionally nitrosated and/or nitrosylated. In another embodiment, the patient can be administered a therapeutically effective amount of at least one COX-2 selective inhibitor, that is optionally nitrosated and/or nitrosylated, and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one COX-2 selective inhibitor, that is optionally nitrosated and/or nitrosylated, and at least one therapeutic agent, including but not limited to, steroids, a nonsterodal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, 3-hydroxy-3-methylglutaryl coenzyme A (HMG-CoA) inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and, optionally, at least one compound that donates, transfers or releases nitric oxide, or elevates levels of endogenous EDRF or nitric oxide, or is a substrate for nitric oxide synthase. The compounds can be administered separately or in the form of a composition.

Disorders resulting from elevated levels of COX-2 (e.g., COX-2 mediated disorders) include, but are not limited to, for example, angiogenesis, arthritis, asthma, bronchitis, menstrual cramps, premature labor, tendinitis, bursitis; skin-related conditions, such as, for example, psoriasis, eczema, surface wounds, burns and dermatitis; post-operative inflammation including from ophthalmic surgery, such as, for example, cataract surgery and refractive surgery, and the like; treatment of neoplasia, such as, for example, brain cancer, bone cancer, epithelial cell-derived neoplasia (epithelial carcinoma), such as, for example, basal cell carcinoma, adenocarcinoma, gastrointestinal cancer, such as, for example, lip cancer, mouth cancer, esophageal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body, benign and cancerous tumors, growths, polyps, adenomatous polyps, including, but not limited to, familial adenomatous polyposis, fibrosis resulting from radiation therapy, and the like; treatment of inflammatory processes in diseases, such as, for example, vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like; treatment of ophthalmic diseases and disorders, such as, for example, retinitis, retinopathies, uveitis, ocular photophobia, acute injury to the eye tissue, glaucoma, inflammation of the eye and elevation of intraocular pressure and the like; treatment of pulmonary inflammation, such as, for example, those associated with viral infections and cystic fibrosis, and the like; treatment of central nervous system disorders, such as, for example, cortical dementia including Alzheimer's disease, vascular dementia, multi-infarct dementia, pre-senile dementia, alcoholic dementia, senile dementia, and central nervous system damage resulting from stroke, ischemia and trauma, and the like; treatment of allergic rhinitis, respiratory distress syndrome, endotoxin shock syndrome, atherosclerosis; treatment of inflammations and/or microbial infections including, for example, inflammations and/or infections of the eyes, ears, nose, throat, and/or skin; treatment and/or prevention of cardiovascular disorders, such as, for example, coronary artery disease, aneurysm, arteriosclerosis, atherosclerosis, including, but not limited to, cardiac transplant atherosclerosis, myocardial infarction, hypertension, ischemia, embolism, stroke, thrombosis, venous thrombosis, thromboembolism, thrombotic occlusion and reclusion, restenosis, angina, unstable angina, shock, heart failure, coronary plaque inflammation, bacterial-induced inflammation, such as, for example, *Chlamydia*-induced inflammation, viral induced inflammation, inflammation associated with surgical procedures, such as, for example, vascular grafting, coronary artery bypass surgery, revascularization procedures, such as, for example, angioplasty, stent placement, endarterectomy, vascular procedures involving arteries, veins, capillaries, and the like; treatment and/or prevention of urinary and/or urological disorders, such as, for example, incontinence and the like; treatment and/or prevention of endothelial dysfunctions, such as, for example, diseases accompanying these dysfunctions, endothelial damage from hypercholesterolemia, endothelial damage from hypoxia, endothelial damage from mechanical and chemical noxae, especially during and after drug, and mechanical reopening of stenosed vessels, for example, following percutaneous transluminal angiography (PTA) and percuntaneous transluminal coronary angiography (PTCA), endothelial damage in postinfarction phase, endothelium-mediated reocculusion following bypass surgery, blood supply disturbances in peripheral arteries, as well as, cardiovascular diseases, and the like; methods for treating and/or preventing tissue deterioration, such as, for example, for organ transplants, and the like; disorders treated by the inhibition and/or prevention of activation, adhesion and infiltration of neutrophils at the site of inflammation; and disorders treated by the inhibition and/or prevention of platelet aggregation. The compounds and compositions of the invention can also be used as a pre-anesthetic medication in emergency operations to reduce the danger of aspiration of acidic gastric contents.

Another embodiment of the invention provides methods for improving the cardiovascular profile of COX-2 selective inhibitors by administering to a patient in need thereof a therapeutically effective amount of the compounds and/or compositions described herein. For example, the patient can be administered a therapeutically effective amount of at least one nitrosated and/or nitrosylated COX-2 selective inhibitor of the invention. In another embodiment, the patient can be administered a therapeutically effective amount of at least one COX-2 selective inhibitor, that is optionally nitrosated and/or nitrosylated, and at least one nitric oxide donor. In yet another embodiment, the patient can be administered a therapeutically effective amount of at least one COX-2 selective inhibitor, that is optionally nitrosated and/or nitrosylated, at least one of 3-hydroxy-3-methylglutaryl coenzyme A (HMG-CoA) inhibitors, antiplatelet agents, thrombin inhibitors, thromboxane inhibitors, and, optionally, at least one nitric oxide donor. The compounds can be administered separately or in the form of a composition.

When administered separately, the COX-2 selective-inhibitor, that is optionally nitrosated and/or nitrosylated, can be administered about the same time as part of the overall treatment regimen i.e., as a combination therapy. "About the same time" includes administering the COX-2 selective inhibitor, that is optionally nitrosated and/or nitrosylated, simultaneously, sequentially, at the same time, at different times on the same day, or on different days, as long as they are administered as part of an overall treatment regimen, i.e., combination therapy or a therapeutic cocktail.

When administered in vivo, the compounds and compositions of the invention can be administered in combination with pharmaceutically acceptable carriers and in dosages described herein. When the compounds and compositions of the invention are administered as a combination of at least one COX-2 selective inhibitor and/or at least one nitrosated and/or nitrosylated COX-2 selective inhibitor and/or at least one nitric oxide donor and/or therapeutic agent, they can also be used in combination with one or more additional compounds which are known to be effective against the specific disease state targeted for treatment. The nitric oxide donors, therapeutic agents and/or other additional compounds can be administered simultaneously with, subsequently to, or prior to administration of the COX-2 selective inhibitor and/or nitrosated and/or nitrosylated COX-2 selective inhibitor.

The compounds and compositions of the invention can be administered by any available and effective delivery system including, but not limited to, orally, bucally, parenterally, by inhalation spray, by topical application, by injection, transdermally, or rectally (e.g., by the use of suppositories) in dosage unit formulations containing conventional nontoxic pharmaceutically acceptable carriers, adjuvants, and vehicles, as desired. Parenteral includes subcutaneous injections, intravenous, intramuscular, intrasternal injection, or infusion techniques.

Transdermal compound administration, which is known to one skilled in the art, involves the delivery of pharmaceutical compounds via percutaneous passage of the compound into the systemic circulation of the patient. Topical administration can also involve the use of transdermal administration such as transdermal patches or iontophoresis devices. Other components can be incorporated into the transdermal patches as well. For example, compositions and/or transdermal patches can be formulated with one or more preservatives or bacteriostatic agents including, but not limited to, methyl hydroxybenzoate, propyl hydroxybenzoate, chlorocresol, benzalkonium chloride, and the like. Dosage forms for topical administration of the compounds and compositions can include creams, sprays; lotions, gels, ointments, eye drops, nose drops, ear drops, and the like. In such dosage forms, the compositions of the invention can be mixed to form white, smooth, homogeneous, opaque cream or lotion with, for example, benzyl alcohol 1% or 2% (wt/wt) as a preservative, emulsifying wax, glycerin, isopropyl palmitate, lactic acid, purified water and sorbitol solution. In addition, the compositions can contain polyethylene glycol 400. They can be mixed to form ointments with, for example, benzyl alcohol 2% (wt/wt) as preservative, white petrolatum, emulsifying wax, and tenox II (butylated hydroxyanisole, propyl gallate, citric acid, propylene glycol). Woven pads or rolls of bandaging material, e.g., gauze, can be impregnated with the compositions in solution, lotion, cream, ointment or other such form can also be used for topical application. The compositions can also be applied topically using a transdermal system, such as one of an acrylic-based polymer adhesive with a resinous crosslinking agent impregnated with the composition and laminated to an impermeable backing.

Solid dosage forms for oral administration can include capsules, tablets, effervescent tablets, chewable tablets, pills, powders, sachets, granules and gels. In such solid dosage forms, the active compounds can be admixed with at least one inert diluent such as sucrose, lactose or starch. Such dosage forms can also comprise, as in normal practice, additional substances other than inert diluents, e.g., lubricating agents such as magnesium stearate. In the case of capsules, tablets, effervescent tablets, and pills, the dosage forms can also comprise buffering agents. Soft gelatin capsules can be prepared to contain a mixture of the active compounds or compositions of the invention and vegetable oil. Hard gelatin capsules can contain granules of the active compound in combination with a solid, pulverulent carrier such as lactose, saccharose, sorbitol, mannitol, potato starch, corn starch, amylopectin, cellulose derivatives of gelatin. Tablets and pills can be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Suppositories for vaginal or rectal administration of the compounds and compositions of the invention, such as for treating pediatric fever and the like, can be prepared by mixing the compounds or compositions with a suitable nonirritating excipient such as cocoa butter and polyethylene glycols which are solid at room temperature but liquid at rectal temperature, such that they will melt in the rectum and release the drug.

Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be used are water, Ringer's solution, and isotonic sodium chloride solution. Sterile fixed oils are also conventionally used as a solvent or suspending medium.

The compositions of this invention can further include conventional excipients, i.e., pharmaceutically acceptable organic or inorganic carrier substances suitable for parenteral application which do not deleteriously react with the active compounds. Suitable pharmaceutically acceptable carriers include, for example, water, salt solutions, alcohol, vegetable oils, polyethylene glycols, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/or dextran. Optionally, the suspension may also contain stabilizers.

The composition, if desired, can also contain minor amounts of wetting agents, emulsifying agents and/or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, and the like.

Various delivery systems are known and can be used to administer the compounds or compositions of the invention, including, for example, encapsulation in liposomes, microbubbles, emulsions, microparticles, microcapsules and the like. The required dosage can be administered as a single unit or in a sustained release form.

The bioavailabilty of the compositions can be enhanced by micronization of the formulations using conventional techniques such as grinding, milling, spray drying and the like in the presence of suitable excipients or agents such as phospholipids or surfactants.

The preferred methods of administration of the COX-2 selective inhibitors and compositions for the treatment of gastrointestinal disorders are orally, bucally or by inhalation. The preferred methods of administration for the treatment of inflammation and microbial infections are orally, bucally, topically, transdermally or by inhalation.

The compounds and compositions of the invention can be formulated as pharmaceutically acceptable salt forms. Pharmaceutically acceptable salts include, for example, alkali metal salts and addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids include, but are not limited to, hydrochloric, hydrobromic, hydroiodic, nitric, carbonic, sulfuric and phosphoric acid and the like. Appropriate organic acids include, but are not limited to, aliphatic, cycloaliphatic, aromatic, heterocyclic, carboxylic and sulfonic classes of organic acids, such as, for example, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesuifonic, sulfanilic, stearic, algenic, β-hydroxybutyric, cyclohexylaminosulfonic, galactaric and galacturonic acid and the like. Suitable pharmaceutically-acceptable base addition salts include, but are not limited to, metallic salts made from aluminum, calcium, lithium, magnesium, potassium, sodium and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound.

While individual needs may vary, determination of optimal ranges for effective amounts of the compounds and/or compositions is within the skill of the art. Generally, the dosage required to provide an effective amount of the compounds and compositions, which can be adjusted by one of ordinary skill in the art, will vary depending on the age, health, physical condition, sex, diet, weight, extent of the dysfunction of the recipient, frequency of treatment and the nature and scope of the dysfunction or disease, medical condition of the patient, the route of administration, pharmacological considerations such as the activity, efficacy, pharmacokinetic and toxicology profiles of the particular compound used, whether a drug delivery system is used, and whether the compound is administered as part of a drug combination.

The amount of a given COX-2 selective inhibitor of the invention that will be effective in the treatment of a particular disorder or condition will depend on the nature of the disorder or condition, and can be determined by standard clinical techniques, including reference to Goodman and Gilman, supra; The Physician's Desk Reference, Medical Economics Company, Inc., Oradell, N.J., 1995; and Drug Facts and Comparisons, Inc., St. Louis, Mo., 1993. The precise dose to be used in the formulation will also depend on the route of administration, and the seriousness of the disease or disorder, and should be decided by the physician and the patient's circumstances.

The amount of nitric oxide donor in a pharmaceutical composition can be in amounts of about 0.1 to about 10 times the molar equivalent of the COX-2 selective inhibitor. The usual daily doses of the COX-2 selective inhibitors are about 0.001 mg to about 140 mg/kg of body weight per day, preferably 0.005 mg to 30 mg/kg per day, or alternatively about 0.5 mg to about 7 g per patient per day. For example, inflammations may be effectively treated by the administration of from about 0.01 mg to 50 mg of the compound per kilogram of body weight per day, or alternatively about 0.5 mg to about 3.5 g per patient per day. The compounds may be administered on a regimen of up to 6 times per day, preferably 1 to 4 times per day, and most preferably once per day. Effective doses may be extrapolated from dose-response curves derived from in vitro or animal model test systems and are in the same ranges or less than as described for the commercially available compounds in the Physician's Desk Reference, supra.

The invention also provides pharmaceutical kits comprising one or more containers filled with one or more of the ingredients of the pharmaceutical compounds and/or compositions of the invention, including, at least, one or more of the novel COX-2 selective inhibitors, that is optionally nitrosated and/or nitrosylated, and one or more of the NO donors described herein. Associated with such kits can be additional therapeutic agents or compositions (e.g., steroids, NSAIDs, 5-lipoxygenase (5-LO) inhibitors, leukotriene $B_4$ ($LTB_4$) receptor antagonists and leukotriene $A_4$ ($LTA_4$) hydrolase inhibitors, 5-HT agonists, HMG-CoA inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, Helicobacter pylori inhibitors, proton pump inhibitors, isoprostane inhibitors, and the like), devices for administering the compositions, and notices in the form prescribed by a governmental agency regulating the manufacture, use or sale of pharmaceuticals or biological products which reflects approval by the agency of manufacture, use or sale for humans.

EXAMPLES

The following non-limiting examples further describe and enable one of ordinary skill in the art to make and use the invention. In each of the examples, flash chromatography was performed on 40 micron silica gel (Baker).

Example 1

1-(1-Cyclooctyl-3-((nitrooxy)methyl)pyrazol-5-yl)-4-(methylsulfonyl)benzene

1a. N-(Azacyclooctylidenemethyl)(tert-butoxy)carboxamide

Cyclooctanone (5 g, 39.6 mmol) and t-butyl carbazate (5.24 g, 39.6 mmol) in methanol (140 mL) was stirred at room temperature for 1 hour. The solvent was evaporated and the resulting solid dried under vacuo to give a white solid in quantitative yield. Mp 133° C. $^1$H NMR (300 MHz, $CDCl_3$) δ 7.45 (br s, 1H), 2.35-2.40 (m, 2H), 2.27-2.35 (m, 2H), 1.60-1.82 (m, 4H), 1.51 (s, 9H), 1.32-1.58 (m, 6H); $^{13}$C NMR (75 MHz, $CDCl_3$) δ 158.3, 152.9, 80.8, 36.5, 28.4, 27.4, 27.3, 26.5, 25.4, 24.6, 24.5. Mass spectrum (API-TIS) m/z 241 ($MH^+$). Anal. calcd. for $C_{13}H_{24}N_2O_2$: C, 64.97; H, 10.07; N, 11.66. Found: C, 64.74; H, 9.98; N, 11.64.

1b. (tert-Butoxy)-N-(cyclooctylamino)carboxamide

Sodium cyanoborohydride (2.48 g, 39.6 mmol) was added portion-wise to a suspension of the product of Example 1a (9.5 g, 39.6 mmol) in 50% acetic acid (100 mL) at room temperature. The resultant clear solution was stirred for 2 hours at room temperature. The reaction mixture was neutralized with 1N NaOH, extracted with $CH_2Cl_2$, washed with saturated $NaHCO_3$, dried, filtered and evaporated to give the title compound as a colorless oil in quantitative yield. The crude product was used without further purification.

1c. Cyclooctyl hydrazine trifluoroacetate

Trifluoroacetic acid (20 mL) was added drop-wise to a solution of the product of Example 1b (5.6 g, 36.9 mmol) in $CH_2Cl_2$ (20 mL). The reaction mixture was stirred at room temperature for 1 hour. The solvent was evaporated to give the trifluoroacetate salt of the title compound as a colorless oil in quantitative yield. $^1$H NMR (300 MHz, $CDCl_3$) δ 6.00-6.25 (br s, 1H), 3.70-3.95 (br s, 1H), 2.95-3.13 (m, 1H), 1.53 (s, 9H), 1.40-1.85 (m, 14H). $^{13}$C NMR (75 MHz, $CDCl_3$) δ 157.0, 80.4, 60.0, 30.4, 28.5, 27.4, 25.7, 23.9. Mass spectrum (API-TIS) m/z 243 ($MH^+$).

1d. Methyl (2Z)-2-hydroxy-4-(4-methylthiophenyl)-4-oxobut-2-enoate

Dimethyloxalate (26 g, 180.7 mmol) was added to a stirred suspension of sodium methoxide (9.75 g, 180.7 mmol) in dry toluene (200 mL) at 0° C. The white suspension was stirred for 15 min at 0° C. A solution of 4'-(methylthio)acetophenone (15 g, 90.4 mmol) in dry toluene (150 mL) was then added drop-wise over 15 minutes giving a yellow suspension which was stirred for 2 hours at room temperature. The thick yellow suspension was transferred to a 2 liter flask and stirred vigorously with 10% HCl (250 mL) and EtOAc (200 mL) to dissolve all the solid present. The organic layer was separated and the aqueous layer was extracted with EtOAc (100 mL). The combined organic extracts were washed with water (250 mL), dried over $Na_2SO_4$ and the solvent was evaporated under reduced pressure to give thick brown oil. The brown oil was dissolved in $CH_2Cl_2$ (25 mL) and hexane (125 mL) and left in a freezer at −20° C. for 16 hours to give the title compound (18 g, 79% yield) as orange color solid. Mp 81° C. $^1$H NMR (300 MHz, $CDCl_3$) δ 7.83 (d, J=8.6 Hz, 2H), 7.23 (d, J=8.6 Hz, 2H), 6.97 (s, 1H), 3.89 (s, 3H), 2.47 (s, 3H); $^{13}$C NMR (75 MHz, $CDCl_3$). Mass spectrum (API-TIS) m/z 253 ($MH^+$). Anal calcd. for $C_{12}H_{12}O_4S$: C, 57.13; H, 4.79; S, 12.71. Found: C, 56.85; H, 4.76; S, 12.43.

1e Methyl 1-cyclooctyl-5-(4-methylthiophenyl)pyrazol-3-carboxylate

A mixture of the product Example 1d (2 g, 7.9 mmol) and the product of Example 1c (3.65 g, 10.3 mmol) in methanol (40 mL) was heated at 70° C. for 2 hours and cooled to room temperature. The mixture was made basic with 5% $Na_2CO_3$ and extracted with EtOAc which was then washed with saturated $NaHCO_3$ and water. The organic extracts were dried over Na$_2$SO$_4$ and the solvent was evaporated under reduced pressure to give a thick oil, which was purified by chromatography over silica gel eluting with 1:2 EtOAc:Hex to give the title compound as a colorless oil (2.8 g, 99% yield). $^1$H NMR (300 MHz, CDCl$_3$) δ 7.34 (dd, J=1.7 and 6.4 Hz, 2H), 7.26 (dd, J=1.9 and 4.7 Hz, 2H), 6.75 (s, 1H), 4.35-4.55 (m, 1H), 3.92 (s, 3H), 2.54 (s, 3H), 2.20-2.38 (m, 2H), 1.15-1.90 (m, 12H); $^{13}$C NMR (75 MHz, CDCl$_3$) δ 163.3, 143.5, 142.6, 140.3, 129.7, 126.7, 126.4, 108.8, 60.4, 59.6, 52.1, 34.2, 30.3, 27.3, 26.5, 25.7, 24.8, 23.7, 15.5. Mass spectrum (API-TIS) m/z 359 (MH$^+$).

1f. (1-Cyclooctyl-5-(4-methylthiophenyl)pyrazol-3-yl)methan-1-ol

Lithium aluminum hydride (6.78 mL of 1M solution in THF, 0.26 g, 6.78 mmol) was added drop-wise to a solution of the product of Example 1e (2.43 g, 6.78 mmol) in THF (40 mL) at 0° C. The yellow solution was stirred at room temperature for 1 hour. Solid Na$_2$SO$_4$.10H$_2$O was added portionwise to the reaction mixture at 0° C., followed by few drops of water and 0.1 N NaOH. The solid was filtered and washed with EtOAc. The residue, obtained after evaporation of the filtrate, was purified by chromatography over silica gel eluting with 1:1 EtOAc:Hex to give the title compound (1.64 g, 73% yield) as an oil. $^1$H NMR (300 MHz, CDCl$_3$) δ 7.32 (dd, J=2.0 and 6.6Hz, 2H), 7.26 (dd, J=1.6 and 6.6Hz, 2H), 6.19 (s, 1H), 4.79 (bd, J=3.4 Hz, 2H), 4.27-4.40 (m, 1H), 2.58-2.72 (m, 1H), 2.53 (s, 3H), 2.08-2.25 (m, 2H), 1.20-1.88 (m, 12H); $^{13}$C NMR (75 MHz, CDCl$_3$) δ 151.3, 143.1, 139.5, 129.5, 127.7, 126.4, 104.1, 59.3, 58.5, 34.1, 26.6, 26.3, 24.8, 15.6. Mass spectrum (API-TIS) m/z 331 (MH$^+$), 313 (M-OH). Anal. calcd. for C$_{19}$H$_{20}$N$_2$OS: C, 69.05; H, 7.93; N, 8.48. Found: C, 68.81; H, 8.06; N, 8.59.

1g. 1-(1-Cyclooctyl-3-(hydroxymethyl)pyrazol-5-yl)-4-methylsulfonyl)benzene

The product of Example 1f (1.54 g, 4.67 mmol) was dissolved in MeOH (90 mL). OXONE® (5.74 g, 9.33 mmol) in water (20 mL) was added at room temperature. The reaction mixture was stirred for 1 hour and the resulting solid was removed by filtration. CH$_2$Cl$_2$ was added to the filtrate, that was washed with saturated NaHCO$_3$, water, dried over Na$_2$SO$_4$, and filtered. The residue after evaporation of the solvent was recrystallized from CH$_2$Cl$_2$/EtOAc/Hexane to give the title compound as white needles (1.4 g, 83% yield). Mp 127-128° C. $^1$H NMR (300 MHz, CDCl$_3$) δ 8.05 (d, J=8.3 Hz, 2H), 7.57 (d, J=8.3 Hz, 2H), 7.26 (s, 1H), 4.73 (d, J=5.7 Hz, 2H), 4.25-4.37 (m, 1H), 3.13 (s, 3H), 2.08-2.30 (m, 2H), 1.22-1.92 (m, 12H); $^{13}$C NMR (75 MHz, CDCl$_3$) δ 151.7, 141.6, 140.5, 136.8, 130.0, 128.0, 105.1, 59.2, 59.1, 44.6, 34.1, 26.7, 26.2, 24.8. Mass spectrum (API-TIS) m/z 363 (MH$^+$). Anal. calcd. for C$_{19}$H$_{26}$N$_2$O$_3$S: C, 62.96; H, 7.23; N, 7.73; S, 8.84. Found: C, 62.99; H, 7.30; N, 7.67; S, 8.87.

1h. 1-(1-Cyclooctyl-3-((nitrooxy)methyl)pyrazol-5-yl)-4-methylsulfonyl)benzene

The product of Example 1g (0.52 g, 1.43 mmol) in CHCl$_3$ was added to a mixture of fuming HNO$_3$ (0.30 mL, 0.45 g, 7.13 mmol) and Ac$_2$O (1.1 mL, 1.16 g, 11.4 mmol) at −10° C. and stirred at −10° C. for 20 minutes. The reaction mixture was quenched with ice cold water and extracted with CH$_2$Cl$_2$. The extracts were washed with ice cold saturated NaHCO$_3$, water, dried over Na$_2$SO$_4$, filtered and the solvent evaporated under reduced pressure. The residue obtained was recrystallized from CH$_2$Cl$_2$/EtOAc/Hex to give the title compound as a white solid (0.36 g, 63% yield). Mp 110-111° C. $^1$H NMR (300 MHz, CDCl$_3$) δ 8.06 (dd, J=1.8 and 6.7 Hz, 2H), 7.56 (dd, J=1.8 and 6.5 Hz, 2H), 6.38 (s, 1H), 5.50 (s, 2H), 4.27-4.40 (m, 1H), 3.13 (s, 3H), 2.12-2.30 (m, 2H), 1.27-1.96 (m, 12H); $^{13}$C NMR (75 MHz, CDCl$_3$) δ 143.3, 141.9, 140.9 136.2, 130.0, 128.1, 107.3, 68.8, 59.5, 44.6, 33.9, 26.7, 26.1, 24.6. Mass spectrum (API-TIS) m/z 408 (MH$^+$). Anal. calcd. for C$_{19}$H$_{25}$N$_3$O$_5$S: C, 56.00; H, 6.18; N, 10.31; S, 7.87. Found: C, 56.12; H, 6.30; N, 10.27; S, 7.84.

Example 2

1-(1-Cycloheptyl-3-((nitrooxy)methyl)pyrazol-5-yl)-4-(methylsulfonyl)benzene

2a. Methyl 1-cycloheptyl-5-(4-methylthiophenyl)pyrazol-3-carboxylate

The title compound was prepared from the product of Example 1d, (tert-butoxy)-N-(cycloheptylamino)carboxamide, TFA, using the procedure for Example 1e. $^1$H NMR (300 MHz, CDCl$_3$) δ 7.34 (d, J=8.4 Hz, 2H), 7.26 (d, J=8.4 Hz, 2H), 7.65 (s, 1H), 4.29 (m, 1H), 3.93 (s, 3H), 2.54 (s, 3H), 1.39-1.96 (m, 12H). Mass spectrum (API-TIS) m/z 345 (MH$^+$).

2b. Methyl 1-cycloheptyl-5-(4-(methylsulfonyl)phenyl)pyrazol-3-carboxylate

The product of Example 2a (150 mg, 0.44 mmol) was dissolved in CH$_2$Cl$_2$ (2 mL) and cooled to 0° C. The oxidant, m-CPBA (240 mg, 0.96 mmol), was added and the cooling bath was removed. The reaction mixture was stirred at room temperature for 1 hour. The reaction mixture was diluted with EtOAc (15 mL), washed with 1N Na$_2$CO$_3$ (2×5) followed by brine (1×5), dried over Na$_2$SO$_4$, and concentrated. This gave a solid that was recrystallized from EtOAc (300 µL) and hexane (450 µL) to give the title compound (90 mg, 54% yield) as a white solid.

Mp 115-117° C. $^1$H NMR (300 MHz, CDCl$_3$) δ 8.07 (d, J=8.0 Hz, 2H), 7.56 (d, J=8.0 Hz, 2H), 6.53 (s, 1H), 4.25 (pentet, J=6.0 Hz, 1H), 3.93 (s, 3H), 3.13 (s, 3H), 1.40-2.32 (m, 12).

Mass spectrum (API-TIS) m/z 377 (MH$^+$). Anal calcd. for C$_{19}$H$_{24}$N$_2$O$_4$S: C, 60.62; H, 6.43; N, 7.44. Found C, 60.43; H, 6.36; N, 7.47.

2c. 1-(1-Cycloheptyl-3-(hydroxymethyl)pyrazol-5-yl)-4-(methylsulfonyl)benzene

The product of Example 2b (1.8 g, 4.9 mmol) was dissolved in THF (20 mL) and cooled to 0° C. Solid lithium aluminum hydride (280 mg, 7.5 mmol) was added all at one time. Stirring was continued at 0° C. for 30 minutes followed by 30 minutes at room temperature. The reaction mixture was cooled to 0° C. and excess lithium aluminum hydride was destroyed by the sequential addition of H$_2$O (350 µL), 15% NaOH (350 µL), H$_2$O (1 mL). The precipitate that formed was removed by filtration through Celite, washed with EtOAc (2×25). The combined filtrates were dried over Na$_2$SO$_4$ and concentrated. Trituration of the solid residue with hexane (6 mL) and EtOAc (3 mL) gave the title compound (1.0 g, 60% yield) as a white solid. Mp 116-118° C. $^1$H NMR (300 MHz, CDCl$_3$) δ 8.04 (d, J=8.2 Hz, 2H), 7.55 (d, J=8.2 Hz, 2H), 6.29 (s, 1H), 4.73 (d, J=5.6 Hz, 2H), 4.19 (pentet, J=4.6 Hz, 1H), 3.12 (s, 3H), 1.26-2.24 (m, 12).

Mass spectrum (API-TIS) m/z 349 (MH$^+$). Anal calcd. for C$_{18}$H$_{24}$N$_2$O$_3$S: C, 62.04; H, 6.94; N, 8.04. Found C, 61.87; H, 6.94; N, 7.99.

2d. 1-(1-Cycloheptyl-3-((nitrooxy)methyl)pyrazol-5-yl)-4-(methylsulfonyl)benzene Fuming nitric acid 90% (350 μL, 7.5 mmol) was added to acetic anhydride (1.1 mL, 12 mmol) and the mixture stirred at room temperature for 30 minutes, it was then cooled to 0° C. and diluted with EtOAc (10 mL). The product of Example 2c in EtOAc and the above mentioned mixture were stirred for 2 hours at 0° C. The reaction mixture was partitioned between EtOAc (20 mL) and saturated $NaHCO_3$ (20 mL) by stirring for 20 minutes. The organic layer was removed and the aqueous layer was extracted with EtOAc (40 mL). The combined organic layers were dried over $Na_2SO_4$ and concentrated. Trituration of the residue in hexane (1.6 mL) and EtOAc (0.4 μL) gave the title compound (400 mg, 70% yield) as a white solid. Mp 119-120° C. $^1$H NMR (300 MHz, $CDCl_3$) δ 8.06 (d, J=8.3 Hz, 2H), 7.55 (d, J=8.4 Hz, 2H), 6.38 (s, 1H), 5.50 (s, 2H), 4.22 (pentet, J=4.6 Hz, 1H), 3.13 (s, 3H), 1.42-2.20 (m, 12). Mass spectrum (API-TIS) m/z 394 (MH$^+$). Anal calcd. for $C_{18}H_{23}N_3O_5S$: C, 54.95; H, 5.89; N, 10.68. Found C, 54.97; H, 5.99; N, 10.42.

Example 3

1-(1-Cyclohexyl-5-(4-(methylsulfonyl)phenyl)pyrazol-3-yl)-4-(nitrooxy)butan-1-one

3a. Methyl(2Z)-2-hydroxy-4-(4-(methylsulfonyl)phenyl)-4-oxobut-2-enoate

OXONE® (4.39 g, 7.1 mmol) in water (14 mL) was added drop-wise to a solution of Example 1d (1.5 g, 6.0 mmol) in a mixture of MeOH (30 mL) and $CH_2Cl_2$ (2 mL) at 0° C. The resultant suspension was slowly allowed to warm to room temperature over a period of 1 hour. The solid was filtered off and the filtrate was diluted with $CH_2Cl_2$, washed with saturated $NaHCO_3$, water, dried ($Na_2SO_4$) and filtered. The solvent was evaporated to give the product (0.8 g, 47% yield). Mass spectrum (API-TIS) m/z 285 (MH$^+$), 302 ($MNH_4^+$).

3b. Methyl-1-cyclohexyl-5-(4-methylsulfonylphenyl)pyrazol-3-carboxylate

The product of Example 3a (7.4 g, 26 mmol) and cyclohexyl hydrazine hydrochloride (4.3 g, 29 mmol) were heated at reflux in MeOH (100 mL) for 6 hours. The reaction mixture was cooled to room temperature and a few drops of acetone was added to initiate crystallization. The resulting thick slurry was diluted with $H_2O$ (90 mL) and 1N HCl (20 mL), then cooled to −20° C. in a freezer. The solid was isolated by filtration and washed with $H_2O$ (2×50), dried in vacuo at room temperature to give the title compound (8.3 g, 88% yield) as a tan solid. Mp 108° C. $^1$H NMR (300 MHz, CDCl3) δ 8.09 (d, J=8.4 Hz, 2H), 7.59 (d, J=8.4 Hz, 2H), 6.88 (s, 1H), 4.06-4.10 (m, 1H),3.97 (s, 3H), 3.16 (s, 3H), 1.26-2.19 (m, 10H). $^{13}$C NMR (75 MHz $CDCl_3$) δ 162.5, 142.5, 141.9, 140.8, 135.2, 129.7, 127.8, 109.3, 59.0, 51.8, 44.2, 33.1, 25.2, 24.5. Mass spectrum (API-TIS) m/z 363 (MH$^+$).

3c. (1-Cyclohexyl-5-(4-(methylsulfonyl)phenyl)pyrazol-3-yl)-N-methoxy-N-methylcarboxamide Trimethylaluminum (5.52 mL of 2M solution in hexane, 0.80 g, 11.1 mmol,) was added drop-wise to a suspension of dimethylhydroxylamine hydrochloride in $CH_2Cl_2$ (10 mL) at 0° C. The clear solution was stirred at 0° C. for 45 minutes and then at room temperature for 40 minutes. To this solution the product of Example 3b (2.06 g, 5.7 mmol) in $CH_2Cl_2$ (4 mL) was added drop-wise. The stirring was continued for 2 hours at room temperature. The reaction mixture was cooled to 0° C. and 10% HCl was carefully added drop-wise. The aqueous phase was extracted with EtOAc, washed with water, brine, dried over $Na_2SO_4$ and filtered. The residue obtained after evaporation of the solvent was dissolved in $CH_2Cl_2$, filtered through a silica gel pad and was washed with EtOAc. The combined filtrate and washings were evaporated to give the title compound (1.48 g, 67% yield) as a white solid. Mp 53° C. $^1$H NMR (300 MHz, $CDCl_3$) δ 8.28 (d, J=8.3 Hz, 2H), 7.58 (d, J=8.3 Hz, 2H), 6.81 (s, 1H), 4.00-4.20 (m, 1H), 3.85 (s, 3H), 3.48 (br s, 3H), 3.13 (s, 3H), 1.78-2.20 (m, 7H), 1.13-1.37 (m, 3H); $^{13}$C NMR (75 MHz, $CDCl_3$) δ 144.6, 141.3, 140.9, 136.0, 130.0, 128.1, 109.5, 61.7, 59.0, 44.6, 33.5, 25.6, 25.1, 14.7, 14.2. Mass spectrum (API-TIS) m/z 392 (MH$^+$). Anal. calcd. for $C_{19}H_{25}N_3O_4S$: C, 58.29; H, 6.44; N, 10.73. Found: C, 57.98; H, 6.45; N, 10.35.

3d. 1-(1-Cyclohexyl-5-(4-(methylsulfonyl)phenyl)pyrazol-3-yl)-4-(1,1,2,2-tetramethyl-1-silapropoxy)butan-1-one To a solution of the product of Example 3c (1.0 g, 2.56 mmol) in THF (20 mL) was added drop-wise the Grignard reagent prepared from 3-bromo-1-(1,1,2,2-tetramethyl-1-silapropoxy)propane (5 g, 19.8 mmol) and magnesium turnings (1.02 g, 42.5 mmol) in THF (50 mL) at 0° C. under nitrogen. The reaction mixture was gradually allowed to warm to room temperature. After all the starting material had been consumed, saturated aqueous $NH_4Cl$ solution was added drop-wise at 0° C. The reaction mixture was diluted with EtOAc and the layers were separated. The aqueous layer was extracted with EtOAc and the combined organic layers were washed with water, dried ($Na_2SO_4$) and filtered. The residue obtained after evaporation of the solvent was purified by chromatography over silica gel eluting first with 1:10 to 2:10, then with 1:2 to 1:1 and lastly with 2:1 EtOAc:hexane to give the title compound (1.27 g, 98% yield) as a white solid. Mp 131-133° C. $^1$H NMR (300 MHz, $CDCl_3$) δ 8.08 (d, J=8.4 Hz, 2H), 7.58 (d, J=8.4 Hz, 2H), 6.82 (s, 1H), 3.95-4.25 (m, 1H), 3.74 (t, J=6.3 Hz, 2H), 3.16 (s, 3H), 3.13 (t, J=7.4 Hz, 2H), 1.80-2.20 (m, 7H and 2H), 1.22-1.40 (m, 3H), 0.91 (s, 9H), 0.08 (s, 6H); $^{13}$C NMR (75 MHz, $CDCl_3$) δ 96.5, 150.3, 142.4, 141.0, 135.9, 130.0, 128.1, 107.1, 62.7, 59.0, 44.6, 35.3, 33.4, 27.6, 26.1, 25.5, 25.1, 18.5, −5.2. Mass spectrum (API-TIS) m/z 505 (MH$^+$). Anal. calcd. for $C_{26}H_{40}N_2O_4SSi$: C, 61.87; H, 7.99; N, 5.55. Found: C, 61.81; H, 7.70; N, 5.48.

3e. 1-(1-Cyclohexyl-5-(4-(methylsulfonyl)phenyl)pyrazol-3-yl)-4-hydroxybutan-1-one Tetrabutyl ammonium fluoride (2.57 mL of 1 M solution in THF, (0.67 g, 2.57 mmol) was added drop-wise to a solution of the product of Example 3d (1.04 g, 2.06 mmol) in THF (24 mL) at 0° C. The resultant solution was stirred at 0° C. for 2 hours and then at room temperature for 3 hours. The residue obtained after evaporation of the solvent was purified by chromatography over silica gel eluting with 1:1 to 2:1 EtOAc:hexane to give an oil which was recrystallized from $CH_2Cl_2$/EtOAc/Hexane to give the title compound (0.64 g, 79% yield). Mp 112-114° C. $^1$H NMR (300 MHz, $CDCl_3$) δ 8.07 (d, J=8.3 Hz, 2H), 7.57 (dd, J=1.7 and 6.7 Hz, 2H), 6.83 (s, 1H), 4.00-4.20 (m, 1H), 3.65-3.80 (m, 2H), 3.19 (t, J=6.9 Hz, 2H), 3.14 (s, 3H), 2.32 (t, J=5.8 Hz, 1H), 2.03 (p, J=6.8 Hz, 2H), 1.68-1.97 (m, 6H), 1.18-1.40 (m, 4H).

$^{13}$C NMR (75 MHz, $CDCl_3$) δ 196.9, 150.4, 142.7, 141.1, 135.7, 130.0, 128.2, 107.3, 62.3, 59.2, 44.6, 35.4, 33.5, 27.8, 25.5, 25.1. Mass spectrum (API-TIS) m/z 391 (MH$^+$), 373 (M-OH). Anal. calcd. for $C_{20}H_{26}N_2O_4S$: C, 61.52; H, 6.71; N, 7.17. Found: C, 61.25; H, 6.66; N, 7.08.

3f. 1-(1-Cyclohexyl-5-(4-(methylsulfonyl)phenyl) pyrazol-3-yl)-4-(nitrooxy)butan-1-one The title compound was prepared as a white solid from the product of Example 3e using the procedure for Example 1h. Mp 122-124° C. $^1$H NMR (300 MHz, CDCl$_3$) δ 8.07 (d, J=8.2 Hz, 2H), 7.56 (d, J=8.2 Hz, 2H), 6.81 (s, 1H), 4.59 (t, J=6.4 Hz, 2H), 4.04-4.09 (m, 1H), 3.21 (t, J=7.1 Hz, 2H), 3.13 (s, 3H), 2.15-2.24 (m, 2H), 1.67-2.13 (m, 7H), 1.12-1.42 (m, 3H); $^{13}$C NMR (75 MHz, CDCl$_3$) δ 194.7, 149.9, 142.6, 141.1, 135.7, 130.0, 128.2, 107.2, 72.8, 59.2, 44.6, 34.5, 33.4, 25.5, 25.1, 21.5. Mass spectrum (API-TIS) m/z 435 (MH$^+$). Anal. calcd. for C$_{20}$H$_{25}$N$_3$O$_6$S: C, 55.16; H, 5.79; N, 9.65. Found: C, 54.93; H, 5.62; N, 9.49.

Example 4

1-(3-((1Z)-4-(Nitrooxy)but-1-enyl)-1-cyclohexylpyrazol-5-yl)-4-(methylsulfonyl)benzene

4a. Methyl-1-cyclohexyl-5-(4-methylthiophenyl) pyrazol-3-carboxylate

A mixture of the product of Example 1d (1.98 g, 7.8 mmol) and cyclohexylhydrazine hydrochloride (1.54 g, 10.2 mmol) in methanol (40 mL) was heated at 70° C. for 3 hours and then cooled to room temperature. The mixture was made basic with 10% Na$_2$CO$_3$ and extracted with EtOAc (3×25 mL). The organic extracts were dried over Na$_2$SO$_4$ and the solvent was evaporated under reduced pressure to give a thick oil. The oil was dissolved in CH$_2$Cl$_2$ (4 mL) and hexane (20 mL) and left in a freezer at −10° C. for 16 hours to give the title compound (2.2 g, 85% yield) as a white solid. Mp 84° C. $^1$H NMR (300 MHz, CDCl$_3$) δ 7.33 (d, J=8.3 Hz, 2H), 7.26 (d, J=8.3 Hz, 2H), 6.76 (s, 1H), 4.08-4.13 (m, 1H), 3.93 (s, 3H), 2.54 (s, 3H), 2.07-2.20 (m, 2H), 1.80-1.95 (m, 4H), 1.62-1.72 (m, 1H), 1.20-1.30 (m, 3H); $^{13}$C NMR (75 MHz, CDCl$_3$) δ 163.1, 143.6, 142.3, 140.1, 129.4, 126.4, 126.2, 108.8, 58.7, 51.9, 33.1, 25.5, 24.8, 15.3. Mass spectrum (API-TIS), m/z 331 (MH$^+$). Anal. calcd. for C$_{18}$H$_{22}$N$_2$O$_2$S: C, 65.43; H, 6.71; N, 8.48; S, 9.70. Found: C, 65.28; H, 6.66; N, 8.47; S, 9.61.

4b. 1-Cyclohexyl-5-(4-methylthiophenyl)pyrazol-3-yl)methan-1-ol

A solution of lithium aluminum hydride (1 M in THF, 2 mL, 2 mmol) was added to a stirred solution of the product of Example 4a (0.7 g, 2.1 mmol) in THF (15 mL) at 0° C. The resulting clear solution was stirred at room temperature for 1 hour. Solid Na$_2$SO$_4$·10H$_2$O (2 g) was added in small portions with stirring until a thick precipitate formed. Methanol in CH$_2$Cl$_2$ (10%, 50 mL) was added and the mixture was filtered. The solid was washed with additional methanol in CH$_2$Cl$_2$ (10%, 50 mL) and the combined filtrates were evaporated to give the title compound (0.61 g, 95% yield) as a white solid. Mp 97° C. $^1$H NMR (300 MHz, CDCl$_3$) δ 7.31 (d, J=8.3 Hz, 2H), 7.24 (d, J=8.3 Hz, 2H), 6.20 (s, 1H), 4.71 (d, J=4.8 Hz, 2H), 4.00-4.15 (m, 1H), 2.53 (s, 3H), 1.65-2.10 (m, 7H), 1.15-1.30 (m, 3H); $^{13}$C NMR (75 MHz, CDCl$_3$) δ 151.0, 143.2, 139.3, 129.3, 127.5, 126.3, 104.1, 59.0, 57.7, 33.2, 25.6, 25.1, 15.4. Mass spectrum (API-TIS) m/z 303 (MH$^+$).

4c. Methyl-1-cyclohexyl-5-(4-methylthiophenyl) pyrazol-3-carboxyladehyde

To a stirred solution of oxalyl chloride (0.66 mL, 0.96 g, 6.1 mmol) in CH$_2$Cl$_2$ (2.5 mL) at −78° C. under nitrogen was added DMSO (1.08 mL, 15.2 mmol) in CH$_2$Cl$_2$ (2 mL) drop-wise over a period of 20 min. To this solution the product of Example 4b (1.84 g, 6.1 mmol) in CH$_2$Cl$_2$ (12 mL) was added drop-wise over a period of 40 minutes at −78° C. The mixture was stirred at −78° C. for 1.5 hours. Triethylamine (4.25 mL, 3.08 g, 30.5 mmol) in CH$_2$Cl$_2$ (2.6 mL) was then added drop-wise over a period of 45 minutes at −78° C. The resultant mixture was stirred at 0° C. for 20 minutes. To this mixture, water (2 mL) was added drop-wise followed by CH$_2$Cl$_2$ (50 mL). The organic layer was separated and the aqueous layer was extracted with CH$_2$Cl$_2$. The combined organic extracts were washed with 5% HCl, dried over Na$_2$SO$_4$ and filtered. The residue after evaporation of the solvent was recrystallized from CH$_2$Cl$_2$/EtOAc/Hexane to give the title compound (1.4 g, 77% yield) as a white solid. Mp 63° C. $^1$H NMR (300 MHz, CDCl$_3$) δ 9.97 (s, 1H), 7.32 (d, J=8.3 Hz, 2H), 7.24 (d, J=8.3 Hz, 2H), 6.71 (s, 1H), 4.00-4.18 (m, 1H), 2.52 (s, 3H), 1.50-1.90 (m, 7H), 1.15-1.25 (m, 3H). $^{13}$C NMR (75 MHz, CDCl$_3$) δ 186.8, 150.4, 144.4, 140.4, 129.3, 126.2, 105.4, 58.7, 33.2, 25.5, 24.5, 15.2. mass spectrum (API-TIS) m/z 301 (MH$^+$).

4d. 1-((3Z)-4-(1-Cyclohexyl-5-(4-methylthiophenyl) pyrazol-3-yl)but-3-enyloxy)-1,1,2,2-tetramethyl-1-silapropane n-Butyl lithium (2.5 M solution in hexane, 2.25 mL, 0.36 g, 5.6 mmol), was added drop-wise to solution of (3-((1,1-dimethylethyl)-dimethylsilyl)-oxy)propyl)-triphenylphosphonium bromide (2.45 g, 4.76 mmol) in THF (13 mL) at −78° C. The resultant solution was stirred at −78° C. for 1 hour. To this solution the product of Example 4c (1.3 g, 4.3 mmol) in THF (13 mL) was added drop-wise. The reaction mixture was stirred at −78° C. for 1 hour. The reaction mixture was gradually allowed to warm to room temperature and stirred for 24 hours. Water was added and the reaction mixture extracted with EtOAc, which was then washed with water, dried over Na$_2$SO$_4$ and filtered. The residue obtained after evaporation of the solvent was purified by chromatography over silica gel eluting with 0.5:10 EtOAc:Hexane to give the pure Z-isomer (1.2 g, 61% yield) as a colorless oil and minor E-isomer (0.1 g, 5% yield). Z-isomer: $^1$H NMR (300 MHz, CDCl$_3$) δ 7.33 (d, J=8.4 Hz, 2H), 7.28 (d, J=8.5 Hz, 2H), 6.47 (d, J=11.7 Hz, 1H), 6.28 (s, 1H), 5.65-5.77 (m, 1H), 3.98-4.12 (m, 1H), 3.76 (t, J=6.9 Hz, 2H), 2.72 (q, J=6.1 Hz, 2H), 2.54 (s, 3H), 1.60-2.18 (m, 7H), 1.15-1.40 (m, 3H), 0.90 (s, 9H), 0.07 (s, 6H); $^{13}$C NMR (75 MHz, CDCl$_3$) δ 148.4, 142.8, 139.3, 129.5, 128.7, 127.8, 126.4, 122.7, 105.9, 62.9, 57.8, 33.5, 33.1, 26.1, 25.8, 25.3, 18.5, 15.6, −5.0. Mass spectrum (API-TIS) m/z 457 (MH$^+$).

4e. 1-(3-((1Z)-4-(Hydroxy)but-1-enyl)-1-cyclohexylpyrazol-5-yl-4-methylsulfonyl)benzene The product of Example 4d (1.17 g, 2.6 mmol) was dissolved in MeOH (51 mL). OXONE® (4.73 g, 7.7 mmol) in water (11 mL) was added at room temperature. The reaction mixture was stirred for 1 hour and then filtered to remove the solid. CH$_2$Cl$_2$ was added to the filtrate which was washed with saturated NaHCO$_3$, water, dried over Na$_2$SO$_4$ and filtered. The residue after evaporation of the solvent was recrystallized from CH$_2$Cl$_2$/EtOAc/Hexane to give the product (0.88 g, 92% yield) as a white solid. Mp 170-172° C. $^1$H NMR (300 MHz, CDCl$_3$) δ 8.05 (d, J=8.3 Hz, 2H), 7.56 (d, J=8.3 Hz, 2H), 6.50 (d, J=11.5 Hz, 1H), 6.27 (s, 1H), 5.80-5.94 (m, 1H), 3.90-4.10 (m, 1H), 3.87 (q, J=5.7 Hz, 2H), 3.79 (t, J=4.7 Hz, 1H), 3.13 (s, 3H), 2.75 (q, J=5.9 Hz, 2H), 1.62-2.18 (m, 7H), 1.18-1.40 (m, 3H); $^{13}$C NMR (75 MHz, CDCl$_3$) δ148.1, 141.5, 140.7, 136.5, 130.4, 129.9, 128.1, 123.1, 107.1, 62.6, 58.5, 44.6, 33.6, 32.4, 25.7, 25.1. mass spectrum (API-TIS) m/z 375 (MH$^+$). Anal. calcd. for C$_{20}$H$_{26}$N$_2$O$_3$S: C, 64.14; H, 7.00; N, 7.48; S, 8.56. Found: C, 63.89; H, 7.07; N, 7.40; S, 8.60.

4f. 1-(3-((1Z)-4-(Nitrooxy)but-1-enyl)-1-cyclohexylpyrazol-5-yl)-4-(methylsulfonyl)benzene The title compound was prepared as a white crystalline solid from the product of Example 4e by following the procedure for Example 1h. Mp 137-138° C. $^1$H NMR (300 MHz, CDCl$_3$) δ 8.05 (dd, J=1.5 and 8.4 Hz, 2H), 7.57 (dd, J=1.7 and 6.7 Hz, 2H), 6.48 (d, J=10.2 Hz, 1H), 6.27 (s, 1H), 5.62-5.74 (m, 1H), 4.64 (t, J=6.9 Hz, 2H), 3.93-4.10 (m, 1H), 3.13 (s, 3H), 3.00-305 (m, 2H), 1.78-2.14 (m, 6H), 1.62-1.77 (m, 1H), 1.19-1.38 (m, 3H); $^{13}$C NMR (75 MHz, CDCl$_3$) δ 148.0, 141.3, 140.6, 136.6, 129.9, 128.1, 125.7, 124.1, 107.2, 72.7, 58.5, 44.6, 33.5, 27.3, 25.7, 25.2. Mass spectrum (API-TIS) m/z 420 (MH$^+$). Anal. calcd. for C$_{20}$H$_{25}$N$_3$O$_5$S.¼ mol H$_2$O: C, 56.66; H, 6.06; N, 9.91. Found: C, 56.80; H, 5.99; 9.85.

Example 5

4-(methylsulfonyl)-1-(3-((3-(nitrooxy)propoxy)methyl)-1-phenylpyrazol-5-yl)benzene

5a. Methyl 5-(4-(methylsulfonyl)phenyl)-1-phenylpyrazol-3-carboxylate

The phenyl hydrazine hydrochloride (2.9 g, 20 mmol) and the product of Example 3a (4.5 g, 16 mmol) were added to MeOH and the solution heated at reflux for 4 hours. The reaction mixture was cooled to room temperature and H$_2$O was added until the solution became turbid and a precipitate formed. The precipitate was isolated by filtration and washed with H$_2$O (1×40). The solid was recrystallized from MeOH (2×300) to give the title compound (3 g, 50% yield) as a white solid. Mp 190-193° C. $^1$H NMR (300 MHz, CDCl$_3$) δ 7.89 (d, J=8.5 Hz, 2H), 7.34-7.43 (m, 5H), 7.30-7.33 (m, 2H), 7.15 (s, 1H), 3.99 (s, 3H), 3.07 (s, 3H). Mass spectrum (API-TIS) m/z 357 (MH$^+$). Anal calcd. for C$_{18}$H$_{16}$N$_2$O$_4$S: C, 60.66; H, 4.53; N, 7.86. Found C, 60.60; H, 4.46; N, 7.77.

5b. 4-(3-(Hydroxymethyl)-1-phenylpyrazol-5-yl)-1-(methylsulfonyl)benzene

A flask was charged with lithium aluminum hydride (320 mg, 8.4 mmol) in THF (8 mL) and cooled to 0° C. The product of Example 5a (1.85 mg, 5.2 mmol) in THF (10 mL) was added slowly. The reaction mixture was stirred at 0° C. for 15 minutes then allowed to warm to room temperature while stirring and then stirred for 3 hours at room temperature. The excess lithium aluminum hydride was destroyed by adding sequentially H$_2$O (500 µL), 15% NaOH (500 µL), H$_2$O (1.5 mL). The precipitate that formed was removed by filtration through Celite, the filter cake was washed with EtOAc (2×20). The combined filtrates were dried over Na$_2$SO$_4$ and concentrated. This gave the title compound (1.6 mg, 93% yield) as a white solid. $^1$H NMR (300 MHz, CDCl$_3$) δ 7.85 (d, J=8.7 Hz, 2H), 7.34-7.41 (m, 5H), 7.23-7.27 (m, 2H), 6.62 (s, 1H), 4.79 (s, 2H), 3.06 (s, 3H).

5c. 4-(3-(Bromomethyl)-1-phenylpyrazol-5-yl)-1-(methylsulfonyl)benzene

The product of Example 5b (1.6 g, 4.9 mmol) was dissolved in CH$_2$Cl$_2$ (25 mL) and cooled to 0° C. Phosphorous tribromide (470 µL, 4.9 mmol) was added and the mixture was stirred at room temperature for 2.5 hours. The reaction mixture was diluted with CH$_2$Cl$_2$ and washed with H$_2$O (2×20) and dried over Na$_2$SO$_4$. Evaporation of the solvent gave a residue that was purified chromatography over silica gel eluting with Hexane:EtOAc 1:1 to give the title compound (1.2 g, 63% yield). $^1$H NMR (300 MHz, CDCl$_3$) δ 7.87 (d, J=8.7 Hz, 2H), 7.36-7.43 (m, 5H), 7.24-7.28 (m, 2H), 6.68 (s, 1H), 4.58 (s, 2H), 3.06 (s, 3H).

5d. 4-(3-((3-Hydroxypropoxy)methyl)-1-phenylpyrazol-5-yl)-1-(methylsulfonyl)benzene To a slurry of 95% NaH (210 mg, 8.4 mmol) in THF (15 mL) at 0° C. was added 3-benzyloxypropanol (850 mL, 5.6 mmol). The mixture was stirred at room temperature for 40 minutes by which time effervescence had ceased. The product of Example 5c (2 mg, 5.1 mmol) in THF (10 mL) was added and the reaction mixture was stirred at room temperature for 18 hours. Excess NaH was quenched with 1N HCl (40 mL), and the reaction mixture was extracted with EtOAc (2×40). The combined extracts were washed with brine, dried over Na$_2$SO$_4$, and concentrated. The residue was taken up in EtOH (30 mL) and TFA (250 µL) and the hydrogenation was performed using 10% Pd/C (1 g) at 50 psi of hydrogen for 18 hours. The reaction mixture was filtered through Celite to remove the catalyst and was washed with EtOAc (2×25). The combined filtrate was concentrated and redissolved in CHCl$_3$ (60 mL). The chloroform solution was washed with H$_2$O (2×30), dried over Na$_2$SO$_4$, and concentrated. Chromatography of the residue over silica gel eluting with EtOAc gave the title compound (600 mg, 30% yield). $^1$H NMR (300 MHz, CDCl$_3$) δ 7.86 (d, J=8.6 Hz, 2H), 7.41 (d, J=8.6 Hz, 2 H), 7.25-7.38 (m, 5H), 6.63 (s, 1H), 4.65 (s, 2H), 3.81 (t, J=5.9 Hz, 2H), 3.79 (t, J=5.9 Hz, 2H), 3.06 (s, 3H), 1.90 (pentet, J=5.7 Hz, 2H). Mass spectrum (API-TIS) m/z 387 (MH$^+$). Anal calcd. for C$_{20}$H$_{22}$N$_2$O$_4$S: C, 62.16; H, 5.74; N, 7.25. Found C, 62.39; H, 5.58; N, 7.16.

5e. 4-(3-((3-(Nitrooxy)propoxy)methyl)-1-phenylpyrazol-5-yl)-1-(methylsulfonyl)benzene Fuming HNO$_3$ (1.0 mL, 26 mmol) was cooled to 0° C. The product of Example 5d (400 mg, 1 mmol) in CHCl$_3$ was added and the mixture stirred at 0° C. for 30 minutes. The reaction mixture was poured in to saturated aqueous NaHCO$_3$ (20 mL). The aqueous mixture was extracted with CHCl$_3$ (3×15). The combined extracts were dried over Na$_2$SO$_4$, and concentrated. The residue was purified chromatography over silica gel eluting with Hexane:EtOAc 1:1 to give the title compound (300 mg) as a clear oil. $^1$H NMR (300 MHz, CDCl$_3$) δ 7.87 (d, J=8.3 Hz, 2H), 7.42 (d, J=8.3 Hz, 2 H), 7.25-7.39 (m, 5H), 6.63 (s, 1H), 4.63 (s, 2H), 4.61 (t, J=6.4 Hz, 2H), 3.69 (t, J=5.9 Hz, 2H), 3.06 (s, 3H), 2.06 (pentet, J=6.2 Hz, 2H). Mass spectrum (API-TIS) m/z 432 (MH$^+$). Anal calcd. for C$_{20}$H$_{21}$N$_3$O$_6$S: C, 55.68; H, 4.914; N, 9.74. Found C, 54.72; H, 4.58; N, 9.46.

Example 6

1-(3-(Difluoro(3-(nitrooxy)propoxy)methyl)-1-phenylpyrazol-5-yl)-4-(methylsulfonyl)benzene

6a. (4-(Methylsulfonyl)phenyl)-1-phenylpyrazol-3-carboxylic acid

The product of Example 5a (1.0 g, 2.8 mmol) and NaOH (130 mg, 3.2 mmol) in MeOH (10 mL) were heated to reflux for 8 hours. The reaction mixture was cooled to room temperature and partitioned between EtOAc (30 mL) and 0.5 N HCl (30 mL). The aqueous layer was extracted with EtOAc (2×15). The combined organic layers were washed with brine, dried over Na$_2$SO$_4$, and concentrated. This gave the title compound (1 g, 100% yield) as a solid. Mp 207-208° C. $^1$H NMR (300 MHz, CDCl$_3$) δ 7.90 (d, J=8.1 Hz, 2H), 7.40-7.44 (m, 5H), 7.26-7.35 (m, 2H), 7.20 (s, 1H), 3.06 (s, 3H).

6b. 3-(Phenylmethoxy)propyl 5-(4-(methylsulfonyl) phenyl)-1-phenylpyrazol-3-carboxylate The product of Example 6a. (7.5 g, 22 mmol) was dissolved in toluene (50 mL) containing DMF (25 µL). Oxalyl chloride (2M/CH$_2$Cl$_2$, 22 mL, 44 mmol) was added drop-wise. The reaction mixture was allowed to stir at room temperature for 1.5 hours, then concentrated to thick oil. A solution of benzyloxypropanol (3.6 mL, 22 mmol) and pyridine (1.7 mL, 22 mmol) in CH$_2$Cl$_2$ (40 mL) was prepared and cooled to 0° C. The acid chloride prepared above was dissolved in CH$_2$Cl$_2$ (10 mL) and added drop-wise to the alcohol/pyridine mixture. The reaction mixture was allowed to warm to room temperature and stirred for 18 hours. The reaction mixture was diluted with CH$_2$Cl$_2$ (60 mL); washed with 1N HCl, saturated NaHCO$_3$, and H$_2$O (1×30); dried over Na$_2$SO$_4$; and concentrated to give the title compound (10.3 g, 95% yield) as an oil. $^1$H NMR (300 MHz, CDCl$_3$) δ 7.88 (d, J=8.1 Hz, 2H), 7.39-7.42 (m, 6H), 7.29-7.34 (m, 8H), 7.09 (s, 1H), 4.53 (t, J=6.6 Hz, 2H), 4.53, (s, 2H), 3.65 (t, J=6.3 Hz, 2H), 3.07 (s, 3H). 1.88 (pentet, J=6.3 Hz, 2H).

6c. 1-(Methylsulfonyl)-4-(1-phenyl-3-((3-(phenylmethoxy)propoxy)thioxomethyl)pyrazol-5-yl)benzene The product of Example 6b (10.3 g, 21 mmol) and Lawesson's reagent (32 g, 80 mmol) were heated to reflux in toluene (120 mL) for 5 days. As the reaction mixture was cooled to 0° C. a precipitate formed. The solid was removed by filtration and the filtrate was concentrated to a heavy oil. The oil was triturated with Hexane:EtOAc 1:1 (100 mL). A second precipitate formed which was also removed by filtration and the filtrate was concentrated to an oil. The oily residue was filtered through silica gel eluting with CHCl$_3$ to 5% MeOH/CHCl$_3$ to give the title compound (3.8 g, 36% yield). $^1$H NMR (300 MHz, CDCl$_3$) δ 7.88 (d, J=8.1 Hz, 2H), 7.39-7.42 (m, 6H), 7.26-7.34 (m, 8H), 7.09 (s, 1H), 4.87 (t, J=6.6 Hz, 2H), 4.54, (s, 2H), 3.68 (t, J=5.7 Hz, 2H), 3.07 (s, 3H). 2.25 (pentet, J=6.0 Hz, 2H). Mass spectrum (API-TIS) m/z 507 (MH$^+$).

6d. 4-(3-(Difluoro(3-(phenylmethoxy)propoxy)methyl)-1-phenylpyrazol-5-yl)-1-(methylsulfonyl)benzene The product of Example 6c (3.8 g, 7.5 mmol) and SbCl$_3$ (90 mg, 0.4 mmol) were dissolved in CH$_2$Cl$_2$ (40 mL) and cooled to 0° C. (Bis(2-methoxyethyl)amino)sulfur trifluoride (2.1 mL, 11.3 mmol) was added and the mixture was allowed to warm to room temperature with stirring for 3 hours. The reaction mixture was cooled to 0° C. and excess reagent was quenched with saturated aqueous NaHCO$_3$. Addition of NaHCO$_3$ (25 mL) was drop-wise until effervescence subsided then more rapid. The aqueous layer was separated and extracted with CH$_2$Cl$_2$. The combined organic layers were washed with 1N HCl and H$_2$O, dried over Na$_2$SO$_4$, and concentrated. The residue was purified by chromatography over silica gel eluting with Hexane:EtOAc 1:1 to give the title compound (2.4 g, 62% yield). $^1$H NMR (300 MHz, CDCl$_3$) δ 7.87 (d, J=8.4 Hz, 2H), 7.25-7.42 (m, 12H), 6.77 (s, 1H), 4.53, (s, 2H), 4.24 (t, J=6.3 Hz, 2H), 3.64 (t, J=6.3 Hz, 2H), 3.06 (s, 3H). 2.06 (pentet, J=6.3 Hz, 2H). Mass spectrum (API-TIS) m/z 513 (MH$^+$).

6e. 1-(3-(Difluoro(3-hydroxypropoxy)methyl)-1-phenylpyrazol-5-yl)-4-(methylsulfonyl)benzene The product of Example 6d (1.05 g, 2.05 mmol) and NaIO$_4$ (2.7 g, 12.3 mmol) were taken up in a biphasic mixture of CCl$_4$ (20 mL), CH$_3$CN (20 mL), and H$_2$O (30 mL). Ruthenium chloride (20 mg, 0.1 mmol) was added to the mixture which was stirred at room temperature for 18 hours. The reaction mixture was transferred to a separatory funnel with CHCl$_3$ (20 mL) and saturated with NaCl. The organic layer was separated and the aqueous layer was extracted with CHCl$_3$ (3×25). The combined organic extracts were dried over Na$_2$SO$_4$ and concentrated. The residue was taken up in MeOH (20 mL) containing NaOH (200 mg, mmol) and stirred at room temperature for 5 hours. The MeOH was evaporated and replaced with H$_2$O (100 mL). The aqueous mixture was extracted with EtOAc (4×25). The combined organic extracts were washed with H$_2$O (2×25) and brine (1×25), dried over Na$_2$SO$_4$, and concentrated. The residue was purified by chromatography over silica gel eluting with Hexane:EtOAc 1:2 to give the title compound (390 mg, 50% yield) as a clear oil. $^1$H NMR (300 MHz, CDCl$_3$) δ 7.87 (d, J=8.5 Hz, 2H), 7.38-7.43 (m, 5H), 7.27-7.37 (m, 2H), 6.80 (s, 1H), 4.25 (t, J=6.1 Hz, 2H), 3.84 (t, J=5.9 Hz, 2H), 3.06 (s, 3H). 2.0 (pentet, J=6.3 Hz, 2H). Mass spectrum (API-TIS) m/z 423 (MH$^+$). Anal calcd for C$_{20}$H$_{20}$F$_2$N$_2$O$_4$S: C, 56.86; H, 4.77; N, 6.63. Found C, 56.60; H, 4.54; N, 6.40.

6f. 1-(3-(Difluoro(3-(nitrooxy)propoxy)methyl)-1-phenylpyrazol-5-yl)-4-(methylsulfonyl)benzene Acetyl nitrate was prepared by addition of AgNO$_3$ (250 mg, 1.5 mmol) to AcCl (110 µL, 1.5 mmol) in CH$_3$CN (3 mL) and stirring at room temperature for 15 minutes. The AgCl precipitate was removed by filtration through a cotton plug. A 2 mL portion of the filtered AcONO$_2$ solution was added to the product of Example 6e in CH$_3$CN (6 mL), and stirred at room temperature for 2 hours. The reaction mixture was diluted with Hexane:EtOAc 1:1 (60 mL). The organic mixture was extracted with satd NaHCO$_3$ (1×25) and brine (1×25), dried over Na$_2$SO$_4$, and concentrated. The residue was purified by chromatography over silica gel eluting with Hexane:EtOAc 3:2 to give the title compound (100 mg, 36% yield) as an oil along with 3-(nitrooxy)propyl 5-(4-(methylsulfonyl)phenyl)-1-phenylpyrazol-3-carboxylate (150 mg, 54% yield). $^1$H NMR (300 MHz, CDCl$_3$) δ 7.88 (d, J=8.5 Hz, 2H), 7.38-7.44 (m, 5H), 7.27-7.33 (m, 2H), 6.80 (s, 1H), 4.64 (t, J=6.3 Hz, 2H), 4.22 (t, J=6.0 Hz, 2H), 3.06 (s, 3H). 2.18 (pentet, J=6.2 Hz, 2H). Mass spectrum (API-TIS) m/z 468 (MH$^+$).

Example 7

1-(1-(4-Chlorophenyl)-3-((3-nitrooxy)propoxy)methyl)pyrazol-5-yl)-4-methylsulfonyl)benzene

7a. Methyl 1-(4-chlorophenyl)-5-(4-(methylsulfonyl) phenyl)pyrazol-3-carboxylate A mixture of the product of Example 3a (5.0 g, 17.6 mmol) and 4-chlorophenylhydrazine hydrochloride (3.46 g, 19.35 mmol) in MeOH (100 mL) was heated at 70° C. for 18 hours and then cooled to room temperature. The solvent was removed and the residue was redissolved in CH$_2$Cl$_2$. The organic solution was washed with water and brine, and dried over magnesium sulfate. Evaporation of solvent provided a solid, which was recrystallized from CH$_2$Cl$_2$/Hexane to give the title compound as a pale yellow solid (4.27 g, 62% yield). Mp 169-171° C. $^1$H NMR (300 MHz, CDCl$_3$) δ 7.93 (d, J=8.4 Hz, 2H), 7.44 (d, J=8.4 Hz, 2H), 7.39 (d, J=8.7 Hz, 2H), 7.27 (d, J=8.7 Hz, 2H), 7.15 (s, 1H), 3.40 (s, 3H), 3.09 (s, 3H). Mass spectrum (API-TIS) m/z 319 (MH$^+$). Anal. calcd. for C$_{18}$H$_{15}$ClN$_2$O$_4$S: C, 55.32; H, 3.87; N, 7.17. Found: C, 55.27; H, 3.69; N, 7.14.

7b. 1-(1-(4-Chlorophenyl)-3-(hydroxymethyl)pyrazol-5-yl)-4-(methylsulfonyl)benzene The title compound (2.5 g, 61% yield) was prepared from the product of Example 7a by following the procedure for Example 5b. Mp 96-100° C. $^1$H NMR (300 MHz, CDCl$_3$) δ 7.89 (d, J=8.2 Hz, 2H), 7.41 (d, J=8.2 Hz, 2H), 7.34 (d, J=8.6 Hz, 2H), 7.20 (d, 8.6, J=8.63 Hz, 2H), 6.62 (s, 1H), 4.80 (d, J=5.7 Hz, 2H), 3.07 (s, 3H), 2.07 (br s, 1H). Mass spectrum (API-TIS) m/z 363 (MH$^+$).

7c. 1-(3-(Bromomethyl)-1-(4-chlorophenyl)pyrazol-5-yl)-4-(methylsulfonyl)benzene The title compound (2.1 g, 96% yield) was prepared from the product of Example 7b by following the procedure for Example 5c. Mp 60-64° C. $^1$H NMR (300 MHz, CDCl$_3$) δ7.90 (d, J=8.5 Hz, 2H), 7.42 (d, J=8.5 Hz, 2H), 7.36 (d, J=8.8 Hz, 2H), 7.21 (d, J=8.8 Hz, 2H), δ 6.68 (s, 1H), 4.56 (s, 2H), 3.07 (s, 3H). Mass spectrum (API-TIS) m/z 426 (MH$^+$).

7d. 1-(1-(4-Chlorophenyl)-3-((3-hydroxypropoxy)methyl)pyrazol-5-yl)-4-(methylsulfonyl)benzene The title compound (531.4 mg, 57% yield) was prepared from the product of Example 7c by following the procedure for Example 5d except 3-benzyloxy propanol was substituted for 2-benzyloxy ethanol. $^1$H NMR (300 MHz, CDCl$_3$) δ 7.87 (d, J=8.4 Hz, 2H), 7.41 (d, J=8.4 Hz, 2H), 7.34 (d, J=8.7 Hz, 2H), 7.20 (d, J=8.7 Hz, 2H), 6.61 (s, 1H), 4.64 (d, J=4.1 Hz, 2H), 3.80 (t, J=5.7 Hz, 2H), 3.78 (t, J=5.7 Hz, 2H), 3.07 (s, 3H), 1.89 (q, J=5.7 Hz, 2H). Mass spectrum (API-TIS) m/z 421 (MH$^+$).

7e. 1-(1-(4-Chlorophenyl)-3-((3-(nitrooxy)propoxy)methyl)pyrazol-5-yl)-4-(methylsulfonyl)benzene The title compound (35.0 mg, 39% yield) was prepared from the product of Example 7d by following the procedure for Example 5e. $^1$H NMR (300 MHz, CDCl$_3$) δ 7.89 (d, J=8.3 Hz, 2H), 7.41 (d, J=8.3 Hz, 2H), 7.34 (d, J=8.7 Hz, 2H), 7.20 (d, J=8.7 Hz, 2H), 6.62 (s, 1H), 4.60 (s, 2H), 4.59 (t, J=6.1 Hz, 2H), 3.67 (t, J=6.1 Hz, 2H), 3.07 (s, 3H), 2.04 (q, J=6.1 Hz, 2H). Mass spectrum (API-TIS) m/z 466 (MH$^+$).

Example 8

1-(1-(4-Methylphenyl)-3-((3-nitrooxy)propoxy)methyl)pyrazol-5-yl)-4-methylsulfonyl)benzene

8a. Methyl 1-(4-methylphenyl)-5-(4-(methylsulfonyl)phenyl)pyrazol-3-carboxylate The title compound was prepared from the product of Example 3a (5.0 g, 17.6 mmol) and 4-methylphenylhydrazine hydrochloride (3.63 g, 22.9 mmol) in methanol (120 mL) was heated at 70° C. for 18 hours and cooled to room temperature. The solvent was removed by rotary evaporation, and the residue was redissolved in methylene chloride. The organic solution was washed with water and brine, and dried over magnesium sulfate. Evaporation of solvent provided a solid, which was shown by NMR to be a mixture of regioisomers. The crude product was purified by chromatography over silica gel, eluting with 50% ethyl acetate:hexane, to 100% ethyl acetate (gradient). The slower eluting compound was recrystallized from CH$_2$Cl$_2$/hexane to give the title compound (4.3 g, 66% yield) as a white solid. Mp 173-175° C. $^1$H NMR (300 MHz, CDCl$_3$) δ7.87 (d, J=8.3 Hz, 2H), 7.41 (d, J=8.3 Hz, 2H), 7.17 (s, 4H), 7.13 (s, 1H), 3.97 (s, 3H), 3.06 (s, 3H), 2.38 (s, 3H). Mass spectrum (API-TIS) m/z 371 (MH$^+$).

Anal. calcd. for C$_{19}$H$_{18}$N$_2$O$_4$S: C, 61.61; H, 4.90; N, 7.56. Found: C, 61.62; H, 4.77; N, 7.61.

8b. 1-(3-(Hydroxymethyl)-1-(4-methylphenyl)pyrazol-5-yl)-4-(methylsulfonyl)benzene The title compound (2.7 g, 80% yield) was prepared from the product of Example 8a by following the procedure for Example 5b. $^1$H NMR (300 MHz, CDCl$_3$) δ 7.86 (d, J=8.5 Hz, 2H), 7.41 (d, J=8.5 Hz, 2H), 7.18-7.11 (m, 4H), 6.61 (s, 1H), 4.80 (d, J=5.9 Hz, 2H), 3.08 (s, 3H), 2.38 (s, 3H). Mass spectrum (API-TIS) m/z 342 (MH$^+$)

8c. 1-(3-(Bromomethyl)-1-(4-methylphenyl)pyrazol-5-yl)-4-(methylsulfonyl)benzene The title compound (2.7 g, 86% yield) was prepared from the product of Example 8b by following the procedure for Example 5c. $^1$H NMR (300 MHz, CDCl$_3$) δ 7.87 (d, J=8.6 Hz, 2H), 7.41 (d, J=8.6 Hz, 2H), 7.18-7.12 (m, 4H), 6.67 (s, 1H), 4.58 (s, 2H), 3.06 (s, 3H), 2.38 (s, 3H).

Mass spectrum (API-TIS) m/z 374 (MH$^+$)

8d. 1-(3-((3-Hydroxypropoxy)methyl)-1-(4-methylphenyl)pyrazol-5-yl)-4-(methylsulfonyl)benzene The title compound (2.7 g, 80% yield) was prepared from the product of Example 8c by following the procedure for Example 5d. (910 mg, 83% yield). $^1$H NMR (300 MHz, CDCl$_3$) δ 7.85 (d, J=8.4 Hz, 2H), 7.40 (d, J=8.4 Hz, 2H), 7.17-7.10 (m, 4H), 6.59 (s, 1H), 4.63 (s, 2H), 3.79 (t, J=5.7 Hz, 2H), 3.78 (t, J=5.7 Hz, 2H), 3.05 (s, 3H), 2.36 (s, 3H), 1.87 (q, J=5.7 Hz, 2H). Mass spectrum (API-TIS) m/z 401 (MH$^+$)

8e. 1-(1-(4-methylphenyl)-3-((3-(nitrooxy)propoxy)methyl)pyrazol-5-yl)-4-(methylsulfonyl)benzene The title compound (460 mg, 64% yield) was prepared from the product of Example 8d by following the procedure for Example 5e. $^1$H NMR (300 MHz, CDCl$_3$) δ 7.86 (d, J=8.5 Hz, 2H), 7.41 (d, J=8.5 Hz, 2H), 7.18-7.11 (m, 4H), 6.61 (s, 1H), 4.61 (s, 2H), 4.60 (t, J=6.1 Hz, 2H), 3.68 (t, J=6.1 Hz, 2H), 3.07 (s, 3H), 2.37 (s, 3H), 2.04 (q, J=6.1 Hz, 2H). Mass spectrum (API-TIS) m/z 446 (MH$^+$)

Example 9

4-(Methylsulfonyl)-1-(3-((3-nitrooxy)propoxy)methyl)-1-(4-trifluoromethyl)phenyl)pyrazol-5-yl)benzene

9a. Methyl 5-(4-(methylsulfonyl)phenyl)-1-(4-(trifluoromethyl)phenyl)pyrazol-3-carboxylate The title compound was prepared from the product of Example 3a (5.0 g, 17.6 mmol) and 4-(trifluoromethyl)phenylhydrazine hydrochloride (4.03 g, 22.9 mmol) in acetic acid (120 mL) was heated at 70° C. for 18 hours and then cooled to room temperature. The solvent was removed by rotary evaporation, and the residue was redissolved in CH$_2$Cl$_2$. The organic solution was washed with water and brine, and dried over magnesium sulfate. Evaporation of solvent provided a solid, which was recrystallized from CH$_2$Cl$_2$/hexane to give the title compound as pale yellow needles (5.38 g, 72% yield). Mp 204-207° C. $^1$H NMR (300 MHz, CDCl3) δ 7.95 (d, J=8.4 Hz, 2H), 7.68 (d, J=8.5 Hz, 2H), 7.48 (d, J=8.5 Hz, 2H), 7.45 (d, J=8.4 Hz, 2H), 7.17 (s, 1H), 4.01

(s, 3H), 3.10 (s, 3H). Mass spectrum (API-TIS) m/z 425 (MH⁺), 442 (M+18⁺). Anal. calcd. for $C_{19}H_{15}F_3N_2O_4S$: C, 53.77; H, 3.56; N, 6.60; Found: C, 53.72; H, 3.52; N, 6.54.

9b. 1-(3-(Hydroxymethyl)-1-(4-(trifluoromethyl)phenyl)pyrazol-5-yl-4-(methylsulfonyl)benzene The title compound (4.0 g, 86% yield) was prepared from the product of Example 9a by following the procedure for Example 5b. ¹H NMR (300 MHz, CDCl₃) δ 7.92 (d, J=8.4 Hz, 2H), 7.64 (d, J=8.4 Hz, 2H), 7.43 (d, J=8.5 Hz, 2H), 7.39 (d, J=8.5 Hz, 2H), 6.65 (s, 1H), 4.81 (s, 2H), 3.08 (s, 3H). Mass spectrum (API-TIS) m/z 397 (MH⁺).

9c. 1-(3-(Bromomethyl)-1-(4-(trifluoromethyl)phenyl)pyrazol-5-yl-4-(methylsulfonyl)benzene The title compound (3.7 g, 80% yield) was prepared from the product of Example 9b by following the procedure for Example 5c. ¹H NMR (300 MHz, CDCl₃) δ 7.93 (d, J=8.4 Hz, 2H), 7.64 (d, J=8.4 Hz, 2H), 7.44-7.36 (m, 4H), 6.69 (s, 1H), 4.56 (s, 2H), 3.08 (s, 3H). Mass spectrum (API-TIS) m/z 459 (MH⁺).

9d. 1-(3-((3-Hydroxypropoxy)methyl)-1-(4-(trifluoromethyl)phenyl)pyrazol-5-yl)-4-(methylsulfonyl)benzene The title compound (920 mg, 79% yield) was prepared from the product of Example 9a by following the procedure for Example 5d except 2-benzyloxy ethanol was used instead of 3-benzyloxy propanol. ¹H NMR (300 MHz, CDCl₃) δ 7.92 (d, J=8.4 Hz, 2H), 7.63 (d, J=8.4 Hz, 2H), 7.44-7.28 (m, 4H), 6.64 (s, 1H), 4.64 (s, 2H), 3.81 (t, J=5.8 Hz, 2H), 3.79 (t, J=5.8 Hz, 2H), 3.08 (s, 3H), 1.90 (q, J=5.8 Hz, 2H). Mass spectrum (API-TIS) m/z 455 (MH⁺).

9e. 4-(Methylsulfonyl)-1-(3-((3-(nitrooxy)propoxy)methyl)-1-(4-(trifluoromethyl)phenyl)pyrazol-5-yl)benzene The title compound (189.3 mg, 22% yield) was prepared from the product of Example 9d by following the procedure for Example 5e. ¹H NMR (300 MHz, CDCl₃) δ 7.91 (d, J=8.5 Hz, 2H), 7.63 (d, J=8.5 Hz, 2H), 7.44-7.38 (m, 4H), 6.64 (s, 1H), 4.61 (s, 2H), 4.59 (t, J=5.9 Hz, 2H), 3.68 (t, J=5.8 Hz, 2H), 3.07 (s, 3H), 2.04 (q, J=5.9 Hz, 2H). Mass spectrum (API-TIS) m/z 500 (MH⁺)

Example 10

1-(1-(4-Methoxy-3-nitrophenyl)-3-((3-nitrooxy)propoxy)methyl)pyrazol-5-yl)-4-methylsulfonyl)benzene

10a. Methyl 1-(4-methoxyphenyl)-5-(4-(methylsulfonyl)phenyl)pyrazol-3-carboxylate The title compound was prepared as a white solid (3.99 g, 59% yield) by following the procedure for Example 8a. with a mixture of the product of Example 3a (5.0 g, 17.6 mmol) and 4-methoxyphenyl hydrazine hydrochloride (4.00 g, 22.9 mmol) in methanol (150 mL). Mp 136-138° C. ¹H NMR (300 MHz, CDCl₃) δ 7.88 (d, J=8.5 Hz, 2H), 7.41 (d, J=8.5 Hz, 2H), 7.22 (d, J=8.9 Hz, 2H), 7.13 (s, 1H), 6.89 (d, J=8.9 Hz, 2H), 3.98 (s, 3H), 3.84 (s, 3H), 3.07 (s, 3H).
Mass spectrum (API-TIS) m/z 387 (MH⁺); Anal. calcd. for $C_{19}H_{18}N_2O_5S$: C, 59.06; H, 4.70; N, 7.25. Found: C, 58.84; H, 4.63; N, 7.26.

10b. 1-(3-(Hydroxymethyl)-1-(4-methoxyphenyl)pyrazol-5-yl)-4-(methylsulfonyl)benzene The title compound (3.2 g, 97% yield) was prepared from the product of Example 10a by following the procedure for Example 5b. ¹H NMR (300 MHz, CDCl₃) δ 7.84 (d, J=8.4 Hz, 2H), 7.38 (d, J=8.4 Hz, 2H), 7.15 (d, J=8.9 Hz, 2H), 6.86 (d, J=8.9 Hz, 2H), 6.59 (s, 1H), 4.75 (s, 2H), 3.80 (s, 3H), 3.04 (s, 3H). Mass spectrum (API-TIS) m/z 359 (MH⁺).

10c. 1-(3-(Bromomethyl)-1-(4-methoxyphenyl)pyrazol-5-yl)-4-(methylsulfonyl)benzene The title compound (1.7 g, 46% yield) was prepared from the product of Example 10b by following the procedure for Example 5c. ¹H NMR (300 MHz, CDCl₃) δ 7.85 (d, J=8.4 Hz, 2H), 7.38 (d, J=8.4 Hz, 2H), 7.18 (d, J=8.9 Hz, 2H), 6.88 (d, J=8.9 Hz, 2H), 6.61 (s, 1H), 4.56 (s, 2H), 3.80 (s, 3H), 3.05 (s, 3H). Mass spectrum (API-TIS) m/z 422 (MH⁺).

10d. 1-(3-((3-Hydroxypropoxy)methyl)-1-(4-methoxyphenyl)pyrazol-5-yl)-4-(methylsulfonyl)benzene The title compound (770 mg, 47% yield) was prepared from the product of Example 10c by following the procedure for Example 5d except 2-benzyloxy ethanol was used instead of 3-benzyloxy propanol. ¹H NMR (300 MHz, CDCl₃) δ 7.84 (d, J=8.5 Hz, 2H), 7.39 (d, J=8.5 Hz, 2H), 7.17 (d, J=8.9 Hz, 2H), 6.87 (d, J=8.9 Hz, 2H), 6.59 (s, 1H), 4.62 (s, 2H), 3.81 (s, 3H), 3.80-3.75 (m, 4H), 3.04 (s, 3H), 1.88 (q, J=5.7 Hz, 2H). Mass spectrum (API-TIS) m/z 417 (MH⁺).

10e. 1-(1-(4-Methoxy-3-nitrophenyl)-3-((3-(nitrooxy)propoxy)methyl)pyrazol-5-yl)-4-(methylsulfonyl)benzene The title compound (120.5 mg, 72% yield) was prepared from the product of Example 10d by following the procedure for Example 5e. ¹H NMR (300 MHz, CDCl₃) δ 7.90 (d, J=8.3 Hz, 2H), 7.83 (d, J=2.7 Hz, 1H), 7.43 (d, J=8.3 Hz, 2H), 7.36 (dd, J=2.7 Hz, 1H), 7.05 (d, J=9.0 Hz, 1H), 6.62 (s, 1H), 4.59 (s, 2H), 4.58 (t, J=6.0, 2H), 3.96 (s, 3H), 3.66 (t, J=6.0, 2H), 3.06 (s, 3H), 2.03 (q, J=6.0 Hz, 2H). Mass spectrum (API-TIS) m/z 507 (MH⁺)

Example 11

1-(3-((1Z)-4-(Nitrooxy)but-1-enyl)-1-phenylpyrazol-5-yl)-4-(methylsulfonyl)benzene and 1-(3-((1E)-4-(Nitrooxy)but-1-enyl)-1-phenylpyrazol-5-yl)-4-(methylsulfonyl)benzene

11a. Methyl 5-(4-methylthiophenyl)-1-phenylpyrazol-3-carboxylate

A mixture of the product of Example 1d (10 g, 39.6 mmol) and phenylhydrazine hydrochloride (7.45 g, 51.6 mmol) in methanol (200 mL) was heated at 70° C. for 5 hours and cooled to room temperature. The mixture was made basic with 10% Na₂CO₃ and extracted with EtOAc (3×25 mL). The organic extracts were dried over Na₂SO₄ and filtered. The residue, after evaporation of the solvent, was recrystallized from CH₂Cl₂/EtOAc/hexane to give the title compound (8.8 g, 68% yield) as a white solid. Mp 94-96° C. ¹H NMR (300 MHz, CDCl₃) δ 7.30-7.41 (m, 5H), 7.17 (d, J=8.8 Hz, 2H), 7.12 (d, J=8.2 Hz, 2H), 7.03 (s, 1H), 3.97 (s, 3H), 2.48 (s, 3H); ¹³C NMR (75 MHz, CDCl₃) δ 162.9, 144.4, 144.1, 140.1, 139.6, 129.2, 129.1, 128.5, 126.0, 125.9, 125.8, 109.8, 52.2, 15.3. Mass spectrum (API-TIS) m/z 325 (MH+). Anal. Calcd. for $C_{18}H_{16}N_2O_2S$: C, 66.65; H, 4.97; N, 8.64. Found: C, 66.45; H, 4.92; N, 8.83.

11b. (5-(4-methylthiophenyl)-1-phenylpyrazol-3-yl)-methanol

The title compound was prepared as a white solid from the product of Example 1f by following the procedure for Example 1f. Mp 105-106° C. $^1$H NMR (300 MHz, CDCl$_3$) 7.26-7.39 (m, 5H), 7.09-7.18 (m, 4H), 6.49 (s, 1H), 4.78 (d, J=5.9 Hz, 2H), 2.47 (s, 3H), 2.26 (t, J=6.0 Hz, 1H); $^{13}$C NMR (75 MHz, CDCl$_3$) δ 153.1, 143.8, 140.0, 139.3, 129.1, 129.1, 127.1, 126.9, 126.1, 125.4, 106.2, 59.1, 15.4. Mass spectrum (API-TIS) m/z 297 (MH+), 279 (M-OH). Anal. calcd. for $C_{17}H_{16}N_2O_1S$: C, 68.89; H, 5.44; N, 9.45. Found: C, 68.80; H, 5.34; N, 9.34.

11c. 1-((3Z)-4-(5-(4-methylthiophenyl)-1-phenylpyrazol-3-yl)but-3-enyloxy)-1,1,2,2-tetramethyl-1-silapropane and 1-((3E)-4-(5-(4-methylthiophenyl)-1-phenylpyrazol-3-yl)but-3-enyloxy)-1,1,2,2-tetramethyl-1-silapropane Activated MnO$_2$ (4.49 g, 51.6 mmol) was dried under high vacuum for 2 days at 70° C. Dried MnO$_2$ (2 g, 23.0 mmol) was then added to a solution of the product of Example 11a (3.08 g, 10.4 mmol), (3-((1,1-dimethylethyl)-dimethylsilyl)oxy) propyl)-triphenylphosphonium bromide (5.9 g, 11.5 mmol), 1,3,4,6,7,8-hexahydro-1-methyl-2H-pyrimido(1,2-a)pyrimidine (3.45 g, 22.5 mmol), Ti(i-OPr)$_4$ (2.95 g, 10.4 mmol) in dry THF (250 mL) which was heated to reflux under nitrogen. A second portion of MnO$_2$ (2.49 g, 28.6 mmol) was added after 1 h and the reaction mixture was heated for 4 h. The reaction mixture was allowed to cool to room temperature and then filtered through the Celite pad and washed with EtOAc. The residue obtained after evaporation of the solvent, was purified by chromatography over silica gel eluting with 1:2 EtOAc:Hexane to give the title compounds as a colorless oil. Z-isomer: (1.84 g, 39% yield), and E-isomer (0.3 g, 6% yield). Z-isomer: $^1$H NMR (300 MHz, CDCl$_3$) δ 7.25-7.40 (m, 5H), 7.10-7.20 (m, 4H), 6.57 (s, 1H), 6.52 (d, J=11.7 Hz, 1H), 5.78-5.88 (m, 1H), 3.79 (t, J=6.8 Hz, 2H), 2.77 (q, J=1.3 Hz, 2H), 2.48 (s, 3H), 0.91 (s, 9H), 0.08 (s, 6H); $^{13}$C NMR (75 MHz, CDCl$_3$) δ 150.2, 143.1, 140.2, 139.2, 130.5, 129.2, 129.1, 127.5, 127.2, 126.1, 125.3, 122.1, 108.0, 62.8, 33.1, 26.1, 18.5, 15.5, −5.0. Mass spectrum (API-TIS) m/z 451 (MH+).

11d. 1-(3-((1Z)-4-(Hydroxy)but-1-enyl)-1-phenylpyrazol-5-yl)-4-methylsulfonyl)benzene The title compound was prepared as a white solid from the product of Example 11c by following the procedure for Example 3e. Mp 104-105° C. $^1$H NMR (300 MHz, CDCl$_3$) δ 7.87 (dd, J=1.8 and 8.5 Hz, 2H), 7.42 (dd, J=1.8 and 8.4 Hz, 2H), 7.32-7.38 (m, 3H), 7.22-7.29 (m, 2H), 6.60 (s, 1H), 6.55 (d, J=11.6 Hz, 1H), 5.87-5.98 (m, 1H), 3.84 (q, J=5.9 Hz, 2H), 3.06 (s, 3H), 2.93 (t, J=5.0 Hz, 1H), 2.83 (q, J=5.0 Hz, 2H). $^{13}$C NMR (75 MHz, CDCl$_3$) δ 150.0, 141.6, 140.2, 139.4, 135.8, 131.4, 129.5, 129.5, 128.3, 127.8, 125.3, 122.6, 109.4, 62.5, 44.6, 32.6. Mass spectrum (API-TIS) m/z 369 (MH+). Anal. calcd. for $C_{20}H_{20}N_2O_3S$: C, 65.20; H, 5.47; N, 7.60. Found: C, 65.01; H, 5.21; N, 7.53.

11e. 1-(3-((1Z)-4-(Nitrooxy)but-1-enyl)-1-phenylpyrazol-5-yl)-4-(methylsulfonyl)benzene Fuming HNO$_3$ (2.2 mL, 3.28 g, 52.1 mmol) was added drop-wise to a solution of the product of Example 11d (0.64 g, 1.7 mmol) in CHCl$_3$ at 0° C. and then stirred at room temperature for 30 min. The solution was extracted with CH$_2$Cl$_2$, washed with saturated NaHCO$_3$, water, dried over Na$_2$SO$_4$, and filtered. The residue after evaporation of the solvent purified by chromatography over silica gel eluting with 1:2 EtOAc:Hexane to give the product as a pale yellow foam (0.72 g, ~100% yield). $^1$H NMR (300 MHz, CDCl$_3$) δ 7.88 (d, J=8.2 Hz, 2H), 7.43 (d, J=8.2 Hz, 2H), 7.23-7.40 (m, 5H), 6.60 (s, 1H), 6.54 (d, J=11.5 Hz, 1H), 5.73-5.87 (m, 1H), 4.64 (t, J=6.7 Hz, 2H), 3.07 (s, 3H), 2.61-2.65 (m, 2H); $^{13}$C NMR (75 MHz, CDCl$_3$) δ 149.6, 141.5, 140.2, 139.5, 135.8, 129.4, 129.4, 128.2, 127.7, 127.4, 125.2, 123.3, 109.5, 72.5, 44.5, 27.3. Mass spectrum (API-TIS) m/z 414 (MH+). Anal. calcd. for $C_{20}H_{19}N_3O_5S$·0.85 mol $H_2O$: C, 56.02; H, 4.86; N, 9.80. Found: C, 56.28; H, 4.85; N, 9.41.

11f. 1-(3-((1E)-4-(Nitrooxy)but-1-enyl)-1-phenylpyrazol-5-yl)-4-(methylsulfonyl)benzene Prepared as in Example 11e to give the title compound as a white foam. $^1$H NMR (300 MHz, CDCl$_3$) δ 7.86 (d, J=8.3 Hz, 2H), 7.41 (d, J=8.3 Hz, 2H), 7.20-7.48 (m, 5H), 6.68 (s, 1H), 6.61 (d, J=16.0 Hz, 1H), 6.25-6.40 (m, 1H), 4.58 (t, J=6.6 Hz, 2H), 3.06 (s, 3H), 2.68 (q, J=6.6 Hz, 2H); $^{13}$C NMR (75 MHz, CDCl$_3$) δ 150.8, 142.0, 140.1, 139.5, 135.7, 129.4, 129.3, 128.2, 127.7, 126.7, 125.3, 125.1, 105.9, 72.1, 44.4, 30.5. Mass spectrum (API-TIS) m/z 414 (MH+). Anal. Calcd. for $C_{20}H_{19}N_3O_5S$: C, 58.10; H, 4.63; N, 10.16. Found: C, 58.36; H, 4.75; N, 9.88.

Example 12

1-(1-(4-Methylphenyl)-5-(4-(methylsulfonyl)phenyl)pyrazol-3-yl)-4-(nitrooxy)butan-1-one

12a. Methyl 1-(4-methylphenyl)-5-(4-methylthiophenyl)pyrazol-3-carboxylate

The title compound was prepared as a white solid (4.258 g, 63% yield) from the product of Example 1d (5.05 g, 20 mmol) and 4-methylphenylhydrazine hydrochloride (4.12 g, 26 mmol) following the procedure of Example 8a. Mp 113-115° C. $^1$H NMR (300 MHz, CDCl$_3$) δ 7.29-7.13 (m, 8H), 7.04 (s, 1H), 3.99 (s, 3H), 2.50 (s, 3H), 2.40 (s, 3H). Mass spectrum (API-TIS) m/z 339 (MH+). Anal. calcd. for $C_{19}H_{18}N_2O_2S$: C, 67.43; H, 5.36; N, 8.28. Found: C, 67.62; H, 5.27; N, 8.20.

12b. N-Methoxy-N-methyl(1-(4-methylphenyl)-5-(4-methylthiophenyl)pyrazol-3-yl)carboxamide The title compound was prepared as a white solid from the product of Example 12a by following the procedure for Example 3c. $^1$H NMR (300 MHz, CDCl$_3$) δ 7.14-7.30 (m, 8H), 6.98 (s, 1H), 3.87 (s, 3H), 3.53 (br s, 3H), 2.49 (s, 3H), 2.39 (s, 3H); $^{13}$C NMR (75 MHz, CDCl$_3$) δ 145.8, 143.3, 139.6, 138.1, 137.4, 129.7, 129.1, 126.4, 126.0, 125.3, 109.9, 61.7, 35.0, 21.2, 15.4.

Mass spectrum (API-TIS) m/z 368 (MH+). Anal. calcd. for $C_{20}H_{21}N_3O_2S$: C, 65.37; H, 5.76; N, 11.43. Found: C, 65.03; H, 5.54; N, 11.17.

12c. 1-(1-(4-Methylphenyl)-5-(4-methylthiophenyl)pyrazol-3-yl)-4-(1,1,2,2-tetramethyl-1-silapropoxy)butan-1-one The title compound was prepared as a white solid from the product of Example 12b by following the procedure for Example 3d. $^1$H NMR (300 MHz, CDCl$_3$) δ 7.13-7.26 (m, 8H), 6.96 (s, 1H), 3.71 (t, J=6.4 Hz, 2H), 3.15 (t, J=7.3 Hz, 2H), 2.48 (s, 3H), 2.38 (s, 3H), 1.92-2.05 (m, 2H), 0.86 (s, 9H), 0.05 (s, 6H). $^{13}$C NMR (75 MHz, CDCl$_3$) δ 196.6, 151.4, 144.3, 139.8, 138.4, 137.4, 129.8, 129.1, 126.3, 126.0, 125.3, 107.4, 62.7, 35.2, 27.5, 26.1, 21.2, 18.4, 15.3, −5.2.

Mass spectrum (API-TIS) m/z 481 (MH$^+$). Anal. calcd. for C$_{27}$H$_{36}$N$_2$O$_2$SSi: C, 67.46; H, 7.55; N, 5.83. Found: C, 67.40; H, 7.76; N, 5.74.

12d. 4-Hydroxy-1-(1-(4-methylphenyl)-5-(4-(methylsulfonyl)phenyl)pyrazol-3-yl)butan-1-one The product of Example 12c (1.64 g, 3.42 mmol) was dissolved in MeOH (60 mL). OXONE® (6.30 g, 10.25 mmol) in water (20 mL) was added at room temperature. The reaction mixture was stirred for 1 hour and the resulting solid was removed by filtration. The filtrate was diluted with CH$_2$Cl$_2$, washed with saturated NaHCO$_3$ and water, dried over Na$_2$SO$_4$. and filtered. The residue, after evaporation of the solvent,was purified by chromatography over silica gel eluting with 1:2 to 1:1 to 2:1 EtOAc:Hexane to give the title compound (0.8 g, 59% yield) as a white solid. Mp 159-161° C. $^1$H NMR (300 MHz, CDCl$_3$) δ 7.88 (dd, J=1.7 and 6.8 Hz, 2H), 7.41 (dd, J=1.7 and 6.8 Hz, 2H), 7.16-7.23 (m, 4H), 7.10 (s, 1H), 3.73 (q, J=6.0 Hz, 2H), 3.23 (t, J=6.95 Hz, 2H), 3.07 (s, 3H), 2.41 (s, 3H), 2.10 (bt, J=5.70 Hz, 1H), 2.06 (p, J=6.5 Hz, 2H); $^{13}$C NMR (75 MHz, CDCl$_3$) δ 196.4, 152.0, 143.0, 141.0, 138.1, 134.7, 132.8, 129.6, 128.1, 127.0, 123.0, 109.2, 62.4, 44.5, 35.6, 27.3. Mass spectrum (API-TIS) m/z 399 (MH$^+$), 381 (M-OH). Anal. calcd. for C$_{21}$H$_{22}$N$_2$O$_4$S·½ H$_2$O: C, 61.90; H, 5.68; N, 6.87. Found: C, 62.29; H, 5.41; N, 6.82.

12e. 1-(1-(4-Methylphenyl)-5-(4-(methylsulfonyl)phenyl)pyrazol-3-yl)-4-(nitrooxy)butan-1-one The title compound was prepared as a white solid from the product of Example 12d by following the procedure for Example 1h. Mp 107-109° C. $^1$H NMR (300 MHz, CDCl$_3$) δ 7.89 (dd, J=1.7 and 6.8 Hz, 2H), 7.42 (dd, J=2.9 and 8.5 Hz, 2H), 7.16-7.24 (m, 4H), 7.10 (s, 1H), 4.58 (t, J=6.4 Hz, 2H), 3.26 (t, J=7.1 Hz, 2H), 3.07 (s, 3H), 2.42 (s, 3H), 2.22 (p, J=6.8 Hz, 2H); $^{13}$C NMR (75 MHz, CDCl$_3$) δ 194.3, 151.2, 143.1, 140.7, 139.4, 136.7, 135.1, 130.2, 129.6, 127.9, 125.4, 108.6, 72.7, 44.5, 34.6, 21.3. Mass spectrum (API-TIS) m/z 444 (MH$^+$). Anal. calcd. for C$_{21}$H$_{21}$N$_3$O$_6$S: C, 56.88; H, 4.77; N, 9.48. Found: C, 56.87; H, 4.69; N, 9.39.

Example 13

1-(1-(4-Fluorophenyl)-5-(4-(methylsulfonyl)phenyl)pyrazol-3-yl)-4-(nitrooxy)butan-1-one

13a. Methyl 1-(4-fluorophenyl)-5-(4-methylthiophenyl)pyrazol-3-carboxylate

The title compound was prepared from the product of Example 1d (5.05 g, 20 mmol) and 4-fluorophenylhydrazine hydrochloride (4.23 g, 26 mmol) in methanol (120 mL) using the procedure of Example 10a. Separation of the regioisomers and recrystallization gave the title compound (5.124 g, 75% yield) as a white solid. Mp 117-119° C. $^1$H NMR (300 MHz, CDCl$_3$) δ 7.37-7.31 (m, 2H), 7.22-7.05 (m, 7H), 4.00 (s, 3H), 2.51 (s, 3H). Mass spectrum (API-TIS) m/z 343 (MH$^+$). Anal. calcd. for C$_{18}$H$_{15}$FN$_2$O$_2$S: C, 63.14; H, 4.42; N, 8.18; Found: C, 63.08; H, 4.41; N, 8.19.

13b. (1-(4-Fluorophenyl)-5-(4-methylthiophenyl)pyrazol-3-yl)-N-methoxy-N-methylcarboxamide The title compound was prepared as a white solid from the product of Example 13a using the procedure of Example 3c. Mp 91-93° C. $^1$H NMR (300 MHz, CDCl$_3$) δ 7.02-7.33 (m, 8H), 6.96 (s, 1H), 3.84 (s, 3H), 3.50 (br s, 3H), 2.48 (s, 3H). $^{13}$C NMR (75 MHz, CDCl$_3$) δ 162.1 (J=248.5 Hz), 146.1, 143.5, 140.1, 136.0, 129.2, 127.4, 127.3, 126.1 (J=5.2 Hz), 116.1 (J=23.1 Hz), 110.1, 61.8, 34.0, 15.4. Mass spectrum (API-TIS) m/z 372 (MH$^+$), 394 (MNa$^+$). Anal. calcd. for C$_{19}$H$_{18}$FN$_3$O$_2$S: C, 61.44; H, 4.88; N, 11.31. Found: C, 61.35; H, 4.86; N, 11.25.

13c. 1-(1-(4-Fluorophenyl)-5-(4-methylthiophenyl)pyrazol-3-yl)-4-(1,1,2,2-tetramethyl-1-silapropoxy)butan-1-one The title compound was prepared as a white solid from the product of Example 13b using the procedure of Example 3d. Mp 46-47° C. $^1$H NMR (300 MHz, CDCl$_3$) δ 7.02-7.42 (m, 8H), 6.96 (s, 1H), 3.72 (t, J=6.4 Hz, 2H), 3.15 (t, J=7.3 Hz, 2H), 2.48 (s, 3H), 1.99 (p, J=7.0 Hz, 2H), 0.88 (s, 9H), 0.05 (s, 6H); $^{13}$C NMR (75 MHz, CDCl$_3$) δ 196.5, 162.2 (J$_{C-F}$=248.8 Hz), 151.6, 144.6, 140.2, 136.0, 135.9, 129.1, 127.4, 127.3, 126.0 (J$_{C-F}$=11.4 Hz), 116.2 (J$_{C-F}$=116.2 Hz), 107.8, 62.7, 35.3, 27.5, 26.1, 18.5, 15.3, −5.1. Mass spectrum (API-TIS) m/z 485 (MH$^+$). Anal. calcd. for C$_{26}$H$_{33}$FN$_2$O$_2$SSi: C, 64.43; H, 6.86; N, 5.78. Found: C, 64.29; H, 6.72; N, 5.70.

13d. 1-(1-(4-Fluorophenyl)-5-(4-(methylsulfonyl)phenyl)pyrazol-3-yl)-4-hydroxybutan-1-one The title compound was prepared as a white solid from the product of Example 13c using the procedure of Example 12d. Mp 164-166° C. $^1$H NMR (300 MHz, CDCl$_3$) δ 7.91 (d, J=8.5 Hz, 2H), 7.40 (d, J=6.6 Hz, 2H), 7.27-7.34 (m, 2H), 7.08-7.17 (m, 2H), 7.11 (s, 1H), 3.74 (q, J=6.0 Hz, 2H), 3.23 (t, J=7.0 Hz, 2H), 3.08 (s, 3H), 1.97-2.07 (m, 3H); $^{13}$C NMR (75 MHz, CDCl$_3$) δ196.4, 162.5 (J$_{C-F}$=250.4 Hz), 151.7, 143.1, 140.9, 135.3, 134.7, 129.6, 128.0, 127.5 (J$_{C-F}$=8.8 Hz), 116.7 (J$_{C-F}$=23.2 Hz), 108.9, 62.3, 44.4, 35.5, 27.3. Mass spectrum (API-TIS) m/z 403 (MH$^+$), 385 (M-OH). Anal. Calcd. for C$_{20}$H$_{19}$FN$_2$O$_4$S: C, 59.69; H, 4.76; N, 6.96. Found: C, 59.40; H, 4.84; N, 6.71.

13e. 1-(1-(4-Fluorophenyl)-5-(4-(methylsulfonyl)phenyl)pyrazol-3-yl)-4-(nitrooxy)butan-1-one The title compound was prepared as a white solid from the product of Example 13d using the procedure of Example 1h. Mp 134-136° C. $^1$H NMR (300 MHz, CDCl$_3$) δ 7.91 (d, J=6.8 Hz, 2H), 7.41 (d, J=6.7 Hz, 2H), 7.25-7.37 (m, 2H), 7.13-7.16 (m, 2H), 7.11 (s, 1H), 4.59 (t, J=6.4 Hz, 2H), 3.26 (t, J=7.1 Hz, 2H), 3.08 (s, 3H), 2.22 (p, J=6.8 Hz, 2H); $^{13}$C NMR (75 MHz, CDCl$_3$) δ 194.4, 162.6 (J$_{C-F}$=250.3 Hz), 151.4, 143.3, 141.0, 135.3, 134.7, 129.6, 128.1, 127.5 (J$_{C-F}$=8.8 Hz), 116.8 (J$_{C-F}$=23.2 Hz), 108.9, 72.6, 44.5, 34.7, 21.3. Mass spectrum (API-TIS) m/z 448 (MH$^+$), 465 (MNH$_4^+$), 470 (MNa$^+$). Anal. calcd. for C$_{20}$H$_{18}$FN$_3$O$_6$S: C, 53.69; H, 4.05; N, 9.39. Found: C, 53.47; H, 4.05; N, 9.26.

Example 14

1-(1-(4-Bromophenyl)-5-(4-(methylsulfonyl)phenyl)pyrazol-3-yl)-4-(nitrooxy)butan-1-one

14a. Methyl 1-(4-bromophenyl)-5-(4-methylthiophenyl)pyrazol-3-carboxylate

The title compound was prepared from the product of Example 1d (5.05 g, 20 mmol) and 4-bromophenylhydrazine hydrochloride (5.81 g, 26 mmol) in methanol (120 mL) using the procedure for Example 8a. Separation of the regioisomers and recrystallization provided the title compound (6.798 g, 84% yield) as a white solid. Mp 138-140° C. $^1$H NMR (300 MHz, CDCl$_3$) δ 7.49 (d, J=8.6 Hz, 2H), 7.25 (d, J=8.9 Hz, 2H), 7.19 (d, J=8.9 Hz, 2H), 7.11 (d, J=8.6 Hz, 2H), 7.01 (s, 1H), 3.97 (s, 3H), 2.49 (s, 3H). Mass spectrum (API-TIS) m/z 405 (MH$^+$). Anal. calcd. for C$_{18}$H$_{15}$BrN$_2$O$_2$S: C, 53.61; H, 3.75; N, 6.95; found: C, 53.67; H, 3.60; N, 6.89.

14b. (1-(4-Bromophenyl)-5-(4-methylthiophenyl) pyrazol-3-yl)-N-methoxy-N-methylcarboxamide The title compound was prepared as a white solid from the product of Example 14a using the procedure of Example 3c. Mp 151-153° C. $^1$H NMR (300 MHz, CDCl$_3$) δ 7.47 (d, J=6.8 Hz, 2H), 7.15-7.25 (m, 6H), 6.95 (s, 1H), 3.84 (s, 3H), 3.49 (br s, 3H), 2.48 (s, 3H); $^{13}$C NMR (75 MHz, CDCl$_3$) δ 141.0, 138.1, 134.9, 133.5, 126.9, 123.8, 121.5, 120.8, 120.6, 116.5, 105.1, 56.4, 29.0, 10.0. Mass spectrum (API-TIS) m/z 432/434 (MH$^+$). Anal. calcd. for C$_{19}$H$_{18}$BrN$_3$O$_2$S: C, 52.79; H, 4.20; N, 9.72. Found: C; 52.67; H, 4.15; N, 9.70.

14c. 1-(1-(4-Bromophenyl)-5-(4-methylthiophenyl) pyrazol-3-yl)-4-(1,1,2,2-tetramethyl-1-silapropoxy) butan-1-one The title compound was prepared as a colorless oil from the product of Example 14b using the procedure of Example 3d. $^1$H NMR (300 MHz, CDCl$_3$) δ 7.50 (d, J=6.9 Hz, 2H), 7.08-7.27 (m, 6H), 6.96 (s, 1H), 3.72 (t, J=6.4 Hz, 2H), 3.14 (t, J=7.31 Hz, 2H), 2.49 (s, 3H), 1.99 (p, J=6.9 Hz, 2H), 0.86 (s, 9H), 0.05 (s, 6H). $^{13}$C NMR (75 MHz, CDCl$_3$) δ 196.5, 151.8, 144.5, 140.4, 138.8, 132.4, 129.2, 126.9, 126.2, 125.9, 122.2, 108.0, 62.7, 35.4, 27.5, 26.1, 18.5, 15.3, −5.1. Mass spectrum (API-TIS) m/z 545/547 (MH$^+$). Anal. calcd. for C$_{26}$H$_{33}$BrN$_2$O$_2$SSi: C, 57.24; H, 6.10; N, 5.13. Found: C, 56.95; H, 6.02; N, 4.97.

14d. 1-(1-(4-Bromophenyl)-5-(4-(methylsulfonyl) phenyl)pyrazol-3-yl)-4-hydroxybutan-1-one The title compound was prepared as a white solid from the product of Example 14c using the procedure of Example 12d. Mp 136-137° C. $^1$H NMR (300 MHz, CDCl$_3$) δ 7.93 (d, J=8.3 Hz, 2H), 7.56 (d, J=8.6 Hz, 2H), 7.42 (d, J=8.3 Hz, 2H), 7.19 (dd, J=1.7 and 8.6 Hz, 2H), 7.10 (s, 1H), 3.74 (m, 2H), 3.23 (t, J=6.97 Hz, 2H), 3.09 (s, 3H), 2.04 (p, J=6.6 Hz, 2H), 1.93 (t, J=5.6 Hz, 1H); $^{13}$C NMR (75 MHz, CDCl$_3$) δ 196.4, 152.0, 143.0, 141.0, 138.1, 134.7, 132.8, 129.6, 128.1, 127.0, 123.0, 109.2, 62.4, 44.5, 35.6, 27.3. Mass spectrum (API-TIS) m/z 463/465 (MH$^+$). Anal. calcd. for C$_{20}$H$_{19}$BrN$_2$O$_4$S: C, 51.84; H, 4.13; N, 6.05. Found: C, 51.57; H, 4.07; N, 5.79.

14e. 1-(1-(4-Bromophenyl)-5-(4-(methylsulfonyl) phenyl)pyrazol-3-yl)-4-(nitrooxy)butan-1-one The title compound was prepared as a white solid from the product of Example 14d using the procedure of Example 1h. Mp 150-152° C. $^1$H NMR (300 MHz, CDCl$_3$) δ 7.96 (dd, J=1.7 and 6.8 Hz, 2H), 7.59 (dd, J=1.9 and 6.9 Hz, 2H), 7.45 (dd J=1.7 and 8.5 Hz, 2H), 7.23 (dd, J=2.8 and 8.8 Hz, 2H), 7.13 (s, 1H), 4.61 (t, J=6.4 Hz, 2H), 3.28 (t, J=7.08 Hz, 2H), 3.12 (s, 3H), 2.24 (p, J=6.6 Hz, 2H). $^{13}$C NMR (75 MHz, CDCl$_3$) δ 194.3, 151.6, 143.1, 141.1, 138.1, 134.7, 132.8, 129.6, 128.1, 127.0, 123.1, 109.1, 72.6, 44.5, 34.7, 21.3. Mass spectrum (API-TIS) m/z 508/510 (MH$^+$). Anal. Calcd. for C$_{20}$H$_{18}$BrN$_3$O$_6$S: C, 47.26; H, 3.57; N, 8.27. Found: C, 47.55; H, 3.47; N, 7.96.

Example 15

1-(1-Cyclohexyl-3-((2-(nitrooxy)ethoxy)methyl) pyrazol-5-yl)-4-(methylsulfonyl)benzene

15a. 4-(1-Cyclohexyl-3-(hydroxymethyl)pyrazol-5-yl)-1-(methylsulfonyl)benzene The product of Example 4b (0.6 g, 2.0 mmol) was dissolved in a mixture of MeOH (20 mL) and water (8 mL) and cooled to 0° C. OXONE® (3 g) was added and the resulting suspension was stirred at 0° C. for 1 hour. Water (25 mL) and 15% NH$_4$OH (25 mL) were added. The mixture was extracted with EtOAC (3×25 mL) and the organic extracts were dried over Na$_2$SO$_4$. The solvent was evaporated under reduced pressure to give white solid which was recrystallized from CH$_2$Cl$_2$ (5 mL) and hexane (20 mL) to give the title compound (0.62 g, 94% yield) as a white solid. Mp 148° C. $^1$H NMR (300 MHz, CDCl$_3$) δ 8.03 (d, J=8.3 Hz, 2H), 7.56 (d, J=8.3 Hz, 2H), 6.31 (s, 1H), 4.73 (s, 2H), 3.90-4.10 (m, 1H), 3.13 (s, 3H), 2.45 (s, 1H, OH), 1.66-2.05 (m, 7H), 1.10-1.25 (m, 3H); $^{13}$C NMR (75 MHz, CDCl$_3$) δ151.4, 141.7, 140.4 136.5, 129.7, 127.9, 105.0, 59.0, 58.2, 44.4, 33.3, 25.6, 25.0. Mass spectrum (API-TIS), m/z 335 (MH$^+$).

15b. 1-(3-(Bromomethyl)-1-cyclohexylpyrazol-5-yl)-4-(methylsulfonyl)benzene

The product of Example 15a (2.0 g, 5.9 mmol) and PBr$_3$ (1.1 mL, 11.7 mmol) were taken up in CH$_2$Cl$_2$ (10 mL) and stirred at room temperature overnight. Aqueous work-up followed by drying over MgSO$_4$ and evaporation of the solvent under reduced pressure gave the title compound (1.9 g, 83% yield) as a yellow solid. $^1$H NMR (300 MHz, CDCl$_3$) δ 8.04 (d, J=8.4 Hz, 2H), 7.56 (d, J=8.4 Hz, 2H), 6.36 (s, 1H), 4.53 (s, 2H), 3.99-3.44 (m, 1H), 3.12 (s, 3H), 2.03-1.87 (m, 5H), 1.67 (m, 2H), 1.28-1.26 (m, 3H). Mass spectrum (API-TIS) m/z 398 (MH$^+$).

15c. 1-(1-Cyclohexyl-3-((2-(phenylmethoxy)ethoxy) methyl)pyrazol-5-yl)-4-(methylsulfonyl)benzene 2-Benzyloxy-1-ethanol (1.5 g, 10.1 mmol) was added to a stirred solution of NaH (240.8 mg, 10.1 mmol) in dry THF (10 mL) and the reaction mixture stirred for 15 minutes. The product of Example 15b (2.0 g, 5.0 mmol) was added and the mixture stirred overnight. The sample was diluted with CH$_2$Cl$_2$ (10 mL) and washed with saturated NH$_4$Cl and brine. The sample was dried over Mg$_2$SO$_4$ and the solvent evaporated under reduced pressure. The resulting residue was purified by chromatography over silica gel eluting with 3:1 Hexanes/EtOAc to give the title compound (1.3 g, 51% yield) as a yellow oil. $^1$H NMR (300 MHz, CDCl$_3$) δ 8.02 (d, J=8.3 Hz, 2H), 7.54 (d, J=8.3 Hz, 2H), 7.36-7.27 (m, 5H), 6.35 (s, 1H), 4.61 (s, 2H), 4.57 (s, 2H), 3.99-3.94 (m, 1H), 3.75-3.72 (m, 2H), 3.68-3.65 (m, 2H), 3.12 (s, 3H), 2.04-1.98 (m, 3H), 1.88-1.83 (m, 4H), 1.65-1.60 (m, 3H). Mass spectrum (API-TIS) m/z 469 (MH$^+$).

15d. 1-(1-Cyclohexyl-3-((2-hydroxyethoxy)methyl) pyrazol-5-yl)-4-(methylsulfonyl)benzene The product of Example 15c (1.3 g, 2.8 mmol) was dissolved in EtOH (100 mL) and placed in a Parr shaker. Pd/C (500 mg) was added and the sample flushed with nitrogen 4 times. The sample was then flushed several times with H$_2$ (25-30 psi). The hydrogenation was performed at 30 psi in a H$_2$ atmosphere for 30 minutes. The catalyst was removed via filtration through Celite and washed with additional EtOH.

The combined filtrate was evaporated under reduced pressure, to give the title compound (513.7 mg, 49% yield) as a yellow oil. $^1$H NMR (300 MHz, CDCl$_3$) δ 8.04 (d, J=8.4 Hz, 2H), 7.56 (d, J=8.4 Hz, 2H), 6.30 (s, 1H), 4.62 (s, 2H), 4.03-3.94 (m, 1H), 3.78-3.76 (m, 2H), 3.69-3.67 (m, 2H), 3.13 (s, 3H), 2.66 (br s, 1H), 2.06-1.99 (m, 2H), 1.90-1.86 (m, 2H), 1.66-1.62 (m, 3H), 1.28-1.22 (m, 3H). Mass spectrum (API-TIS) m/z 379 (MH$^+$).

15e. 1-(1-Cyclohexyl-3-((2-nitrooxy)ethoxy)methyl)pyrazol-5-yl)-4-(methylsulfonyl)benzene Fuming nitric acid (5 mL) was cooled to 0° C. and the product of Example 15d (175.0 mg, 0.46 mmol) was added drop-wise. The reaction mixture was stirred at 0° C. for 1 hour. Water (5 mL) was added followed by Na$_2$CO$_3$ until the mixture was neutralized. CH$_2$Cl$_2$ was added and the organics separated. The aqueous portion was extracted with additional CH$_2$Cl$_2$ and the combined organic fractions were washed with water, dried over MgSO$_4$ and the solvent was evaporated under reduced pressure to give the title compound (93.5 mg, 48% yield) as a pale yellow solid. $^1$H NMR (300 MHz, CDCl$_3$) δ 8.04 (d, J=8.4 Hz, 2H), 7.57 (d, J=8.4 Hz, 2H), 6.33 (s, 1H), 4.65-4.61 (m, 2H), 4.60 (s, 2H), 3.99-3.93 (m, 1H), 3.84-3.81 (m, 2H), 3.13 (s, 3H), 2.04-1.98 (m, 2H), 1.89-1.86 (m, 3H), 1.58-1.53 (m, 2H), 1.28-1.22 (m, 3H). Mass spectrum (API-TIS) m/z 424 (MH$^+$).

Example 16

1-(1-Cyclohexyl-3-((3-(nitrooxy)propoxy)methyl)pyrazol-5-yl)-4-(methylsulfonyl)benzene

16a. 1-(1-Cyclohexyl-3-((3-phenoxypropoxy)methyl)pyrazol-5-yl)-4-(methylsulfonyl)benzene 3-Benzyloxy-1-propanol (1.5 g, 9.6 mmol) was added to a stirred solution of NaH (228.7 mg, 9.6 mmol) in dry THF (10 mL) and the reaction mixture stirred for 15 minutes at room temperature. The product of Example 15b(1.9 g, 4.8 mmol) was added and the mixture stirred overnight. The sample was diluted with CH$_2$Cl$_2$ (10 mL) and washed with saturated NH$_4$Cl, brine, dried over Mg$_2$SO$_4$ and the solvent was evaporated under reduced pressure. The resulting residue was purified by chromatography over silica gel eluting with 3:1 Hexanes/EtOAc to give the title compound (1.2 g, 50% yield) as a yellow oil. $^1$H NMR (300 MHz, CDCl$_3$) δ 8.02 (d, J=8.4 Hz, 2H), 7.54 (d, J=8.4 Hz, 2H), 7.32-7.26 (m, 5H), 6.31 (s, 1H), 4.54 (s, 2H), 4.50 (s, 2H), 3.99-3.94 (m, 1H), 3.66 (t, J=6.4 Hz, 2H), 3.59 (t, J=6.4 Hz, 2H), 3.12 (s, 3H), 2.07-2.04 (m, 2H), 1.94 (q, J=6.4 Hz, 2H), 1.65-1.61 (m, 3H), 1.28-1.22 (m, 3H). Mass spectrum (API-TIS) m/z 483 (MH$^+$)

16b. 1-(1-Cyclohexyl-3-((3-hydroxypropoxy)methyl)pyrazol-5-yl)-4-(methylsulfonyl)benzene The product of Example 16a (1.3 g, 2.3 mmol) was dissolved in EtOH (100 mL) and placed in a Parr shaker. Pd/C (500 mg) was added and the sample flushed with nitrogen 4 times. The sample was then flushed several times with H$_2$ (25-30 psi). The flask was refilled to 30 psi with H$_2$ and the sample shaken for 30 minutes. The solid was removed via filtration through Celite and washed with additional EtOH. The filtrate was collected, dried over MgSO$_4$ and the solvent was evaporated under reduced pressure to give the title compound (727.9 mg, 80% yield) as a yellow oil. $^1$H NMR (300 MHz, CDCl$_3$) δ 8.04 (d, J=8.5 Hz, 2H), 7.55 (d, J=8.5 Hz, 2H), 6.29 (s, 1H), 4.57 (s, 2H), 4.03-3.94 (m, 2H), 3.79-3.76 (m, 1H), 3.75 (t, J=5.8 Hz, 2H), 3.12 (s, 3H), 2.58 (br s, 1H), 2.07-2.03 (m, 2H), 1.99-1.83 (m, 3H), 1.87 (q, J=5.8 Hz, 2H), 1.65-1.59 (m, 2H), 1.28-1.21 (m, 3H). Mass spectrum (API-TIS) m/z 393 (MH$^+$).

16c. 1-(1-Cyclohexyl-3-((3-(nitrooxy)propoxy)methyl)pyrazol-5-yl)-4-(methylsulfonyl)benzene Fuming nitric acid (5 ml) was cooled to 0° C. and the product of Example 16b (105.5 mg, 0.27 mmol) in EtoAc was added drop-wise. The reaction mixture was stirred at 0° C. for 1 hour. Water (5 mL) was added followed by Na$_2$CO$_3$ until the mixture was neutralized. CH$_2$Cl$_2$ was added and the organics separated. The aqueous portion was extracted with additional CH$_2$Cl$_2$ and the combined organic fractions were washed with water, dried over MgSO$_4$ and the solvent was evaporated under reduced pressure to give the title compound (49.1 mg, 41% yield) as a pale yellow solid. $^1$H NMR (300 MHz, CDCl$_3$) δ 8.03 (d, J=8.3 Hz, 2H), 7.30 (d, J=8.3 Hz, 2H), 6.30 (s, 1H), 4.56 (t, J=6.0 Hz, 2H), 4.53 (s, 2H), 4.02-3.94 (m, 1H), 3.62 (t, J=6.0 Hz, 2H), 3.11 (s, 3H), 2.04-1.97 (m, 3H), 2.01 (q, J=6.0 Hz, 2H), 1.88-1.86 (m, 3H), 1.65 (br s, 1H), 1.27-1.21 (m, 3H). Mass spectrum (API-TIS) m/z 438 (MH$^+$).

Example 17

1-(1-Cyclohexyl-3-((3-((nitrooxy)methyl)phenoxy)methyl)pyrazol-5-yl)-4-(methylsulfonyl)benzene

17a. Ethyl 3-((1-cyclohexyl-5-(4-(methylsulfonyl)phenyl)pyrazol-3-)methoxy)benzoate The product of Example 15b (562.2 mg, 1.4 mmol), ethyl-3-hydroxybenzoate (259.5 mg, 1.6 mmol), K$_2$CO$_3$ (294.2 mg, 2.1 mmol), and NaI (233.8 mg, 1.6 mmol) were taken up in acetone (10 mL) and stirred at reflux overnight. Aqueous work-up followed by drying over MgSO$_4$ and removal of the solvent under reduced pressure gave the title compound (377.1 mg, 55% yield) as a white foam. $^1$H NMR (300 MHz, CDCl$_3$) δ 8.03 (d, J=8.3 Hz, 2H), 7.69 (br s, 1H), 7.63 (d, J=7.6 Hz, 1H), 7.56 (d, J=8.3 Hz, 2H), 7.33 (t, J=8.3 Hz, 1H), 7.19 (dd, J=2.1 Hz, 8.3, 1H), 6.40 (s, 1H), 5.14 (s, 2H), 4.35 (q, J=7.1 Hz, 2H), 4.05-3.98 (m, 1H), 3.11 (s, 3H), 2.06-2.00 (m, 2H), 1.91-1.84 (m, 4H), 1.65 (br s, 1H), 1.37 (t, J=7.1 Hz, 3H), 1.31-1.26 (m, 3H). Mass spectrum (API-TIS) m/z 483 (MH$^+$).

17b. 1-(1-Cyclohexyl-3-((3-(hydroxymethyl)phenoxy)methyl)pyrazol-5-yl)-4-(methylsulfonyl)benzene The product of Example 17a (377.1 mg, 0.78 mmol) was dissolved in dry THF (7 mL) and cooled to 0° C. A 1 M lithium aluminum hydride solution (1.02 mL, 1.02 mmol) was added drop-wise and the mixture stirred at 0° C. for 3.5 hours. Solid Na$_2$SO$_4$.10H$_2$O was added until a solid formed. The precipitate was removed via filtration and washed with 10% MeOH/CH$_2$Cl$_2$. The filtrate was collected, dried over Mg$_2$SO$_4$, and the solvent was evaporated under reduced pressure. The resulting residue was purified by chromatography over silica gel eluting with 2.5% MeOH/CHCl$_3$ to give the title compound (214.1 mg, 62% yield) as a clear oil. $^1$H NMR (300 MHz, CDCl$_3$) δ 8.00 (d, J=8.3 Hz, 2H), 7.54 (d, J=8.3 Hz, 2H), 7.22 (d, J=7.9 Hz, 2H), 7.01 (br s, 1H), 6.93-6.86 (m, 2H), 6.38 (s, 1H), 5.10 (s, 2H), 4.62 (d, J=4.6 Hz, 2H), 4.04-3.97 (m, 1H), 3.08 (s, 3H), 2.04-1.97 (m, 2H), 1.89-1.80 (m, 4H), 1.64 (br s, 1H), 1.29-1.24 (m, 3H).

Mass spectrum (API-TIS) m/z 441 (MH$^+$).

17c. 1-(3-((3-(Bromomethyl)phenoxy)methyl)-1-cyclohexylpyrazol-5-yl)-4-(methylsulfonyl)benzene The product of Example 17b (204.8 mg, 0.46 mmol) and PBr$_3$ (88.4 µL, 0.93 mmol) were taken up in CH$_2$Cl$_2$ (3 mL) and stirred overnight. Aqueous work-up followed by drying over MgSO$_4$ and removal of the solvent under reduced pressure afforded the title compound (161.6 mg, 69% yield) as a clear oil. $^1$H NMR (300 MHz, CDCl$_3$) δ 8.02 (d, J=8.2 Hz, 2H), 7.55 (d, J=8.2 Hz, 2H), 7.22 (t, J=7.9 Hz, 2H), 6.96-6.92 (m, 2H), 6.40 (s, 1H), 5.10 (s, 2H), 4.43 (s, 2H), 4.06-3.98 (m, 1H), 3.09 (s, 3H), 2.06-2.03 (m, 3H), 1.91-1.87 (m, 3H), 1.65 (br s, 1H), 1.29-1.22 (m, 3H). Mass spectrum (API-TIS) m/z 504 (MH$^+$).

17d. 1-(1-Cyclohexyl-3-((3-((nitrooxy)methyl)phenoxy)methyl)pyrazol-5-yl)-4-(methylsulfonyl)benzene The product of Example 17c (161.6 mg, 0.32 mmol) was dissolved in acetonitrile (5 mL) and AgNO$_3$ (109.3 mg, 0.64 mmol) was added. The mixture was shielded from light and stirred at room temperature overnight. 1N HCl (4 mL) was added and the precipitate removed via filtration through Celite. The aqueous layer was separated and extracted with methylene chloride. The combined extracts were washed with water, dried over MgSO$_4$ and the solvent evaporated under reduced pressure to give the title compound (67.0 mg, 43% yield) as a yellow oil. $^1$H NMR (300 MHz, CDCl$_3$); δ 8.04 (d, J=8.2 Hz, 2H), 7.57 (d, J=8.2 Hz, 2H), 7.31 (t, J=7.6 Hz, 1H), 7.06-7.03 (m, 2H), 6.98 (d, J=7.6 Hz, 1H), 6.40 (s, 1H), 5.39 (s, 2H), 5.13 (s, 2H), 4.06-3.98 (m, 1H), 3.12 (s, 3H), 2.07-2.02 (m, 3H), 1.92-1.88 (m, 3H), 1.67 (br s, 1H), 1.34-1.26 (m, 3H). Mass spectrum (API-TIS) m/z 487 (MH$^+$).

Example 18

1-(1-(4-Fluorphenyl)-3-((3-nitrooxy)propoxy)methyl)pyrazol-5-yl)-4-methylsulfonyl)benzene

18a. Methyl 1-(4-fluorophenyl)-5-(4-(methylsulfonyl)phenyl)pyrazol-3-carboxylate The title compound was prepared from the product of Example 3a (5.68 g, 20 mmol) and 4-fluorophenylhydrazine hydrochloride (4.23 g, 26 mmol) in methanol (120 mL) using the procedure of Example 10a. Separation of the regioisomers and recrystallization gave the title compound as a white solid (4.16 g, 55% yield). Mp 224-227° C. $^1$H NMR (300 MHz, CDCl$_3$) δ 7.94 (d, J=8.3 Hz, 2H), 7.44 (d, J=8.3 Hz, 2H), 7.33 (m, 2H), 7.17 (s, 1H), 7.13 (m, 2H), 4.01 (s, 3H), 3.10 (s, 3H). Mass spectrum (API-TIS) m/z 375 (MH$^+$), 392 (M+18$^+$). Anal. calcd. for C$_{18}$H$_{15}$FN$_2$O$_4$S: C, 57.75; H, 4.04; N, 7.48; found: C, 57.66; H, 3.88; N, 7.48.

18b. 1-(1-(4-Fluorophenyl)-3-(hydroxymethyl)pyrazol-5-yl)-4-(methylsulfonyl)benzene The title compound (0.4 g, 77% yield) was prepared from the product of Example 18a by following the procedure for Example 5b. $^1$H NMR (300 MHz, CDCl$_3$) δ 7.88 (d, J=8.5 Hz, 2H), 7.40 (d, J=8.5 Hz, 2H), 7.26-7.22 (m, 2H), 7.07 (m, 2H), 6.62 (s, 1H), 4.80 (d, J=5.8 Hz, 2H), 3.06 (s, 3H), 2.19 (d, J=5.8 Hz, 2H). Mass spectrum (API-TIS) m/z 347 (MH$^+$).

18c. 1-(3-(Bromomethyl)-1-(4-fluorophenyl)pyrazol-5-yl)-4-(methylsulfonyl)benzene The title compound (3.3 g, 82% yield) was prepared from the product of Example 18b by following the procedure for Example 5c. $^1$H NMR (300 MHz, CDCl$_3$) δ 7.88 (d, J=8.5 Hz, 2H), 7.40 (d, J=8.5 Hz, 2H), 7.26-7.22 (m, 2H), 7.07 (m, 2H), 6.62 (s, 1H), 4.80 (d, J=5.8 Hz, 2H), 3.06 (s, 3H), 2.19 (t, J=5.8 Hz, 1H). Mass spectrum (API-TIS) m/z 459 (MH$^+$).

18d. 1-(1-(4-Fluorophenyl)-3-((3-hydroxypropoxy)methyl)pyrazol-5-yl)-4-(methylsulfonyl)benzene The title compound (0.32 g, 25% yield) was prepared from the product of Example 18c by following the procedure for Example 5d except 2-benzyloxy ethanol was used instead of 3-benzyloxy propanol. $^1$H NMR (300 MHz, CDCl$_3$) δ 7.86 (d, J=8.4 Hz, 2H), 7.39 (d, J=8.4 Hz, 2H), 7.24-7.21 (m, 2H), 7.05 (m, 2H), 6.61 (s, 1H), 4.62 (s, 2H), 3.78 (t, J=5.8 Hz, 2H), 3.76 (t, J=5.8 Hz, 2H), 3.43 (br s, 1H), 3.05 (s, 3H), 1.88 (q, J=5.8 Hz, 2H). Mass spectrum (API-TIS) m/z 407 (MH$^+$).

18e. 1-(1-(4-Fluorophenyl)-3-((3-(nitrooxy)propoxy)methyl)pyrazol-5-yl)-4-(methylsulfonyl)benzene The title compound (69.3 mg, 74% yield) was prepared from the product of Example 18d by following the procedure for Example 5e. $^1$H NMR (300 MHz, CDCl$_3$) δ 7.88 (d, J=8.5 Hz, 2H), 7.40 (d, J=8.5 Hz, 2H), 7.27-7.22 (m, 2H), 7.07 (m, 2H), 6.62 (s, 1H), 4.60 (s, 2H), 4.58 (t, J=6.1 Hz, 2H), 3.68 (t, J=6.1 Hz, 2H), 3.06 (s, 3H), 2.04 (q, J=6.1 Hz, 2H). Mass spectrum (API-TIS) m/z 450 (MH$^+$).

Example 19

4-(methylsulfonyl)-1-(3-((3-(nitrooxy)butoxy)methyl)-1-phenylpyrazol-5-yl)benzene

19a. 4-(Methylsulfonyl)-1-(1-phenyl-3-((3-phenoxybutoxy)methyl)pyrazol-5-yl)benzene 4-Benzyloxy-1-butanol (540.6 mg, 3.1 mmol) was added to a stirred solution of NaH (133.3 mg, 5.6 mmol) in dry THF (10 mL) and the reaction mixture stirred for 15 minutes. The product of Example 5c (1.1 g, 2.8 mmol) was added and the mixture stirred overnight. The sample was diluted with CH$_2$Cl$_2$ (10 mL) and washed with saturated NH$_4$Cl and brine. The sample was dried over MgSO$_4$ and the solvent was evaporated under reduced pressure. The resulting residue was purified by chromatography over silica gel eluting with 2:1 Hexanes/EtOAc followed by preparatory plate chromatography eluting with 1:1 Hexanes/EtOAc to give the title compound (564.5 mg, 42% yield) as a yellow oil. $^1$H NMR (300 MHz, CDCl$_3$) δ 7.85 (d, J=8.5 Hz, 2H), 7.40 (d, J=8.5 Hz, 2H), 7.39-7.32 (m, 5H), 7.30-7.24 (m, 5H), 6.64 (s, 1H), 4.60 (s, 2H), 4.52 (s, 2H), 3.62 (t, J=5.9 Hz, 2H), 3.50 (t, J=5.9 Hz, 2H), 3.05 (s, 3H), 1.74-1.66 (m, 4H). Mass spectrum (API-TIS) m/z 491 (MH$^+$).

19b. 1-(3-((3-Hydroxybutoxy)methyl)-1-phenylpyrazol-5-yl)-4-(methylsulfonyl)benzene The product of example 19a (564.5 mg, 1.2 mmol) was dissolved in EtOH (100 mL) and placed in a Parr shaker. Pd/C (1.3 g) was added and the sample flushed with nitrogen 4 times. The sample was then flushed several times with H$_2$ (25-30 psi). The hydrogenation was performed at 30 psi for 30 minutes. The catalyst was removed via filtration through Celite and washed with EtOH. The combined filtrate was evaporated under reduced pressure to give the title compound (0.23 g, 51% yield) as a yellow oil. $^1$H NMR (300 MHz, CDCl$_3$) δ 7.83 (d, J=8.4 Hz, 2H), 7.41 (d, J=8.4 Hz, 2H), 7.37-7.35 (m, 2H), 7.28-7.25 (m, 3H), 6.65 (s, 1H), 4.64 (s, 2H), 3.69-3.62 (m, 4H), 3.06 (s, 3H), 1.78-1.66 (m, 4H). Mass spectrum (API-TIS) m/z 401 (MH$^+$).

19c. 4-(Methylsulfonyl)-1-(3-((3-(nitrooxy)butoxy)methyl)-1-phenylpyrazol-5-yl)benzene The product of Example 19b (46.5 mg, 0.116 mmol) was dissolved in acetonitrile (3 mL) and added drop-wise to 5 ml of cold fuming HNO$_3$. The mixture was stirred at 0° C. for 3 hours. Water (10 mL) was added followed by Na$_2$CO$_3$ until the mixture was neutralized. Methylene chloride was added and the organics separated. The aqueous portion was extracted with additional methylene chloride and the combined organic fractions were washed with water, dried over MgSO$_4$ and the solvent was evaporated under reduced pressure to give the title compound (37.6 mg, 73% yield) as a yellow oil. $^1$H NMR (300 MHz, CDCl$_3$) δ 7.89 (d, J=8.2 Hz, 2H), 7.45 (d, J=8.2 Hz, 2H), 7.39-7.37 (m, 2H), 7.31-7.29 (m, 2H), 6.67 (s, 1H), 4.65 (s, 2H), 4.53 (t, J=6.4 Hz, 2H), 3.66 (t, J=6.4 Hz, 2H), 3.09 (s, 3H), 1.93-1.86 (m, 2H), 1.83-1.77 (m, 2H). Mass spectrum (API-TIS) m/z 446 (MH$^+$).

Example 20

4-(5-(4-Methylphenyl)-3-((3-(nitrooxy)propoxy)methyl)pyrazolyl)-benzenesulfonamide

20a. Methyl 4-(4-methylphenyl)-2,4-dioxobutanoate

The title compound was prepared from dimethyloxalate (47.24 g, 400 mmol) and 4'-methylacetophenone (26.84 g, 200 mmol) using the procedure for Example 1d. Work-up and recrystallization provided the title compound as white needles (32.6 g, 74% yield). Mp 82-84° C. $^1$H NMR (300 MHz, CDCl$_3$) δ 15.36 (br.s, 1H), 7.92 (d, J=8.3 Hz, 2H), 7.32 (d, J=8.3 Hz, 2H), 7.08 (s, 1H), 3.96 (s, 3H), 2.46 (s, 3H). Mass spectrum (API-TIS) m/z 221 (MH$^+$). Anal calcd. for C$_{12}$H$_{12}$O$_4$: C, 65.45; H, 5.49. Found: C, 65.46; H, 5.53.

20b. 4-Hydrazinobenzenesulfonamide

A stirred solution of 4-chlorobenzenesulfonamide (38.33 g, 200 mmol) and anhydrous hydrazine (31.4 mL, 1.0 mol) was heated at reflux for 30 hours. After cooling to room temperature, the mixture was poured into water (500 mL) with swirling. The resulting precipitate was collected by filtration, washed thoroughly with water several times, air-dried, and dried under vacuum to give the title compound (35.5 g, 95% yield) as a white solid. Mp 169-171° C. $^1$H NMR (300 MHz, THF-d$_8$) δ 7.59 (d, J=8.8 Hz, 2H), 6.77 (d, J=8.8 Hz, 2H), 6.62 (br, 1H), 5.99 (br, 2H), 3.87 (br, 2H). Mass spectrum (API-TIS) m/z 188 (MH$^+$).

20c. Methyl 5-(4-methylphenyl)-1-(4-sulfamoylphenyl)pyrazol-3-carboxylate

To a stirred solution of the product of Example 20a (6.25 g, 28.4 mmol) in MeOH (200 mL) was added the product of Example 20b (5.31 g, 28.4 mmol), followed by 12N HCl (2.4 mL). The mixture was heated at reflux for 6 hours and then concentrated. The resulting solid was crystallized from MeOH:EtOAc (1:9) to give the title compound as white plates (10.1 g, 96% yield). Mp 138-139° C. $^1$H NMR (300 MHz, THF-d$_8$) δ 7.86 (m, 2H), 7.48 (m, 2H), 7.17 (s, 4H), 6.99 (s, 1H), 6.55 (br, 2H), 3.86 (s, 3H), 2.34 (s, 3H). Mass spectrum (API-TIS) m/z 372 (MH$^+$).

20d. 4-(3-(Hydroxymethyl)-5-(4-methylphenyl)pyrazolyl)benzenesulfonamide

To a stirred solution of the product of Example 20c (5.55 g, 14.96 mmol) in THF (500 mL) was added lithium aluminum hydride (1.0 M in THF, 37 mL, 37 mmol) drop-wise. After stirring at room temperature for 3 hours, the mixture was poured onto crushed ice, acidified with 12N HCl (20 mL), extracted with EtOAc, dried over Na$_2$SO$_4$, filtered, and concentrated. The resulting solid was crystallized from EtOAc: Hexane (2:1) to give the title compound as white prisms (4.60 g, 89% yield). Mp 130° C. $^1$H NMR (300 MHz, THF-d$_8$) δ 7.79 (d, J=8.5 Hz, 2H), 7.34 (d, J=8.5 Hz, 2H), 7.14 (d, J=8.0 Hz, 2H), 7.07 (d, J=8.0 Hz, 2H), 6.50 (s, 1H), 5.4 (br s, 2H), 4.79 (s, 2H), 2.36 (s, 3H), 2.1 (br s, 1H). Mass spectrum (API-TIS) m/z 344 (MH$^+$).

20e. (5-(4-Methylphenyl)-1-(4-sulfamoylphenyl)pyrazol-3-yl)methyl methylsulfonate To a stirred solution of the product of Example 20d (4.79 g, 13.97 mmol) and N,N-diisopropylethylamine (2.96 mL, 17 mmol) in THF (120 mL) was added methanesulfonyl chloride (1.08 mL, 14 mmol). After stirring at room temperature for 1 hour, the mixture was poured into 2N HCl, extracted with EtOAc, dried over Na$_2$SO$_4$, filtered, and concentrated to give the title compound as a white foam (5.21 g), which was used for the next step without further purification. $^1$H NMR (300 MHz, CDCl$_3$) δ 7.78 (d, J=8.5 Hz, 2H), 7.30 (d, J=8.5 Hz, 2H), 7.12 (d, J=8.0 Hz, 2H), 7.05 (d, J=8.0 Hz, 2H), 6.63 (s, 1H), 5.8 (br s, 2H), 5.34 (s, 2H), 3.09 (s, 3H), 2.33 (s, 3H). Mass spectrum (API-TIS) m/z 422 (MH$^+$).

20f. 4-(3-((3-Hydroxypropoxy)methyl)-5-(4-methylphenyl)pyrazolyl)benzenesulfonamide Sodium (0.66 g, 28.7 mmol) was stirred in 1,3-propanediol (8 mL) while heating (50° C.) until complete dissolution. The product of Example 20e (1.26 g, 3.00 mmol) in THF (15 mL) was added, and the resulting solution was heated at reflux for 2 hours. The mixture was poured into ice-cooled aqueous NH$_4$Cl, extracted with EtOAc, washed with brine, dried over Na$_2$SO$_4$, filtered, and concentrated. Chromatography of the residue over silica gel eluting with a 0-5% gradient MeOH in CHCl$_3$ furnished the title compound as a white solid (1.08 g, 94% yield over two steps). Mp 85-86° C. $^1$H NMR (300 MHz, CDCl$_3$) δ 7.73 (d, J=8.6 Hz, 2H), 7.25 (d, J=8.6 Hz, 2H), 7.09 (d, J=8.2 Hz, 2H), 7.03 (d, J=8.2 Hz, 2H), 6.47 (s, 1H), 6.15 (br s, 2H), 4.59 (s, 2H), 3.72 (m, 4H), 3.25 (br, 1H), 2.31 (s, 3H), 1.83 pentet, J=5.8 Hz, 2H). Mass spectrum (API-TIS) m/z 402 (MH$^+$).

20g. 4-(5-(4-Methylphenyl)-3-((3-(nitrooxy)propoxy)methyl)pyrazolyl)benzenesulfonamide A mixture of 90% HNO$_3$ (1.17 mL, 25 mmol) and Ac$_2$O (7 mL) was stirred at –10° C. (ice-MeOH bath) for 30 min. The product of Example 20f (2.09 g, 5.21 mmol) in THF (12 mL) was added. After being stirred at –10° C. for 20 minutes, the mixture was poured into ice containing aqueous Na$_2$CO$_3$, extracted with EtOAc, washed with brine, dried over Na$_2$SO$_4$, filtered, and concentrated. Chromatography of the residue over silica gel eluting with EtOAc:Hexane 2:1 afforded the title compound as a tan solid (1.61 g, 69% yield). Mp 62° C. $^1$H NMR (300 MHz, CDCl$_3$) δ 7.76 (d, J=8.7 Hz, 2H), 7.32 (d, J=8.7 Hz, 2H), 7.13 (d, J=8.1 Hz, 2H), 7.08 (d, J=8.1 Hz, 2H), 6.51 (s, 1H), 5.75 (br s, 2H), 4.62 (s, 2H), 4.60 (t, J=6.3 Hz, 2H), 3.69 (t, J=6.0 Hz, 2H), 2.34 (s, 3H), 2.07-2.02 (m, 2H); $^{13}$C NMR (75 MHz, CDCl$_3$) δ 151.3, 144.7, 142.8, 140.6, 140.0, 129.5, 128.6, 127.2, 126.7, 124.9, 108.0, 70.5, 66.4, 66.2, 27.2, 21.2. Mass spectrum (API-TIS) m/z 447 (MH$^+$).

Example 21

1-(3-((1E)-4-(Nitrooxy)but-1-enyl)-1-cyclohexylpyrazol-5-yl)-4-(methylsulfonyl)benzene 21a. 1-((3E)-4-(1-Cyclohexyl-5-(4-methylthiophenyl)pyrazol-3-yl)but-3-enyloxy)-1,1,2,2-tetramethyl-1-silapropane n-Butyl lithium (2.25 mL of 2.5 M solution in hexane, 0.36 g, 5.6 mmol), was added drop-wise to solution of phosphonium salt ((3-((1,1-dimethylethyl)-dimethylsilyl)-oxy)propyl)-triphenylphosphonium bromide) (2.45 g, 4.76 mmol) in THF (13 mL) at −78° C. The resultant solution was stirred at −78° C. for 1 hour. To this solution product of the Example 4c (1.3 g, 4.3 mmol) in THF (13 mL) was added drop-wise and the stirring continued at −78° C. for 1 hour. The reaction mixture was gradually warmed to room temperature and stirred at room temperature for 24 hour. Water was added and extracted with EtOAc which was then washed with water, dried and filtered. The residue, after evaporation of the solvent, was purified by chromatography over silica gel eluting with 0.5:10 EtOAc:Hex to give pure Z-isomer (1.2 g, 61% yield) as a colorless oil and E-isomer (0.1 g, 5% yield). E-isomer: $^1$H NMR (300 MHz, CDCl$_3$) δ 7.22-7.35 (m, 4H), 6.51 (d, J=16.1 Hz, 1H), 6.26 (s, 1H), 6.12-6.25 (m, 1H), 3.92-4.08 (m, 1H), 3.72 (t, J=7.10 Hz, 2H), 2.53 (s, 3H), 2.37-2.48 (m, 2H), 1.56-2.10 (m, 7H), 1.16-1.30 (m, 3H), 0.91 (s, 9H), 0.07 (s, 6H). $^{13}$C NMR (75 MHz, CDCl$_3$) δ 149.8, 143.3, 139.3, 129.5, 128.1, 127.9, 126.5, 124.4, 102.1, 63.3, 57.8, 36.7, 33.5, 26.1, 25.8, 25.3, 18.5, 15.6, −5.0. mass spectrum (API-TIS) m/z 457 (MH$^+$).

21b. 1-(3-((1E)-4-(Hydroxy)but-1-enyl)-1-cyclohexylpyrazol-5-yl)-4-methylsulfonyl)benzene The title compound was prepared as a white solid from the product of Example 21a by following the procedure for Example 12d. Mp 129-130° C. $^1$H NMR (300 MHz, CDCl$_3$) δ 8.04 (d, J=8.2 Hz, 2H), 7.55 (d, J=8.2 Hz, 2H), 6.07 (d, J=16.0 Hz, 1H), 6.37 (s, 1H), 6.16-6.30 (m, 1H), 3.89-4.08 (m, 1H), 3.77 (q, J=6.0 Hz, 2H), 3.13 (s, 3H), 2.49 (q, J=6.5 Hz, 2H), 1.42-2.12 (m, 7H), 1.10-1.37 (m, 3H). $^{13}$C NMR (75 MHz, CDCl$_3$) δ 149.9, 141.8, 140.6, 136.8, 129.9, 128.2, 128.1, 125.1, 103.4, 62.2, 58.4, 44.7, 36.5, 33.5, 25.8, 25.2. mass spectrum (API-TIS) m/z 375 (MH$^+$). Anal. Calcd. for C$_{20}$H$_{26}$N$_2$O$_3$S.¼ mol H$_2$O: C, 63.38; H, 7.04; N, 7.39; S, 8.46. Found: C, 63.35; H, 7.13; N, 7.13; S, 8.44.

21c. 1-(3-((1E)-4-(Nitrooxy)but-1-enyl)-1-cyclohexylpyrazol-5-yl)-4-(methylsulfonyl)benzene The title compound was prepared as a white foam from the product of Example 21b by following the procedure for Example 1h. $^1$H NMR (300 MHz, CDCl$_3$) δ 8.05 (dd, J=1.5 and 8.4 Hz, 2H), 7.57 (dd, J=1.7 and 6.7 Hz, 2H), 6.57 (d, J=16.0 Hz, 1H), 6.37 (s, 1H), 6.09-6.23 (m, 1H), 4.57 (t, J=6.7 Hz, 2H), 3.90-4.12 (m, 1H), 3.13 (s, 3H), 2.55-2.68 (m, 2H), 1.60-2.12 (m, 7H), 1.12-1.35 (m, 3H). $^{13}$C NMR (75 MHz, CDCl$_3$) δ 149.3, 141.9, 140.6, 136.6, 129.9, 128.0, 125.9, 125.1, 103.5, 72.3, 58.4, 44.6, 33.5, 31.7, 30.5, 25.7, 25.1. mass spectrum (API-TIS) m/z 420 (MH$^+$). Anal. Calcd. for C$_{20}$H$_{25}$N$_3$O$_5$S: C, 57.26; H, 6.01; N, 10.02. Found: C, 56.98; H, 6.00; N, 9.75.

Example 22

1-(1-Cyclohexyl-5-(4-(methylsulfonyl)pyrazol-3-yl)-6-(nitrooxy)hexan-1-one 22a. (1-Cyclohexyl-5-(4-(methylthiophenyl)pyrazol-3-yl)-N-methoxy-N-methylcarboxamide The title compound was prepared as a white solid from the product of Example 4a by following the procedure for Example 3c. Mp 80-82° C. $^1$H NMR (300 MHz, CDCl$_3$) δ 7.34 (d, J=6.4 Hz, 2H), 7.27 (d, J=8.0 Hz, 2H), 6.71 (s, 1H), 4.05-4.20 (m, 1H), 3.84 (s, 3H), 3.48 (s, 3H), 2.54 (s, 3H), 1.80-2.10 (m, 6H), 1.56-1.70 (m, 1H), 1.17-1.32 (m, 3H). $^{13}$C NMR (75 MHz, CDCl$_3$) δ 144.2, 142.9, 139.9, 129.5, 126.9, 126.4, 108.6, 61.6, 58.4, 33.4, 25.6, 25.2, 15.5. Mass spectrum (API-TIS) m/z 360 (MH$^+$). Anal. Calcd. for C$_{19}$H$_{25}$N$_3$O$_2$S: C, 63.48; H, 7.01; N, 11.69. Found: C, 63.72; H, 7.05; N, 11.75.

22b. 1-(1-Cyclohexyl-5-(4-methylthiophenyl)-pyrazol-3-yl)-6-(1,1,2,2-tetramethyl-1-silapropoxy)hexanone-1-one To a solution of the product of Example 22a (6.0 g, 16.7 mmol) in THF (40 mL) was added drop-wise the Grignard reagent prepared from 3-bromo-1-(1,1,2,2-tetramethyl-1-silapropoxy)pentane (6.15 g, 21.8 mmol) and magnesium turnings (1.1 g, 46.0 mmol) in THF (40 mL) at room temperature under nitrogen. The reaction mixture was stirred at room temperature for 5 hours, and then quenched by the addition of saturated aqueous NH$_4$Cl at 0° C. The reaction mixture was diluted with EtOAc and the layers were separated. The aqueous layer was extracted with EtOAc and the combined organic layers were washed with water, dried (Na$_2$SO$_4$) and filtered. The residue obtained after evaporation of the solvent was purified by chromatography over silica gel eluting with 1:10 to 2: 10 EtOAc:Hexane to give the title compound (3.79 g, 48% yield) as a colorless oil. $^1$H NMR (300 MHz, CDCl$_3$) δ 7.33 (d, J=8.4 Hz, 2H), 7.26 (d, J=8.4 Hz, 2H), 6.71 (s, 1H), 4.00-4.18 (m, 1H), 3.63 (t, J=6.5 Hz, 2H), 3.03 (t, J=7.4 Hz, 2H), 2.54 (s, 3H), 1.82-2.13 (m, 7H), 1.76 (p, J=7.6 Hz, 2H), 1.52-1.64 (m, 2H), 1.36-1.52 (m, 2H), 1.20-1.36 (m, 3H), 0.91 (s, 9H), 0.06 (s, 6H). $^{13}$C NMR (75 MHz, CDCl$_3$) δ197.1, 150.1, 143.9, 140.1, 129.5, 126.8, 126.4, 106.3, 63.3, 58.5, 38.7, 33.4, 32.9, 26.1, 25.8, 25.6, 25.2, 24.5, 18.5, 15.5, −5.1. Mass spectrum (API-TIS) m/z 501 (MH$^+$). Anal. calcd. for C$_{28}$H$_{44}$N$_2$O$_2$SSi: C, 67.15; H, 8.86; N, 5.59. Found: C, 67.14; H, 8.68; N, 5.59.

22c. 1-(1-Cyclohexyl-5-(4-(methylsulfonyl)phenyl)-pyrazol-3-yl)-6-hydroxyhexan-1-one The title compound was prepared as a white solid from the product of Example 22b by following the procedure for Example 12d. Mp 125-127° C. $^1$H NMR (300 MHz, CDCl$_3$) δ 8.06 (d, J=8.4 Hz, 2H), 7.56 (d, J=8.4 Hz, 2H), 6.80 (s, 1H), 3.98-4.12 (m, 1H), 3.68 (q, J=6.3 Hz, 2H), 3.13 (s, 3H), 3.07 (t, J=7.3 Hz, 2H), 1.83-2.14 (m, 7H), 1.79 (p, J=7.5 Hz, 2H), 1.60-1.72 (m, 3H), 1.40-1.57 (m, 2H), 1.18-1.37 (m, 3H). $^{13}$C NMR (75 MHz, CDCl$_3$) δ 196.8, 150.4, 142.4, 141.0, 135.9, 130.0, 128.1, 107.2, 62.9, 59.1, 44.6, 38.6, 33.4, 32.7, 25.6, 25.5, 25.1, 24.1. Mass spectrum (API-TIS) m/z 419 (MH$^+$), 401 (M-OH). Anal. calcd. for C$_{22}$H$_{30}$N$_2$O$_4$S: C, 63.13; H, 7.22; N, 6.69. Found: C, 63.19; H, 7.08; N, 6.67.

22d. 1-(1-Cyclohexyl-5-(4-(methylsulfonyl)pyrazol-3-yl)-6-(nitrooxy)hexan-1-one The title compound was prepared as a white solid from the product of Example 22c by following the procedure for Example 1h. Mp 111-113° C. $^1$H NMR (300 MHz, CDCl$_3$) δ 8.07 (dd, J=1.9 and 8.5 Hz, 2H), 7.57 (d, J=8.4 Hz, 2H), 6.81 (s, 1H), 4.48 (t, J=6.7 Hz, 2H), 3.98-4.15 (m, 1H), 3.14 (s, 3H), 3.07 (t, J=7.3 Hz, 2H), 1.67-2.16 (m, 8H), 1.81 (p, J=8.0 Hz, 2H), 1.45-1.61 (m, 3H), 1.19-1.38 (m, 3H). $^{13}$C NMR (75 MHz, CDCl$_3$) δ 196.2, 150.2, 142.5, 141.0, 135.8, 130.0, 128.1, 107.1, 73.3, 59.0, 44.5, 38.2, 33.4, 26.7, 25.5, 25.4, 25.0, 23.8. Mass spectrum (API-TIS) m/z 464 (MH$^+$). Anal. calcd. for C$_{22}$H$_{29}$N$_3$O$_6$S: C, 57.00; H, 6.31; N, 9.06. Found: C, 57.07; H, 6.24; N, 8.97.

Example 23

1-(5-(4-(Methylsulfonyl)phenyl)-1-(4-(trifluoromethyl)phenyl)pyrazol-3-yl)-4-(nitrooxy)butan-1-one

23a. Methyl 5-(4-methylthiophenyl)-1-(4-(trifluoromethyl)phenyl)pyrazol-3-carboxylate The title compound was prepared from the product of Example 1d (5.0 g, 20 mmol) and 4-(trifluoromethyl)phenyl-hydrazine hydrochloride (4.58 g, 26 mmol) in acetic acid (120 mL) in a manner similar to Example 7a. Work-up and recrystallization provided the title compound as a white solid (4.05 g, 52% yield). Mp 108-110° C. $^1$H NMR (300 MHz, CDCl$_3$) δ 7.66 (d, J=8.5 Hz, 2H), 7.51 (d, J=8.5 Hz, 2H), 7.23 (d, J=8.5 Hz, 2H), 7.15 (d, J=8.5 Hz, 2H), 7.06 (s, 1H), 4.01 (s, 3H), 2.52 (s, 3H). Mass spectrum (API-TIS) m/z 393 (MH$^+$). Anal. calcd. for C$_{19}$H$_{15}$F$_3$N$_2$O$_2$S: C, 58.16; H, 3.85; N, 7.14; found: C, 58.26; H, 3.73; N, 7.10.

23b. N-Methoxy-N-methyl(5-(4-methylthiophenyl)-1-(4-(trifluoromethyl)phenyl)-pyrazolyl)carboxamide The title compound was prepared from the product of Example 23a by following the procedure for Example 3c. Mp 142-144° C. $^1$H NMR (300 MHz, CDCl$_3$) δ 7.62 (d, J=8.4 Hz 2H), 7.47 (d, J=8.5 Hz, 2H) 7.21 (dd, J=2.1 and 6.5 Hz, 2H), 7.14 (dd, J=2.1 and 6.5 Hz, 2H), 6.97 (s, 1H), 3.86 (s, 3H), 3.50 (br s, 3H), 2.50 (s, 3H); $^{13}$C NMR (75 MHz, CDCl$_3$) δ 146.1, 143.3, 140.0, 138.1, 133.6, 129.0 (J$_{C-F}$=9.4 Hz), 126.4, 125.9, 125.7, 110.1, 61.6, 34.0, 15.1. Mass spectrum (API-TIS) m/z 422 (MH$^+$). Anal. calcd. for C$_{20}$H$_{18}$F$_3$N$_3$O$_2$S: C, 57.00; H, 4.31; N, 9.97. Found: C, 56.78; H, 4.12; 9.76.

23c. 1-(5-(4-Methylthiophenyl)-1-(4-(trifluoromethyl)phenyl)pyrazol-3-yl)-4-(1,1,2,2-tetramethyl-1-silapropoxy)butan-1-one The title compound was prepared as a white solid from the product of Example 23b by following the procedure for Example 3d. Mp 102-103° C. $^1$H NMR (300 MHz, CDCl$_3$) δ 7.59 (d, J=8.6 Hz, 2H), 7.43 (d, J=8.4 Hz, 2H) 7.15 (d, J=8.4 Hz, 2H), 7.07 (d, J=8.4 Hz, 2H), 6.93 (s, 1H), 3.68 (t, J=6.3 Hz, 2H), 3.11 (t, J=7.3 Hz, 2H), 2.44 (s, 3H), 1.88-2.05 (m, 2H), 0.84 (s, 9H), 0.01 (s, 6H). $^{13}$C NMR (75 MHz, CDCl$_3$) δ196.4, 152.1, 144.7, 142.5, 140.7, 130.1 (J$_{C-F}$=32.9 Hz), 129.2, 126.4 (J$_{C-F}$=3.7 Hz), 126.2, 125.8, 125.6, 125.4, 108.5, 62.6, 35.4, 27.5, 26.1, 18.5, 15.3, −5.2. Mass spectrum (API-TIS) m/z 535 (MH$^+$). Anal. calcd. for C$_{27}$H$_{33}$F$_3$N$_2$O$_2$SSi: C, 60.65; H, 6.22; N, 5.24. Found: C, 60.49; H, 6.13; 5.09.

23d. 4-Hydroxy-1-(5-(4-(methylsulfonyl)phenyl)-1-(4-(trifluoromethyl)-phenyl)pyrazol-3-yl)butan-1-one The title compound was prepared as a white solid from the product of Example 23c by following the procedure for Example 12d. Mp 60-63° C. $^1$H NMR (300 MHz, CDCl$_3$) δ 7.95 (dd, J=1.7 and 6.7 Hz, 2H), 7.69 (d, J=8.4 Hz, 2H), 7.42-7.47 (m, 4H), 7.12 (s, 1H), 3.74 (t, J=5.9 Hz, 2H), 3.24 (t, J=7.0 Hz, 2H), 3.09 (s, 3H), 1.97-2.12 (m, 2H), 1.85-1.97 (br s, 1H), $^{13}$C NMR (75 MHz, CDCl$_3$) δ 196.4, 152.3, 143.2, 141.9, 141.3, 134.7, 130.8, 129.7, 128.2, 126.9 (J$_{C-F}$=3.6 Hz), 125.6, 109.7, 62.4, 44.5, 35.6, 27.2. Mass spectrum (API-TIS) m/z 453 (MH$^+$), 435 (M-OH). Anal. calcd. for C$_{21}$H$_{19}$F$_3$N$_2$O$_4$S: C, 55.75; H, 4.23; N, 6.19. Found: C, 55.59; H, 4.14; 5.91.

23e. 1-(5-(4-(Methylsulfonyl)phenyl)-1-(4-(trifluoromethyl)phenyl)pyrazol-3-yl)-4-(nitrooxy)butan-1-one The title compound was prepared as a white solid from the product of Example 23d by following the procedure for Example 1h. Mp 152-154° C. $^1$H NMR (300 MHz, CDCl$_3$) δ 7.95 (d, J=8.3 Hz, 2H), 7.70 (d, J=8.6 Hz, 2H), 7.42-7.47 (m, 4H), 7.13 (s, 1H), 4.59 (t, J=6.3 Hz, 2H), 3.26 (t, J=7.0 Hz, 2H), 3.10 (s, 3H), 2.23 (p, J=6.7 Hz, 2H). $^{13}$C NMR (75 MHz, CDCl$_3$) δ 194.3, 151.9, 143.3, 141.8, 141.3, 134.6, 131.3, 129.7, 128.2, 126.9 (J$_{(C-F)}$=3.8 Hz), 125.6, 125.4, 109.6, 72.6, 44.5, 34.7, 21.3. Mass spectrum (API-TIS) m/z 498 (MH$^+$), 515 (MNa$^+$). Anal. calcd. for C$_{21}$H$_{18}$F$_3$N$_3$O$_6$S: C, 50.71; H, 3.65; N, 8.45. Found: C, 50.60; H, 3.49; 8.20.

Example 24

1-(1-(4-Methoxyphenyl)-5-(4-(methylsulfonyl)phenyl)pyrazol-3-yl)-4-(nitrooxy)butan-1-one

24a. Methyl 1-(4-methoxyphenyl)-5-(4-methylthiophenyl)pyrazole-3-carboxylate The title compound was prepared from the product of Example 1d (5.05 g, 20 mmol) and 4-methoxyphenylhydrazine hydrochloride (4.54 g, 26 mmol) in methanol (120 mL) by following the procedure of Example 8a. Separation of the regioisomers and recrystallization gave the title compound as white needles (5.45 g, 15.4 mmol, 77% yield). Mp 106-108° C.; 1H NMR (300 MHz, CDCl3) δ7.27 (d, J=8.9 Hz, 2H), 7.19 (d, J=8.6 Hz, 2H), 7.14 (d, J=8.6 Hz, 2H), 7.04 (s, 1H), 6.89 (d, J=8.9 Hz, 2H), 3.99 (s, 3H), 3.85 (s, 3H), 2.50 (s, 3H). Mass spectrum (API-TIS) m/z 355 (MH$^+$); Anal. calcd. for C$_{19}$H$_{18}$N$_2$O$_3$S: C, 64.39; H, 5.12; N, 7.90; found: C, 64.39; H, 5.05; N, 7.79.

24b. N-Methoxy-(1-(4-methoxyphenyl)-5-(4-methylthiophenyl)-pyrazol-3-yl)-N-methylcarboxamide The title compound was prepared as a white solid from the product of Example 24a by following the procedure for Example 3c. Mp 131-133° C. $^1$H NMR (300 MHz, CDCl$_3$) δ 7.25-7.29 (m, 2H), 7.14-7.20 (m, 4H), 6.98 (s, 1H), 6.89 (d, J=8.2 Hz, 2H), 3.87 (s, 3H), 3.84 (s, 3H), 3.53 (br s, 3H), 2.49 (s, 3H). $^{13}$C NMR (75 MHz, CDCl$_3$) δ 159.4, 145.7, 143.3, 139.6, 133.1, 129.1, 126.9, 126.4, 126.1, 114.3, 109.7, 61.7, 55.6, 34.0, 15.4. mass spectrum (API-TIS) m/z 384 (MH$^+$). Anal. Calcd. for C$_{20}$H$_{21}$N$_3$O$_3$S: C, 62.64; H, 5.52; N, 10.96. Found: C, 62.44; H, 5.29; N, 10.75.

24c. 1-(1-(4-Methoxyphenyl)-5-(4-methylthiophenyl)pyrazol-3-yl)-4-(1,1,2,2-tetramethyl-1-silapropoxy)butan-1-one The title compound was prepared as a white solid from the product of Example 24b by following the procedure for Example 3d. mp 51-53° C. $^1$H NMR (300 MHz, CDCl$_3$) δ 7.24 (d, J=8.8Hz, 2H), 7.16 (d, J=8.4Hz, 2H), 7.11 (d, J=8.5Hz, 2H), 6.96 (s, 1H), 6.89 (d, J=8.8 Hz, 2H), 3.83 (s, 3H), 3.72 (t, J=6.4 Hz, 2H), 3.15 (t, J=7.3 Hz, 2H), 2.47 (s, 3H), 1.99 (p, J=6.9 Hz, 2H), 0.89 (s, 9H), 0.05 (s, 6H). $^{13}$C NMR (75 MHz, CDCl$_3$) δ 196.6, 159.5, 151.3, 144.4, 139.8, 133.0, 129.1, 126.9, 126.3, 126.0, 114.4, 107.3, 62.7, 55.6, 35.3, 27.5, 26.1, 18.4, 15.3, −5.2. mass spectrum (API-TIS) m/z 497 (MH$^+$). Anal. Calcd. for C$_{27}$H$_{36}$N$_2$O$_3$SSi: C, 65.29; H, 7.30; N, 5.64. Found: C, 65.06; H, 7.40; N, 5.52.

24d. 4-Hydroxy-1-(1-(4-methoxyphenyl)-5-(4-(methylsulfonyl)phenyl)-pyrazol-3-yl)butan-1-one The title compound was prepared as a white solid from the product of Example 24c by following the procedure for Example 3e. Mp 125-127° C. $^1$H NMR (300 MHz, CDCl$_3$) δ 7.89 (d, J=8.4 Hz, 2H), 7.40 (d, J=6.8 Hz, 2H), 7.22 (dd, J=2.1 and 8.9 Hz, 2H), 7.10 (s, 1H), 6.91 (dd, J=2.1 and 8.9 Hz, 2H), 3.85 (s, 3H), 3.73 (t, J=6.0 Hz, 2H), 3.23 (t, J=6.9 Hz, 2H), 3.07 (s, 3H), 2.04 (p, J=6.9 Hz, 2H). $^{13}$C NMR (75 MHz, CDCl$_3$) δ 196.6, 160.0, 151.4, 143.0, 140.5, 132.0, 132.1, 129.5, 127.8, 126.9, 114.7, 108.4, 62.2, 55.7, 44.4, 35.5, 27.4. mass spectrum (API-TIS) m/z 415 (MH$^+$), 397 (M-OH). Anal. Calcd. for C$_{21}$H$_{22}$N$_2$O$_5$S: C, 60.86; H, 5.35; N, 6.76. Found: C, 60.66; H, 5.27; N, 6.59.

24e. 1-(1-(4-Methoxyphenyl)-5-(4-(methylsulfonyl)phenyl)pyrazol-3-yl-4-(nitrooxy)butan-1-one The title compound was prepared as a white solid from the product of Example 24d by following the procedure for Example 1h. Mp 132-134° C. $^1$H NMR (300 MHz, CDCl$_3$) δ 7.89 (d, J=8.3 Hz, 2H), 7.41 (d, J=8.3 Hz, 2H), 7.20-7.27 (m, 2H), 7.10 (s, 1H), 6.91-6.95 (m, 2H), 4.58 (t, J=6.4 Hz, 2H), 3.85 (s, 3H), 3.26 (t, J=7.1 Hz, 2H), 3.07 (s, 3H), 2.21 (p, J=6.7 Hz, 2H). $^{13}$C NMR (75 MHz, CDCl$_3$) δ 194.5, 160.1, 151.1, 143.1, 140.6, 135.1, 132.2, 129.5, 127.9, 127.0, 114.8, 108.4, 72.6, 55.8, 44.5, 34.6, 21.3. mass spectrum (API-TIS) m/z 460 (MH$^+$). Anal. Calcd. for C$_{21}$H$_{21}$N$_3$O$_7$S: C, 54.90; H, 4.61; N, 9.15. Found: C, 54.63; H, 4.43; N, 8.97.

Example 25

1-(3-((1Z)-4-(nitrooxy)but-1-enyl)-5-(3-pyridyl)pyrazolyl)-4-(methylsulfonyl)benzene

25a. Methyl 2,4-dioxo-4-(3-pyridyl)butanoate

Sodium methoxide (5.4 g, 100 mmol) and dimethyloxalate (11.8 g, 100 mmol) were dissolved in anhydrous methanol (700 mL) and stirred at room temperature under nitrogen until a suspension was formed. To this mixture, 3-acetylpyridine (5.5 mL, 50 mmol) was added and the stirring was continued for 3 days at room temperature. The reaction was quenched with enough 5% aqueous KHSO$_4$ until all solids have dissolved. The methanol was removed under reduced pressure, and the residue was extracted with ethyl acetate (3×200 mL). The combined organic layers were washed with water (2×200 mL), brine and dried (NaSO$_4$) followed by the removal of solvent under reduced pressure to give the title compound (8.67 g, 84% yield) as a yellow solid. $^1$H NMR (CDCl$_3$, 300 MHz) δ 9.21-9.20 (m, 1H), 8.84-8.82 (m, 1H), 8.30-8.26 (m, 1H), 7.50-7.45 (m, 1H), 7.08 (s, 1H), 3.96 (s, 3H). $^{13}$C NMR (CDCl$_3$, 75 MHz) δ 188.5, 170.4, 162.2, 153.9, 149.0, 135.2, 130.5, 123.8, 98.0, 53.3. mass spectrum (APIMS) m/z 208 (M+1)$^+$.

25b. Methyl 1-(4-(methylsulfony)phenyl)-5-(3-pyridyl)pyrazol-3-carboxalate

A mixture of the product of Example 25a (295 mg, 1.4 mmol) and 4-methylsulfonyl phenylhydrazine hydrochloride (528 mg, 2.8 mmol) was dissolved in anhydrous methanol (10 mL) and refluxed (70° C.) overnight under nitrogen. Solvent was removed under reduced pressure and the residue was partitioned with ethyl acetate and saturated aqueous solution of sodium bicarbonate (50 mL each). The organic layer was washed with water, brine and dried (NaSO$_4$). The solvent was removed under reduced pressure and purification by silica gel flash column chromatography with 1% methanol in dichloromethane yielded the title compound (350 mg, 69% yield) as an orange colored solid. $^1$H NMR (CDCl$_3$, 300 MHz) δ 8.66-8.65 (m, 1H), 8.58-8.57 (m, 1H), 7.99-7.96 (m, 2H), 7.59-7.54 (m, 3H), 7.37-7.33 (m, 1H)7.16 (s, 1H), 3.99 (s, 3H), 3.10 (s, 3H). $^{13}$C NMR (CDCl$_3$, 75 MHz) δ161.9, 150.3, 149.1, 145.2, 142.9, 141.5, 140.3, 135.8, 128.6, 125.8, 125.0, 123.5, 111.4, 52.3,44.3. LRMS (APIMS) m/z 715 (2M+1)$^+$, 358 (M+1)$^+$.

25c. 1-(3-(Hydroxymethyl)-5-(3-pyridyl)pyrazoyl)-4-(methylsulfonyl)benzene

The product of Example 25b (600 mg, 1.7 mmol) was dissolved in anhydrous dichloromethane (50 mL). To this solution, DIBAL-H (1M in toluene, 3.4 mL, 3.4 mmol) was added drop-wise under nitrogen and stirred at room temperature for 15 min. The reaction was quenched with saturated ammonium chloride, filtered and the layers were separated. The organic layer was washed with water (1×50 mL), brine and dried (NaSO$_4$) and the solvent was removed under reduced pressure. Purification by silica gel flash column chromatography with 3% methanol in dichloromethane yielded the title compound (310 mg, 57% yield) as a white solid. $^1$H NMR (CDCl$_3$, 300 MHz) δ 8.64-8.61 (m, 1H), 8.57-8.56 (m, 1H), 7.94-7.89 (m, 2H), 7.53-7.45 (m, 3H), 7.38-7.27 (m, 1H), 6.65 (s, 1H), 4.81 (s, 2H), 3.07 (s, 3H), 2.69 (br s, 1H), $^{13}$C NMR (CDCl$_3$, 75 MHz) δ 154.6, 150.0, 149.1, 143.6, 141.0, 139.2, 135.9, 128.6, 126.2, 125.1, 123.6, 108.5, 58.8, 44.5. mass spectrum (APIMS) m/z 659 (2M+1)$^+$, 330 (M+1)$^+$.

25d. 1-(4-(Methylsulfonyl)phenyl)-5-(3-pyridyl)pyrazol-3-carbaldehyde

The product of Example 25c (200 mg, 0.6 mmol) was dissolved in anhydrous dichloromethane (30 mL) and alumina (1 g) was added and stirred under nitrogen. Pyridinium chlorochromate (380 mg, 1.8 mmol) was added and continued stirring for 20 min. The reaction mixture was filtered, then washed with saturated aqueous solution of sodium bicarbonate (3×30 mL), water (1×30 mL), brine (1×30 mL), dried (NaSO$_4$), filtered and solvent removed under reduced pressure. The product was purified on silica gel flash column choromatography with 3% methanol in dichloromethane to give the pure title compound (80 mg, 41% yield) as a solid.

$^1$H NMR (CDCl$_3$, 300 MHz) δ 10.10 (s, 1H), 8.69-8.67 (m, 1H), 8.58-8.57 (m, 1H), 8.02 (s, 1H), 7.99 (s, 1H), 7.61-7.52 (m, 3H), 7.37-7.34 (m, 1H), 7.12 (s, 1H), 3.10 (s, 3H). Mass spectrum (APIMS) m/z 328 (M+1)$^+$.

25e. 1-(3-((1Z)-4-Hydroxybut-1-enyl)-5-(3-pyridnyl) pyrazolyl)-4-(methylsulfonyl)benzene 1-t-Butyldimethylsilyloxypropyl-3-triphenylphosphonium bromide (310 mg, 0.6 mmol, 2.5 eq.) and anhydrous THF (10 mL) was stirred and cooled to −78° C. under nitrogen. To this suspension, n-BuLi (1.6 M in hexanes, 300 μL, 2 mmol) was added and stirred for 20 minutes until the dark orange color was observed. To this solution the product of Example 25d (80 mg, 0.24 mmol) dissolved in anhydrous THF (5 mL) was added and stirred for 30 minutes. The reaction mixture was stirred for another 2 hours at room temperature. The reaction was quenched with saturated ammonium chloride (3 mL) and layers were separated. The aqueous layer was diluted until all solids dissolved and further extracted with ethyl acetate (2×30 mL). The combined organic layers were washed with brine and dried (NaSO$_4$), filtered and solvent removed under reduced pressure. The product was purified by chromatography over silica gel and then it was dissolved in THF and tetrabutyl ammonium fluoride (1M, 2 mL, 2 mmol) was added and mixture stirred under nitrogen overnight. The solvent was removed under reduced pressure, and the residue was partitioned with dichloromethane and water (30 mL each) and layers separated. The organic layer was washed with brine and dried (NaSO$_4$), filtered and solvent removed under reduced pressure. The product was purified by silica gel flash column chromatography using 1% methanol in dichloromethane to yield the title compound (40 mg, 52% yield) as a colorless foam. $^1$H NMR (CDCl$_3$, 300 MHz) δ 8.64 (d, J=3.8 Hz, 1H), 8.59 (br s, 1H), 7.92 (d, J=8.6 Hz, 2H), 7.55-7.47 (m, 3H), 7.37-7.32 (m, 1H), 6.64 (s, 1H), 6.53 (d, 1H, J=11.6 Hz), 6.02-5.93 (m, 1H), 3.85 (t, J=6.2 Hz, 2H), 3.07 (s, 1H), 2.87-2.80 (m, 2H). $^{13}$C NMR (CDCl$_3$, 75 MHz) δ 151.0, 149.9, 149.1, 143.5, 140.5, 139.1, 135.9, 132.2, 128.6, 126.0, 124.9, 123.5, 121.8, 110.5, 62.0, 44.4, 32.6. mass spectrum (APIMS) m/z 370 (M+1)$^+$.

25f. 1-(3-((1Z)-4-(Nitrooxy)but-1-enyl)-5-(3-pyridyl)pyrazolyl)-4-(methylsulfonyl)benzene The product of Example 25e (40 mg, 0.11 mmol) was dissolved in a mixture of ethyl acetate (3 mL) and dichloromethane (2 mL). The solution was cooled to 0° C. In a separate flask, acetic anhydride (620 μL) and fuming nitric acid (190 μL) was mixed together at 0° C. The Ac$_2$O/HNO$_3$ mixture (270 μL) was added to the solution of starting material and stirred at 0° C. for 10 min and at room temperature for 5 min. The reaction was quenched by pouring over crushed ice, layers separated and the aqueous layer was further extracted with ethyl acetate (2×25 mL). The combined organic layers were washed with water (3×25 mL), brine (1×25 mL) and dried (NaSO$_4$). The solution was filtered and solvent was removed under reduced pressure to give the title compound (38 mg, 84% yield) as a colorless foam. $^1$H NMR (CDCl$_3$, 300 MHz) δ 8.70 (br s, 2H), 7.98 (d, J=8.6 Hz, 2H), 7.67-7.65 (m, 1H), 7.55 (d, J=8.6 Hz, 2H), 7.46 (br s, 1H), 6.66 (s, 1H), 6.56 (d, J=12 Hz, 1H), 5.94-5.85 (m, 1H), 4.69 (t, J=6.8 Hz, 2H), 3.16-3.10 (m, 2H), 3.13 (s, 3H). $^{13}$C NMR (CDCl$_3$, 75 MHz) δ 155.2, 148.9, 148.2, 143.5, 139.9, 139.4, 136.9, 128.7, 128.5, 125.0, 122.6, 110.9, 72.2, 44.5, 27.3. Mass spectrum (APIMS) m/z 415 (M+1)$^+$.

Example 26

4-(5-(3-Nitrooxy)propoxy)-methyl)-3-phenylisoxazol-4-yl)benzenesulfonamide

26a. 4-(5-(3-Hydroxypropoxy)methyl)-3-phenylisoxazol-4-yl)benzenesulfonamide Sodium (0.50 g, 22 mmol) was dissolved in 1,3-propanediol (10 mL) and to this was added a solution of 4-(5-(chloromethyl)-3-phenylisoxazol-4-yl)benzenesulfonamide (1.11 g, 3.18 mmol, prepared according to the method of Talley, J. J., et. al. *J. Med. Chem.* 2000, 43, 775-777) in THF (20 mL). The resulting mixture was heated at reflux for 4 hours, then poured into ice containing aqueous NH$_4$Cl and extracted with EtOAc. The combined extracts were washed with water, dried over Na$_2$SO$_4$, filtered, and concentrated. Flash chromatography (silica gel, 1:1 EtOAc:THF) of the residue afforded the title compound as a white solid, (1.08 g, yield 87% yield). $^1$H NMR (300 MHz, DMSO-d$_6$) δ 7.87 (d, J=8.3 Hz, 2H), 7.6-7.3 (m, 9H), 4.59 (s, 2H), 4.43 (t, J=5.1 Hz, 1H, OH), 3.55 (t, J=6.4 Hz, 2H), 3.46 (m, 2H), 1.67 (pentet, J=6.3 Hz, 2H). Mass spectrum (API-TIS) m/z 389 (MH$^+$).

26b. 4-(5-(3-Nitrooxy)propoxy)methyl)-3-phenyl-isoxazol-4-yl)benzenesulfonamide HNO$_3$ (90%, 1 mL) was added to Ac$_2$O (6 mL) at −10° C. (ice-MeOH bath), and the solution was stirred at the same temperature for 30 min. The product of Example 26a (910 mg, 2.34 mmol) in THF (10 mL) was added, and the resulting solution was stirred at −10° C. for 20 min. The mixture was then poured into ice containing aqueous Na$_2$CO$_3$ and extracted with EtOAc. The combined extracts were washed with brine, dried over Na$_2$SO$_4$, filtered, and concentrated. Flash chromatography (silica gel, 2:1 EtOAc:Hexane) gave the title compound as a white solid (0.9 g, 86% yield), $^1$H NMR (300 MHz, DMSO-d$_6$) δ 7.87 (d, J=6.1 Hz, 2H), 7.5-7.3 (m, 9H), 4.63 (s, 2H), 4.56 (t, J=6.4 Hz, 2H), 3.58 (t, J=6.1 Hz, 2H), 1.94 (pentet, J=6.2 Hz, 2H). Mass spectrum (API-TIS) m/z 434 (MH$^+$).

Example 27

4-(5-(2-Nitrooxy)ethoxy)methyl)-3-phenylisoxazol-4-yl)benzene-sulfonamide

27a. 4-(5-(2-Hydroxyethoxy)methyl)-3-phenylisoxazol-4-yl)benzenesulfonamide Sodium (0.828 g, 36 mmol) was dissolved in ethylene glycol (15 mL) and to this was added a solution of 4-(5-(chloromethyl)-3-phenylisoxazol-4-yl)benzenesulfonamide (1.80 g, 5.17 mmol, prepared according to the procedure of Talley, J. J., et. al. *J. Med. Chem.* 2000, 43, 775-777.)) in THF (15 mL). The resulting mixture was heated at reflux for 4 hours, then poured into ice containing aqueous NH$_4$Cl, extracted with EtOAc. The combined extracts were washed with water, dried over Na$_2$SO$_4$, filtered, and concentrated. Flash chromatography (silica gel, 1:1 EtOAc:THF) of the residue afforded the title compound as a white solid (1.65 g, 85% yield). $^1$H NMR (300 MHz, CDCl$_3$) δ 7.88 (d, J=8.5 Hz, 2H), 7.38-7.27 (m, 7H), 5.53 (br, 2H), 4.59 (s, 2H), 3.70 (t, J=3.8 Hz, 2H), 3.63 (t, J=3.8 Hz, 2H), 2.63 (br, 1H). Mass spectrum (API-TIS) m/z 375 (MH$^+$).

27b. 4-(5-(2-Nitrooxy)ethoxy)methyl-3-phenylisoxazol-4-yl)benzenesulfonamide Fuming HNO₃ (90%, 1 mL) was added to Ac₂O (6 mL) at −10° C. (ice-MeOH bath), and the solution was stirred at the same temperature for 30 min. The product of Example 27a (1.00 g mg, 2.67 mmol) in THF (10 mL) was added, and the resulting solution was stirred at −10° C. for 20 min. The mixture was then poured into ice containing aqueous Na₂CO₃ and extracted with EtOAc. The combined extracts were washed with brine, dried over Na₂SO₄, filtered, and concentrated. Flash chromatography (silica gel, 2:1 EtOAc:Hexane) gave the title compound as a white solid (0.81 g, 72% yield). $^1$H NMR (300 MHz, CDCl₃) δ 7.89 (d, J=8.4 Hz, 2H), 7.38-7.30 (m, 7H), 5.46 (br, 2H), 4.60 (t, J=3.0 Hz, 2H), 4.58 (s, 2H), 3.83 (t, J=3.0 Hz, 2H), $^{13}$C NMR (75 MHz, CDCl₃) δ 165.5, 161.2, 141.7, 133.6, 130.3, 129.9, 128.4, 127.7, 126.7, 117.4, 71.7, 66.9, 62.3. Mass spectrum (API-TIS) m/z 420 (MH⁺).

Example 28

4-(5-(4-Chlorophenyl)-3-((3-(nitrooxy)propoxy)methyl)pyrazolyl)benzenesulfonamide

28a. 4-(5-(4-Chlorophenyl)-3-((3-hydroxypropoxy)methyl)pyrazolyl)benzenesulfonamide The title compound was prepared using the procedure of Example 20f. $^1$H NMR (300 MHz, CDCl₃) δ 7.76 (d, J=8.5 Hz, 2H), 7.31-7.25(m, 4H), 7.11 (d, J=8.5 Hz, 2H), 6.51 (s, 1H), 6.07 (br, 2H), 4.58 (s, 2H), 3.8-3.7 (m, 4H), 3.1 (br, 1H), 1.9-1.8 (m, 2H). Mass Spectrum (API-TIS) m/z 421 (MH⁺).

28b. 4-(5-(4-Chlorophenyl)-3-((3-(nitrooxy)propoxy)methyl)pyrazolyl)benzenesulfonamide The title compound was prepared from the product of Example 28a using the procedure of Example 20g. $^1$H NMR (300 MHz, CDCl₃) δ 7.80 (d, J=8.4 Hz, 2H), 7.34-7.29(m, 4H), 7.14 (d, J=8.4 Hz, 2H), 6.55 (s, 1H), 5.67 (br, 2H), 4.62-4.57 (m, 4H), 3.7-3.6 (m, 2H), 2.1-2.0 (m, 2H).). Mass spectrum (API-TIS) m/z 467 (MH⁺).

Example 29

4-(3-((3-(Nitrooxy)propoxy)methyl)-5-phenylpyrazolyl)benzenesulfonamide

29a 4-(3-((3-Hydroxypropoxy)methyl)-5-phenylpyrazolyl)benzenesulfonamide

The title compound was prepared using the procedure of Example 20f. $^1$H NMR (300 MHz, CDCl₃) δ 7.74 (d, J=8.8 Hz, 2H), 7.33-7.27 (m, 5H), 7.171 (d, J=8.8 Hz, 2H), 6.52 (s, 1H), 5.95 (br, 2H), 4.62 (s, 2H), 3.8-3.7 (m, 4H), 3.2 (br, 1H), 1.9-1.8 (m, 2H). Mass spectrum (API-TIS) m/z 387 (MH⁺).

29b. 4-(3-((3-(Nitrooxy)propoxy)methyl)-5-phenylpyrazolyl)benzenesulfonamide The title compound was prepared from the product of Example 29a using the procedure of Example 20g. $^1$H NMR (300 MHz, CDCl₃) δ 7.82-7.79 (m, 2H), 7.40-7.33 (m, 5H), 7.23-7.20 (m, 2H), 6.55 (s, 1H), 5.23 (br, 2H), 4.63-4.58 (m, 4H), 3.7-3.6 (m, 2H), 2.1-2.0 (m, 2H). Mass spectrum (API-TIS) m/z 432 (MH⁺).

Example 30

4-(1-Cyclohexyl-3-(2-(nitrooxy)ethyl)pyrazol-5-yl)-1-(methylsulfonyl)benzene

30a. 4-(1-Cyclohexyl-3-vinylpyrazol-5-yl)-1-methylthiobenzene

A solution of BuLi (5.07 mL of 1.6 M solution in hexane, 8.1 mmol) was added to a stirred solution of methyltriphenylphosphoniumbromide (2.3 g, 6.5 mmol) in THF (20 mL) at −78° C. under N₂. The resulting solution was stirred for 30 minutes and then a solution of the product of Example 4c (1.3 g, 4.3 mmol) in THF (10 mL) was added. The cold bath was removed and the mixture was stirred at room temperature for 2 hours. Saturated NH₄Cl (50 mL) was added and the mixture was extracted with EtOAc. The combined organic extracts were dried over Na₂SO₄. The solvent was evaporated and crude product was chromatographed on silica gel eluting with (0.5:10) EtOAC:Hexane to give the title compound (0.92 g, 71% yield) as an oil. $^1$H NMR (300 MHz, CDCl₃) δ 7.21 (d, J=8.4 Hz, 2H), 7.16 (d, J=8.3 Hz, 2H), 6.68 (dd, J=11 and 17.7 Hz, 1H), 6.25 (s, 1H), 5.58 (d, J=17.7 Hz, 1H), 5.16 (d, J=11 Hz, 1H), 3.85-3.96 (m, 1H), 2.42 (s, 3H), 1.50-2.00 (m, 7H), 1.05-1.20 (m, 3H); $^3$C NMR (75 MHz, CDCl₃) δ 149.7, 143.1, 139.2, 129.5, 129.2, 127.4, 126.2, 114.4, 102.1, 57.6, 33.2, 25.5, 25.0, 15.3. Mass spectrum (API-TIS) m/z 299 (MH⁺). Anal. Calcd. for C₁₈H₂₂N₂O₂S.¼ mol H₂O: C, 64.54; H, 6.77; N, 8.36. Found: C, 64.26; H, 6.45; N, 8.32.

30b. 2-(1-Cyclohexyl-5-(4-methylthiophenyl)pyrazol-3-yl)-1-ethan-1-ol

A solution of 1M BH₃.THF complex (6 mL, 6 mmol) was added drop-wise to a stirred solution of product of Example 30a (0.9 g, 3 mmol) in THF at 0° C. and stirred for 45 minutes at 0° C. 10% NaOH (6 mL) followed by 30% H₂O₂ solution (6 mL) were added drop-wise. The product was extracted with EtOAc, dried over Na₂SO₄ and concentrated under reduced pressure. The crude material was chromatographed on silica gel eluting with (1:1) EtOAc:Hexane to give the title compound (0.18 g, 19% yield) as an oil. $^1$H NMR (300 MHz, CDCl₃) δ 7.23 (d, J=8.3 Hz, 2H), 7.17 (d, J=8.3 Hz, 2H), 5.95 (s, 1H), 3.82-3.96 (m, 1H), 3.84 (t, J=5.7 Hz, 2H), 3.30 (br s, 1H), 2.80 (t, J=5.7 Hz, 2H), 2.44 (s, 3H), 1.05-1.95 (m, 10H); $^3$C NMR (75 MHz, CDCl₃) δ 149.5, 142.8, 139.2, 129.2, 127.5, 126.2, 104.7, 61.9, 57.5, 33.3, 30.9, 25.6, 25.1, 15.4.
Mass spectrum (API-TIS) m/z 317 (MH⁺).

30c. 2-(1-Cyclohexyl-3-(2-hydroxyethyl)pyrazol-5-yl)-1-(methylsulfonyl)benzene The title compound-compound (0.18 g, 96% yield) was prepared from the product of Example 30b (0.17 g, 0.53 mmol) and OXONE® (0.66 g, 1.07 mmol) using the procedure for Example 1g. Mp 108° C. $^1$H NMR (300 MHz, CDCl₃) δ 7.95 (d, J=8.1 Hz, 2H), 7.48 (d, J=8.1 Hz, 2H), 6.07 (s, 1H), 3.81-3.94 (m, 1H), 3.83 (t, J=5.9 Hz, 2H), 3.33 (br s, 1H), 3.05 (s, 3H), 2.81 (t, J=5.9 Hz, 2H), 1.50-2.05 (m, 7H), 1.05-1.25 (m, 3H); $^{13}$C NMR (75 MHz, CDCl₃) 149.8, 141.2, 140.1, 136.4, 129.5, 127.7, 105.6, 61.7, 57.9, 44.3, 33.2, 30.9, 25.4, 24.9. Mass spectrum (API-TIS) m/z 349 (MH⁺).

30d. 4-(1-Cyclohexyl-3-(2-(nitrooxy)ethyl)pyrazol-5-yl)-1-(methylsulfonyl)benzene The title compound (0.12 g, 66% yield) was prepared from the product of Example 30c (0.16 g, 0.45 mmol), fuming HNO$_3$ (94 µL, 0.14 g, 2.24 mmol) and Ac$_2$O (0.34 mL, 0.37 g, 3.58 mmol) using the procedure for Example 1h. Mp 117° C. $^1$H NMR (300 MHz, CDCl$_3$) δ 7.98 (d, J=8.3 Hz, 2H), 7.50 (d, J=8.3 Hz, 2H), 6.15 (s, 1H), 4.70 (t, J=6.7 Hz, 2H), 3.85-4.05 (m, 1H), 3.07 (s, 3H), 3.04-3.08 (m, 2H), 1.60-2.00 (m, 7H), 1.10-1.30 (m, 3H); $^{13}$C NMR (75 MHz, CDCl$_3$) δ 146.5, 141.9, 140.6, 135.9, 129.7, 127.8, 106.0, 71.9, 58.4, 44.3, 33.1, 26.0, 25.5, 24.8. Mass spectrum (API-TIS) m/z 394 (MH$^+$).

Example 31

4-(1-Cyclohexyl-3-(3-(nitrooxy)propyl)pyrazol-5-yl)-1-(methylsulfonyl)benzene

31a. Methyl (2E)-3-(1-cyclohexyl-5-(4-methylthiophenyl)pyrazol-3-yl)prop-2-enoate A solution of BuLi (3.2 mL of 1.6 M solution in hexane, 5.2 mmol) was added to a stirred solution of trimethylphosphonoacetate (0.92 g, 5.08 mmol) in THF (10 mL) at −78° C. under N$_2$. The resulting solution was stirred for 30 minutes and a solution of the product of Example 4c (1.22 g, 4.06 mmol) in THF (10 mL) was added. The cold bath was removed and the mixture was stirred at room temperature for 2 hours. Water (50 mL) was added and the mixture was extracted with EtOAc. The combined organic extracts were dried over Na$_2$SO$_4$. The solvent was evaporated and crude product was chromatographed on silica gel eluting with (1:9) EtOAc:Hexane to give the title compound (1.12 g, 77% yield) as an oil. $^1$H NMR (300 MHz, CDCl$_3$) δ 7.71 (d, J=16 Hz, 1H), 7.32 (d, J=6.5 Hz, 2H), 7.23 (d, J=6.8 Hz, 2H), 6.43 (s, 1H), 6.38 (d, J=16 Hz, 1H), 4.03-4.08 (m, 1H), 3.93 (s, 3H), 2.52 (s, 3H), 1.55-2.00 (m, 7H), 1.22-1.28 (m, 3H); $^{13}$C NMR (75 MHz, CDCl$_3$) δ 167.4, 146.8, 143.7, 139.8, 137.4, 129.3, 126.7, 126.2, 118.0, 104.6, 58.1, 51.4, 33.2, 25.5, 25.0, 15.3. Mass spectrum (API-TIS) m/z 357 (MH$^+$).

31b. (2E)-3-(1-Cyclohexyl-5-(4-methylthiophenyl)pyrazol-3-yl)prop-2-en-1-ol

The title compound (0.62 g, 60% yield) was prepared from the product of Example 31a (1.12 g, 3.4 mmol) and lithium aluminum hydride (3.4 mL of 1M solution in THF, 0.13 g, 3.4 mmol) using the procedure for Example 1f. Mp 90° C. $^1$H NMR (300 MHz, CDCl$_3$) δ 7.25-7.35 (m, 4H), 6.68 (d, J=16 Hz, 1H), 6.32-6.39 (m, 1H), 6.31 (s, 1H), 4.30 (d, J=5.5 Hz, 2H), 3.98-4.06 (m, 1H), 2.53 (s, 3H), 1.60-1.95 (m, 7H), 1.10-1.30 (m, 3H); $^{13}$C NMR (75 MHz, CDCl$_3$) δ 148.8, 143.3, 139.4, 129.6 129.3, 127.5, 123.9, 102.6, 63.6, 57.7, 33.3, 25.6, 25.1, 15.4. Mass spectrum (API-TIS) m/z 329 (MH$^+$).

31c. 4-(3-((1E)-3-Hydroxyprop-1-enyl)-1-cyclohexylpyrazol-5-yl)-1(methylsulfonyl)benzene The title compound (0.52 g, 76% yield) was prepared from the product of Example 31b (0.62 g, 1.89 mmol) and OXONE® (1.45 g, 2.36 mmol) using the procedure for Example 1g. Mp 121° C. $^1$H NMR (300 MHz, CDCl$_3$) δ 7.99 (d, J=8.4 Hz, 2H), 7.52 (d, J=8.4 Hz, 2H), 6.49 (d, J=16 Hz, 1H), 6.35 (s, 1H), 6.29-6.38 (m, 1H), 4.27 (d, J=5.5 Hz, 2H), 3.90-3.98 (m, 1H), 3.09 (s, 3H), 1.60-2.10 (m, 7H), 1.10-1.30 (m, 3H); $^{13}$C NMR (75 MHz, CDCl$_3$) δ 149.1, 141.7, 140.4, 136.4, 130.3, 129.7, 127.8, 123.2, 103.6, 63.4, 58.2, 44.4, 33.3, 25.5, 24.9. Mass spectrum (API-TIS) m/z 361 (MH$^+$).

31d. 4-(1-Cyclohexyl-3-(3-hydroxypropyl)pyrazol-5-yl)-1-(methylsulfonyl)benzene

The product of Example 31c (0.52 g, 1.44 mmol) was dissolved in EtOH (20 mL) and degassed with N$_2$. 10% Pd/C (2 spatula) was added and hydrogenated (20 p.s.i.) for 3 hours. The carbon residue was removed by filtration and the solvent was removed under reduced pressure. The crude material was chromatographed on silica gel eluting with (2:1) EtOAc:Hexane to give the title compound (0.37 g, 71% yield) as a white solid. Mp 138° C. $^1$H NMR (300 MHz, CDCl$_3$) δ 8.03 (d, J=8.2 Hz, 2H), 7.54 (d, J=8.1 Hz, 2H), 6.11 (s, 1H), 3.90-4.00 (m, 1H), 3.75 (t, J=5.8 Hz, 2H), 3.30 (br s, 1H), 3.13 (s, 3H), 2.81 (t, J=6.9 Hz, 2H), 1.60-2.10 (m, 9H), 1.15-1.30 (m, 3H); $^{13}$C NMR (75 MHz, CDCl$_3$) δ 151.7, 141.4, 140.2, 136.6, 129.6, 127.8, 105.5, 62.7, 58.0., 44.4, 33.4, 31.5, 25.5, 24.9. Mass spectrum (API-TIS) m/z 363 (MH$^+$).

31e. 4-(1-Cyclohexyl-3-(3-(nitrooxy)propyl)pyrazol-5-yl)-1-(methylsulfonyl)benzene The title compound (0.11 g, 70% yield) was prepared from the product of Example 31d (0.14 g, 0.38 mmol), fuming HNO$_3$ (81 µL, 0.12 g, 1.93 mmol) and Ac$_2$O (0.29 mL, 0.31 g, 3.09 mmol) by following the procedure for the Example 1h. Mp 77° C. $^1$H NMR (300 MHz, CDCl$_3$) δ 8.04 (d, J=8.1 Hz, 2H), 7.55 (d, J=8.1 Hz, 2H), 6.19 (s, 1H), 4.53 (t, J=6.4 Hz, 2H), 3.95-4.07 (m, 1H), 3.11 (s, 3H), 2.85 (t, J=7.45 Hz, 2H), 1.69-2.20 (m, 9H), 1.10-1.30 (m, 3H); $^{13}$C NMR (75 MHz, CDCl$_3$) δ 150.1, 142.5, 140.9, 135.2, 129.7, 127.9, 105.7, 72.4, 58.8, 44.3, 32.8, 26.4, 25.4, 24.6, 23.7. Mass spectrum (API-TIS) m/z 408 (MH$^+$).

Example 32

4-(5-((2,2-Difluoro-3-(nitrooxy)propoxy)methyl)-3-phenylisoxazol-4-yl)benzenesulfoamide 32a. 2,2-Difluoropropane-1,3-diol To a stirred solution of diethyldifluoromalonate (5.00 g, 25.5 mmol) in THF (100 mL) at 0° C. was added lithium aluminum hydride (1.0 M in THF, 61 mL, 61 mmol) dropwise under nitrogen atmosphere. The reaction mixture was stirred for 3 hours, and then cautiously quenched by solid sodium sulfate decahydrate (15 g). The resulting mixture was aged for 30 minutes, filtered, and the filter cake was thoroughly rinsed with 1:1 mixture of methanol and THF. The combined filtrates were dried over magnesium sulfate, filtered, and concentrated to give the title compound (1.58 g, 55% yield) as a white solid which required no further purification (the yield can be improved up to 82% when the reaction was performed at −78° C.): $^1$H NMR (300 MHz, DMSO-d$_6$) δ 5.41 (br, 2H), 3.66 (t, J ($^{19}$F, $^1$H)=13.8 Hz, 4H); $^{13}$C NMR (75 MHz, DMSO-d$_6$) 6123.7 (t, J ($^{19}$F, $^3$C)=242 Hz), 60.9 (t, J ($^{19}$F, $^{13}$C)=29.4 Hz); LRMS (API-TIS) m/z 113.2 ((M+H)$^+$).

32b. 4-(5-(Chloromethyl)-3-phenylisoxazol-4-yl)benzenesulfonamide

This compound was prepared according to the method of Talley, J. J. et al. *J. Med. Chem.* 43, 775-777, 2000.

32c. 4-(5-((2,2-Difluoro-3-hydroxypropoxy)methyl)-3-phenylisoxazol-4-yl)benzenesulfonamide To a stirred solution of the product of Example 32a (3.37 g, 30 mmol) in THF (100 mL) was added NaH (0.72 g, 30 mmol)

portionwise. The mixture was stirred at ambient temperature until gas evolution was no longer observed (ca. 15 min). The product of Example 32b (2.09 g, 6.00 mmol) in THF (20 mL) was added, and the reaction mixture was heated at reflux for 35 minutes, at which point the starting chloride was completely consumed as indicated by TLC. Upon cooling, the mixture was poured into aqueous ammonium chloride, extracted with ethyl acetate (2×). The combined organic layers were washed with water (3×), dried over sodium sulfate, filtered, and concentrated. Chromatography of the residue (silica gel, 5% methanol in dichloromethane) gave the title compound (1.96 g, 77% yield) as a beige solid. Mp 93-94° C. $^1$H NMR (300 MHz, DMSO-$d_6$) δ 7.91 (d, J=8.5 Hz, 2H), 7.52-7.40 (m, 9H), 5.64 (t, J=6.2 Hz, 1H), 4.78 (s, 2H), 3.89 (t, J ($^{19}$F, $^1$H)=13.5 Hz, 2H), 3.68 (td, J ($^{19}$F, $^1$H)=13.8 Hz, J ($^1$H, $^1$)=6.2 Hz, 2H). LRMS (API-TIS) m/z 425.2 ((M+H)$^+$).

32d. 4-(5-((2,2-Difluoro-3-(nitrooxy)propoxy)methyl)-3-phenylisoxazol-4-yl)benzenesulfoamide Nitric acid (90%, 1.41 mL, 30 mmol, 20 equiv.) was added to stirred acetic anhydride (4.3 mL) at 0° C. After 15 minutes, a pre-cooled (0° C.) solution of the product of Example 32c (0.637 g, 1.50 mmol) in THF (5 mL) was added, and the reaction mixture was stirred at the same temperature for 45 minutes. TLC indicated complete conversion of the starting alcohol. The mixture was diluted with ethyl acetate, washed with ice-cooled 2M aqueous sodium carbonate (2×), and water. The organic layer was dried over sodium sulfate, filtered, and concentrated. The resulting semisolid was purified by crystallization from dichloromethane/hexanes (1:1) to give the title compound (0.605 g, 86% yield) as white needles. Mp 69° C.; $^1$H NMR (300 MHz, CDCl$_3$) δ 7.94 (d, J=8.5 Hz, 2H), 7.42-7.35 (m, 7H), 5.11 (br, 2H), 4.77 (t, J ($^{19}$F, $^1$H)=11.9 Hz, 2H), 4.69 (s, 2H), 3.87 (t, J ($^{19}$F, $^1$H)=12.0 Hz, 2H); LRMS (API-TIS) m/z 470.0 ((M+H)$^+$).

Example 33

4-(3-Phenyl-5-((2,2,3,3-tetrafluoro-4-(nitrooxy)butoxy)methyl)isoxazol-4-yl)benzenesulfonamide

33a. 4-(3-Phenyl-5-(2,2,3,3-tetrafluoro-4-hydroxy)methyl)isoxazol-4-yl)benzenesulfonamide To a stirred solution of 2,2,3,3-tetrafluorobutane-1,4-diol (5.78 g, 35.7 mmol) in THF (150 mL) was added NaH (0.857 g, 35.7 mmol) portionwise at room temperature. After 15 minutes, the product of Example 32b (2.49 g, 7.14 mmol) in THF (20 mL) was added, and the reaction mixture was heated at reflux under nitrogen atmosphere for 55 minutes, at which point the starting chloride was no longer observable by TLC. Upon cooling, the mixture was diluted with ethyl acetate, washed with aqueous ammonium chloride, water, and brine. The organic layer was dried over sodium sulfate, filtered, and concentrated. Crystallization of the residue from ethyl acetate gave the title compound (2.66 g, 79% yield) as white flakes. Mp 70° C.; $^1$H NMR (300 MHz, DMSO-$d_6$) δ 7.86 (d, J=8.3 Hz, 2H), 7.53-7.36 (m, 9H), 5.88 (t, J=4.8 Hz, 1H), 4.79 (s, 2H), 4.12 (t, J ($^{19}$F, $^1$H)=15.5 Hz, 2H), 3.81 (td, J ($^{19}$F, $^1$H)=15.2 Hz, J ($^1$H, $^1$H)=4.8 Hz, 2H); LRMS (API-TIS) m/z 475.2 ((M+H)$^+$).

33b. 4-(3-Phenyl-5-(2,2,3,3-tetrafluoro-4-hydroxy)methyl)isoxazol-4-yl)benzenesulfonamide Nitric acid (90%, 4.66 mL, 100 mmol, 18 equiv.) was added to stirred acetic anhydride (14 mL) at 0° C. After 15 min, a pre-cooled (0° C.) solution of the product of Example 33a (2.66 g, 5.60 mmol) in THF (30 mL) was added, and the reaction mixture was stirred under ambient atmosphere for 75 minutes. TLC indicated complete conversion of the starting alcohol. The mixture was diluted with ethyl acetate, washed with ice plus 2M aqueous sodium carbonate (2×), and water. The organic layer was dried over sodium sulfate, filtered, and concentrated. The resulting solid was purified by crystallization from dichloromethane/hexanes (1:1) to furnish the title compound (2.36 g, 81% yield) as white prisms. Mp 46° C. $^1$H NMR (300 MHz, CDCl$_3$) δ 7.92 (d, J=8.5 Hz, 2H), 7.41-7.33 (m, 7H), 5.37 (br, 2H), 4.95 (t, J ($^{19}$F, $^1$H)=13.7 Hz, 2H), 4.71 (s, 2H), 4.05 (t, J ($^{19}$F, $^1$H)=13.2 Hz, 2H). LRMS (API-TIS) m/z 520.2 ((M+H)$^+$).

Example 34

4-(5-((2,2,3,3,4,4-Hexafluoro-5-(nitrooxy)pentyloxy)methyl)-3-phenylisoxazol-4-yl)benzenesulfonamide

34a. 4-(5-((2,2,3,3,4,4-Hexafluoro-5-hydroxypentyloxy)methyl)-3-phenylisoxazol-4-yl)benzenesulfonamide To a stirred solution of 2,2,3,3,4,4-hexafluoropentane-1,5-diol (6.36 g, 30 mmol) in THF (100 mL) was added sodium hydride (0.72 g, 30 mmol) in small portions. The mixture was stirred at ambient temperature until hydrogen evolution had ceased (ca. 10 min). The product of Example 32b (2.12 g, 6.09 mmol) in THF (25 mL) was added, and the reaction mixture was heated at reflux under nitrogen atmosphere for 80 minutes, at which point the starting chloride. was completely converted as judged by TLC. The mixture was poured into ice plus aqueous ammonium chloride with swirling, and extracted with ethyl acetate (2×). The combined organic extracts were washed with water, dried over sodium sulfate, filtered, and concentrated. Chromatography of the residue (silica gel, 5% ethanol in ethyl acetate) afforded the title compound (2.62 g, 82% yield) as a white crystalline solid. Mp 50-51° C.; $^1$H NMR (300 MHz, DMSO-$d_6$) δ 7.90 (d, J=8.3 Hz, 2H), 7.57-7.41 (m, 9H), 6.00 (t, J=5.6 Hz, 1H), 4.86 (s, 2H), 4.27 (t, J ($^{19}$F, $^1$H)=15.2 Hz, 2H), 3.97 (td, J ($^{19}$F, $^1$H)=15.7 Hz, J ($^1$H, $^1$H)=5.6 Hz, 2H); LRMS (API-TIS) m/z 525.2 ((M+H)$^+$).

34b. 4-(5-((2,2,3,3,4,4-Hexafluoro-5-(nitrooxy)pentyloxy)methyl)-3-phenylisoxazol-4-yl)benzenesulfonamide Nitric acid (90%, 4.19 mL, 90 mmol, 30 equiv.) was added to stirred acetic anhydride (12.6 mL) at 0° C. After 15 min, a pre-cooled (0° C.) solution of the product of Example 34a (1.58 g, 3.01 mmol) in THF (20 mL) was added, and the reaction mixture was stirred at 0° C. under ambient atmosphere for 105 minutes. TLC indicated complete conversion of the starting alcohol. The mixture was diluted with ethyl acetate, washed with ice water plus 2M aqueous sodium carbonate (2×), and water. The organic layer was dried over sodium sulfate, filtered, and concentrated. The resulting oil was purified by crystallization twice from dichloromethane/hexanes (1:1) to give the title compound (1.25 g, 73% yield) as a white solid.

Mp 38-39° C. $^1$H NMR (300 MHz, CDCl$_3$) δ 7.93 (dd, J=6.9, 1.7 Hz, 2H), 7.45-7.33 (m, 7H), 5.23 (br, 2H), 4.99 (t, J ($^{19}$F, $^1$H)=13.5 Hz, 2H), 4.72 (s, 2H), 4.10 (t, J ($^{19}$F, $^1$H)=13.7 Hz, 2H). LRMS (API-TIS) m/z 570.2 ((M+H)$^+$).

Example 35

1-(5-(4-(Methysulfonyl)phenyl)-1-(2-pyridyl)pyrazol-3-yl)-2-(nitrooxy)ethan-1-one

35a. 2-Bromo-1-(5-(4-methylthiophenyl)-1-(2-pyridyl)pyrazol-3-yl)ethan-1-one To a stirred solution of methyl 5-(4-methylthiophenyl)-1-(2-pyridyl)pyrazole-3-carboxylate (prepared as described in Penning, T. D. et al. *J. Med. Chem.* 1997, 40, 1347-1365.; 0.39 g, 1.2 mmol) and dibromomethane (0.17 mL, 2.4 mmol) in THF (10 mL) at −78° C. under nitrogen atmosphere was added methyllithium (1.6 M in ether, 1.4 mL, 2.2 mmol). After being stirred at the same temperature for 90 minutes, the solution was quenched with aqueous sodium bicarbonate, and extracted with ethyl acetate. The combined organic extracts were dried over sodium sulfate, filtered, and concentrated. Chromatography of the residue on silica gel (2:1 EtOAc:hexane) gave the title compound (0.32 g, 69% yield) as a white foam. $^1$H NMR (300 MHz, CDCl$_3$) δ 8.42-8.40 (m, 1H), 7.83 (m, 1H), 7.55-7.51 (m, 1H), 7.17-7.09 (m, 4H), 7.02 (s, 1H), 4.70 (s, 2H), 2.46 (s, 3H); LRMS (API-TIS) m/z 388 and 390 (MH$^+$).

35b. 2-Bromo-1-(5-(4-(methylsulfonyl)pyrazol-3-yl)ethan-1-one

To a stirred solution of the product of Example 35a (0.32 g, 0.823 mmol) in methanol (15 mL) was added OZONE® (1.01 g, 1.65 mmol) in water (10 mL). After being stirred at ambient temperature for 30 minutes, the mixture was extracted with ethyl acetate, dried over sodium sulfate, filtered, and concentrated. Chromatography of the residue on silica gel (2:1 EtOAc:hexane) gave the title compound (0.34 g) as a white solid. Mp 116° C. $^1$H NMR (300 MHz, CDCl$_3$) δ 8.32-8.30 (m, 1H), 7.95-7.91 (m, 3H), 7.79-7.76 (m, 1H), 7.50-7.36 (m, 3H), 7.14 (s, 1H), 4.70 (s, 2H), 3.10 (s, 3H). LRMS (API-TIS) m/z 420 and 422 (MH$^+$).

35c. 1-(5-(4-(Methysulfonyl)phenyl)-1-(2-pyridyl)pyrazol-3-yl)-2-(nitrooxy)ethan-1-one To a stirred solution of the product of Example 35b (0.21 g, 0.499 mmol) in acetonitrile (10 mL) was added silver nitrate (0.425 g, 2.5 mmol). After being stirred at ambient temperature for 20 hours, the mixture was concentrated and chromatographed on silica gel (1:1 EtOAc:hexane) to give the title compound (0.19 g) as a white solid. Mp 82-84° C. $^1$H NMR (300 MHz, CDCl$_3$) δ 8.34-8.33 (m, 1H), 7.95-7.91 (m, 3H), 7.75-7.72 (m, 1H), 7.50-7.22 (m, 3H), 7.15 (s, 1H), 5.78 (s, 2H), 3.10 (s, 3H). LRMS (API-TIS) m/z 403.2 (MH$^+$).

Example 36

4-(5-(Chlorophenyl)-3-((3-(nitrooxy)propoxy)methyl)benzene-sulfonamide

36a. 5-(4-Chlorophenyl)-1-(4-sulfamoylphenyl)pyrazol-3-yl)methyl methylsulfonate To a stirred solution of 4-(5-(4-chlorophenyl)-3-(hydroxymethyl)pyrazoyl)-benzenesulfonamide (prepared as described in Penning, T. D. et al. *J. Med. Chem.* 1997, 40, 1347-1365; 8.50 g, 23.2 mmol) in THF (200 mL) were added MeSO$_2$Cl (1.80 mL, 232 mmol), di-isopropylethylamine (4.36 mL, 25 mmol). After being stirred at room temperature for 90 minutes, the mixture was concentrated, poured into 2 N HCl, and extracted with ethyl acetate. The organic layer was dried over sodium sulfate, filtered, and concentrated to give the title compound (10 g) as a white foam, which was used without further purification.

36b. 4-(5-(4-Chlorophenyl)-3-((3-hydroxypropoxy)methyl)pyrazolyl)-benzenesulfonamide Sodium (0.69 g, 30 mmol) was dissolved in 1,3-dihydroxypropane (15 mL). The product of Example 36b (4.21 g, 10 mmol) in THF (50 mL) was added, and the mixture was heated at reflux for 5 hours, and then poured into ice plus aqueous ammonium chloride. The mixture was extracted with ethyl acetate, washed with brine, dried over sodium sulfate, filtered, and concentrated. The resulting solid was purified by crystallization from 1:5 MeOH:CHCl$_3$ to give the title compound (2.12 g) as white needles. Mp 96° C. $^1$H NMR (300 MHz, CDCl$_3$) δ 7.77 (d, J=8.7 Hz, 2H), 7.31-7.25 (m, 4H), 7.13-7.09 (m, 2H), 6.51 (s, 1H), 6.07 (br, 2H), 4.58 (s, 2H), 3.75-3.70 (m, 4H), 3.18 (br, 1H), 1.85-1.80 (m, 2H). LRMS (API-TIS) m/z 422.2 (MH$^+$).

36c. 4-(5-(Chlorophenyl)-3-((3-(nitrooxy)propoxy)methyl)benzene-sulfonamide Nitric acid (90%, 1.2 mL, 25 mmol) and acetic anhydride (3.6 mL) were mixed and stirred at 0° C. for 15 min, the product of Example 36b (1.23 g, 2.92 mmol) in THF (10 mL) was then added. After being stirred at 0° C. for 20 minutes, the mixture was poured into ice plus 2M sodium carbonate, extracted with ethyl acetate, washed with brine, dried over sodium sulfate, filtered, and concentrated. The residue was purified by crystallization from 1:1 dichloromethane:hexanes to give the title compound (1.11 g) as a yellow solid. Mp 88° C. $^1$H NMR (300 MHz, CDCl$_3$) δ 7.80 (d, J=8.6 Hz, 2H), 7.34-7.29 (m, 4H), 7.14 (d, J=8.6 Hz, 2H), 6.55 (s, 1H), 5.67 (br s, 2H), 4.61-4.57 (m, 4H), 3.68 (t, J=5.9 Hz, 2H), 2.04 (m, 2H). LRMS (API-TIS) m/z 467 (MH$^+$).

Example 37

4-(5-((2-(Nitrooxy)ethyl)sulfonyl)ethoxy)methyl)-3-phenylisoxazol-4-yl)benzenesulfonamide

37a. 4-(5-((2-(2-Hydroxyethylthio)ethoxy)methyl)-3-phenylisoxazol-4-yl)benzenesulfonamide Sodium (0.69 g, 30 mmol) was dissolved in 2,2'-thiodiethanol (10 mL) at 50° C. 4-((5-Chloromethyl-3-phenyl)-4-isoxazolyl)benzenesulfonamide (synthesized as described in Talley et al.; *J. Med. Chem.* 2002, 43, 775-777; 1.19 g, 3.41 mmol) in THF (25 mL) was added, and the solution was heated at reflux under nitrogen atmosphere for 150 minutes. The mixture was poured into aqueous ammonium chloride, extracted with EtOAc, washed with water, dried over sodium sulfate, filtered, and concentrated to give an oil (2.38 g), which was used without further purification.

37b. 4-(5-((2-((2-Hydroxyethyl)sulfonyl)ethoxy)methyl)-3-phenylisoxazol-4-yl)benzenesulfonamide To a stirred solution of the product of Example 37a (2.38 g crude) in methanol (150 mL) was added OXONE® (16.4 g, 26.6 mmol) in water (150 mL). After being stirred at room temperature for 95 minutes, the mixture was poured into water, and extracted with ethyl acetate. The combined organic extracts were washed with water, dried over sodium sulfate, filtered, and concentrated. Chromatography of the residue on silica gel (EtOAc) gave the title compound (1.28 g), as a white solid. Mp 81° C. $^1$H NMR (300 MHz, THF-d$_8$) δ 7.97 (d, J=8.6 Hz, 2H), 7.7-7.4 (m, 7H), 6.22 (br, 2H), 4.75 (s, 2H), 4.03-3.88 (m, 4H), 3.49-3.40 (m, 2H), 3.19-3.08 (m, 2H), 3.03 (br, 1H). LRMS (API-TIS) m/z 467.2 (MH$^+$).

37c. 4-(5-((2-(Nitrooxy)ethyl)sulfonyl)ethoxy)methyl)-3-phenylisoxazol-4-yl)benzenesulfonamide Nitric acid (90%, 2.5 mL, 51 mmol) and acetic anhydride (8 mL) were mixed and stirred at 0° C. for 15 minutes, the product of Example 37b (1.08 g, 2.31 mmol) in THF (10 mL) was then added. After being stirred at 0° C. for 20 minutes, the mixture was poured into ice plus 2M sodium carbonate, extracted with ethyl acetate, washed with brine, dried over sodium sulfate, filtered, and concentrated. The residue was purified by crystallization from 3:1 dichloromethane:hexanes to give the title compound (0.81 g) as a white solid. Mp 62-63° C. $^1$H NMR (300 MHz, THF-d$^8$) δ 7.77 (d, J=8.3 Hz, 2H), 7.32-7.19 (m, 7H), 6.47 (br, 2H), 4.74 (t, J =5.9 Hz, 2H), 4.53 (s, 2H), 3.83 (t, J=6.0 Hz, 2H), 3.41 (t, J=5.8 Hz, 2H), 3.25 (t, J=5.8 Hz, 2H). LRMS (API-TIS) m/z 467.2 (MH$^+$). LRMS (API-TIS) m/z 512.2 (MH$^+$).

Example 38

1-(1-Cyclohexyl-3-(((2-hydroxyethyl)amino)methyl)pyrazol-5-yl)-4-(methylsulfonyl)benzene

38a. 1-(1-Cyclohexyl-3-(hydroxymethyl)pyrazol-5-yl)-4-(methylsulfonyl)benzene The product of Example 4b (1.64 g, 5.43 mmol) was dissolved in MeOH/H$_2$O (6 mL/1 mL) and OXONE® was added (6.67 g, 10.86 mmol) and the mixture stirred at room temperature overnight. The resulting solid was removed via filtration and washed with CH$_2$Cl$_2$. The filtrate was collected and diluted with additional CH$_2$Cl$_2$ (10 mL) and the organic layer separated, dried, and the solvent removed under reduced pressure to give the title compound as a yellow solid (1.55 g, 86% yield). $^1$H NMR (300 MHz, CDCl$_3$) δ 8.04 (d, 2H, J=8.3), 7.55 (d, 2H, J=8.3), 6.31 (s, 1H), 4.73 (s, 2H), 3.99 (m, 1H), 3.12 (s, 3H), 2.04-2.02 (m, 2H), 1.89-1.86 (m, 4H), 1.66 (m, 2H), 1.27-1.25 (m, 2H). Mass spectrum (API-TIS) m/z 335 (M+1).

38b. 1-(3-(Bromomethyl)-1-cyclohexylpyrazol-5-yl)-4-(methylsulfonyl)benzene The product of Example 38a (1.5o g, 4.49 mmol) was dissolved in CH$_2$Cl$_2$ (10 mL) and PBr$_3$ (853.1 mg, 8.98 mmol) was added. The mixture was stirred overnight at room temperature. Water (10 mL) was slowly added and the organics separated, washed with brine, and dried (MgSO$_4$). The solvent was removed under reduced pressure to give of the title compound as a white solid (1.29 g, 72% yield). $^1$H NMR (300 MHz, CDCl$_3$) δ 8.03 (d, 2H, J=7.4), 7.55 (d, 2H, J=7.4), 6.34 (s, 1H), 4.51 (s, 2H), 4.01-3.92 (m, 1H), 3.11 (s, 3H), 2.02-1.98 (m, 2H), 1.88-1.85 (m, 4H), 1.64 (m, 2H), 1.24 (m, 2H). Mass spectrum (API-TIS) ml/z 398 (M+1).

38c. 1-(1-Cyclohexyl-3-(((2-hydroxyethyl)amino)methyl)pyrazol-5-yl)-4-(methylsulfonyl)benzene The product of Example 38b (480 mg, 1.209 mmol) and ethanolamine (109.4 uL, 1.813 mmol) were dissolved in acetonitrile (10 mL) and stirred at room temperature for 48 hours. The acetonitrile was removed under reduced pressure and the resulting residue dissolved in CH$_2$Cl$_2$ (15 mL). The sample was washed with water (2×8 mL) and brine and dried (MgSO$_4$). The solvent was removed under reduced pressure to give of the title compound as a yellow oil (37 mg, 8% yield). $^1$H NMR (300 MHz, CDCl$_3$) δ 8.03 (d, 2H, J=8.3), 7.54 (d, 2H, J=8.3), 6.22 (s, 1H), 3.97 (br m, 1H), 3.86 (s, 2H), 3.67 (t, 2H, J=5.1), 3.46 (s, 1H), 3.11 (s, 3H), 2.88 (t, 2H, J=5.1), 2.04-2.01 (m, 2H), 1.88-1.85 (m, 4H), 1.65 (m, 2H), 1.27-1.25 (m, 2H). Mass spectrum (API-TIS) m/z 378 (M+1).

Example 39

4-(1-(4-Methoxyphenyl)-3-((3-(nitrooxy)propoxy)methyl)pyrazol-5-yl)-1-(methylsulfonyl)benzene Nitric acid (3 mL) was cooled to 0° C. and the product of Example 10d (31.2 mg, 0.075 mmol) in CH$_3$CN (2 mL) was added drop-wise. The mixture was stirred at 0° C. for 6 hours and diluted with H$_2$O (3 mL). The sample was neutralized with solid Na$_2$CO$_3$ and the aqueous portion extracted with CH$_2$Cl$_2$ (3×10 mL). The combined organic extracts were dried (MgSO$_4$), evaporated to give the title compound as a yellow oil (30.0 mg, 87 % yield). $^1$H NMR (300 MHz, CDCl$_3$) δ 7.84 (d, 2H, J=8.5), 7.40 (d, 2H, J=8.5), 7.17 (d, 2H, J=8.9), 6.87 (d, 2H, J=8.9) 6.60 (s, 1H), 4.61-4.56 (m, 4H), 3.81 (s, 3H), 3.67 (t, 2H, J=6.1), 3.04 (s, 3H), 2.05-2.01 (t, 2H, J=6.1). Mass spectrum (API-TIS) m/z 462 (M+1).

Example 40

4-(1-(4-Methyl-3-nitrophenyl)-3-((3-(nitrooxy)propoxy)methyl)pyrazol-5-yl)-1-(methylsulfonyl)benzene The product of Example 8d (41.9 mg, 0.105 mmol) was cooled to 0° C. and cold HNO$_3$ (5 mL) was added drop-wise. The mixture was stirred at 0° C. for 2.5 hours and diluted with H$_2$O (10 mL). The sample was neutralized with solid Na$_2$CO$_3$ and the aqueous layer extracted with CH$_2$Cl$_2$ (3×10 mL). The combined organic extracts were dried (MgSO$_4$), evaporated to give the title compound as a yellow oil (5 mg, 10% yield). $^1$H NMR (300 MHz, CDCl$_3$) δ 7.92 (d, 2H, J =8.3), 7.91 (s, 1H), 7.44 (d, 2H, J=8.3), 7.45-7.43 (m, 1H), 7.33-7.32 (m, 1H), 6.63 (s, 1H), 4.63-4.56 (m, 4H), 3.68 (t, 2H, J=6.0), 3.07 (s, 3H), 2.61 (s, 3H), 2.05 (t, 2H, J=6.0). Mass spectrum (API-TIS) m/z 491 (M+1).

Example 41

1-(3-((1E)-3-(Nitrooxy)prop-1-enyl)-1-cyclohexylpyrazol-5-yl)-4-(methylsulfonyl)benzene The title compound was prepared as a white foam from the product of Example 31c (33 mg, 0.09 mmol) in CHCl$_3$ (0.3 mL), fuming HNO$_3$ (19 μL, 29 mg, 0.46 mmol) and Ac$_2$O (69 μL, 74.9 mg, 0.73 mmol) following the procedure for the preparation of Example 1h. $^1$H NMR (300 MHz, CDCl$_3$) δ 8.06 (d, J=8.3 Hz, 2H), 7.57 (d, J=6.7 Hz, 2H), 6.84 (d, J=16.0 Hz, 1H), 6.44 (s, 1H), 6.20-6.30 (m, 1H), 5.07 (d, J=6.8 Hz, 2H), 3.89-4.10 (m, 1H), 3.14 (s, 3H), 1.92-2.10 (m, 2H), 1.78-1.92 (m, 4H), 1.57-1.75 (m, 2H), 1.15-1.35 (m, 2H). Mass spectrum (API-TIS) m/z 406 (MH$^+$).

Example 42

4-(5-(4-(Methylsulfonyl)phenyl)-3-(4-(nitrooxy))pyrazolyl)benzene carbonitrile

42a. Methyl 1-(4-cyanophenyl)-5-(4-methylthiophenyl)pyrazole-3-carboxylate

The title compound was prepared from the product of Example 1d (5 g, 20 mmol) and 4-cyanophenylhydrazine hydrochloride (4.4 g, 26 mmol) in acetic acid (120 mL) following the procedure for the preparation of Example 1e. Purification gave a yellow solid (5.3 g, 76% yield). Mp 177-179° C. $^1$H NMR (300 MHz, CDCl$_3$) δ 7.66 (d, J=8.7 Hz, 2H), 7.48 (d, J=8.7 Hz, 2H), 7.21 (d, J=8.5 Hz, 2H), 7.11 (d, J=8.5 Hz, 2H), 7.03 (s, 1H), 3.98 (s, 3H), 2.50 (s, 3H); Mass spectrum (API-TIS) m/z 350 (MH$^+$); Anal. calcd for C$_{19}$H$_{15}$N$_3$O$_2$S: C, 65.31; H, 4.33; N, 12.03. Found: C, 65.37; H, 4.12; N, 12.01.

42b. 1-(4-Cyanophenyl)-5-(4-methylthiophenyl)-pyrazol-3-yl)carboxamido-N-methoxy-N-methyl The title compound was prepared from the product of Example 42a (1.77 g, 5.05 mmol), trimethylaluminum (5.05 mL of 2M solution in hexane, 0.73 g, 10.1 mmol) and dimethylhydroxylamine hydrochloride (0.99 g, 10.1 mmol) following the procedure for the preparation of Example 3c. Purification gave a white solid (1.8 g, 94% yield). Mp 146-147° C. $^1$H NMR (300 MHz, CDCl$_3$) δ 7.66 (d, J=8.2 Hz, 2H), 7.49 (d, J=8.3 Hz, 2H), 7.23 (d, J=8.2 Hz, 2H), 7.15 (d, J=8.2 Hz, 2H), 6.98 (s, 1H), 3.85 (s, 3H), 3.49 (br s, 3H), 2.51 (s, 3H); $^{13}$C NMR (75 MHz, CDCl$_3$) δ 147.1, 143.7, 143.0, 140.8, 133.1, 129.2, 126.2, 125.6, 125.4, 118.1, 111.5, 111.2, 61.8, 34.0, 15.2; Mass spectrum (API-TIS) m/z 379 (MH$^+$). Anal. calcd for C$_{20}$H$_{18}$N$_4$O$_2$S.¼ mol H$_2$O: C, 62.72; H, 4.87; N, 14.63. Found: C, 62.70; H, 4.82; N, 14.57.

42c. 4-(5-(4-Methylthiophenyl)-3-(4-(1,1,2,2-tetramethyl-1-silapropoxy)butanoyl)pyrazolyl)benzene carbonitrile The title compound was prepared from the product of Example 42b (1.56 g, 4.12 mmol), the Grignard reagent (35 mL) (prepared from 3-bromo-1-(1,1,2,2-tetramethyl-1-silapropoxy)propane (25 g, 98.8 mmol) and magnesium turnings (4.98 g, 0.21 mol) in THF (180 mL) following the procedure for the preparation of Example 3d. Purification gave a white solid (1.5 g, 73% yield). Mp 91-93° C. $^1$H NMR (300 MHz, CDCl$_3$) δ 7.67 (d, J=8.6 Hz, 2H), 7.48 (d, J=8.5 Hz, 2H), 7.21 (d, J=8.4 Hz, 2H), 7.11 (d, J=8.3 Hz, 2H), 6.98 (s, 1H), 3.72 (t, J=6.3 Hz, 2H), 3.15 (t, J=7.3 Hz, 2H), 2.50 (s, 3H), 1.99 (p, J=7.0 Hz, 2H), 0.88 (s, 9H), 0.05 (s, 6H); $^{13}$C NMR (75 MHz, CDCl$_3$) δ 196.3, 152.4, 144.8, 143.1, 141.0, 133.2, 129.2, 126.2, 125.5, 125.5, 118.1, 111.7, 108.8, 62.6, 35.4, 27.4, 26.1, 18.4, 15.2, −5.2; Mass spectrum (API-TIS) m/z 492 (MH$^+$). Anal. calcd. for C$_{27}$H$_{33}$N$_3$O$_2$SSi: C, 65.95; H, 6.76; N, 8.55. Found: C, 65.89; H, 6.69; N, 8.44.

42d. 4-(3-(4-Hydroxybutanoyl)-5-(4-(methylsulfonyl)phenyl)pyrazolyl)benzenecarbonitrile The title compound was prepared from the product of Example 42c (1.5 g, 3.06 mmol) in MeOH (54 mL) and OXONE® (5.6 g, 9.17 mmol) in water (18 mL) following the procedure for the preparation of Example 12d. Purification gave a white solid (0.64 g, 52% yield). Mp 169-171° C. $^1$H NMR (300 MHz, CDCl$_3$) δ 7.97 (dd, J=1.9 and 6.7 Hz, 2H), 7.72 (dd, J=2.0 and 10.8 Hz, 2H), 7.40-7.50 (m, 4H), 7.12 (s, 1H), 3.76 (q, J=6.0 Hz, 2H), 3.24 t, J=7.0 Hz, 2H), 3.10 (s, 3H), 2.06 (p, J=6.3 Hz, 2H), 1.79 (t, J=3.2 Hz, 1H); $^{13}$C NMR (75 MHz, CDCl$_3$) δ 196.2, 152.5, 143.3, 142.4, 141.5, 134.5, 133.6, 129.7, 128.3, 125.7, 117.7, 112.7, 110.1, 62.4, 44.5, 35.7, 27.1; Mass spectrum (API-TIS) m/z 410 (MH$^+$), 392 (M-OH). Anal. calcd. for C$_{21}$H$_{19}$N$_3$O$_4$S: C, 61.60; H, 4.68; N, 10.26. Found: C, 61.34; H, 4.50; N, 10.18.

42e. 4-(5-(4-(Methylsulfonyl)phenyl)-3-(4-(nitrooxy)butanoyl)pyrazolyl)benzenecarbonitrile The title compound was prepared from the product of Example 42d (0.4 g, 0.98 mmol) in CHCl$_3$ (3.2 mL), fuming HNO$_3$ (0.21 mL, 0.31 g, 4.89 mmol) and Ac$_2$O (0.74 mL, 0.80 g, 7.8 mmol) following the procedure for the preparation of Example 1h. Purification gave a white solid (0.32 g, 72% yield). Mp 148-149° C. $^1$H NMR (300 MHz, CDCl$_3$) δ 7.96 (d, J=8.3 Hz, 2H), 7.72 (dd, J=1.8 and 8.5 Hz, 2H), 7.40-7.50 (m, 4H), 7.12 (s, 1H), 4.59 (t, J=6.3 Hz, 2H), 3.25 (t, J=7.1 Hz, 2H), 3.10 (s, 3H), 2.22 (p, J=6.9 Hz, 2H); $^{13}$C NMR (75 MHz, CDCl$_3$) δ 194.2, 152.2, 143.4, 142.3, 141.5, 134.4, 133.6, 129.7, 128.3, 125.7, 117.7, 112.8, 110.0, 72.5, 44.5, 34.7, 21.3; Mass spectrum (API-TIS) m/z 455 (MH$^+$), 472 (MNH$_4^+$). Anal. cacld. for C$_{21}$H$_{18}$N$_4$O$_6$S.0.1 mol EtOAc: C, 55.48; H, 4.09; N, 12.09. Found: C, 55.36; H, 4.02; N, 11.78.

Example 43

4-(1-Cyclohexyl-3-(4-(nitrooxy)butanoyl)pyrazol-5-yl)benzenesulfonamide

43a. (1-Cyclohexyl-5-(4-(methylthiophenyl)pyrazol-3-yl)-N-methoxy-N-methyl carboxamide The title compound was prepared from Example 4a (7 g, 21.2 mmol), trimethylaluminum (21.1 mL of 2M solution in hexane, 3.05 g, 42.4 mmol) and dimethylhydroxylamine hydrochloride (4.13 g, 42.4 mmol) following the procedure for the preparation of Example 3c. Purification gave a white solid (7.1 g, 93% yield). Mp 80-82° C. $^1$H NMR (300 MHz, CDCl$_3$) δ 7.34 (d, J=6.4 Hz, 2H), 7.27 (d, J=8.0 Hz, 2H), 6.71 (s, 1H), 4.05-4.20 (m, 1H), 3.84 (s, 3H), 3.48 (s, 3H), 2.54 (s, 3H), 1.80-2.10 (m, 6H), 1.56-1.70 (m, 1H), 1.17-1.32 (m, 3H); $^{13}$C NMR (75 MHz, CDCl$_3$) δ 144.2, 142.9, 139.9, 129.5, 126.9, 126.4, 108.6, 61.6, 58.4, 33.4, 25.6, 25.2, 15.5; Mass spectrum (API-TIS) m/z 360 (MH$^+$). Anal. calcd. for C$_{19}$H$_{25}$N$_3$O$_2$S: C, 63.48; H, 7.01; N, 11.69. Found: C, 63.72; H, 7.05; N, 11.75.

43b. 1-(1-Cyclohexyl-5-(4-methylthiophenyl)pyrazol-3-yl)-4-(1,1,2,2-tetramethyl-1-silapropoxy)butan-1-one The title compound was prepared from the product of Example 43a (3.9 g, 11.0 mmol) in THF (30 mL), the Grignard reagent prepared from 3-bromo-1-(1,1,2,2-tetramethyl-1-silapropoxy)propane (25 g, 98.8 mmol) and magnesium turnings (5.0 g, 20.8 mol) in THF (180 mL) following the procedure for preparation of Example 3d. Purification gave a colorless oil (3.79 g, 48% yield). $^1$H NMR (300 MHz, CDCl$_3$) δ 7.20-7.38 (m, 4H), 6.71 (s, 1H), 4.02-4.20 (m, 1H), 3.72 (t, J=6.4 Hz, 2H), 3.10 (t, J=7.3 Hz, 2H), 2.54 (s, 3H), 1.72-2.05 (m, 10H), 1.19-1.32 (m, 2H), 0.91 (s, 9H), 0.06 (s, 6H); Mass spectrum (API-TIS) m/z 473 (MH$^+$).

43c. 1-(1-Cyclohexyl-5-(4-(methylsulfinyl)phenyl)pyrazol-3-yl)-4-(1,1,2,2-tetramethyl-1-silapropoxy)butan-1-one The product of Example 43b (3.23 g, 6.84 mmol) was dissolved in CH$_2$Cl$_2$ (48 mL) and MeOH (15 mL). Magnesium monoperoxyphathalate hexahydrate (MMPP) (1.83 g, 3.69 mmol) was added in five equal portions at 1 minute intervals. The resulting heterogeneous solution was stirred at room temperature for 1 hour. Saturated NaHCO$_3$ was added. The organic layer was separated, dried over Na$_2$SO$_4$ and the solvent was evaporated in vacuo to give the crude product.

The crude product was chromatographed on silica gel eluting with 10% MeOH/CH$_2$Cl$_2$ to give the title compound (1.5 g, 45% yield) as an oil. $^1$H NMR (300 MHz, CDCl$_3$) δ 7.77 (d, J=8.3 Hz, 2H), 7.51 (d, J=8.3 Hz, 2H), 6.78 (s, 1H), 3.98-4.20 (m, 1H), 3.72 (t, J=6.4 Hz, 2H), 3.12 (t, J=7.3 Hz, 2H), 2.81 (s, 3H), 1.78-2.10 (m, 10H), 1.14-1.33 (m, 2H), 0.90 (s, 9H), 0.06 (s, 6H); $^{13}$C NMR δ (75 MHz, CDCl$_3$) 196.6, 150.2, 146.7, 143.0, 133.3, 130.0, 124.3, 106.8, 62.7, 58.8, 44.0, 35.3, 33.4, 27.6, 26.1, 25.6, 25.1, 18.4, −5.3; Mass spectrum (API-TIS) m/z 488 (MH$^+$). Anal. calcd. for C$_{26}$H$_{39}$N$_2$O$_3$SSi: C, 64.03; H, 8.06; N, 5.74. Found: C, 63.86; H, 8.05; N, 5.74.

43d. (4-(1-Cyclohexyl-3-(4-(1,1,2,2-tetramethyl-1-silapropoxy)butanoyl)pyrazol-5-yl)phenylthio)methyl acetate The product of Example 43c (1.5 g, 3.1 mmol) was dissolved in acetic anhydride (12 mL). Powdered sodium acetate (1.1 g, 13.4 mmol) was added and the solution was refluxed for 8 hour. The solvent was evaporated in vacuo. The residue was taken up in EtOAc:CH$_2$Cl$_2$ (1:0.5), washed with saturated NH$_4$Cl, brine and dried over Na$_2$SO$_4$. The solvent was removed under vacuo to give the title compound (0.9 g, 56% yield) as oil. $^1$H NMR (300 MHz, CDCl$_3$) δ 7.54 (d, J=8.3 Hz, 2H), 7.31 (d, J=8.3 Hz, 2H), 6.73 (s, 1H), 5.49 (s, 2H), 4.00-4.18 (m, 1H), 3.73 (t, J=6.4 Hz, 2H), 3.11 (t, J=7.3 Hz, 2H), 2.15 (s, 3H), 1.83-2.00 (m, 10H), 1.12-1.32 (m, 2H), 0.91 (s, 9H), 0.06 (s, 6H); $^{13}$C NMR (75 MHz, CDCl$_3$) δ 196.8, 170.3, 150.1, 143.5, 136.3, 129.8, 129.2, 106.5, 67.4, 62.8, 58.6, 35.3, 33.4, 27.7, 26.1, 25.6, 25.2, 21.2, 18.4, −5.2; Mass spectrum (API-TIS) m/z 531 (MH$^+$). Anal. calcd. for C$_{28}$H$_{42}$N$_2$O$_4$SSi: C, 63.36; H, 7.98; N, 5.28. Found: C, 63.32; H, 7.81; N, 5.19.

43e. ((4-(1-Cyclohexyl-3-(4-(1,1,2,2-tetramethyl-1-silapropoxy)butanoyl)pyrazol-5-yl)phenyl)sulfonyl)methyl acetate The product of Example 43d (0.9 g, 1.7 mmol) and MMPP (0.92 g, 1.86 mmol) were mixed in CH$_2$Cl$_2$ (16 mL) and MeOH (5 mL) and was stirred at room temperature for 16 hours. The reaction mixture was neutralized with saturated NaHCO$_3$ and the solvent was evaporated to half of its volume. The residue was extracted into CH$_2$Cl$_2$, washed with saturated NaHCO$_3$, water, dried over Na$_2$SO$_4$, filtered and evaporated to give the title compound (0.74 g, 78% yield) as an oil. $^1$H NMR (300 MHz, CDCl$_3$) δ 8.05 (d, J=8.3 Hz, 2H), 7.58 (d, J=8.3 Hz, 2H), 6.83 (s, 1H), 5.21 (s, 2H), 3.98-4.12 (m, 1H), 3.73 (t, J=6.3 Hz, 2H), 3.12 (t, J=7.4 Hz, 2H), 2.13 (s, 3H), 1.82-2.10 (m, 9H), 1.20-1.35 (m, 1H), 1.20-1.35 (m, 2H), 0.89 (s, 9H), 0.06 (s, 6H); $^{13}$C NMR (75 MHz, CDCl$_3$) δ 196.4, 168.3, 150.4, 142.2, 137.3, 136.7, 130.0, 129.6, 107.3, 62.7, 59.1, 35.3, 34.8, 33.4, 31.7, 27.6, 26.1, 25.5, 25.1, 22.8, 20.4, 18.4, 14.2, −5.1; Mass spectrum (API-TIS) m/z 563 (MH$^+$). Anal. calcd. for C$_{28}$H$_{42}$N$_2$O$_6$SSi: C, 59.76; H, 7.52; N, 4.98. Found: C, 59.67; H, 7.37; N, 4.94.

43f. 4-(1-Cyclohexyl-3-(4-(1,1,2,2-tetramethyl-1-silapropoxy)butanoyl)pyrazol-5-yl)benzenesulfonamide Sodium acetate (0.77 g, 9.4 mmol) was added to a solution of the product of Example 43e (0.66 g, 1.17 mmol) in methanol (14 mL). The resultant mixture was stirred at room temperature for 15 minutes K$_2$CO$_3$ (0.46 g, 3.3 mmol) was added and the stirring was continued for 1.5 hours. To this solution, hydroxyaminosulfonic acid (0.53 g, 4.69 mmol) was added. The mixture was stirred at room temperature for 2 hours, diluted with EtOAc and saturated NaHCO$_3$ was added. The solvent was evaporated to a small volume, more EtOAc was added. The organic layer was washed with saturated NaHCO$_3$, brine, dried over Na$_2$SO$_4$ and filtered. The residue after evaporation of the solvent was chromatographed on silica gel eluting with 1:2 to 1:1 EtOAc:Hexane to give the title compound (0.38 g, 64% yield) as a white solid. Mp 151-153° C. $^1$H NMR (300 MHz, CDCl$_3$) δ 8.04 (d, J=8.4 Hz, 2H), 7.50 (d, J=8.4 Hz, 2H), 6.78 (s, 1H), 4.96 (s, 2H), 3.92-4.10 (m, 1H), 3.72 (t, J=6.3 Hz, 2H), 3.12 (t, J=7.3 Hz, 2H), 1.75-2.10 (m, 8H), 1.48-1.60 (m, 2H), 1.20-1.38 (m, 2H), 0.90 (s, 9H), 0.06 (s, 6H); Mass spectrum (API-TIS) m/z 506 (MH$^+$).

43g. 4-(1-Cyclohexyl-3-(4-hydroxybutanoyl)pyrazol-5-yl)benzenesulfonamide

Tetrabutylammonium fluoride (0.75 mL of 1M solution in THF, 0.20 g, 0.75 mmol) was added dropwise to a solution of the product of Example 43f (0.38 g, 0.75 mmol) in THF (9 mL). The reaction mixture was stirred at room temperature for 16 hours. The residue after evaporation of the solvent was chromatographed on silica gel eluting with 1:1 EtOAc:CH$_2$Cl$_2$ to give the title compound (0.23 g, 78% yield) as a white solid. Mp 152-154° C. $^1$H NMR (300 MHz, d$_6$-DMSO) δ 7.95 (d, J=8.4 Hz, 2H), 7.68 (d, J=8.4 Hz, 2H), 6.84 (s, 1H), 4.48 (t, J=5.2 Hz, 2H), 4.08-4.22 (m, 1H), 3.42-3.49 (m, 2H), 3.02 (t, J=7.4 Hz, 2H), 1.82-2.00 (m, 4H), 1.70-1.82 (m, 4H), 1.19-1.38 (m, 2H); $^{13}$C NMR (75 MHz, d$_6$-DMSO) δ 195.2, 149.5, 144.4, 143.0, 132.6, 129.6, 126.3, 106.6, 60.2, 58.1, 34.9, 32.9, 27.0, 24.8, 24.7; Mass spectrum (API-TIS) m/z 374 (M-OH), 392 (MH$^+$). LCMS (94.3%).

43h. 4-(1-Cyclohexyl-3-(4-(nitrooxy)butanoyl)pyrazol-5-yl)benzenesulfonamide The title compound was prepared from the product of Example 43g (0.15 g, 0.38 mmol), fuming nitric acid (80 μL, 0.12 g, 1.92 mmol) and acetic anhydride (0.28 mL, 0.31 g, 3.1 mmol) following the procedure for the preparation of Example 1h. Purification gave a white solid (0.12 g, 74% yield). Mp 45-47° C. $^1$H NMR (300 MHz, d$_6$-DMSO) δ 8.05 (d, J=8.3 Hz, 2H), 7.51 (d, J=8.2 Hz, 2H), 6.80 (s, 1H), 4.75-4.90 (m, 2H), 4.59 (t, J=6.3 Hz, 2H), 3.90-4.20 (m, 1H), 3.21 (t, J=7.1 Hz, 2H), 2.15-2.24 (m, 2H), 1.75-1.92 (m, 4H), 1.92-2.15 (m, 2H), 1.40-1.60 (m, 2H), 1.18-1.32 (m, 2H); $^{13}$C NMR (75 MHz, d$_6$-DMSO) δ 194.9, 149.9, 142.8, 142.6, 134.7, 129.8, 127.2, 107.1, 72.8, 59.1, 34.6, 33.4, 25.5, 25.1, 21.5; Mass spectrum (API-TIS) m/z 437 (MH$^+$). LCMS (94.6%).

Example 44

1-(1-(4-Chlorophenyl)-5-(4-(methylsulfonyl)phenyl)pyrazol-3-yl)-4-(nitrooxy)butan-1-one

44a. Methyl 1-(4-chlorophenyl)-5-(4-methylthiophenyl)pyrazol-3-carboxylate

The title compound was prepared from the product of Example 1d (5 g, 20 mmol) and 4-chlorophenylhydrazine hydrochloride (4.7 g, 26 mmol) in MeOH (120 mL) following the procedure for the preparation of Example 1e. Purification gave a white solid (5.7 g, 79% yield). Mp 140-143° C. $^1$H NMR (300 MHz, CDCl$_3$) δ 7.34 (d, J=8.8 Hz, 2H), 7.28 (d, J=8.8 Hz, 2H), 7.19 (d, J=8.4 Hz, 2H), 7.11 (d, J=8.4 Hz, 2H), 7.01 (s, 1H), 3.97 (s, 3H), 2.49 (s, 3H); Mass spectrum (API-TIS) m/z 359 (MH$^+$). Anal. calcd. for C$_{18}$H$_{15}$ClN$_2$O$_2$S: C, 60.25; H, 4.21; N, 7.81. Found: C, 60.47; H, 4.10; N, 7.80.

44b. (1-(4-Chlorophenyl)-5-(4-methylthiophenyl) pyrazol-3-yl)-N-methoxy-N-methylcarboxamide The title compound was prepared from the product of Example 44a (2.5 g, 7.0 mmol), trimethylaluminum (7.0 mL of 2M solution in hexane, 1.00 g, 13.9 mmol) and dimethylhydroxylamine hydrochloride (1.36 g,13.9 mmol) following the procedure for the preparation of Example 3c. Purification gave a white solid (2.3 g, 85% yield). Mp 128-129° C. $^1$H NMR (300 MHz, CDCl$_3$) δ 7.08-7.35 (m, 8H), 6.96 (s, 1H), 3.85 (s, 3H), 3.50 (br s, 3H), 2.49 (s, 3H). $^{13}$C NMR (75 MHz, CDCl$_3$) δ 162.6, 146.1, 143.3, 140.1, 138.1, 133.7, 129.1, 129.0, 126.4, 125.9, 110.2, 61.6, 15.1; Mass spectrum (API-TIS) m/z 388 (MH$^+$). Anal. calcd. for C$_{19}$H$_{18}$ClN$_3$O$_2$S: C, 58.83; H, 4.68; N, 10.83. Found: C, 58.58; H, 4.64; N, 10.66.

44c. 1-(1-(4-Chlorophenyl)-5-(4-methylthiophenyl) pyrazol-3-yl)-4-(1,1,2,2-tetramethyl-1-silapropoxy) butan-1-one The title compound was prepared from the product of Example 44b (2.3 g, 5.9 mmol), the Grignard reagent (81 mL) (prepared from 3-bromo-1-(1,1,2,2-tetramethyl-1-silapropoxy)propane (68 g, 0.27 mol) and magnesium turnings (13.5 g, 0.56 mol) in THF (500 mL) following the procedure for the preparation of Example 3d. Purification gave a white solid (1.9 g, 65% yield). Mp 64-65° C. $^1$H NMR (300 MHz, CDCl$_3$) δ 7.02-7.42 (m, 8H), 6.96 (s, 1H), 3.72 (t, J=6.3 Hz, 2H), 3.15 (t, J=7.3 Hz, 2H), 2.49 (s, 3H), 1.99 (p, J=6.8 Hz, 2H), 0.89 (s, 9H), 0.05 (s, 6H); $^{13}$C NMR (75 MHz, CDCl$_3$) δ 196.5, 151.8, 144.5, 140.4, 138.3, 134.2, 129.4, 129.1, 126.6, 126.2, 125.9, 108.0, 62.6, 35.3, 27.5, 26.1, 18.5, 15.3, −5.2; Mass spectrum (API-TIS) m/z 502 (MH$^+$). Anal. calcd. for C$_{26}$H$_{33}$ClN$_2$O$_2$SSi.¼ mol CHCl$_3$: C, 59.38; H, 6.31; N, 5.28. Found: C, 59.00; H, 6.25; N, 5.04.

44d. 1-(1-(4-Chlorophenyl)-5-(4-(methylsulfonyl) phenyl)pyrazol-3-yl)-4-hydroxybutan-1-one The title compound was prepared from the product of Example 44c (1.9 g, 3.8 mmol) in MeOH (57 mL) and OXONE® (7.0 g, 11.4 mmol) in water (19 mL) following the procedure for the preparation of Example 12d. Purification gave a white solid (0.47 g, 29% yield). Mp 147-148° C. $^1$H NMR (300 MHz, CDCl$_3$) δ 7.92 (d, J=8.3 Hz, 2H), 7.35-7.46 (m, 4H), 7.20-7.29 (m, 2H), 7.10 (s, 1H), 3.74 (q, J=6.0 Hz, 2H), 3.23 (t, J=7.0 Hz, 2H), 3.08 (s, 3H), 2.00-2.11 (m, 2H), 1.96 (t, J=5.6 Hz, 1H); $^{13}$C NMR (75 MHz, CDCl$_3$) δ 196.4, 151.9, 143.1, 141.0, 135.0, 134.8, 129.9, 129.6, 128.1, 126.7, 109.2, 62.4, 44.5, 35.6, 27.3; Mass spectrum (API-TIS) m/z 419 (MH$^+$), 401 (M-OH). Anal. calcld. for C$_{20}$H$_{19}$ClN$_2$O$_4$S: C, 57.35; H, 4.57; N, 6.69. Found: C, 56.97; H, 4.49; N, 6.36.

44e. 1-(1-(4-Chlorophenyl)-5-(4-(methylsulfonyl) phenyl)pyrazol-3-yl)-4-(nitrooxy)butan-1-one The title compound was prepared from the product of Example 44d (0.19 g, 0.45 mmol) in CHCl$_3$ (2 mL), fuming HNO$_3$ (95.4 µL, 0.14 g, 2.27 mmol) and Ac$_2$O (0.34 mL, 0.37 g, 3.6 mmol) following the procedure for the preparation of Example 1h. Purification gave a white solid. Mp 131-132° C. $^1$H NMR (300 MHz, CDCl$_3$) δ 7.92 (d, J=8.1 Hz, 2H), 7.30-7.48 (m, 4H), 7.15-7.30 (m, 2H), 7.10 (s, 1H), 4.58 (t, J=6.3 Hz, 2H), 3.25 (t, J=7.0 Hz, 2H), 3.08 (s, 3H), 2.22 (p, J=6.6 Hz, 2H); $^{13}$C NMR (75 MHz, CDCl$_3$) δ 194.3, 151.5, 143.1, 141.0, 137.6, 135.1, 134.7, 129.8, 129.6, 128.0, 126.7, 109.1, 72.6, 44.5, 34.6, 21.2; Mass spectrum (API-TIS) m/z 464 (MH$^+$). Anal. calcd. for C$_{20}$H$_{18}$ClN$_3$O$_6$S: C, 51.78; H, 3.91; N, 9.06. Found: C, 51.54; H, 3.86; N, 8.87.

Example 45

(1-Cyclohexyl-5-(4-(methylsulfonyl)phenyl)pyrazol-3-yl)-N-(2-(nitrooxy)ethyl)carboxamide (NMI-1693)

45a. (1-Cyclohexyl-5-(4-methylthiophenyl)pyrazol-3-yl)-N-(2-hydroxyethyl)carboxamide The product of Example 4b (1.8 g, 5.45 mmol) and ethanolamine (12 ml, 198.82 mmol) were heated at 60° C. for 2 hours. The mixture was allowed to warm to room temperature and acidified with 1N HCl. The reaction mixture was extracted with ether (3×10 mL) and the organics separated, dried over MgSO$_4$ and the solvent removed under reduced pressure to give a yellow oil. The sample was triturated in Et$_2$O to give the title compound as a pale yellow solid (998 mg, 50% yield). Mp 149-151 0° C. $^1$H NMR (300 MHz, CDCl$_3$); δ7.33 (d, J=8.3, 2H), 7.25 (d, J=8.3, 2H), 6.73 (s, 1H), 4.07-4.06 (m, 1H) 3.84 (t, J=4.9, 2H), 3.64-3.59 (m, 3H), 2.53 (s, 3H), 1.95-1.90 (m, 3H), 1.86-1.85 (m, 3H), 1.28-1.25 (m, 3H). Mass spectrum (API-TIS) m/z 360 (M+1).

45b. (1-Cyclohexyl-5-(4-(methylsulfonyl)phenyl) pyrazol-3-yl)-N-(2-hydroxyethyl)carboxamide The product of Example 45a (540 mg, 1.50 mmol) was cooled to 0° C. and dissolved in MeOH/H$_2$O (20 mL/10 mL). OXONE® was added (1.20 g, 1.95 mmol) and the mixture stirred at 0° C. for 1 hour. The mixture was allowed to warm to room temperature and stirred for an additional hour. The resulting solid was removed by filtration and the filtrate made basic with saturated Na$_2$CO$_3$ solution. Additional H$_2$O (10 mL) was added and the sample extracted with EtOAc (3×30 mL). The combined organic extracts were dried over MgSO$_4$ and the solvent removed under reduced pressure to give the title compound as a solid (94.5 mg, 15% yield). Mp 199-201° C. $^1$H NMR (300 MHz, CDCl$_3$); δ8.06 (d, J=8.1, 2H), 7.56 (d, J=8.1, 2H), 7.56-7.32 (m, 1H), 6.84 (s, 1H), 4.06-4.02 (m, 1H) 3.85-3.83 (m, 2H), 3.65-3.60 (m, 2H), 3.12 (s, 3H), 2.03-2.02 (m, 2H), 1.98-1.87 (m, 2H), 1.70 (br s, 1H), 1.61 (br s, 1H), 1.27-1.25 (m, 3H). Mass spectrum (API-TIS) m/z 392 (M+1).

45c. (1-Cyclohexyl-5-(4-(methylsulfonyl)phenyl) pyrazol-3-yl)-N-(2-(nitrooxy)ethyl)carboxamide Fuming nitric acid (700 µL, 17.55 mmol) was added to acetic anhydride (756.6 µL, 8.01 mmol) at 0° C. and the mixture stirred for 10 minutes. The mixture was then added to a solution of the product of Example 45b ( 85.9 mg, 0.22 mmol) in EtOAc (15 mL) at 0° C. and the mixture stirred for 2 hours. Saturated NaHCO$_3$ was added to basify the mixture and the organic layer was separated. The aqueous layer was washed with additional EtOAc (2×10 mL) and the combined organic layers were dried over MgSO$_4$ and the solvent removed under reduced pressure to give the title compound (69.7 mg, 73% yield)as a solid. Mp 168-170° C. $^1$H NMR (300 MHz, CDCl$_3$); δ8.06 (d, J=8.2, 2H), 7.56 (d, J=8.2, 2H), 7.20-7.16 (m, 1H), 6.83 (s, 1H), 4.67 (t, J=5.3, 2H), 4.08-4.00 (m, 1H) 3.81 (q, J=5.3, 2H), 3.11 (s, 3H), 2.10-1.89 (m, 5H), 2.10 (br s, 1H), 1.17 (br s, 1H), 1.28-1.25 (m, 3H). Mass spectrum (API-TIS) m/z 437 (M+1).

Example 46

(1-Cyclohexyl-5-(4-(methylsulfonyl)phenyl)pyrazol-3-yl)-N-(3-(nitrooxy)propyl)carboxamide

46a. (1-Cyclohexyl-5-(4-methylthiophenyl)pyrazol-3-yl)-N-(3-hydroxypropyl)carboxamide The product of Example 4b (540.0 mg, 1.64 mmol) and propanolamine (7 ml, 91.5 mmol) were heated at 60° C. overnight. The sample was allowed to cool to room temperature and diluted with EtOAc (30 mL). The solution was pulled through a silica gel plug to remove any excess propanolamine. The filtrate was collected and the solvent removed under reduced pressure to give an oil, which upon standing at room temperature yielded an oil/crystal mixture. $Et_2O$ was added and the crystals collected via filtration. The sample was purified via recrystalization from hexanes/$CH_2Cl_2$ to give the title compound (329.8 mg, 54% yield) as white crystals. $^1$H NMR (300 MHz, $CDCl_3$); δ 7.33 (d, J=8.4, 2H), 7.24 (d, J=8.4, 2H), 7.17 (m, 1H), 6.73 (s, 1H), 4.06-4.04 (m, 1H) 3.68 (t, J=5.7, 2H), 3.61 (q, J=5.7, 2H), 2.53 (s, 3H), 1.99-1.95 (m, 2H), 1.91-1.82 (m, 3H), 1.78 (t, J=5.7, 2H), 1.68 (m, 1H), 1.26 (m, 3H). Mass spectrum (API-TIS) m/z 374 (M+1).

46b. (1-Cyclohexyl-5-(4-(methylsulfonyl)phenyl) pyrazol-3-yl)-N-(3-hydroxypropyl)carboxamide The product of Example 46a (392.8 mg, 0.88 mmol) was dissolved in MeOH/$H_2O$ (10 mL/5 mL) and OXONE® was added (3.7 mg, 6.02 mmol). The mixture was stirred at room temperature for 4 hours. The resulting precipitate was removed via filtration and the solid washed with MeOH (2 mL). The filtrate was collected and diluted with additional $CH_2Cl_2$ (10 mL). The organic layer was separated and the aqueous portion extracted with additional $CH_2Cl_2$ (2×10 mL). The combined organic extracts were collected, dried over $MgSO_4$ and the solvent removed under reduced pressure to give the title compound (196.2 mg, 55% yield) as a white solid. Mp 166-168° C. $^1$H NMR (300 MHz, $CDCl_3$); δ 8.04 (d, J=8.0, 2H), 7.54 (d, J=8.0, 2H), 7.24-7.21 (m, 1H), 6.81 (s, 1H), 4.06-3.99 (m, 1H) 3.66-3.49 (m, 4H), 3.11 (s, 3H), 2.00-1.68 (m, 8H), 1.26-1.24 (m, 3H). Mass spectrum (API-TIS) m/z 406 (M+1).

46c. (1-Cyclohexyl-5-(4-(methylsulfonyl)phenyl) pyrazol-3-yl)-N-(3(nitrooxy)propyl)carboxamide Fuming nitric acid (10 mL, 250.7 mmol) was cooled to −10° C. and the product of Example 46b (80.3 mg, 0.19 mmol) was added as a solid. The mixture was stirred at −10° C. for 1.5 hours and diluted with ice water. The mixture was neutralized with a saturated solution of $Na_2CO_3$ and extracted with EtOAc (3×15 mL). The combined organic extracts were washed with brine, and dried over $MgSO_4$. The solvent was removed under reduced pressure to give the title compound (60.8 mg, 68% yield) a pale yellow solid. Mp 168-170° C. $^1$H NMR (300 MHz, $CDCl_3$); δ 8.06 (d, J=8.2, 2H), 7.56 (d, J=8.2, 2H), 7.10-7.08 (m, 1H), 6.82 (s, 1H), 4.59 (t, J=6.5, 2H), 4.07-4.02 (m, 1H) 3.57 (q, J=6.5, 2H), 3.12 (s, 3H), 2.14-1.99 (m, 4H), 2.10 (t, J=6.5, 2H), 1.70 (br s, 1H), 1.63 (br s, 1H), 1.27-1.25 (m, 3H). Mass spectrum (API-TIS) m/z

Example 47

3-(Nitrooxy)propyl 4-(5-(4-(methylsulfonyl)phenyl)-1-(4-(trifluoromethyl)phenyl)pyrazol-3-yl)butanoate

47a. Methyl (6Z)-7-hydroxy-7-(4-methylthiophenyl)-5-oxohept-6-enoate

Lithium diisopropylamide mono(tetrahydrofuran) in cyclohexane (1.5 M; 28 mL, 42 mmol) was added to a solution of 1-(4-methylthiophenyl)ethan-1-one (5.16 g, 31 mmol) in THF (120 mL) and stirred for 30 minutes at −72° C. A solution of methyl 4-(chloroformyl)butyrate (1.78 g, 10.8 mmol) was added to the above solution and stirred for 30 minutes and then warmed slowly from the −72° C. to −45° C. To the reaction mixture was added 3N HCl (50 mL) and extracted with ethyl acetate (100 mL×3). The combined organic layers were washed with water, brine, dried over $Na_2SO_4$, filtered and evaporated. Trituration of the residue with diethyl ether/hexane gave a mixture of the title compound and starting material (~30% yield) as a solid (2.42 g). The crude material was used in the next step without purification. A small quantity of pure sample was obtained at the beginning of the trituation. Mp. 92-93° C.
1H NMR ($CDCl_3$) δ 15.1 (br, 1H), 7.79 (d, J=8.6 Hz, 2H), 7.27 (d, J=8.6 Hz, 2H), 6.13 (s, 1H), 3.69 (s, 3H), 2.52 (s, 3H), 2.48 (t, J=7.4 Hz, 2H), 2.42 (t, J=7.4 Hz, 2H), 2.02 (m, 2H). $^{13}$C NMR ($CDCl_3$) δ 194.8, 183.0, 173.4, 144.9, 131.0, 127.3, 125.2, 95.6, 51.5, 37.9, 33.1, 20.8, 14.8.

47b. Methyl 4-(5-(4-methylthiophenyl)-1-(4-(trifluoromethyl)phenyl)pyrazol-3-yl)butanoate A solution of the product of Example 47a (1.61 g) and 4-(trifluoromethyl)phenylhydrazine hydrochloride (1.28 g, 7.3 mmol) in methanol (50 mL) was heated at reflux for 4 hours. The reaction was concentrated and the residue was separated by silica gel column chromatography eluting with ethyl acetate/hexane (1:4, Rf=0.2) to give a mixture of the title compound with some unknown impurities (~5% yield) as an oil (1.80 g). The crude material was used in the next step without purification. $^1$H NMR ($CDCl_3$) δ 7.57 (d, J=8.4 Hz, 2H), 7.41 (d, J=8.4 Hz, 2H), 7.18 (d, J=8.4 Hz, 2H), 7.13 (d, J=8.4 Hz, 2H), 6.33 (s, 1H), 3.68 (s, 3H), 2.76 (t, J=7.6 Hz, 2H), 2.48 (s, 3H), 2.46 (t, J=7.4 Hz, 2H), 2.09 (m, 2H). $^{13}$C NMR ($CDCl_3$) δ 173.7, 153.8, 143.4, 142.4, 139.6, 128.9, 128.7 ($J_{CF}$=33 Hz), 126.6, 126.0, 125.9, 124.6, 123.8 ($J_{CF}$=270 Hz), 51.4, 33.5, 27.5, 24.5, 15.1. MS(API) m/z 435 $(M+H)^+$.

47c. 4-(5-(4-Methylthiophenyl)-1-(4-(trifluoromethyl)phenyl)pyrazol-3-yl)butanoic acid A solution of the product of Example 47b (1.80 g) and LiOH (0.11 g, 4.47 mmol) in a mixture of water (10 mL), methanol (40 mL) and THF (30 mL) was stirred at room temperature overnight. The reaction mixture was acidified with 3N HCl and then evaporated. The aqueous residue was extracted with $CH_2Cl_2$ (30 mL×2). The combined organic extracts were washed with water, brine, dried over $Na_2SO_4$, filtered and evaporated. The residue was separated by silica gel column chromatography eluting with ethyl acetate/hexane (gradient from 1:2 to 3:2, Rf =0.3 in 3:2) to give the title compound as a white solid (0.82 g). Mp 92-93° C. $^1$H NMR ($CDCl_3$) δ 7.58 (d, J=8.4 Hz, 2H), 7.41 (d, J=8.4 Hz, 2H), 7.19 (d, J=8.4 Hz, 2H), 7.12 (d, J =8.4 Hz, 2H), 6.33 (s, 1H), 2.80 (t, J=7.4 Hz, 2H), 2.50 (t, J=7.4 Hz, 2H), 2.49 (s, 3H) 2.09 (m, 2H). $^{13}$C NMR ($CDCl_3$) δ 179.0, 153.7, 143.6, 142.6, 139.7, 129.1, 128.8 ($J_{CF}$=32 Hz), 126.5, 126.1, 126.0, 124.8, 123.8

($J_{CF}$=270 Hz), 33.5, 27.3, 24.3, 15.2. MS(API) m/e 419 (M–H)⁻. Analysis for $C_{21}H_{19}F_3N_2O_2S$ Calcd. C, 59.99; H, 4.55; N, 6.66. Found C, 59.72; H, 4.34; N, 6.60.

47d. 4-(5-(4-(Methylsulfonyl)phenyl)-1-(4-(trifluoromethyl)phenyl)pyrazol-3-yl)butanoic acid A solution of OXONE® (1.3 g, 2.11 mmol) in water (15 mL) was added to a solution of the product of Example 47c (0.82 g, 1.95 mmol) in methanol (50 mL) and stirred at room temperature for 1.5 hours. The reaction mixture was filtered though Celite and then evaporated. The residue was partitioned between ethyl acetate and water. The organic layer was dried over $Na_2SO_4$, filtered and evaporated. The residue was separated by silica gel column chromatography eluting with ethyl acetate/hexane (gradient from 1:2 to 2:3, Rf=0.1 in 1:2) to give the title compound as an oil. Trituration of the product with ether/hexane gave the title compound as a white solid (0.49 g, 55% yield). Mp 155-156° C.

1H NMR (CDCl₃) δ 7.91 (d, J=8.4 Hz, 2H), 7.63 (d, J=8.4 Hz, 2H), 7.43 (d, J=8.4 Hz, 2H), 7.41 (d, J=8.4 Hz, 2H), 6.48 (s, 1H), 3.10 (s, 3H), 2.82 (t, J=7.4 Hz, 2H), 2.50 (t, J=7.4 Hz, 2H), 2.10 (m, 2H). ¹³C NMR (CDCl₃) δ 178.9, 154.0, 142.1, 141.8, 140.2, 135.4, 129.4 ($J_{CF}$=32 Hz), 129.3, 127.8, 126.3, 124.9, 123.8 ($J_{CF}$=270 Hz), 44.3, 33.3, 27.2, 24.1. MS(API) m/e 451 (M–H)⁻.

47e. 3-(Nitrooxy)propylamine nitric acid salt

A solution of 3-amino-1-propanol (6.17 g, 82.2 mmol) was added, dropwise, to an ice-cooled solution of fuming nitric acid (12 mL) in acetic anhydride (50 mL). The reaction was stirred in an ice-bath for 10 minutes and then at room temperature for 10 minutes. The solvent was evaporated under vacuum at 40° C. The residue was stirred in diethyl ether (200 mL) until the product precipitated. The mixture was filtered and the white crystalline solid was dried in vacuo to give the title compound (12.1 g, 80% yield). ¹H NMR (DMSO-d₆) δ 4.57 (br. t, 2 H), 2.8-3.0 (m, 2H), 1.96 (m, 2H). ¹³C NMR (DMSO-d₆) δ 70.9, 36.1, 24.5. MS(API) m/z 121 (M—NO₃)⁺.

47f. 3-(Nitrooxy)propyl 4-(5-(4-(methylsulfonyl)phenyl)-1-(4-(trifluoromethyl)-phenyl)pyrazol-3-yl)butanoate A solution of the product of Example 47d (0.35 g, 0.78 mmol), Example 47e (0.18 g, 0.98 mmol), 4-dimethylaminopyridine (0.20 g, 0.16 mmol), 1-(3-dimethylaminopropyl)-3-ethylcarbodiimide hydrochloride (0.21 g, 1.11 mmol) and $NEt_3$ (0.4 mL, 2.87 mmol) in $CH_2Cl_2$ (30 mL) was stirred at room temperature overnight. The reaction mixture was partitioned between 3N HCl (50 mL) and $CH_2Cl_2$ (50 mL). The organic layer was washed with water and brine, dried over $Na_2SO_4$, filtered and evaporated. The product was separated by silica gel column chromatography eluting with ethyl acetate (Rf=0.25) to give the title compound as a yellowish foam (0.257 g, 59% yield). ¹H NMR (CDCl₃) δ 7.91 (d, J=8.4 Hz, 2H), 7.63 (d, J=8.4 Hz, 2H), 7.44 (d, J=8.4 Hz, 2H), 7.38 (d, J=8.4 Hz, 2H), 6.49 (s, 1H), 6.39 (br. t, 1H), 4.51 (t, J=6.3 Hz, 2H), 3.37 (q, J=6.3 Hz, 2H), 3.10 (s, 3H), 2.77 (t, J=7.4 Hz, 2H), 2.33 (t, J=7.4 Hz, 2H), 2.05 (m, 2H), 1.94 (m, 2H). ¹³C NMR (CDCl₃) δ 173.0, 154.1, 142.1, 141.7, 140.1, 135.4, 129.3 ($J_{CF}$=32 Hz), 129.2, 127.6, 126.3, 124.7, 123.5 ($J_{CF}$=270 Hz), 71.0, 44.2, 35.9, 35.6, 27.1, 26.9, 25.1, 20.9. MS(API) m/z 555 (M+H)⁺.

Example 48

Assay for Human COX-1 and COX-2 Enzyme Activity in Human Whole Blood

The assay for COX-1 and COX-2 enzyme activity, in the human whole blood was performed as described in Brideau et al., *Inflamm Res.*, 45: 68-74 (1996)). Human blood (≈50 mL) from male or female donors who had not received any aspirin or NSAIDs for 14 days was collected at two local area blood donor centers and placed in polypropylene syringes containing sodium heparin (20 units per mL blood, final concentration). The blood was transported to the laboratory on ice packs and used within 1.5 hours of collection. Upon receipt in the laboratory, the blood was allowed to come to room temperature for 15 minutes prior to distribution in 1 mL aliquots per well of 24 well tissue culture plates. The plates were then placed on a gently rotating platform shaker in a 5% $CO_2$ incubator at 37° C. for 15 minutes. Test compounds were dissolved in DMSO, at 1000 fold the final desired concentration, and further diluted, as indicated, in DMSO. One μL of each dilution of the test compound was added per well, in duplicate wells; wells not receiving test compound (e.g., basal, background or control wells) received 1 μL DMSO.

To induce COX-2, lipopolysaccharide (LPS) from *E. coli* (LPS, serotype 026:B6 or serotype 0127:B8, Sigma Chemical Co., St. Louis, Mo., Catalogue No. L3755 or L3129, respectively) was added at 10 μg/mL (2 μL of 5 mg/mL LPS in DMSO) to appropriate wells 15 minutes after the addition of the test compound. (Basal or background wells not incubated with LPS received 2 μL of DMSO.) For the stimulation of COX-1, the calcium ionophore, A23187 (free acid from Sigma Chemical Co., St. Louis, Mo., Catalogue No. C7522) was added at 25 μM (1 μL of 25 mM stock in DMSO) to separate wells 4.5 hours after the addition of the test compound. (Again, basal, background or control wells not stimulated with A23187 received 1 μL of DMSO.) At 5 hours after the addition of the test compound, all incubations were terminated by placement on ice and the addition of 2 mM EGTA (100 μL of 20 mM EGTA, tetrasodium, in PBS (phosphate buffered saline) without $Ca^{++}$ and $Mg^{++}$, pH 7.2)). The resulting solutions, were transferred by polyethylene transfer pipettes to 15 mL polypropylene centrifuge tubes and centrifuged at 1200 g for 10 minutes at 4° C. One hundred μL of plasma was removed from each blood sample and added to 1 mL of methanol in new 15 mL polypropylene centrifuge tubes, vortexed, and stored overnight at –20° C. The next day, the samples were centrifuged at 2000 g for 10 minutes at 4° C. and the supernatants transferred to glass tubes and evaporated to dryness. The samples were assayed for thromboxane $B_2$ using EIA kits supplied by Cayman Chemical Co. (Ann Arbor, Mich., Catalogue No. 519031) in duplicate wells after reconstitution with EIA Buffer and appropriate dilution (2000 fold for COX-1 and 500 fold for Cox-2 samples).

The % inhibition for COX-1 and COX-2 enzyme activity in human whole blood by the test compounds, at the indicated concentrations, are given in Table 1.

TABLE 1

% INHIBITION OF COX-1 AND COX-2 ENZYME ACTIVITY IN HUMAN WHOLE BLOOD

| Test Compound | COX-1 Inhibition (% at 100 μM) | COX-2 Inhibition (% at 10 μM) | COX-2 Inhibition (% at 1 μM) |
|---|---|---|---|
| Example 1g | 35 | 75 | 35 |
| Example 1h | 60 | 90 | 50 |
| Example 2c | 40 | 25 | 10 |
| Example 2d | 35 | 90 | 60 |

TABLE 1-continued

% INHIBITION OF COX-1 AND COX-2 ENZYME ACTIVITY IN HUMAN WHOLE BLOOD

| Test Compound | COX-1 Inhibition (% at 100 μM) | COX-2 Inhibition (% at 10 μM) | COX-2 Inhibition (% at 1 μM) |
|---|---|---|---|
| Example 3e | 0 | 90 | 60 |
| Example 3f | 20 | 80 | 55 |
| Example 4e | 45 | 70 | 30 |
| Example 4f | 20 | 95 | 70 |
| Example 5d | 25 | 80 | 20 |
| Example 5e | 55 | 85 | 50 |
| Example 6e | 40 | 85 | 50 |
| Example 6f | 80 | 95 | 50 |
| Example 7d | 80 | 95 | 25 |
| Example 7e | 90 | 100 | 65 |
| Example 8d | 70 | 90 | 20 |
| Example 8e | 90 | 95 | 50 |
| Example 9d | 40 | 85 | 30 |
| Example 9e | 45 | 100 | 60 |
| Example 10d | 100 | 100 | 25 |
| Example 10e | 85 | 100 | 70 |
| Example 11d | 25 | 30 | 0 |
| Example 11e | 90 | 100 | 95 |
| Example 11f | 85 | 90 | 55 |
| Example 12d | 0 | 45 | 15 |
| Example 12e | 55 | 95 | 70 |
| Example 13d | 0 | 25 | 25 |
| Example 13e | 40 | 100 | 55 |
| Example 14d | 0 | 70 | 15 |
| Example 14e | 90 | 95 | 70 |
| Example 15d | 10 | 40 | 0 |
| Example 15e | 35 | 75 | 35 |
| Example 16b | 10 | 55 | 20 |
| Example 16c | 10 | 85 | 45 |
| Example 17b | 80 | 100 | 135 |
| Example 17d | 25 | 25 | 0 |
| Example 18d | 40 | 90 | 45 |
| Example 18e | 80 | 95 | 55 |
| Example 19b | 40 | 100 | 20 |
| Example 19c | 35 | 30 | 20 |
| Example 20f | 35 | 65 | 10 |
| Example 20g | 45 | 85 | 20 |
| Example 21b | 10 | 25 | 10 |
| Example 21c | 60 | 90 | 45 |
| Example 22c | 40 | 80 | 25 |
| Example 22d | 75 | 30 | 30 |
| Example 23d | −20 | 10 | 0 |
| Example 23e | 45 | 100 | 35 |
| Example 24d | 85 | 85 | 50 |
| Example 24e | 100 | 100 | 95 |
| Example 25e | 10 | 0 | 15 |
| Example 25f | 55 | 40 | 40 |
| Example 26a | 25 | 85 | 50 |
| Example 26b | 70 | 100 | 55 |
| Example 27a | 45 | 90 | 40 |
| Example 27b | 65 | 100 | 50 |
| Example 28a | 30 | 55 | 30 |
| Example 28b | 55 | 80 | 40 |
| Example 29a | −15 | 65 | 35 |
| Example 29b | 0 | 60 | 0 |
| Example 31c | 10 | 15 | 0 |
| Example 32c | −20 | 75 | 15 |
| Example 32d | 0 | 85 | 20 |
| Example 33a | 75 | 100 | 40 |
| Example 33b | 85 | 100 | 90 |
| Example 34a | 95 | 100 | 90 |
| Example 34b | 75 | 100 | 90 |
| Example 35c | 0 | 30 | 25 |
| Example 36b | 30 | 55 | 30 |
| Example 36c | 55 | 80 | 40 |
| Example 37b | 50 | 90 | 35 |
| Example 37c | −15 | 20 | 20 |
| Example 38c | 10 | 25 | 15 |
| Example 39 | 100 | 100 | 85 |
| Example 41 | 40 | 45 | 0 |
| Example 42d | 0 | 100 | 0 |
| Example 42e | 35 | 55 | 10 |
| Example 43g | 30 | 10 | 0 |
| Example 43h | 50 | 20 | 10 |
| Example 44d | 10 | 60 | 30 |
| Example 44e | 60 | 100 | 30 |
| Example 47f | 85 | 65 | 30 |

The results show that the compounds in Table 1 have COX-2 selectivity.

Example 49

Rat Carrageenan Air-Pouch

The carrageenan air pouch model was performed as described by Sedgwick et al., *Agents Actions* 18, 429-438, (1986) and Masferrer et al, *Proc. Natl. Acad. Sci.* 91, 3228-3232 (1994). Air pouches were produced by subcutaneous injection of 20 ml of sterile air on day (−6) into the intrascapular area of the back of the anesthesia rat (male CD, Charles River, 175-200 g). An additional 10 mL of sterile air was injected into the pouch 3 days later to keep the space open and to assist in the development of the interior membrane. Six days after the initial air injection, 1 mL of a 1% solution of carrageenan (Sigma, lambda fraction) dissolved in pyrogen-free saline was injected directly into the pouch to produce an inflammatory response. The test compound in vehicle (3 mL/rat, 0.5% Methocel) was administered by oral intubation 1 hour prior to carrageenan injection into the inflammatory pouch. After 4 hours the exudate was removed by pipette into a calibrated centrifuge tube and the volume measured. The number of leukocytes in the exudate was determined by cell counting with a Beckman Coulter Particle Counter with the lower threshold set to exclude red blood cells. The exudate samples were assayed without further processing for $PGE_2$ (prostaglandin $E_2$) using $PGE_2$ EIA kit-Monoclonal, from Cayman Chemical Co. (Ann Arbor, Mich., Catalogue No. 514010).

The % inhibition for the cell infiltration and the % inhibition for $PGE_2$ by the test compounds, at the indicated concentrations, are given in Table 2.

TABLE 2

| Test Compound | Cell Infiltration (% Inhibition @ 45 μmol/kg) | PGE-2 (% Inhibition at @ 45 μmol/kg) |
|---|---|---|
| Example 3f | 42 | 45 |
| Example 5e | 10 | 40 |
| Example 13e | 23 | 45 |
| Example 24e | 43 | 78 |

The compounds in Table 2 inhibit cell infiltration with an accompanying decrease in $PGE_2$ levels.

The disclosure of each patent, patent application and publication cited or described in the present specification is hereby incorporated by reference herein in its entirety.

Although the invention has been set forth in detail, one skilled in the art will appreciate that numerous changes and modifications can be made to the invention, and that such changes and modifications can be made without departing from the spirit and scope of the invention.

What is claimed is:

1. A compound of Formula (I), (II) or a pharmaceutically acceptable salt thereof;

wherein the compound of Formula (I) is:

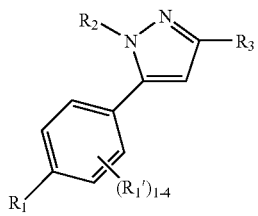

I wherein:
R$_1$ is —S(O)$_2$—CH$_3$;
R$_1$' at each occurrence is independently a hydrogen, a halogen, a methyl or CH$_2$OH;
R$_2$ is a substituted lower alkyl group, a cycloalkyl group, an aryl group or a heteroaryl;
R$_3$ is:
(a) —(C(R$_4$)(R'$_4$))$_k$—Y—(C(R$_4$)(R'$_4$))$_n$—O—V;
(b) —C(Z)-(C(R$_4$)(R'$_4$))$_k$—O—V;
(c) —C(Z)-(C(R$_4$)(R'$_4$))$_k$—Y—(C(R$_4$)(R'$_4$))$_n$—O—V;
(d) —(C(R$_4$)(R'$_4$))$_k$—Y—(C(R$_4$)(R'$_4$))$_n$—C(Z)—(C(R$_4$)(R'$_4$))$_n$—O—V;
(e) —(C(R$_4$)(R'$_4$))$_k$—CH=CH—(C(R$_4$)(R'$_4$))$_p$—O—V;
(g) —(C(R$_4$)(R'$_4$))$_n$—W-Q-(C(R$_4$)(R'$_4$))$_k$—O—V;
(h) —C(Z)-W-Q-(C(R$_4$)(R'$_4$))$_k$—O—V;
(i) —C(O)—N(R$_i$)—O—(C(R$_4$)(R'$_4$))$_n$—O—V;
(j) —(C(R$_4$)(R'$_4$))$_k$—C≡C—(C(R$_4$)(R'$_4$))$_p$—O—V;
(k) —(C(R$_4$)(R'$_4$))$_k$—Y—(C(R$_4$)(R'$_4$))$_k$—Y—(C(R$_4$)(R'$_4$))$_k$—O—V;
(l) —(C(R$_4$)(R'$_4$))$_p$-E-N(R$_i$)—O—W-Q-(C(R$_4$)(R'$_4$))$_k$—O—V;
(m) —(C(R$_4$)(R'$_4$))$_p$-E-N(R$_i$)—O—(C(R$_4$)(R'$_4$))$_k$—O—V;
(n) —(C(R$_4$)(R'$_4$))$_p$—N(R$_i$)—O—(C(R$_4$)(R'$_4$))$_k$—O—V;
(o) —(C(R$_4$)(R'$_4$))$_p$—O—N(R$_i$)—(C(R$_4$)(R'$_4$))$_k$—O—V;
(p) —(C(R$_4$)(R'$_4$))$_p$—O—N(R$_i$)-E-(C(R$_4$)(R'$_4$))$_k$—O—V; or
(q) —(C(R$_4$)(R'$_4$))$_p$—O—N(R$_i$)-E-W-Q-(C(R$_4$)(R'$_4$))$_k$—O—V;

R$_4$ and R'$_4$ at each occurrence are independently a hydrogen, a halogen, a lower alkyl group, or an alkoxy group;
V is —NO, —NO$_2$, or a hydrogen;
Y at each occurrence is independently an oxygen,—S(O)$_o$— or —N(R$_a$)R$_i$—;
Z is an oxo, a thial, an oxime or a hydrazone;
Q is Y or a covalent bond;
W at each occurrence is independently an aryl group, an alkylaryl group, a heterocyclic ring or an alkylheterocyclic ring;
E is —C(O) or —S(O)$_o$;
R$_a$ is a lone pair of electron, a hydrogen or a lower alkyl group;
R$_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an aminoalkyl, an aminoaryl, —(C(R$_4$)(R'$_4$))$_n$—O—V, or —(N$_2$O$_2$—)$^-$•M$^+$, wherein M$^+$is an organic or inorganic cation;
o is an integer from 0 to 2;
k is an integer from 1 to 6;
p at each occurrence is independently an integer from 0 to 10;
n at each occurrence is independently an integer from 2 to 10;
wherein the compound of Formula (II) is:

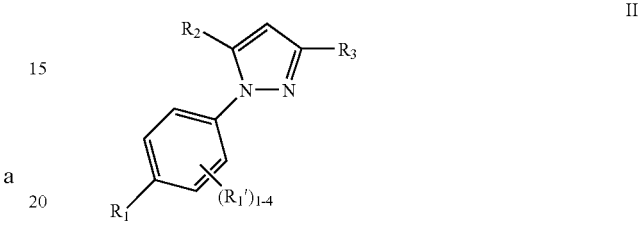

II wherein R$_1$, R$_1$', R$_2$ and R$_3$ are as defined herein.

2. A composition comprising the compound of claim 1 and a pharmaceutically acceptable carrier.

3. The composition of claim 2, further comprising at least one therapeutic agent.

4. The composition of claim 3, wherein the therapeutic agent is a steroid, a nonsteroidal antiinflammatory compound, a 5-lipoxygenase (5-LO) inhibitor, a leukotriene B$_4$ receptor antagonist, a leukotriene A$_4$ hydrolase inhibitor, a 5-HT agonist, a 3-hydroxy-3-methylglutaryl coenzyme A inhibitor, a H$_2$ antagonist, an antineoplastic agent, an antiplatelet agent, a thrombin inhibitor, a thromboxane inhibitor, a decongestant, a diuretic, a sedating or non-sedating antihistamine, an inducible nitric oxide synthase inhibitor, an opioid, an analgesic, a *Helicobacter pylori* inhibitor, a proton pump inhibitor, an isoprostane inhibitor, or a mixture of two or more thereof.

5. The composition of claim 4, wherein the nonsteroidal antiinflammatory compound is acetaminophen, aspirin, diclofenac, ibuprofen, ketoprofen or naproxen.

6. A composition comprising at least one compound of claim 1 and at least one compound that donates, transfers or releases nitric oxide, or induces the production of endogenous nitric oxide or endothelium-derived relaxing factor, or is a substrate for nitric oxide synthase.

7. The composition of claim 6, further comprising a pharmaceutically acceptable carrier.

8. The composition of claim 6, wherein the compound that donates, transfers, or releases nitric oxide, or induces the production of endogenous nitric oxide or endothelium-derived relaxing factor or is a substrate for nitric oxide synthase is an S-nitrosothiol.

9. The composition of claim 8, wherein the S-nitrosothiol is S-nitroso-N-acetylcysteine, S-nitroso-captopril, S-nitroso-N-acetylpenicillamine, S-nitroso-homocysteine, S-nitroso-cysteine, S-nitroso-glutathione, or S-nitroso-cysteinyl-glycine.

10. The composition of claim 8, wherein the S-nitrosothiol is:
(i) HS(C(R$_e$)(R$_f$))$_m$SNO;
(ii) ONS(C(R$_e$)(R$_f$))$_m$R$_e$; or
(iii) H$_2$N—CH(CO$_2$H)—(CH$_2$)$_m$—C(O)NH—CH(CH$_2$SNO)—C(O)NH—CH$_2$—CO$_2$H;

wherein m is an integer from 2 to 20; R$_e$ and R$_f$ are each independently a hydrogen, an alkyl, a cycloalkoxy, a halogen, a hydroxy, an hydroxyalkyl, an alkoxyalkyl, an arylheterocyclic ring, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cyano, an aminoalkyl, an aminoaryl, an aryl, an arylalkyl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, an alkylsulfonyl, an alkylsulfonyloxy, an arylsulfonyl, an arylsulfonyloxy, a urea, a nitro, or -T-Q-, or $R_e$ and $R_f$ taken together are an oxo, a thial, a heterocyclic ring, a cycloalkyl group, an oxime, a hydrazone or a bridged cycloalkyl group; Q is —NO or —NO$_2$; and T is independently a covalent bond, a carbonyl, an oxygen, —S(O)$_o$— or —N(R$_a$)R$_i$—, wherein o is an integer from 0 to 2, $R_a$ is a lone pair of electrons, a hydrogen or an alkyl group; $R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylsulfinyl, an alkylsulfonyl, an alkylsulfonyloxy, an arylsulfinyl, an arylsulfonyloxy, an arylsulfonyl, a sulfonamido, a carboxamido, a carboxylic ester, an aminoalkyl, an aminoaryl, or —(N$_2$O$_2$—)$^-$•M$^+$, wherein M$^+$ is an organic or inorganic cation; with the proviso that when $R_i$ is —(N$_2$O$_2$—)•M$^+$, then "-T-Q" can be a hydrogen, an alkyl group, an alkoxyalkyl group, an aminoalkyl group, a hydroxy group or an aryl group.

11. The composition of claim 6, wherein the compound that donates, transfers, or releases nitric oxide, or induces the production of endogenous nitric oxide or endothelium-derived relaxing factor, or is a substrate for nitric oxide synthase is L-arginine, L-homoarginine, N-hydroxy-L-arginine, nitrosated L-arginine, nitrosylated L-arginine, nitrosated N-hydroxy-L-arginine, nitrosylated N-hydroxy-L-arginine, nitrosated L-homoarginine, nitrosylated L-homoarginine), citrulline, ornithine, glutamine, lysine, an arginase inhibitor or a nitric oxide mediator.

12. The composition of claim 6, wherein the compound that donates, transfers, or releases nitric oxide, or induces the production of endogenous nitric oxide or endothelium-derived relaxing factor, or is a substrate for nitric oxide synthase is:

(i) a compound that comprises at least one ON—O— or ON—N— group;

(ii) a compound that comprises at least one O$_2$N—O—, O$_2$N—N— or O$_2$N—S— or group; or (iii) a N-oxo-N-nitrosoamine having the formula: R$^{1'''}$R$^{2''}$N—N(O—M$^+$)—NO, wherein R$^{1''}$ and R$^{2''}$ are each independently a polypeptide, an amino acid, a sugar, an oligonucleotide, a straight or branched, saturated or unsaturated, aliphatic or aromatic, substituted or unsubstituted hydrocarbon, or a heterocyclic group, and M$^+$ is an organic or inorganic cation.

13. The composition of claim 12, wherein the compound comprising at least one ON—O— or ON—N— group is an ON—O-polypeptide, an ON—N-polypeptide, an ON—O-amino acid, an ON—N-amino acid, an ON—O-sugar, an ON—N-sugar, an ON—O-oligonucleotide, an ON—N-oligonucleotide, a straight or branched, saturated or unsaturated, substituted or unsubstituted, aliphatic or aromatic ON—O-hydrocarbon, a straight or branched, saturated or unsaturated, substituted or unsubstituted, aliphatic or aromatic ON—N-hydrocarbon, an ON—O-heterocyclic compound or an ON—N-heterocyclic compound.

14. The composition of claim 12, wherein compound comprising at least one O$_2$N—O—, O$_2$N—N— or O$_2$N—S— group is an O$_2$N—O-polypeptide, an O$_2$N—N—polypeptide, an O$_2$N—S-polypeptide, an O$_2$N—O-amino acid, O$_2$N—N-amino acid, O$_2$N—S-amino acid, an O$_2$N—O-sugar, an O$_2$N—N-sugar, O$_2$N—S-sugar, an O$_2$N—O-oligonucleotide, an O$_2$N—N-oligonucleotide, an O$_2$N—S-oligonucleotide, a straight or branched, saturated or unsaturated, aliphatic or aromatic, substituted or unsubstituted O$_2$N—O-hydrocarbon, a straight or branched, saturated or unsaturated, aliphatic or aromatic, substituted or unsubstituted O$_2$N—N-hydrocarbon, a straight or branched, saturated or unsaturated, aliphatic or aromatic, substituted or unsubstituted O$_2$N—S-hydrocarbon, an O$_2$N—O-heterocyclic compound, an O$_2$N—N-heterocyclic compound or an O$_2$N—S-heterocyclic compound.

15. The composition of claim 6, further comprising at least one therapeutic agent.

16. The composition of claim 15, wherein the therapeutic agent is a steroid, a nonsteroidal antiinflammatory compound, a 5-lipoxygenase (5-LO) inhibitor, a leukotriene B$_4$ receptor antagonist, a leukotriene A$_4$ hydrolase inhibitor, a 5-HT agonist, a HMG CoA inhibitor, a H$_2$ antagonist, an antineoplastic agent, an antiplatelet agent, a thrombin inhibitor, a thromboxane inhibitor, a decongestant, a diuretic, a sedating or non-sedating anti-histamine, an inducible nitric oxide synthase inhibitor, an opioid, an analgesic, a *Helicobacter pylori* inhibitor, a proton pump inhibitor, an isoprostane inhibitor, or a mixture of two or more thereof.

17. The composition of claim 16, wherein the nonsteroidal antiinflammatory compound is acetaminophen, aspirin, diclofenac, ibuprofen, ketoprofen or naproxen.

18. A kit comprising at least one compound of claim 1.

19. The kit of claim 18, further comprising (i) at least one compound that donates, transfers or releases nitric oxide, induces the production of endogenous nitric oxide or endothelium-derived relaxing factor, or is a substrate for nitric oxide synthase; (ii) at least one therapeutic agent; or (iii) at least one compound that donates, transfers or releases nitric oxide, induces the production of endogenous nitric oxide or endothelium-derived relaxing factor, or is a substrate for nitric oxide synthase and at least one therapeutic agent.

20. The kit of claim 19, wherein the at least one compound that donates, transfers or releases nitric oxide, induces the production of endogenous nitric oxide or endothelium-derived relaxing factor, or is a substrate for nitric oxide synthase; the at least one therapeutic agent; or the at least one compound that donates, transfers or releases nitric oxide, induces the production of endogenous nitric oxide or endothelium-derived relaxing factor, or is a substrate for nitric oxide synthase and at least one therapeutic agent; are in the form of separate components in the kit.

21. A kit comprising the composition of claim 3, 7 or 15.

22. A compound selected from the group consisting of 1-(1-cyclohexyl-5-(4-(methylsulfonyl)phenyl)pyrazol-3-yl)-4-hydroxybutan-1-one;

1-(3-((1Z)-4-(hydroxy)but-1-enyl)-1-cyclohexylpyrazol-5-yl-4-methylsulfonyl)benzene;

4-(3-((3-hydroxypropoxy)methyl)-1-phenylpyrazol-5-yl)-1-(methylsulfonyl)benzene;

1-(3-(difluoro(3-hydroxypropoxy)methyl)-1-phenylpyrazol-5-yl)-4-(methylsulfonyl)benzene;

1-(1-(4-chlorophenyl)-3-((3-hydroxypropoxy)methyl)pyrazol-5-yl)-4-(methylsulfonyl) benzene;

1-(3-((3-hydroxypropoxy)methyl)-1-(4-methylphenyl) pyrazol-5-yl)-4-(methylsulfonyl)benzene;
1-(3-((3-hydroxypropoxy)methyl)-1-(4-(trifluoromethyl) phenyl)pyrazol-5-yl)-4-(methylsulfonyl)benzene;
1-(3-((3-hydroxypropoxy)methyl)-1-(4-methoxyphenyl) pyrazol-5-yl)-4-(methylsulfonyl) benzene;
1-(3-((1Z)-4-(hydroxy)but-1-enyl)-1-phenylpyrazol-5-yl)-4-(methylsulfonyl)benzene;
4-hydroxy- 1-(1-(4-methylphenyl)-5-(4-(methylsulfonyl) phenyl)pyrazol-3-yl)butan-1-one;
1-(1-(4-fluorophenyl)-5-(4-(methylsulfonyl)phenyl)pyrazol-3-yl)-4-hydroxybutan-1-one;
1-(1-(4-bromophenyl)-5-(4-(methylsulfonyl)phenyl)pyrazol-3-yl)-4-hydroxybutan-1-one;
1-(1-cyclohexyl-3-((2-hydroxyethoxy)methyl)pyrazol-5-yl)-4-(methylsulfonyl)benzene;
1-(1-cyclohexyl-3-((3-hydroxypropoxy)methyl)pyrazol-5-yl)-4-(methylsulfonyl)benzene;
1-(1-(4-fluorophenyl)-3-((3-hydroxypropoxy)methyl) pyrazol-5-yl)-4-(methylsulfonyl)benzene;
1-(3-((3-hydroxybutoxy)methyl)-1-phenylpyrazol-5-yl)-4-(methylsulfonyl)benzene;
1-(3-((1E)-4-(hydroxy)but-1-enyl)-1-cyclohexylpyrazol-5-yl)-4-methylsulfonyl)benzene;
1-(1-cyclohexyl-5-(4-(methylsulfonyl)phenyl)-pyrazol-3-yl)-6-hydroxyhexan-1-one;
4-hydroxy-1-(5-(4-(methylsulfonyl)phenyl)-1-(4-(trifluoromethyl)-phenyl)pyrazol-3-yl) butan-1-one;
4-hydroxy-1-(1-(4-methoxyphenyl)-5-(4-(methylsulfonyl)phenyl)-pyrazol-3-yl) butan-1-one;
4(3-((1E)-3-hydroxyprop-1-enyl)-1-cyclohexylpyrazol-5-yl)-1 (methylsulfonyl) benzene;
1-(1-cyclohexyl-3-(((2-hydroxyethyl)amino)methyl) pyrazol-5-yl)-4-(methylsulfonyl)benzene;
4-(3-(4-hydroxybutanoyl)-5-(4-(methylsulfonyl)phenyl) pyrazolyl) benzenecarbonitrile;
1-(1-(4-chloroophenyl)-5-(4-(methylsulfonyl)phenyl) pyrazol-3-yl)-4-hydroxybutan-1-one;
(1-cyclohexyl-5-(4-(methylsulfonyl)phenyl)pyrazol-3-yl)-N-(2-hydroxyethyl)carboxamide;
(1-cyclohexyl-5-(4-(methylsulfonyl)phenyl)pyrazol-3-yl)-N-(3-hydroxypropyl) carboxamide;
1-(3-((1Z)-4-(nitrooxy)but-1-enyl)-1-cyclohexylpyrazol-5-yl)-4-(methylsulfonyl) benzene;
4-(3-((3-(nitrooxy)propoxy)methyl)-1-phenylpyrazol-5-yl)-1-(methylsulfonyl)benzene;
1-(3-(difluoro-(3-(nitrooxy)propoxy)methyl)-1-phenylpyrazol-5-yl)-4-(methylsulfonyl) benzene;
1-(1-(4-chlorophenyl)-3-((3-(nitrooxy)propoxy)methyl) pyrazol-5-yl)-4-(methylsulfonyl) benzene;
1-(1-(4-methylphenyl)-3-((3-(nitrooxy)propoxy)methyl) pyrazol-5-yl)-4-(methylsulfonyl) benzene;
4-(methylsulfonyl)-1-(3-((3-(nitrooxy)propoxy)methyl)-1-(4-(trifluoromethyl)phenyl)pyrazol-5-yl)benzene;
1-(1-(4-methoxy-3-nitrophenyl)-3-((3-(nitrooxy)propoxy)methyl)pyrazol-5-yl)-4-(methylsulfonyl) benzene;
1-(3-((1Z)-4-(nitrooxy)but-1-enyl)-1-phenylpyrazol-5-yl)-4-(methylsulfonyl)benzene;
1-(3-((1E)-4-(nitrooxy)but-1-enyl)-1-phenylpyrazol-5-yl)-4-(methylsulfonyl)benzene;
1-(1-(4-methylphenyl)-5-(4-(methylsulfonyl)phenyl) pyrazol-3-yl)-4-(nitrooxy) butan-1-one;
1-(1-(4-fluorophenyl)-5-(4-(methylsulfonyl)phenyl)pyrazol-3-yl)-4-(nitrooxy) butan-1-one
1-(1-(4-bromophenyl)-5-(4-(methylsulfonyl)phenyl)pyrazol-3-yl)-4-(nitrooxy) butan-1-one;
1-(1-cyclohexyl-3-((2-(nitrooxy)ethoxy)methyl)pyrazol-5-yl)-4-(methylsulfonyl)benzene;
1-(1-cyclohexyl-3-((3-(nitrooxy)propoxy)methyl)pyrazol-5-yl)-4-(methylsulfonyl)benzene;
1-(1-(4-fluorophenyl)-3-((3-(nitrooxy)propoxy)methyl) pyrazol-5-yl)-4-(methylsulfonyl) benzene;
4-(methylsulfonyl)-1-(3-((3-(nitrooxy)butoxy)methyl)-1-phenylpyrazol-5-yl)benzene;
1-(3-((1E)-4-(nitrooxy)but-1-enyl)-1-cyclohexylpyrazol-5-yl)-4-(methylsulfonyl)benzene;
1-(1-cyclohexyl-5-(4-(methylsulfonyl)pyrazol-3-yl)-6-(nitrooxy)hexan-1-one;
1-(5-(4-(methylsulfonyl)phenyl)-1-(4-(trifluoromethyl) phenyl)pyrazol-3-yl)-4-(nitrooxy)butan-1-one;
1-(1-(4-methoxyphenyl)-5-(4-(methylsulfonyl)phenyl) pyrazol-3-yl-4-(nitrooxy) butan-1-one;
1-(5-(4-(methysulfonyl)phenyl)-1-(2-pyridyl)pyrazol-3-yl)-2-(nitrooxy)ethan-1-one;
4-(1-(4-methoxyphenyl)-3-((3-(nitrooxy)propoxy)methyl)pyrazol-5-yl)-1-(methylsulfonyl) benzene;
4-(1-(4-methyl-3-nitrophenyl)-3-((3-(nitrooxy)propoxy) methyl)pyrazol-5-yl)-1-(methylsulfonyl)benzene;
1-(3-((1E)-3-(nitrooxy)prop-1-enyl)-1-cyclohexylpyrazol-5-yl)-4-(methylsulfonyl) benzene;
4-(5-(4-(methylsulfonyl)phenyl)-3-(4-(nitrooxy)butanoyl)pyrazolyl) benzenecarbonitrile;
1-(1-(4-chlorophenyl)-5-(4-(methylsulfonyl)phenyl)pyrazol-3-yl)-4-(nitrooxy) butan-1-one;
(1-cyclohexyl-5-(4-(methylsulfonyl)phenyl)pyrazol-3-yl)-N-(2-(nitrooxy)ethyl)carboxamide;
(1-cyclohexyl-5-(4-(methylsulfonyl)phenyl)pyrazol-3-yl)-N-(3-(nitrooxy)propyl)carboxamide;
3-(nitrooxy)propyl, 4-(5-(4-(methylsulfonyl)phenyl)-1-(4-(trifluoromethyl)-phenyl)pyrazol-3-yl)butanoate;
1-(3-((1Z)-4-hydroxybut-1-enyl)-5-(3-pyridyl)pyrazolyl)-4-(methylsulfonyl)benzene; and
1-(3-((1Z)-4-(nitrooxy)but-1-enyl)-5-(3-pyridyl)pyrazolyl)-4-(methylsulfonyl)benzene;

or a pharmaceutically acceptable salt thereof.

23. A composition comprising at least one compound of claim 22 and a pharmaceutically acceptable carrier.

24. The composition of claim 23, further comprising (i) at least one compound that donates, transfers or releases nitric oxide, induces the production of endogenous nitric oxide or endothelium-derived relaxing factor, or is a substrate for nitric oxide synthase; (ii) at least one therapeutic agent; or (iii) at least one compound that donates, transfers or releases nitric oxide, induces the production of endogenous nitric oxide or endothelium-derived relaxing factor, or is a substrate for nitric oxide synthase and at least one therapeutic agent.

25. A kit comprising at least one compound of claim 22.

* * * * *